(12) United States Patent
Kimba et al.

(10) Patent No.: US 6,855,929 B2
(45) Date of Patent: Feb. 15, 2005

(54) APPARATUS FOR INSPECTION WITH ELECTRON BEAM, METHOD FOR OPERATING SAME, AND METHOD FOR MANUFACTURING SEMICONDUCTOR DEVICE USING FORMER

(75) Inventors: Toshifumi Kimba, Kanagawa (JP); Tohru Satake, Kanagawa (JP); Tsutomu Karimata, Kanagawa (JP); Kenji Watanabe, Kanagawa (JP); Nobuharu Noji, Kanagawa (JP); Takeshi Murakami, Tokyo (JP); Masahiro Hatakeyama, Kanagawa (JP); Mamoru Nakasuji, Kanagawa (JP); Hirosi Sobukawa, Kanagawa (JP); Shoji Yoshikawa, Tokyo (JP); Shin Oowada, Kanagawa (JP); Mutsumi Saito, Kanagawa (JP)

(73) Assignee: Ebara Corporation, Tokyo (JP)

(*) Notice: Subject to any disclaimer, the term of this patent is extended or adjusted under 35 U.S.C. 154(b) by 200 days.

(21) Appl. No.: 09/985,324
(22) Filed: Nov. 2, 2001
(65) Prior Publication Data

US 2002/0148975 A1 Oct. 17, 2002

(30) Foreign Application Priority Data

| Dec. 1, 2000 | (JP) | 2000-367082 |
|---|---|---|
| Dec. 6, 2000 | (JP) | 2000-371078 |
| Jan. 10, 2001 | (JP) | 2001-002234 |
| Feb. 8, 2001 | (JP) | 2001-031901 |
| Feb. 8, 2001 | (JP) | 2001-031906 |
| Feb. 9, 2001 | (JP) | 2001-035599 |
| Feb. 14, 2001 | (JP) | 2001-037212 |
| Mar. 15, 2001 | (JP) | 2001-073374 |
| Mar. 27, 2001 | (JP) | 2001-089107 |
| Apr. 13, 2001 | (JP) | 2001-114999 |
| Apr. 23, 2001 | (JP) | 2001-124244 |
| May 28, 2001 | (JP) | 2001-158662 |
| Jun. 19, 2001 | (JP) | 2001-184733 |

(51) Int. Cl.$^7$ .......................... G01N 23/00; G21K 7/00
(52) U.S. Cl. .................... 250/310; 250/307; 250/492.2
(58) Field of Search .............................. 250/310, 492.2, 250/307

(56) References Cited

U.S. PATENT DOCUMENTS

| 5,986,263 | A | | 11/1999 | Hiroi et al. .................. 250/310 |
|---|---|---|---|---|
| 6,329,826 | B1 | * | 12/2001 | Shinada et al. ............. 324/751 |
| 6,365,897 | B1 | * | 4/2002 | Hamashima et al. ........ 250/310 |
| 6,518,582 | B1 | * | 2/2003 | Kohama .................. 250/492.2 |

FOREIGN PATENT DOCUMENTS

EP  0 312 082  4/1989

(List continued on next page.)

Primary Examiner—John R. Lee
Assistant Examiner—Paul Gurzo
(74) Attorney, Agent, or Firm—Westerman, Hattori, Daniels & Adrian, LLP

(57) ABSTRACT

A substrate inspection apparatus 1-1 (FIG. 1) of the present invention performs the following steps of: carrying a substrate "S" to be inspected into an inspection chamber 23-1 maintaining a vacuum in said inspection chamber; isolating said inspection chamber from a vibration; moving successively said substrate by means of a stage 26-1 with at least one degree of freedom; irradiating an electron beam having a specified width; helping said electron beam reach to a surface of said substrate via a primary electron optical system 10-1; trapping secondary electrons emitted from said substrate via a secondary electron optical system 20-1 and guiding it to a detecting system 35-1; forming a secondary electron image in an image processing system based on a detection signal of a secondary electron beam obtained by said detecting system; detecting a defective location in said substrate based on the secondary electron image formed by said image processing system; indicating and/or storing said defective location in said substrate by CPU 37-1; and taking said completely inspected substrate out of the inspection chamber. Thereby, the defect inspection on the substrate can be performed successively with high level of accuracy and efficiency as well as with higher throughput.

55 Claims, 55 Drawing Sheets

FOREIGN PATENT DOCUMENTS

| | | |
|---|---|---|
| EP | 1 061 359 | 12/2000 |
| JP | 58-018833 | 2/1983 |
| JP | 09-180655 | 7/1997 |
| JP | 11-223662 | 8/1999 |
| JP | 2000-149853 | 5/2000 |
| JP | 2000-161948 | 6/2000 |
| JP | 2000-315712 | 11/2000 |
| JP | 2000-323538 | 11/2000 |

* cited by examiner

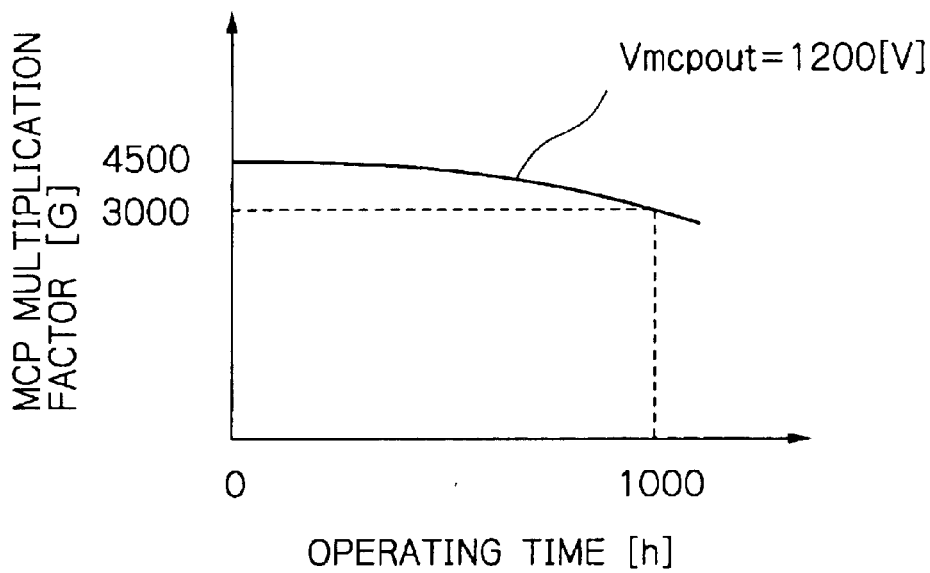
CORRELATION BETWEEN OPERATING TIME
AND MCP MULTIPLICATION FACTOR
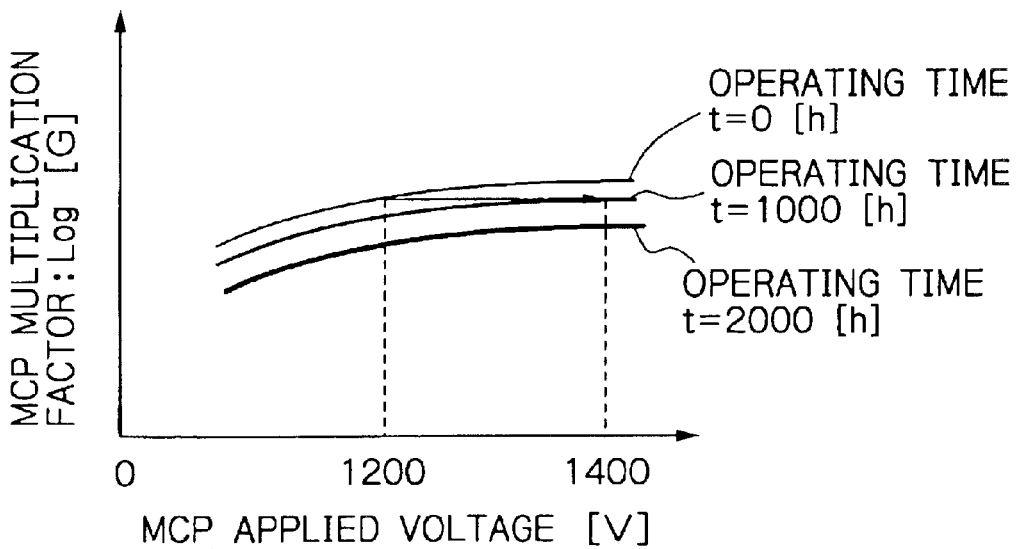
CORRELATION BETWEEN MCP APPLIED VOLTAGE
AND MCP MULTIPLICATION FACTOR (a)

APPARATUS FOR INSPECTION WITH ELECTRON BEAM, METHOD FOR OPERATING SAME, AND METHOD FOR MANUFACTURING SEMICONDUCTOR DEVICE USING FORMER

BACKGROUND OF THE INVENTION

In the field of semiconductor processes, the design rule is going into an age of 100 nm and the production form is on a transition from a mass production with a few models representative of a DRAM into a small-lot production with a variety of models such as a SOC (Silicon on chip). This results in an increase of a number of processes, and thus an improvement in yield for each process becomes essential, which makes more important an inspection for a defect possibly occurring in each process. The present invention relates to an apparatus to be used in the inspection of a wafer after respective processes in the semiconductor processes, and in particular to an inspection method and apparatus using an electron beam and also to a device manufacturing method using the same.

In conjunction with a high integration of semiconductor device and a micro-fabrication of pattern thereof, an inspection apparatus with higher resolution and throughput has been desired. In order to inspect a wafer substrate of 100 nm design rule for any defects, a resolution in size equal to or finer than 100 nm is required, and the increased number of processes resulting from a high integration of the device has called for an increase in the amount of inspection, which consequently requires higher throughput. In addition, as a multi-layer fabrication of the device has been progressed, the apparatus has been further required to have a function for detecting a contact failure in a via for interconnecting wiring between layers (i.e., an electrical defect). In the current trend, an inspection apparatus of optical method has been typically used, but it is expected that an inspection apparatus using an electron beam may soon be of mainstream, substituting for the inspection apparatus of optical method in the viewpoint of resolution and of inspection for contact failure. The inspection apparatus of electron beam method, however, has a weak point in that the inspection apparatus of electron beam method is inferior to the inspection apparatus of optical method in view of throughput.

Accordingly, it would be desirable to develop an apparatus having higher resolution and throughput and being capable of detecting the electrical defects. It is known that the resolution in the inspection apparatus of optical method is limited to ½ of the wavelength of the light to be used, and it is about 0.2 $\mu$m for an exemplary case of a visible light having put to practical use.

On the other hand, in the method using an electron beam, typically a scanning electron microscope (SEM method) has been put to practice, wherein the resolution thereof is 0.1 $\mu$m and the inspection time is 8 hours per wafer (20 cm wafer). The electron microscope method further has a distinctive feature that it is able to inspect for any electrical defects (breaking of wire in the wirings, bad continuity, bad continuity of via). However, the inspection speed (sometime also referred to as inspection speed) thereof is very low, and so the development of an inspection apparatus with higher inspection speed has been expected.

Generally, since an inspection apparatus is expensive and a throughput thereof is rather lower as compared to other processing apparatuses, therefore the inspection apparatus has been used after an important process, for example, after the process of etching, membrane deposition, CMP (Chemical-mechanical polishing) planarization or the like.

The inspection apparatus of scanning method using an electron beam (SEM) will now be described. In the inspection apparatus of SEM method, the electron beam is contracted to be narrower (the diameter of this beam corresponds to the resolution thereof) and this narrowed beam is used to scan a sample so as to radiate it linearly. On the other hand, moving a stage in the direction normal to the scanning direction allows an observation region to be irradiated by the electron beam as a plane area. The scanning width of the electron beam is typically some 100 $\mu$m. Secondary electrons emitted from the sample by the irradiation of said contracted and narrowed electron beam (referred to as a primary electron beam) are detected by a detector (a scintillator plus photo-multiplier (i.e., photoelectron multiplier tube) or a detector of semiconductor type (i.e., a PIN diode type) or the like). A coordinate for an irradiated location and an amount of the secondary electrons (signal intensity) are combined and formed into an image, which is stored in a storage or displayed on a CRT (a cathode ray tube). The above description shows the principle of the SEM (scanning electron microscope), and defects in a semiconductor wafer (typically made of Si) in the course of process may be detected from the image obtained in this method. The inspection speed (corresponding to the throughput) is varied in dependence on an amount of primary electron beam (the current value), a beam diameter, and a response time of the detector. The beam diameter of 0.1 $\mu$m (which may be considered to be equivalent to the resolution), the current value of 100 nA, and the response time of the detector of 100 MHz are the currently highest values, and in the case using those values the inspection speed has been evaluated to be about 8 hours for one wafer having the diameter of 20 cm.

In order to improve the inspection apparatus of said SEM method to work at much higher speed (to increase the throughput), a new method referred to as an image projecting method has been suggested. According to this method, an observation region on a sample is irradiated in block by a primary electron beam (i.e., no scanning but an irradiation covering a certain area), and secondary electrons emitted from the irradiated region are formed into an image in block by a lens system on a detector (a micro-channel plate (MCP) plus fluorescent screen) as an image of electron beam. That image is used in a two-dimensional CCD (charge coupled device) or a TDI-CCD (Time Delayed Integration-CCD) to convert the image data into an electric signal, and from this image data, defects in the sample wafer (the semiconductor (Si) wafer in the course of process) may be detected.

Accordingly, there has arisen a demand for constructing an overall system for inspecting such as a substrate with high level of accuracy and efficiency by using a defect inspection apparatus of said image projecting method having an advantage of higher throughput. Almost no study has made clear an overall structure of such an inspection apparatus that, for example, feeds a sample to inspection as in a clean state to an irradiating location in the image projecting optical apparatus, allowing for an association with the other subsystems to be brought in alignment with it. In addition, in such an environment where the diameter of a wafer subject to inspection has been made larger and larger, there has arisen a demand that the subsystems also should be correspondingly modified to be suitable for the wafer having a large diameter.

In the inspection system, maintaining a vacuum atmosphere within the chamber is one of the important terms. In an apparatus such as a defect inspection apparatus that provides an ultraprecision processing, a stage for accurately positioning a sample in the vacuum atmosphere has been used, wherein in the case where said stage is required to be positioned highly accurately, one structure has been conventionally employed, in which the stage is supported in non-contact manner by a hydrostatic bearing. In this case, the vacuum level in a vacuum chamber is maintained by forming in an extent of the hydrostatic bearing a differential pumping mechanism for exhausting a high pressure gas so that the high pressure gas supplied from the hydrostatic bearing may not be directly exhausted into the vacuum chamber. Aiming at such a stage, specifically a stage including a combination of the hydrostatic bearing and the differential pumping mechanism has been proposed, as shown in FIGS. 29 [A] and [B]. In this configuration, when the stage moves, guide planes 6a-7 and 7a-7 facing to the hydrostatic bearing 9-7 move forth and back between the high pressure gas atmosphere in the hydrostatic section and the vacuum environment within the chamber. For this period, the gas is adsorbed onto the guide plane during it being exposed to the high pressure gas atmosphere and the adsorbed gas is discharged once the guide plane is exposed to the vacuum environment, which will repeatedly occur. Owing to this, every time when the stage moves, there occurs such an event that the vacuum level within the chamber C is deteriorated, which disadvantageously has inhibited the processing including the aforementioned exposure, inspection and process by using the charged particle beam from being performed stably, or otherwise the sample has been contaminated.

Further, there have been such problems in the above-described stage including a combination of the hydrostatic bearing and the differential pumping mechanism that because of the differential pumping mechanism having been added, the structure has become more complicated and the reliability as a stage has decreased in contrast with the increased cost.

As for the electron beam apparatus of the image projecting method by itself, since a plurality of signals from a plurality of pixels on the sample surface can be captured all at once, therefore this method is advantageous in the point of the pattern inspection with the high throughput, while the method is problematic in the point that the sample may be charged due to a plurality of pixels being exposed to the irradiation of the electron beam all at once. On the other hand, in the case where a mark for positioning on the wafer is to be detected during the processes, a field of view may not necessarily be such wide that would be required by the image projection in the pattern inspection but a narrower field of view may be sufficient, wherein it is rather problematic that an insufficiently small pixel size may result in an insufficient mark detection accuracy.

Besides, for the MCP, as a total output charge amount (screen current×time period) is increased over a long-time use, the MCP multiplication factor is decreased, and therefore there has been a problem in that a defective image contrast may change or deteriorate with the same MCP applied voltage upon picking up the defective images successively for a long period in the defect inspection apparatus.

Further, an amplification factor in the image beam current amount is determined by a voltage applied between a first MCP and a second MCP and for example, the amplification factor should be $1 \times 10^4$ with the applied voltage of 1.4 kV. Additionally, a voltage on the order of 3 kV is applied between the second MCP and the fluorescent screen in order to inhibit the expansion of the image beam output from the second MCP. A detector of a conventional electron beam apparatus, in which a camera sensor and a vacuum flange have been separately formed, is disadvantageous in that it has a longer signal line, it is susceptive to signal latency or disturbance, and it prohibits the fast driving of the detector, which has been factors to decrease the throughput in the inspection (a process volume per time).

Further, to perform the defect inspection by using the electron beam, an emission current flow to an electron gun is required to be controlled so as to keep the contrast in the picked-up image at a constant level, and typically the emission current has been controlled by adjusting a voltage applied to the Wehnelt electrode made of such material as $LaB_6$ (lanthanum hexaboride) disposed downstream to the electron gun. FIG. 15 is a graph illustrating a relationship between the voltage (in volt) applied to the Wehnelt electrode and the emission current (in microampere) of the electron gun, and it is seen from this graph that if the voltage applied to the Wehnelt electrode exceeds the level of −300 volt, the emission current increases rapidly.

However, if the electron gun operates for a long time under the condition that the applied voltage to the Wehnelt electrode is maintained at a constant level, an oxide film including La and B emitted from the electron gun may adhere to the inside of the Wehnelt electrode and form an insulating film thereon, which will be positively charged. This is because the electron emitted from the electron gun has an accelerating energy as much as the applied voltage to the Wehnelt electrode, and such electrons impinging upon said insulating film may cause the insulating film to emit the secondary electrons more than the electrons flowing into the Wehnelt electrode. As a matter of fact, there has been a problem in that the applied voltage to the Wehnelt electrode shifting to the positive direction causes a gradual increase in the emission current of the electron gun, which makes it difficult to hold the constant emission current.

On the other hand, advantageously the inspection apparatus having a function as the scanning electron microscope according to the prior art, as compared to the inspection apparatus of the image projecting method, has no such problem that the sample is charged but has a sufficient mark detection accuracy. Individually, either of them has to solve the following problems.

For example, if a sample wafer includes a via formed therein, then a care must be taken upon performing an evaluation procedure for the sample wafer. This is because if a large decelerating electric field as well as the primary electron beam by the amount of not less than a certain value is applied between the objective lens and the wafer, a discharge occurs between the via and the objective lens, and said discharge may possibly cause a damage to a device pattern formed in the wafer. There are a wafer of one type that is apt to incur such a discharge and a wafer of other type that hardly incurs the discharge, wherein the wafer of either type has a different condition of inducing the discharge (different decelerating electric field voltage value and different primary electron beam amount).

Further, it has been known that an edge portion of a pattern is apt to dazzle due to a higher secondary electron emission rate. With the higher secondary electron emission rate, the detection signal of the secondary electron beam to be output by the detector has an increasing signal intensity, and disadvantageously this detection signal results in a masking of a signal generated by a defect, thereby deteriorating the inspection speed.

In an apparatus for evaluating the post-process condition of a wafer according to the prior art, the inspection is performed to encompass the entire area of the wafer, and therefore the wafer is moved within a working chamber so that an arbitrary point on the wafer surface may be positioned in alignment with the optical axis of the electron beam. Accordingly, the evaluation apparatus of the conventional example needs a bottom area extended in the forth and back and the left and right directions by such an amount that can accommodate the movement of the wafer, and inevitably the evaluation apparatus has an enlarged floor area. This enlargement of the floor area is a counter trend toward the effective use of the clean room, thus it is desired to make the evaluation apparatus compact.

Further, said conventional apparatus requires an inspection time of a few hours for a single wafer (a few hours/wafer) to accomplish the inspection covering the entire surface of the wafer. On the other hand, the throughput in the wafer processing apparatus reaches to approximately 100 wafers in 1 hour (about 100 wafers/hour), which means that the inspection time of the wafer is equivalent to dozen times of the process time. Thus, in the circumstance that there is a mismatch between the throughput of the evaluation apparatus and the throughput of the processing apparatus, it would be desirable that those throughputs are matched to each other by reducing the inspection time.

A gate oxide of the semiconductor device is apt to be made thinner year by year, and it has been believed that the thickness of the film may be on the order of 1 nm in the year of 2005 and 0.5 nm in the year of 2005. In addition, the minimum line width "d" of the pattern formed in the sample subject to the inspection is getting narrower, and in proportion to that, it is required to reduce the pixel size used in the evaluation. On the other hand, in order to secure an S/N ratio of the signal at a certain level, it is required to obtain a certain amount of detected secondary electrons per pixel, consequently leading to the trend of increasing the amount of the primary electron per unit area. As a result, the gate oxide is likely to be damaged (including breakdown) as it is getting thinner, while the voltage generated between both sides of the gate oxide increases as the dose increases, thereby the gate oxide is more apt to be damaged. In this viewpoint, it is strongly desired that such an electron beam apparatus be provided which would not give any damage to a thin gate oxide of a sample to be inspected.

Besides, there is a need for improving the throughput as much as possible, and thus it is desired that a sample such as a single wafer (hereafter referred to as a sample for simplicity) may be completely inspected or evaluated within a process time as long as that taken by a process prior to the inspection process. In this regard, it is also conceivable that the inspection time per sample may be reduced by evaluating an arbitrary small number of chips among many chips in a single sample.

Further, there has been no study on how to inhibit an aberration due to forming the primary beam into a multi-beam. In specific, such a method is strongly required that forms the multi-beam by using an optical system which prevents an image field curvature aberration, which is a most serious aberration among aberrations associated with the primary beam.

In conjunction with a defect inspection apparatus described above which uses the image projecting system and the multi-beam scanning method, it has been also suggested that an image recognition technology should be improved so as to achieve a fast and highly accurate defect inspection on a patter of micro-fabrication. However, the prior art has a problem that there may be a position mismatch between an image of the secondary electron beam obtained by irradiating the primary electron beam onto a region to be inspected on a surface of a sample and a reference image which has been prepared in advance, thereby resulting in the deterioration in the accuracy in the defect inspection. This position mismatch could be a serious problem specifically when the irradiating region of the primary electron beam is in the misalignment with respect to the wafer and a part of the inspected pattern falls out of the detected image of the secondary electron beam, which could not be compensated for properly by simply using the technology for optimizing the matching region within the detected image. This problem could be a critical drawback specifically in the inspection of a pattern of high-precision.

An object of the present invention is to provide an inspection method and an apparatus using an electron beam which have overcome those aforementioned problems and can detect a defect in a sample with high level of throughput and accuracy, and also to provide a semiconductor device manufacturing method using these inspection method and apparatus.

SUMMARY OF THE INVENTION

The present invention provides a substrate inspection apparatus comprising:

a. a beam source for generating an electron beam having a specified width;

b. a primary electron optical system for helping said electron beam reach to a surface of a substrate subject to an inspection;

c. a secondary electron optical system for guiding secondary electrons emitted from said substrate to a detecting system;

d. an image processing system for forming a secondary electron image based on a detection signal of a secondary electron beam obtained by said detecting system;

e. a stage for holding said substrate in such a manner that said substrate may be moved successively with at least one degree of freedom;

f. an inspection chamber for said substrate;

g. a substrate conveying mechanism capable of carrying said substrate into said inspection chamber and taking out it therefrom;

h. an image processing analyzer capable of detecting a defective location on the substrate carried into said inspection chamber based on the secondary electron image formed by said image processing system;

i. a vibration isolating mechanism for said inspection chamber;

j. a vacuum system capable of controlling a vacuum atmosphere to be maintained in said inspection chamber; and k. a control system for indicating and/or storing said defective location on said substrate detected by said image processing analyzer.

Further, the present invention provides a substrate inspection method comprising the steps of: carrying a substrate to be inspected into an inspection chamber; maintaining a vacuum in said inspection chamber; isolating said inspection chamber from a vibration; successively moving said substrate with at least one degree of freedom; irradiating an electron beam having a specified width; helping said electron beam reach to a surface of said substrate via a primary electron optical system; trapping secondary electrons emitted from said substrate and guiding them to a detecting system via a secondary electron optical system; forming a secondary electron image in an image processing system based on a detection signal of the secondary electron beam obtained from said detecting system; detecting a defective location on said substrate based on the secondary electron image formed by said image processing system; indicating and/or storing the detected defective location on said substrate; and taking said substrate having been completely inspected out of said inspection chamber.

According to the present invention, since the defect on the substrate can be detected by irradiating the electron beam having the specified width while the substrate being moved successively with at least one degree of freedom, therefore the throughput can be improved. Further, the present invention can construct an integrated defect inspection system which allows the defect inspection to be performed successively with high level of accuracy and efficiency by way of taking the substrate into/out of the inspection chamber, maintaining the vacuum within the inspection chamber and isolating the inspection chamber from the vibration.

According to a preferred embodiment of the present invention, there is provided an alternative substrate inspection apparatus characterized in further comprising: a mini-environment device for inhibiting dust from adhering to the substrate by applying a purge gas flow against said substrate prior to the inspection; and at least two loading chambers which are disposed between said mini-environment device and said inspection chamber and controllable to the vacuum atmosphere respectively and independently, wherein said substrate conveying mechanism includes a loader having one conveying unit capable of conveying said substrate between said mini-environment device and one of said loading chambers and another conveying unit capable of conveying said substrate between one of said loading chambers and said stage, and said vibration isolating mechanism includes a vibration blocking unit interposed between said inspection chamber and said loading chambers. Thereby, the vacuum within the inspection chamber can be maintained appropriately, and thus the adhesion of the dust to the substrate can be prevented appropriately.

According to another preferred embodiment of the present invention, there is provided an alternative substrate inspection apparatus characterized in further comprising a pre-charge unit for irradiating an electron beam onto said substrate disposed in said inspection chamber to reduce non-uniformity level in an electro static charge on said substrate, and a potential applying mechanism for applying a potential to said substrate.

According to still another preferred embodiment of the present invention, there is provided an alternative substrate inspection apparatus characterized in further comprising an alignment control unit for observing a surface of said substrate and controlling an alignment thereof in order to position said substrate in place with respect to said primary electron optical system, and a laser-interferometer for measuring a coordinate of said substrate on said stage, wherein said alignment control unit uses a pattern existing on said substrate to determine the coordinate of a subject to be inspected.

According to still another preferred embodiment of the present invention, there is provided an alternative substrate inspection apparatus characterized in that said detecting system comprises an MCP for amplifying said secondary electron beam, a fluorescent screen for converting said amplified secondary electron beam into an optical signal and a CCD camera or a line sensor for taking out said optical signal as an image data, wherein a voltage applied to said MCP is controlled in association with a change in the amplification factor of the MCP in order to determine an optimal amount of exposure for the image containing said defect. Thus, the deterioration in the image multiplying factor due to a long time use of the MCP can be prevented, and the image defect contrast can be maintained always at a certain constant level.

According to still another preferred embodiment of the present invention, there is provided an alternative substrate inspection apparatus characterized in that said detecting system comprises an MCP for amplifying said secondary electron beam, a fluorescent screen for converting said amplified secondary electron beam into an optical signal and a CCD camera or a line sensor for taking out said optical signal as an image data, wherein an emission current of said electron beam is controlled in association with a change in the amplification factor of the MCP in order to determine an optimal amount of exposure for the image containing said defect.

Alternatively, said voltage applied to said MCP may be determined by referring to a current MCP applied voltage-MCP gain curve. Further alternatively, said MCP applied voltage or the emission current of the beam may be controlled in association with a multiplying factor of the projection of the electron beam or a change in a line rate of said line sensor.

According to still another preferred embodiment of the present invention, there is provided an alternative substrate inspection apparatus characterized in that said detecting system is incorporated with a feed-through unit, said feed-through unit comprising: a feed-through section made of an electrical insulating material; at least one electricity introduction pin fixedly attached to said feed-through section; and a connecting wiring for connecting said at least one electricity introduction pin with a functional element, wherein said functional element includes a sensor, and both a pressure and a kind of gas of an inside of said feed-through section are different from those of an outside thereof, respectively. In that case, the functional element may be arranged on an inner surface of said feed-through section and the functional element may include a CCD or a TDI sensor. The wiring may be formed in a net-like configuration on the surface of said feed-through section. Further, a metal flange may be included therein. Preferably, the electricity introduction pin transmits a signal frequency of not less than 10 MHz.

According to still another preferred embodiment of the present invention, there is provided an alternative substrate inspection apparatus characterized in that said beam source is an electron beam source comprising a Wehnelt electrode, wherein said apparatus further comprises a control section for controlling a voltage applied to said Wehnelt electrode with time so that an emission current flowing to said electron beam source can be maintained at a constant level. Preferably, said electron beam source may comprise an electron gun having a cathode made of $LaB_6$. More preferably, a flat <100> mono-crystalline orientation having a diameter of not less than 100 microns may be arranged in a tip portion of said cathode.

According to still another preferred embodiment of the present invention, there is provided an alternative substrate inspection apparatus characterized in that said stage is provided with a non-contact supporting mechanism by means of a hydrostatic bearing and a vacuum sealing mechanism by means of a differential pumping, and a divider is arranged between a location on said substrate subject to the electron beam irradiation and a hydrostatic bearing supporting section of said stage so as to reduce a conductance, so that a pressure difference may be generated between the electron beam irradiated region and said hydrostatic bearing supporting section. According to the stage of this embodiment, since the non-contact supporting mechanism by means of the hydrostatic bearing is applied to the supporting mechanism of an XY stage on which the sample is loaded and also the vacuum sealing mechanism by means of the differential pumping is provided in the surrounding of the hydrostatic bearing so as to prevent the high pressure gas to be used for said hydrostatic bearing from leaking into the vacuum chamber, therefore the stage unit can exhibit the highly accurate positioning performance within the vacuum atmosphere, and further since even if the gas adsorbed on the surface of the slide portion of the stage is discharged when the slide portion moves from the high pressure gas section into the vacuum environment, the discharged gas hardly reach to the charged particle beam irradiating location due to the blocking by the divider formed between the charged particle beam irradiating location and the stage, therefore it is difficult to increase the pressure at the charged particle beam irradiating location. That is, employing the above configuration can help stabilize the vacuum level at the charged particle beam irradiating location on the sample surface and also drive the stage with high level of accuracy, thereby allowing the process using the charged particle beam against the sample to be performed with high precision as well as without any contamination on the sample surface.

More preferably, said divider may include a differential pumping structure integrated therein. According to this embodiment, since the divider is provided between the hydrostatic bearing supporting section and the charged particle beam irradiating region and the divider is further equipped with the differential pumping function by arranging a vacuum pumping channel inside of the divider, therefore any gas discharged from the hydrostatic bearing supporting section hardly passes over the divider and reaches to the side of the charged particle beam irradiating region. This can help further stabilize the vacuum level at the charged particle beam irradiating location.

Still more preferably, said divider may have a cold trap function. Generally, in a pressure range equal to or lower than $10^{-7}$ Pa, main components of a residual gas in vacuum atmosphere or a discharged gas from the material surface are water molecules. Accordingly, evacuating efficiently those water molecules facilitates a high vacuum level to be maintained stably. Then, since if the cold trap cooled down to approximately $-100°$ C. to $-200°$ C. is provided on said divider, the gas generated on the side of the hydrostatic bearing can be frozen to be trapped with the cold trap, the discharged gas hardly passes through to the side of the charged particle beam irradiating region, and accordingly the vacuum level in said charged particle beam irradiating region is more easily maintained to be stable. It is obvious that said cold trap is not only effective to the water molecules but also effective to trap and remove organic gas molecules of oils or the likes, which are the negative factors against a clean vacuum.

Still further preferably, said divider may be arranged at each of two locations which correspond to the vicinity of the charged particle beam irradiating location and the vicinity of the hydrostatic bearing, respectively. According to this embodiment, since the dividers for reducing the conductance are provided in two locations including the vicinity of the charged particle beam irradiating location and the vicinity of the hydrostatic bearing, the interior of the vacuum chamber is to be partitioned into three chambers comprising a charged particle beam irradiating chamber, a hydrostatic bearing chamber, and an intermediate chamber, which communicate with each other via small conductance. Then, the vacuum pumping system is configured so that the pressure in the charged particle beam irradiating chamber is the lowest, the intermediate chamber medium, and the hydrostatic bearing chamber the highest. By way of this configuration, even if the pressure increase occurs in the hydrostatic bearing chamber by the discharged gas, because of the pressure in this chamber having been originally set to be higher level, the pressure increase in the context of the coefficient of pressure fluctuation is still retained to be low level. Accordingly, the pressure fluctuation in the intermediate chamber can be retained at much lower level by the divider, and accordingly the pressure fluctuation in the charged particle beam irradiating chamber can be further reduced by another step of the divider, so that the pressure fluctuation therein can be reduced substantially to a non-problematic level.

Preferably, the gas supplied to the hydrostatic bearing of said stage may be either of a dry nitrogen or a highly purified inert gas.

Preferably, at least a surface of a component of said stage facing to the hydrostatic bearing may be provided with a surface treatment for reducing any gas emanated therefrom.

According to still another preferred embodiment of the present invention, there is provided an alternative substrate inspection apparatus characterized in that said stage is accommodated in a housing of said inspection chamber and supported by the hydrostatic bearing in a non-contact manner, wherein said housing containing said stage is evacuated to vacuum, and the differential pumping mechanism is arranged in a surrounding of a section irradiating the electron beam onto said substrate surface, for evacuating a region on said substrate subject to an electron beam irradiation. According to this embodiment, the high pressure gas for the hydrostatic bearing leaking into the vacuum chamber is primarily exhausted via a vacuum pumping pipe coupled to the vacuum chamber. Then, by arranging the differential pumping mechanism used to evacuate the region subject to the irradiation of the charged particle beam in the surrounding of the section for irradiating the charged particle beam, the pressure in the charged particle beam irradiating region can be reduced by a great degree as compared to the pressure in the vacuum chamber, thus achieving stably a vacuum level, at which the process using the charged particle beam against the sample can be performed with no trouble. That is, the processing by way of the charged particle beam can be stably applied to the sample on the stage by using the stage having the same configuration with the conventional stage of the hydrostatic bearing type used typically in the atmosphere (the stage supported by the hydrostatic bearing with no differential pumping mechanism).

Preferably, the gas supplied to said hydrostatic bearing of said stage may be either of a dry nitrogen or a highly purified inert gas, wherein said dry nitrogen or said highly purified inert gas, after having been exhausted from said housing containing said stage, may be pressurized and supplied again to said hydrostatic bearing. According to this embodiment, since the main component of the residual gas within the housing in the vacuum atmosphere should be a highly purified inert gas, therefore there is no fear that the surfaces of the components within the vacuum chamber consisting of the sample surface and the housing could be contaminated with water content or oil content, and further since even if the inert gas molecules are adsorbed on the sample surface, they may break way from the sample surface immediately once exposed to the high vacuum section in the differential pumping mechanism or the charged particle beam irradiating region, therefore this embodiment can minimize the affection on the level of vacuum in the charged particle beam irradiating region, and thus can stabilize the process by way of the charged particle beam against the sample.

According to still another preferred embodiment of the present invention, there is provided an alternative substrate inspection apparatus characterized in further having, in addition to an image projecting function comprising the steps of irradiating the electron beam having said specified width onto the substrate and projecting the secondary electron image onto said detecting system by means of said secondary electron optical system, a scanning electron microscopy function comprising the steps of firstly forming an electron beam to be narrower than said specified width, secondarily irradiating said narrower electron beam onto and scanning thereby the substrate surface, and lastly detecting the secondary electron beam emitted from said substrate. Taking advantage of the profit pertaining to each of both functions, that is, the image projecting function and the function for detecting the secondary emission beam, allows a single unit of pattern inspection apparatus to perform the inspection with high level of reliability and throughput as well as the mark detection in the registration to be executed prior to the pattern inspection also with high level of accuracy, by switching the function from either one of said two functions to the other in dependence on the condition that the sample is apt to be charged or hardly to be charged.

Preferably, the function may be switched appropriately between the image projecting function and the scanning electron microscopy function to each other in response to the condition of the substrate during a single substrate being inspected. Further, preferably, on the same substrate, a pattern of a hardly charged sample area is inspected by using said image projecting function and a pattern of an easily charged sample area is inspected by using said scanning electron microscopy function. Yet further, preferably, the scanning electron microscopy function is used in a mark detection for a registration in a wafer processing process, and said image projecting function is used in a subsequent pattern defect inspection.

According to still another preferred embodiment of the present invention, there is provided an alternative substrate inspection apparatus characterized in that said image processing system captures each of images for a plurality of regions to be inspected which have been displaced one from another while being superimposed partially one on another, and said image processing system comprises a storage means for storing a reference image, and a defect determination means for determining the defect in said substrate by comparing the images of said plurality of regions to be inspected which have been captured by said image processing system with said reference image stored in said storage means.

According to this aspect, the image obtaining means obtains respective images for the plurality of regions to be inspected which have been displaced one from another while being superimposed partially one on another, and the defect determination means determines the defect in the sample by comparing the obtained images for the plurality of regions to be inspected with the reference image which has been stored in advance. In this way, since the present invention allows a plurality of images to be taken for the inspection regions of different positions, the inspection images not being offset a lot from the reference image can be selectively used in the following processes so as to prevent the defect detecting accuracy from being deteriorated by the position mismatching. Besides, even if the sample and the image obtaining means have been brought in such a physical relationship that the inspection pattern could partially fall out of the image region to be inspected, there should be extremely higher possibility that every inspection pattern successfully falls in some one of the regions encompassed by the images for a plurality of regions to be inspected which have been displaced one from another, thus preventing any errors in the inspection which otherwise would have been caused by such partial lack of the pattern.

A comparison means performs, for example, what is called the matching operation between obtained respective images for a plurality of regions to be inspected and the reference image, and if there is substantially no difference between at least one image of those images for the plurality of regions to be inspected and the reference image, it determines that said sample has no defect. In contrast, if there is substantially a difference between every one of the images for the plurality of regions to be inspected and the reference image, it determines that said sample has a defect, thus to carry out the defect detection with higher accuracy.

Said beam source may radiate the electron beam onto each of said plurality of regions to be inspected, and said detecting system may detect the secondary electron beam emitted from each of said plurality of regions to be inspected. This can be accomplished by an additionally provided deflecting means for deflecting said electron beam and thereby irradiating sequentially said electron beam onto said plurality of regions to be inspected.

A defect in the substrate may be inspected in the course of process or after having been processed by using the substrate inspection apparatus described above.

Preferred embodiments of an electron beam apparatus of scanning type according to the present invention accomplished in order to solve the aforementioned problems will be described below.

According to a preferred embodiment of the present invention, there is provided an electron beam apparatus for focusing a primary electron beam to scan a sample and detecting a secondary electron beam from said sample, said apparatus having been designed so as to form a decelerating electric field between the sample and an objective lens, said apparatus comprising a detector for detecting a discharge or a precursory phenomenon of the discharge between the sample and the objective lens and then generating a signal, and a means for receiving said signal from said detector to obtain a condition for inhibiting any discharge from occurring.

Said detector may be a PMT for detecting a light occurring at the time of said discharge or said precursory phenomenon of the discharge, or a sample ampere meter for detecting an irregular current occurring at the time of said discharge or said precursory phenomenon of the discharge. Further, said means for obtaining a condition for inhibiting any discharge from occurring may be a means for receiving said signal from said detector and then controlling a voltage of said decelerating electric field or an amount of said primary electron beam so as to inhibit the discharge from occurring. It may be also possible that the detection of said discharge or said precursory phenomenon of the discharge is performed with respect to a part of the region in the sample that would not be used as a finished product.

According to another preferred embodiment of the present invention, there is provided an alternative electron beam apparatus including a plurality of electron optical systems arranged in parallel, each of said electron optical systems having been configured so as to form a primary electron beam into an image on a sample and to form a secondary electron beam emitted from said sample into an image on a detecting means, said apparatus comprising a low-pass filter, wherein said detecting means outputs a detection signal of the secondary electron beam to said low-pas filter. Preferably, said low-pass filter can make a cut-off frequency variable and may change the cut-off frequency in dependence on the sample. In addition, preferably, said electron beam apparatus may further comprise a lens including a plurality of electrodes made of insulating material with a metal coating applied selectively onto surfaces thereof. Yet preferably, said plurality of electrodes may be made of a single insulating material.

According to another preferred embodiment of the present invention, there is provided an evaluation apparatus disposed in the vicinity of at least one processing unit for manufacturing a semiconductor device so as to evaluate a resultant condition of a wafer after having been processed by said processing unit, said apparatus comprising an evaluation condition setting system for setting an evaluation condition such that the resultant condition of a single wafer can be evaluated within a processing time per wafer by the processing unit.

According to still another preferred embodiment of the present invention, there is provided an alternative evaluation apparatus characterized in further comprising an electron gun for emitting an electron beam, a lens system having an electrostatic lens made of insulating material with a metal coating applied onto a surface thereof and a deflector, a secondary electron beam detecting system, and an image forming circuit, wherein an image data is formed by scanning the wafer surface and then detecting the secondary electron beam. More preferably, said evaluation apparatus may comprise a plurality of electron optical columns each including the electron gun for emitting the electron beam, the lens system and the deflector, and the secondary electron beam detector, wherein the image data is formed by scanning the wafer surface with a plurality of electron beams and then detecting the secondary electron beam.

According to still another preferred embodiment of the present invention, there is provided an alternative evaluation apparatus for evaluating a resultant condition of a processed semiconductor device, said apparatus comprising an evaluation condition setting system for setting an evaluation condition such that the resultant condition of one lot can be evaluated within a processing time per lot by the processing unit, wherein said evaluation apparatus further comprises an electron gun for emitting an electron beam, a lens system having an electrostatic lens made of insulating material with a metal coating applied onto a surface thereof and a deflector, a secondary electron beam detecting system, and an image forming circuit, wherein an image data is formed by scanning a wafer surface and then detecting the secondary electron beam.

According to still another preferred embodiment of the present invention, there is provided an alternative electron beam apparatus for evaluating a sample by irradiating a primary electron beam onto a sample while scanning said sample with a predetermined scanning width and then detecting secondary electrons emitted from said sample, wherein after having scanned a certain region on the sample with said predetermined scanning width, the apparatus scans another region adjacent to said certain region by way of a movement of a stage, wherein an amount of said movement of the stage is greater than said predetermined scanning width, so that the sample can be evaluated for a larger region by repeating these steps. The electron beam apparatus according to this embodiment evaluates the sample by irradiating the primary electron beam onto the sample while scanning the sample with a predetermined scanning width and then detecting the secondary electrons emitted from the sample, and the apparatus, after having scanned a certain region on the sample with said predetermined scanning width, scans another region adjacent to said certain region by way of a movement of the stage, and thus repeats these steps so as to accomplish an evaluation of the sample covering the region wider than the scanning width. An mount of the movement of the stage may be made greater than said predetermined scanning width. The electron beam apparatus of the present invention can evaluate the sample in the larger area than the scanning width, while an amount of the movement of the stage is set to be greater than the scanning width so that it can prevent the generation of the overlapped scanning sections even in case of a distortion or position mismatching in the scanning.

According to still another preferred embodiment of the present invention, there is provided an alternative electron beam apparatus for evaluating a sample by irradiating a primary electron beam onto a sample having a pattern of a minimum line width "d" while scanning said sample with a predetermined scanning width and then detecting secondary electrons emitted from said sample, wherein if a beam diameter of the primary electron beam is denoted by "D", then $0.55 \leq D/d \leq 1.0$.

According to still another preferred embodiment of the present invention, there is provided an alternative electron beam apparatus for evaluating a sample by irradiating a primary electron beam onto a sample having a pattern of a minimum line width "d" while scanning said sample with a predetermined scanning width and then detecting secondary electrons emitted from said sample, wherein a beam diameter of the primary electron beam "D" is selected such that a modulation transfer function MTF of a signal at a time when the primary electron beam has observed a cycle pattern having a pitch equivalent to a doubled minimum line width "d" should be $0.42 \leq MTF \leq 0.8$.

According to still another preferred embodiment of the present invention, there is provided an alternative electron beam apparatus for evaluating a sample by irradiating a primary electron beam onto a sample having a gate oxide and then detecting secondary electrons emitted from said sample, wherein assuming that: a time period necessary for evaluating a unit area is denoted by "t"; an amount of irradiation or dose per unit area is denoted by "C" (Coulomb/cm$^2$); a beam current of the primary electron beam is denoted by "$I_p$"; and a modulation transfer function of a signal at a time when the primary electron beam has observed a cycle pattern having a pitch equivalent to a doubled minimum line width "d" is denoted by MTF, then the beam diameter of the primary electron beam is selected such that $1/(C \cdot t)$ or $(MTF)^4 I_p$ can be maximized.

According to an preferred embodiment of the present invention, there is provided an evaluation method using an electron beam for evaluating a sample by irradiating a primary electron beam onto a sample and then detecting a secondary electron beam emitted from said sample by the irradiation of the primary electron beam thereon, wherein the evaluation is performed only with respect to a small number of chips among a large number of chips formed in a single sample. In that case, the number of said small number of chips may be equivalent to the number of electron optical columns for forming the electron beam used for the inspection.

Regarding to an aspect of an apparatus for conducting the evaluation method, there is provided an evaluation apparatus using an electron beam, said apparatus being equipped with an electron beam apparatus comprising: a primary optical system for irradiating a primary electron beam onto a sample; a secondary optical system for delivering secondary electrons emitted from said sample by the irradiation of said primary electron beam; a detecting system for detecting the secondary electrons; and an electron optical column for accommodating said primary and said secondary optical systems, in which said electron optical column has an electrostatic lens including an electrode made of insulating material with a coating applied onto a surface thereof, and an electrostatic deflector or an electrostatic astigmatic correcting lens. Preferably, each of said electron optical columns may form a plurality of electron beams.

For a better understanding of an effect and operation and other advantages of the present invention, reference should be made to the following detailed description of the invention taken in conjunction with the accompanying drawings.

BRIEF DESCRIPTION OF THE DRAWINGS

FIG. 5 is a diagram illustrating a correlation between a total operating time and an MCP multiplication factor according to a third embodiment of the present invention;

FIG. 6 is a diagram illustrating a correlation between a voltage applied to an MCP and an MCP multiplication factor according to the third embodiment of the present invention;

DESCRIPTION OF THE PREFERRED EMBODIMENT

First Embodiment; a Defect Inspection System of Image Projecting Type

Figure 1:
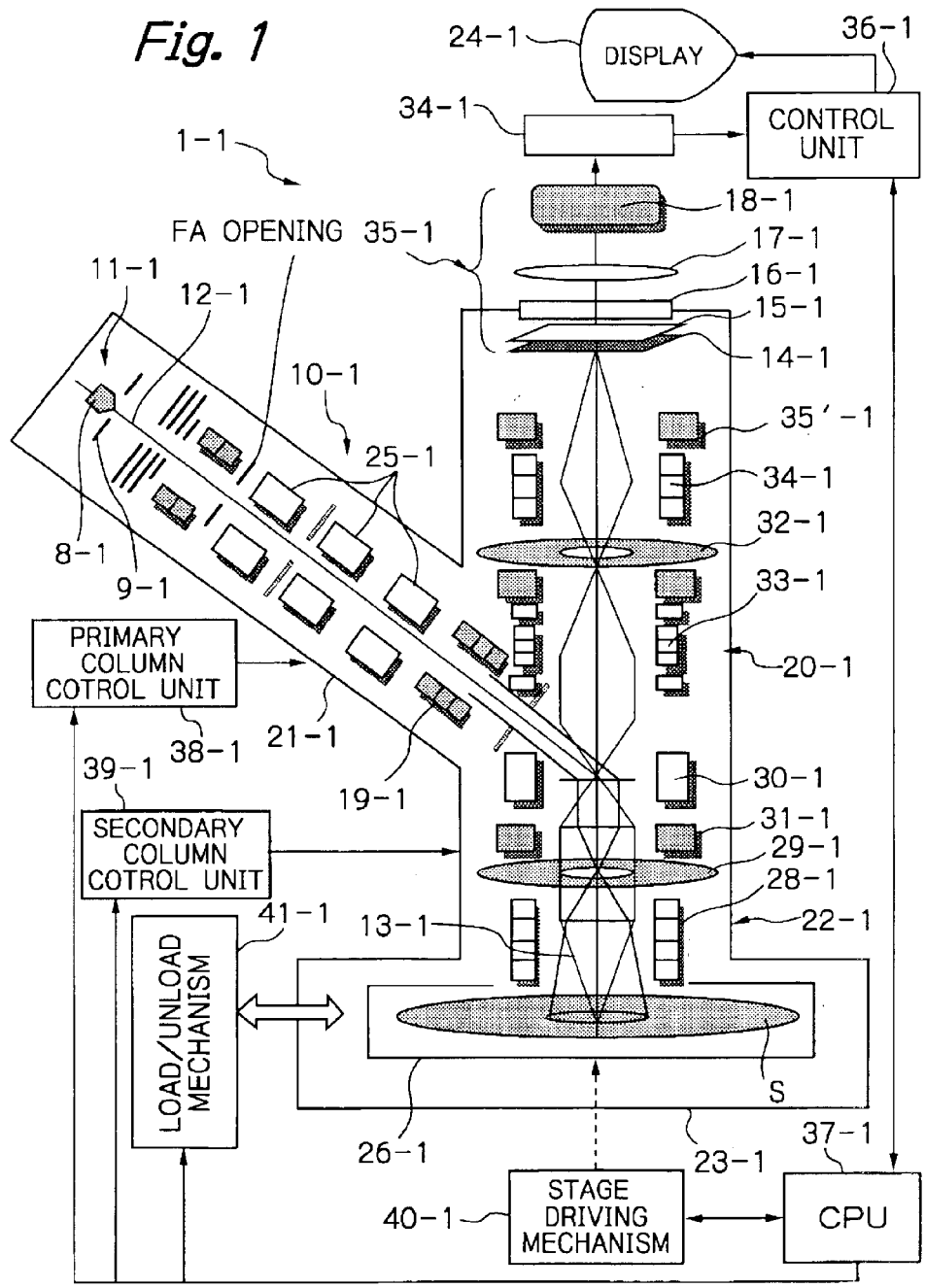
FIG. 1 is a schematic diagram of a defect inspection system using an electron beam apparatus of the image projecting type according to a first embodiment of the present invention.

FIG. 1 shows a schematic general configuration of a defect inspection system using an electron beam apparatus 1-1 of image projecting type according to a first embodiment of the present invention. As shown in FIG. 1, the electron beam apparatus 1-1 comprises a primary column 21-1, a secondary column 22-1 and an inspection chamber 23-1. It is to be appreciated that on the purpose of this application, the context of the term "inspection" includes an evaluation apparatus for evaluating a result of the inspection.

An electron gun 11-1 comprising a cathode 8-1 and an anode 9-1 is arranged in an inside of the primary column 21-1, and an primary optical system 10-1 is arranged along an optical axis of an electron beam 12-1 (a primary electron beam) radiated from the electron gun 11-1. Further, a stage 26 is installed in an interior of the inspection chamber 23-1 and a substrate S (e.g., a wafer) as a sample is loaded on the stage 26.

The primary optical system 10-1 may use an electrostatic (or electromagnetic) lens 25-1 of quadrupole or octopole of rotationally asymmetric type. This lens, can cause a focusing and a divergence in the X- and the Y-axis directions respectively. Such a configuration comprising two or three steps of these lenses to optimize respective lens conditions allows the beam irradiation region on the sample surface to be formed into a rectangular or elliptical shape as desired without any loss of radiated electrons. In specific, in the case of the electrostatic lenses being used, four cylindrical rods may be used. Each two opposite electrodes are made to be equal in potential and reverse voltage characteristics are given thereto. It is to be noted that as a substitute for the quadrupole lens of cylindrical shape, such a lens of configuration formed by dividing a normally used circular plate with an electrostatic deflector. In the latter case, the lens may be made compact.

A thermal electron beam source may be used as an electron gun 11-1. An electron emitting (emitter) material is $LaB_6$. Other materials may be used so far as it has a high melting point (lower vapor pressure at higher temperature) and a low work function. The emitter member with its tip portion formed into cone shape or the emitter member formed into trapezoidal cone shape with the tip portion of the cone having been cut away may be used. The diameter of the tip of the trapezoidal cone may be about 100 $\mu$m. Although in the other method, an electron beam source of an electric field emission type or a thermal field emission type has been used, in such a case where a relatively large area (for example, 100×25 to 400×100 $\mu m^2$) is irradiated with a high current (on the order of 1 $\mu$A) as is the case of the present invention, most preferably the thermal electron source using $LaB_6$ may be employed. (In the SEM method, typically the thermal field emission type electron beam source is used.) It is to be appreciated that the thermal electron beam source is of such a method in which the electron emitting member is heated to emit an electron, while the thermal field emission type electron beam source is of such a method in which a high electric field is applied to the electron emitting member to emit an electron and further the electron beam emitting section is heated so as to stabilize the electron emission.

On the other hand, in an interior of the secondary column 22-1, a secondary optical system 20-1 and a detector 35-1 are arranged, whose optical axes are in alignment with a direction approximately normal to the substrate S (approximately the traveling direction of a secondary electron beam (secondary beam) emitted from the substrate S). In the secondary optical system 20-1, a cathode lens 28-1, a numerical aperture 29-1, a second lens 31-1, an E×B separator unit (a Wien filter) 30-1, a third lens 33-1, a field aperture 32-1, a fourth lens 34-1 and a deflector 35'-1 are arranged. It is to be noted that the numerical aperture 29-1 corresponds to an aperture diaphragm, which is a thin plate made of metal (Mo or the like) having a circular aperture formed therein. Herein, an aperture section is disposed so as to be at a focused location of the primary electron beam and also at a focal point of the cathode lens 28-1. Accordingly, the cathode lens 28-1 and the numerical aperture 29-1 construct a telecentric electron optical system for the secondary electron beam.

Further, the detector 35-1 comprises as main components: a micro channel plate (MCP) 14-1, a fluorescent screen 15-1 for converting the electrons into the light, a vacuum window 16-1 functioning as a relay between the vacuum system and the external component, a fiber optic plate (FOP) 17-1 for transmitting an optical image, and a TDI-CCD 18-1 comprising a large number of elements for detecting the optical image. To explain the principle of the MCP 14-1, the MCP is made of millions of ultra-thin glass capillaries which have been shaped into a thin plate, each of said capillaries having a diameter of 6 to 25 $\mu$m and a length of 0.24 to 1.0 mm, in which each of those capillaries acts as an independent secondary electron amplifier when a predetermined level of voltage is applied thereto, and thereby the capillaries as a whole form a unit of secondary electron amplifier. The TDI-CCD 18-1 is connected to a control unit 36-1 via a memory 34-1.

The control system for controlling generally the defect inspection system of FIG. 1 comprises mainly a control unit 36-1 provided with a man-machine interface and a CPU 37-1 which controls the control unit controlling the respective components while performing a defect inspection from the secondary electron image obtained by the electron beam apparatus 1-1 based on the information entered to the control unit 36-1.

The control unit 36-1 is provided with an operator control panel as the man-machine interface, though not shown, through which an operator can give the defect inspection system a variety of instructions/commands (for example, an entry of recipe, an instruction to start an inspection, a switching between an automatic inspection mode and a manual inspection mode, an input of all of the commands required in the manual inspection mode and so fourth). Further, the control unit 36-1 is interconnected with a display 24-1 by means of a liquid crystal, a CRT or the likes, so as to display a confirmative image for a variety of instructions, an information from the CPU 37-1, and the secondary electron image stored in the memory 34-1.

In the CPU 37-1, sending and receiving operations of a feedback signal to/from the electron optical system and sending and receiving operations of a signal to/from the stage are performed respectively via a primary and a secondary column control units 38-1, 39-1, and a stage controller of a stage driving mechanism 40-1, though not shown.

The primary and the secondary column control units 38-1, 39-1 are mainly in charge of a control of the electron beam optical system (the control of a high precision power supply used for the electron gun, the lens, the aligner, and the Wien filter). In specific, these control units performs, for example, such a control (a cooperative control) operation as an automatic voltage setting for respective lens systems and the aligner in response to respective operation modes, so that a constant electron current may be regularly radiated onto the irradiation region even if the magnification is changed, and the voltage to be applied to respective lens systems, the aligner or the like may be automatically set in response to the magnification.

The stage controller is mainly in charge of a control for a movement of the stage to allow a precise movement in the X- and the Y-directions on the order of $\mu$m (with tolerance of about +/−0.5 $\mu$m). Further, in the present stage, a control in the rotational direction (θ control) is also performed with a tolerance equal to or less than about +/−0.3 seconds.

In addition, the CPU 37-1 also performs such functions as; a control of an conveying controller of a conveying mechanism 41-1, though not shown, a communication with a host computer in a plant, a control of a vacuum pumping system, a conveying of sample such as wafer, a control of position alignment, a transmission of commands to other controlling controllers or the stage controller, and a receipt of information or the like. Further, the CPU 37-1 is also in charge of such functions as: an acquisition of an image signal from an optical microscope; a stage vibration compensating function for compensating for possible deterioration in image by feeding back a fluctuating signal of the stage to the electron optical system; and an automatic focal point compensating function for detecting a displacement of a sample observation point in the Z direction (the direction along the optical axis of the secondary optical system) and feeding it back to the electron optical system so as to automatically compensate for the focal point.

The primary column 21-1, the secondary column 22-1 and the inspection chamber 23-1 are in communication with a vacuum pumping system (not shown). The vacuum pumping system is composed of a vacuum pump, a vacuum valve, a vacuum gauge, a vacuum pipe and the like, and exhausts to vacuum an electron optical system, a detector section, a sample chamber, a load-lock chamber and the like according to a predetermined sequence. In each of those sections, the vacuum valve is controlled so as to accomplish a required vacuum level. The vacuum level is regularly monitored, and in the case of irregularity, an interlock mechanism executes an emergency control such as an interception of communication between the chambers or between the chamber and the exhausting system by an isolation valve to secure the required vacuum level in the respective sections. As for the vacuum pump, a turbo pump may be used for main exhaust, and a dry pump of Root type may be used as a roughing vacuum pump. A pressure at an inspection spot (an electron beam irradiating section) is practically in a range of $10^{-3}$ to $10^{-5}$ Pa, preferably in a range of $10^{-4}$ to $10^{-6}$ Pa as shifted by one digit down.

(Cleaner)

Since, as the electron beam apparatus 1-1 is operated, a target substance is made to float by a proximity interaction (charging of particles in the proximity of a surface) and attracted to a high-voltage region, therefore an organic substance would be deposited on a variety of electrodes used for forming or deflecting an electron beam. Since the insulating material gradually depositing on the surface of the electrodes by the electrostatic charge affects reversely on the forming or deflecting mechanism for the electron beam, accordingly those deposited insulating material must be removed periodically. To remove the insulating material periodically, an electrode adjacent to the region where the insulating material has been deposited is used to generate a plasma of hydrogen, oxygen, fluorine or a compound including those elements, such as HF, $O_2$, $NH_3$, $H_2O$, $C_M F_N$ or the like in the vacuum environment and to control the plasma potential in the space to be a potential level (several kV, for example, 20 V-5 kV) where the spatter would be generated on the electrode surface, thereby allowing only the organic substance to be oxidized, hydrogenated or fluorinated and thereby removed.

(E×B Unit)

A detailed structure of said E×B unit 30-1 (Wien filter) will be described in detail with reference to FIG. 2 and FIG. 3 which is a cross sectional view taken along the line A—A of FIG. 2.

The E×B unit 30-1 is a unit of electromagnetic prism optical system, in which an electrode and a magnetic pole are arranged in the directions orthogonal to each other so that an electric field and a magnetic field are crossed at a right angle. If the electromagnetic field is selectively applied appropriately, such a condition (a Wien condition) can be made where an electron beam entering into the field from one direction is deflected, while in the electron beam entering from the opposite direction, a force applied by the electric field and another force applied by the magnetic field are offset to each other, and thereby the primary electron beam is deflected to be radiated onto the wafer at a right angle and the secondary electron beam is allowed to be advanced approximately straight ahead toward the detector.

Figure 2:
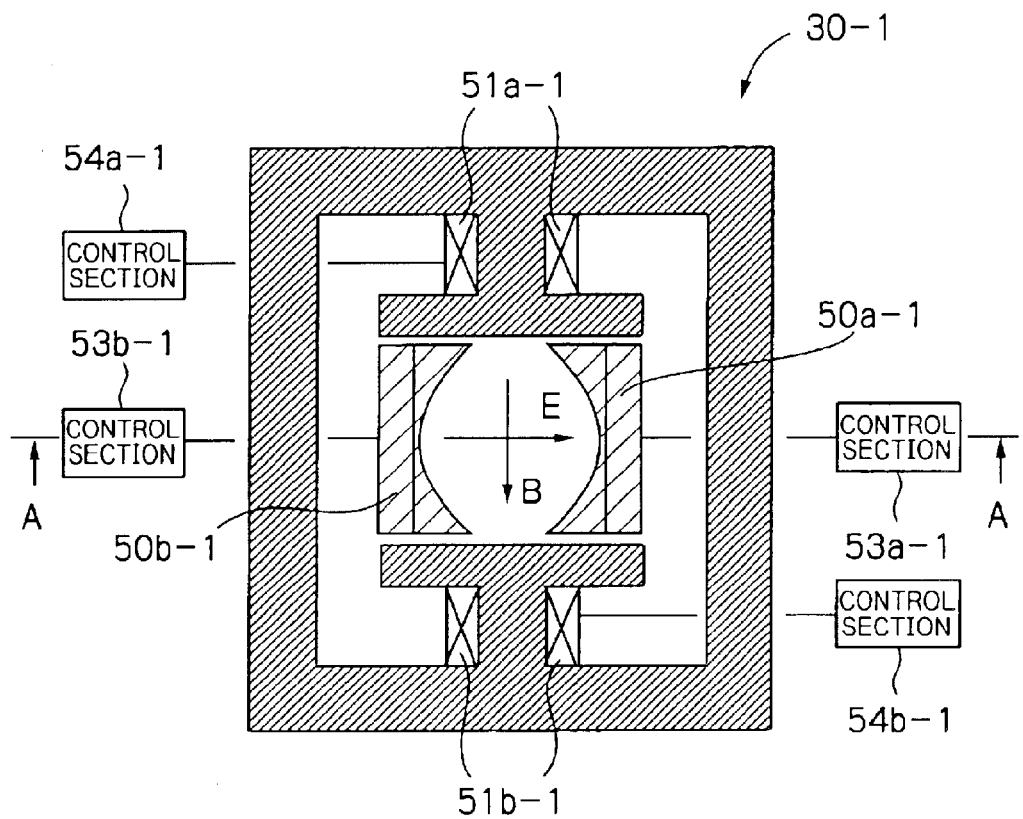
FIG. 2 is a top view illustrating a detailed configuration of an E×B unit used in the electron beam apparatus of FIG. 1.
Figure 3:
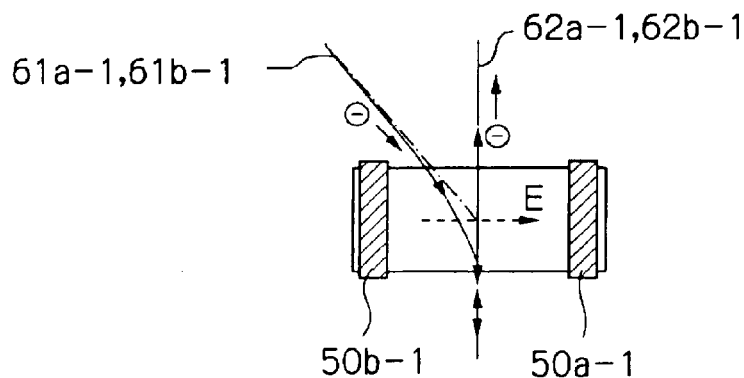
FIG. 3 is a cross sectional view of the E×B unit taken along the line A—A of FIG. 2.

As shown in FIG. 2, a field in the E×B unit 30-1 is made to have such as structure where an electric field is crossed with a magnetic field at a right angel in a plane normal to the optical axis, namely, an E×B structure.

In this regard, the electric field may be generated by electrodes 50a-1 and 50b-1, each having a curved surface of concave shape. The electric fields generated by the electrodes 50a-1 and 50b-1 are respectively controlled by control sections 53a-1 and 53b-1. On the other hand, by arranging the electromagnetic coils 51a-1 and 51b-1 so as to be crossed at a right angel with the electrodes 50a-1 and 50b-1 for generating the electric field, the magnetic field is generated. It is to be noted that those electrodes 50a-1 and 50b-i for generating the electric field are arranged to be point-symmetrical (may also be arranged on concentric circles).

In this case, in order to improve a uniformity of the magnetic field, a magnetic path is formed with a pole piece in a form of parallel plate shape. A behavior of the electron beam on the longitudinal cross sectional plane taken along the A—A line is shown in FIG. 3. The emitted electron beams 61a-i and 61b-1, after having been deflected by the electric field generated by the electrodes 50a-1 and 50b-1 and the magnetic field generated by the electromagnetic coils 51a-1 and 51b-1, enter onto the sample surface in the vertical direction.

In this configuration, the positions and the angles of incidence of the irradiation electron beams 61a-i and 61b-1 to the electron beam deflecting section are unconditionally determined as the energy of the electron is determined. In addition, in order to advance the secondary electrons 62a-1 and 62b-1 straight ahead, the respective control sections 53a-1 and 53b-1, and 54a-1 and 54b-1 control the electric field generated by the electrodes 50a-1 and 50b-i and the magnetic field generated by the electromagnetic coils 51a-1 and 51b-1 so that the condition for the electric field and the magnetic field may be shown as vB=E (i.e., evB=eB; e is the electric charge (C)), and thereby the secondary electrons is allowed to go straight through the electron beam deflecting section 27 into the detecting system. Where, V is a velocity of the electron 32 (m/s), B is the magnetic field (T), and E is the electric field (V/m).

An operation of the electron beam apparatus 1-1 according to the present embodiment will now be described in conjunction with FIG. 1.

In the electron beam apparatus 1-1, an observation region on a sample is irradiated in block by a primary electron beam (i.e., no scanning but an irradiation covering a certain area), and secondary electrons emitted from the irradiated region are formed into an image in block by a lens system on a detector (a micro-channel plate plus fluorescent screen) as an image of the electron beam.

(Primary Electron Beam)

The primary electron beam from the electron gun 11-1 (in a example, $Lab_6$ may be used for a chip of the electron gun, which allows to take out a high current with a rectangular negative electrode) enters the Wien filter 30-1 after having been subject to a lens effect (shaping and image forming) by the primary optical system 10-1, where the beam is subject to the deflecting effect from said Wien filter 30-1 so that an orbit thereof is deflected. In the Wien filter 30-1, the magnetic field is crossed with the electric field at a right angle, and only the charged particles satisfying the Wien condition of E=vB are allowed to be advanced straight forward but the orbits of the other charged particles are deflected, where the electric field is E, the magnetic field B, and the velocity of the charged particle v. A force FB by the magnetic field and another force FE by the electric field may have effect in the same direction on the primary beam, and consequently the beam orbit is deflected. On the other hand, the force FB and the force FE may have effect in the opposite directions on the secondary beam and those forces are offset to each other, so that the secondary beam is allowed to directly go straight forward.

A lens voltage of the primary optical system 10-1 has been determined beforehand such that the primary beam is formed into an image at an aperture portion of the numerical aperture 29-1. That numerical aperture 29-1 prevents any excess electron beams to be dispersed in the apparatus from reaching to the sample surface and thus prevents a charge-up or a contamination in the sample S. Further, since the numerical aperture 29-1 and the cathode lens 28-1 together form the telecentric electron optical system for the secondary beam but not for the primary beam, therefore the primary beams that has passed through the cathode lens 28-1 may turn to be slightly-diffusing beams which are radiated uniformly and similarly onto the sample S. That is to say, this uniform irradiation accomplishes, what is called in an optical microscope, the Koehler illumination.

(Secondary Electron Beam)

When the primary beam is radiated onto the sample, secondary electrons, reflected electrons or back-scattering electrons are generated as the secondary beam from the beam irradiated surface of the sample. The secondary beam passes through the cathode lens 28-1 while being subject to a lens effect from the cathode lens 28-1.

It is to be noted that the cathode lens 28-1 is composed of three pieces of electrodes. Among those electrodes, one at the lowest position is designed to form a positive electric field between the potentials in the sample S side and in itself, and to intake electrons (particularly, secondary electrons with smaller directivities) so that the electrons may be efficiently introduced into the lens.

Further, the lens effect takes place in such a way that voltages are applied to the first and the second electrodes of the cathode lens 28-1 and the third electrode is made to zero potential. Accordingly, a parallel beam of an electron beam emitted from a location other than the center in the field of view (out of the axis) may pass through the numerical aperture 29-1 at the central location thereof without being kicked out any further.

It is to be appreciated that the numerical aperture 29-1 serves to reduce lens aberrations of the second lens 31-1 to the fourth lens 34-1 for the secondary beams. Those secondary beams having passed through the numerical aperture 29-1 may not affected by the deflecting effect from the Wien filter 30-1 but may keep on going straight forward through the filter. It is to be appreciated that although the secondary beam includes secondary electrons, reflected electrons and back-scattering electrons, in this case, the explanation is specifically given to the secondary electrons which has been selected among them.

If the secondary beam is formed into an image only by the cathode lens 28-1, a magnification chromatic aberration and a distortion aberration may become too great. To solve this problem, the cathode lens 28-1 is used in the combination with the second lens 31-1 to perform once an image formation. The secondary beam can be formed into an intermediate image on the Wien filter 30-1 by means of the cathode lens 28-1 in conjunction with the second lens 31-1. In that case, since typically the magnification required to the secondary optical system has been often insufficient, the third lens 33-1 and the fourth lens 34-1 are added to the configuration as the lenses for magnifying the intermediate image. The secondary beam is magnified and formed into an image by the third lens 33-1 and the fourth lens 34-1 respectively, which means that the secondary beam is formed into an image two times in this case. It is to be noted that the beam may be formed into an image only once by using both of the third lens 33-1 and the fourth lens 34-1 (totally one time).

In addition, each of those lenses from the second lens 31-1 to the fourth lens 34-1 should be a lens of rotationally symmetrical type of such kind referred to as a uni-potential lens or Einzell lens. Each lens is composed of three pieces of electrodes, in which typically outer two electrodes have zero potentials and a voltage applied to a central electrode is used to causes a lens effect for controlling. Further, the field aperture 32-1 is disposed in the intermediate image forming point. The field aperture 32-1, which constrains the field of view to be limited to a required range as similar to a field stop in an optical microscope, for the case of an electron beam, blocks any excess beams from entering to the fourth lens 34-1 of the subsequent step so as to prevent the charge-up and/or the contamination of the detector 35-1. It is to be noted that the magnification can be controlled by varying the lens conditions (the focal distances) of the third and the fourth lenses 33-1 and 34-1.

The secondary beam is magnified and projected by the secondary optical system, and then the beam, after having been doubled by the micro channel plate (MCP) 14-1, impinges upon the fluorescent screen 15-1 and is converted into an image of light. The image which has been converted into the light passes through the vacuum window 16-1 and the fiber optic plate (FOP) 171-1 disposed in the atmosphere and is projected on the TDI-CCD 18-1 on one to one basis. The detected image signal is converted into an electric signal, which will be stored in the memory 34-1 temporarily.

The control unit 36-1 reads out the image signal of the sample S from the memory 34-1 and transmits it to the CPU 37-1. At that time, the image data may be output onto the display 24-1. The CPU 37-1 performs a defect inspection of the pattern on the substrate S by way of the template matching, the die-to-die intercomparison and so fourth from the image signal.

While obtaining the secondary electron image, the CPU 37-1 reads a position of the stage 26-1 and outputs a drive control signal to the stage driving mechanism 40-1 to drive the stage 26-1, allowing for a sequential detection and inspection of the images. In the case where the CCD is used as the detecting element, the moving direction of the stage 26-1 extends along the shorter axis (may be along the longer axis), and the movement is made by the step and repeat manner. As for the stage movement in the case where the TDI-CCD is used as the detecting element, the stage is continuously moved in the accumulation direction. Since the TDI-CCD allows the image to be serially obtained, similarly to this embodiment, the TDI-CCD may be used when the defect inspections are to be continuously carried out. The resolution is determined depending on the magnification and the accuracy of an image-forming optical system (a secondary optical system), and in the present embodiment, the resolution of 0.05 $\mu$m has been obtained. In this example, with the resolution of 0.1 $\mu$m and the electron beam irradiation condition of 1.6 $\mu$A for the area of 200 $\mu$m×50 $\mu$m, the inspection time of about one hour per wafer of 20 cm has been accomplished, which is 8 times as high as that in the SEM method. The specification of the TDI-CCD employed has, for example, 2048 pixels×512 arrays with the line rate of 3.3 $\mu$s (at line frequency of 300 kHz). Although the irradiation area in this example has been determined according to the specification of the TDI-CCD 18-1, the irradiation area may be changed depending on the object to be irradiated.

Thus, in the inspection apparatus 1-1 according to the present embodiment, since the light source image is formed in the numerical aperture 29-1 and the FA opening is formed into an image on the sample surface, therefore as to the primary beam, the beam may be radiated uniformly onto the sample. That is, this facilitates to accomplish the Koehler illumination.

Further, as to the secondary beam, since all of the principle beams from the sample S enter the cathode lens 28-1 at a right angle (parallel to the optical axis of the lens) and pass through the numerical aperture 29-1, therefore the peripheral light would not be kicked out, thus preventing deterioration of the image brightness in the periphery of the sample. In addition, although a variation of the energy pertained to the electron gives a different focal position, which causes what is called a magnification chromatic aberration (specially, for the secondary electrons, since the energies thereof are varied to a great extent, the magnification chromatic aberration is rather great), the use of two lenses consisting of the cathode lens 28-1 and the second lens 31-1 for the image formation makes it possible to control the magnification chromatic aberration to be lower.

On the other hand, since a change of the magnification factor is executed after the beam having passed through the numerical aperture 29-1, any changes in the determined magnification factor in the lens condition for the third and the fourth lenses 33-1 and 34-1 still can bring an uniform image over the field of view to be obtained in the detection side. It should be appreciated that although an even and uniform image can be obtained in the present embodiment, typically increasing the magnification factor may problematically cause a deterioration in brightness of the image. Accordingly, in order to improve this problematic condition, when the lens condition for the secondary optical system is changed to vary the magnification factor, the lens condition for the primary optical system should be controlled such that the effective field of view on the sample determined in association with the magnification factor and the electron beam to be radiated on the sample may be equally sized.

That means, as the magnification factor is increased, consequently the field of view gets narrower, but when the irradiation energy density of the electron beam is increased at the same time, the current density of the detected electron can be kept always in a constant level and the brightness of the image may be prevented from being deteriorated even if the beam is magnified and projected in the secondary optical system.

Further, although in the inspection apparatus according to the present embodiment, the Wien filter has been employed, which deflects an orbit of the primary beam but allows the secondary beam to go straight forward, the application is not limited to this but the apparatus may employ the Wien filter with another configuration in which the orbit of the primary beam is deflected at an angle of, for example, 15 degrees and the orbit of the secondary beam is deflected also. In that specific case, most preferably the secondary beam should be deflected at the angle of 5 degrees. Still further, although in the present embodiment, a rectangular negative electrode and a quadrupole lens are used to form a rectangular beam, the application is not limited to this but, for example, a circular beam or an elliptical beam may be formed from a circular negative electrode, or the circular beam may be passed through a slit to extract the rectangular beam.

Alternatively, a plurality of beams may be used for scanning so as to radiate uniformly the entire region to be irradiated. In this case, each of those beams should be adapted to arbitrarily scan a region assigned to respective beam (but in a manner to bring the uniformity in a total irradiation).

(Inspection Procedure)

An inspection procedure for the substrate S by using the defect inspection system of FIG. 1 will now be described.

Generally, since an inspection apparatus using an electron beam is expensive and the throughput thereof is rather lower than that provided by other processing apparatuses, this type of inspection apparatus is currently applied to a wafer after an important process (for example, etching, membrane deposition, or CMP (chemical-mechanical polishing) planarization process) to which it is considered that the inspection is required most.

Figure 4:
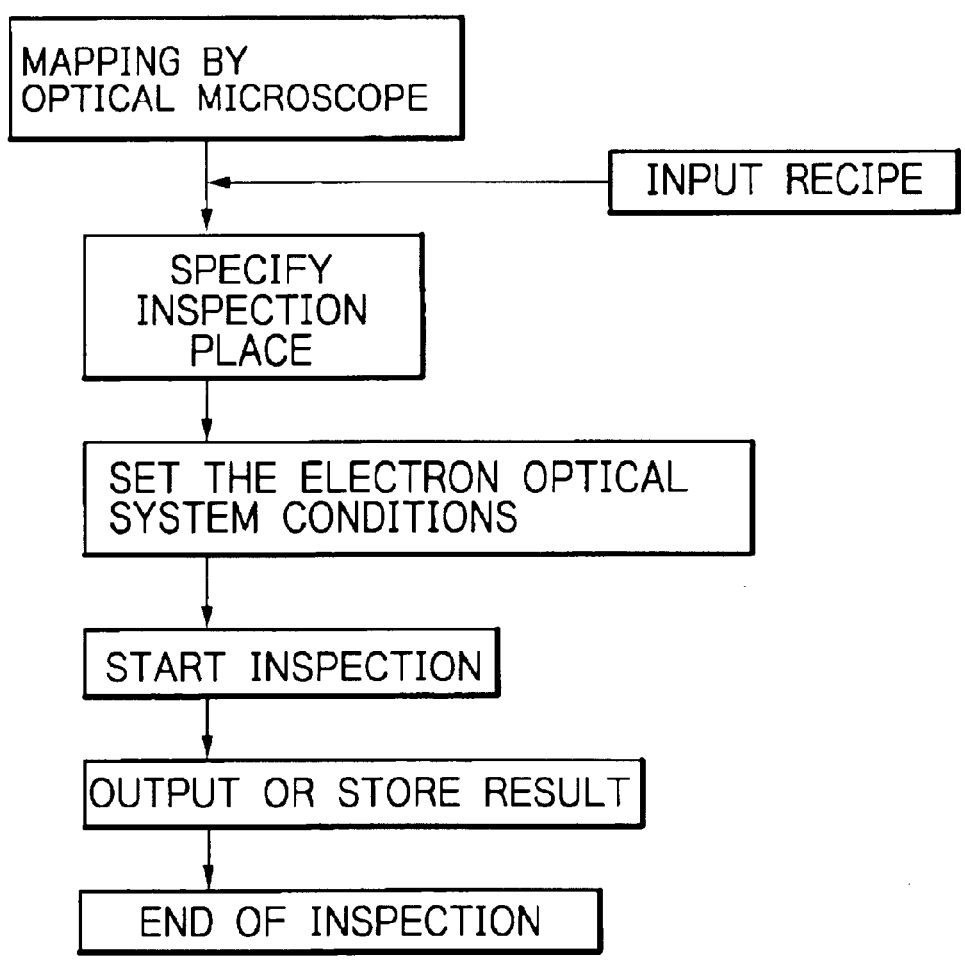
FIG. 4 is a flow chart illustrating a flow of a defect inspection in the electron beam apparatus of FIG. 1.

A substrate S (wafer) to be inspected is, after having been conveyed into the inspection chamber 23-1 through a conveying mechanism 41-1, said inspection chamber being held in a vacuum environment by a vacuum system, and having been positioned on an ultra-precise stage 26-1, secured by an electrostatic chucking mechanism or the like, and then a detect inspection is conducted according to a procedure as shown in FIG. 4 (a flow of inspection), as will be described below. It is to be appreciated that during the inspection a vibration isolating mechanism (not shown) should be preferably used to isolate the inspection chamber from the vibration.

At first, if required, a position of each of dies is checked and/or a height of each location is sensed by using an optical microscope (not shown), and those values are stored. Adding to those, the optical microscope may be used to obtain an optical microscope image in an area of interest possibly including defects or the like, which may also be used in, for example, the comparison with an electron beam image. Then, recipe information corresponding to the kind of the wafer (for example, after which process the inspection should be applied; what is the wafer size, 20 cm or 30 cm, and so on) is entered into the apparatus, and subsequently, after a designation of an inspection place, a setting of an electron optical system and a setting of an inspection condition being established, a defect inspection is conducted according to the operation of the aforementioned electron beam apparatus 1-1 typically at real time while simultaneously obtaining the image. A fast data processing system with an algorithm installed therein executes an inspection, such as the comparisons between cells, between dies or the like, and any results would be output to the display 24-1 or the like and stored in the memory 34-1, if desired. Those defects include a particle defect, an irregular shape (a pattern defect) and an electric defect (a broken wire or via, a bad continuity or the like), and the fast data processing system also can automatically and at real-time distinguish and categorize them according to a defect size, or whether their being a killer defect (a critical defect or the like which disables a chip). The detection of the electric defect may be accomplished by detecting an irregular contrast. For example, since a location having a bad continuity would generally be charged into positive by an electron beam irradiation (about 500 eV) and thereby its contrast would be decreased, the location of bad continuity can be distinguished from normal locations. The electron beam irradiation means in that case typically designates an electron beam source (e.g., means for generating thermal electron, UV/photoelectron) with lower potential energy arranged separately in order to emphasize the contrast by a potential difference, in addition to the electron beam irradiation means used for a regular inspection. Before the electron beam being radiated onto the objective region for inspection, the electron beam having the lower potential is generated and radiated. Further, the defect may be inspected based on the difference in contrast (which is caused by the difference in flowability of elements depending on the forward or backward direction) created by, for example, applying a positive or negative potential relative to a reference potential to a sample such as a wafer or the like. This electron beam source may be applicable to a line-width measuring apparatus and also to an alignment accuracy measurement.

After the inspection for the substrate S has been completed, the substrate S will be taken out of the inspection chamber 23-1 by means of the conveying mechanism 41-1.

Second Embodiment

A pattern inspection apparatus according to a second embodiment has a combination of two functions including a function for image projecting and a function as a scanning electron microscope (i.e., a function for detecting a secondary emission beam generated by scanning with a primary electron beam), in which each of these two functions can be easily switched to each other simply by an electrical operation, as will be described later.

The pattern inspection apparatus according to the second embodiment can be accomplished by employing the configuration of the electron beam apparatus 1-1 shown in FIG. 1, and further adding thereto the function as the scanning electron microscope.

The function for the image projecting is mainly used in a pattern inspection for a hardly-charged sample, while the function as the scanning electron microscope is mainly used in a pattern inspection for an easily-charged sample or in a mark detection in a registration to be preformed prior to the pattern inspection. In this regard, the easily-charged sample material includes, for example, a wafer having a silicon oxide or silicon nitride deposited on a surface thereof, while the hardly-charged sample material includes bare silicon, aluminum coated silicon and so on. Further, whether a sample is easily charged or hardly charged is determined according to the following criterion. That is to say, it is determined based on how many percents of the surface area of the silicon wafer is covered with an insulating material or whether the sample has a conductive film isolated in a island shape or conductive films continued to each other.

The detailed description of the function for the image projection will be omitted since it has been made in conjunction with the first embodiment. It is to be appreciated that in the case where the present embodiment has been applied to the image projecting function, for example, an irradiation region of an electron beam that is formed into an image in a reduced scale on the sample S (e.g., wafer) by the electrostatic objective lens 28-1 may be 250 micron square, and a secondary electron beam may be magnified by the secondary optical system 20-1 in a magnification factor of 300 and then enters the MCP 14-1.

The function as the scanning electron microscope will now be described with reference to FIG. 1. In the pattern inspection apparatus of the second embodiment, a scanning deflector 19-1 capable of deflecting the primary electron beam is arranged in a step subsequent to the electrostatic (or electromagnetic) lens 25-1 in the primary optical system 10-1.

The electron beam 12-1 emitted from the cathode 8-1 is accelerated by the anode 9-1 and shaped to be rectangular in a sectional view in a forming opening arranged at a specified location in the primary optical system 10-1. The appropriately shaped electron beam is then contracted to be narrower when the electrostatic (or electromagnetic) lens 25-1 of a quadrupole or octopole of rotationally asymmetric type is used to adjust the lens condition. That is, the electron beam is adjusted by making a contraction factor for the rectangular shape in a major axis direction especially large while the contracting factor in a minor axis direction remained in a limited range, so that it is calculated that the beam may be shaped into a square of 100 nanometers at a location slightly above the deflection principal plane of the E×B separator 30-1. However, because there is an aberration of the lens in the apparatus used in practice, the beam actually measured is a circular beam having a diameter of 120 nanometers at the location slightly above the deflection principal plane of the E×B separator 30-1. The circular electron beam having entered the E×B separator 30-1 is deflected thereby into the direction perpendicular to the surface of the sample S, and then contracted to be a quarter in size by the electrostatic objective lens 28-1 thus focused to be an electron beam having a diameter of about 30 nanometers on the surface of the sample. When the scanning deflector 19-1 is operated so as for this electron beam having the diameter of 30 nanometers to scan the surface of the sample S in two-dimensional way, accordingly a region of a square of 5 microns or 100 microns can be scanned.

The secondary emission beam emitted from the sample S is accelerated by the accelerating electric field for the secondary emission beam, which has been applied to the electrostatic objective lens 28-1, and then passes through said electrostatic lens 28-1 to enter the E×B separator 30-1. The secondary emission beam having entered the E×B separator 30-1 passes through the electrostatic intermediate lens 31-1 and the electrostatic magnifying lens 33-1 of the secondary optical system 20-1 under the same lens condition as in the case of the function for the image projection, and then enters the MCP 14-1.

The secondary emission beam having entered the MCP 14-1, similarly to the case of the function for the image projection, irradiates the fluorescent screen 15-1 so as to form a pattern image thereon, and then after having passed through the FOP 17-1, the beam is detected by the CCD camera 18-1 and converted into an electric signal. The electric signals from the CCD camera 18-1 are electrically summed over all of the channels so as to obtain a signal intensity. Accordingly, the location data can be obtained from the scanning time.

The switching of the function between the function for the image projection and the function as the scanning electron microscope can be accomplished simply through the electrical operations comprising the steps of: changing a magnification factor of each of the lenses constructing the quadrupole lens 25-1; giving a scanning signal to the scanning deflector 19-1; and determining whether the output signal from the CCD camera 18-1 should be processed by a regular signal processing as the function for the image projection or by a processing for adding the signals electrically for all of the channels as the scanning electron microscope.

According to the second embodiment, the following effects may be brought about.

(1) Since the switching between the function for the image projection and the function as the scanning electron microscope can be accomplished by changing electrically the condition of the quadrupole lens and quadrupole deflector, the operation signal to the scanning deflector, and the signal processing for the signal from the CCD camera, therefore even if there are different kinds of chips formed on a single wafer with easily-charged chips and hardly-charged chips being included on the same wafer, a pattern inspection may be performed efficiently by fast switching between said two functions.

(2) For the mark detection in the registration, highly accurate mark detection can be achieved by using a scanning area reduced to a square of a few microns with a pixel size as small as 5 nanometers.

(3) For the pattern inspection, the pattern inspection with higher throughput can be accomplished by using a pixel size of 50 nanometers, which is determined in conjunction with the pixel of the CCD camera and the magnification factor used in the function for the image projection.

Third Embodiment

Since a defect inspection apparatus according to a third embodiment employs a defect inspection system using the electron beam apparatus 1-1 of FIG. 1, the similar numeric references are used to designate the similar components and a detailed description on the configuration of this defect inspection apparatus will be omitted.

Figure 7:
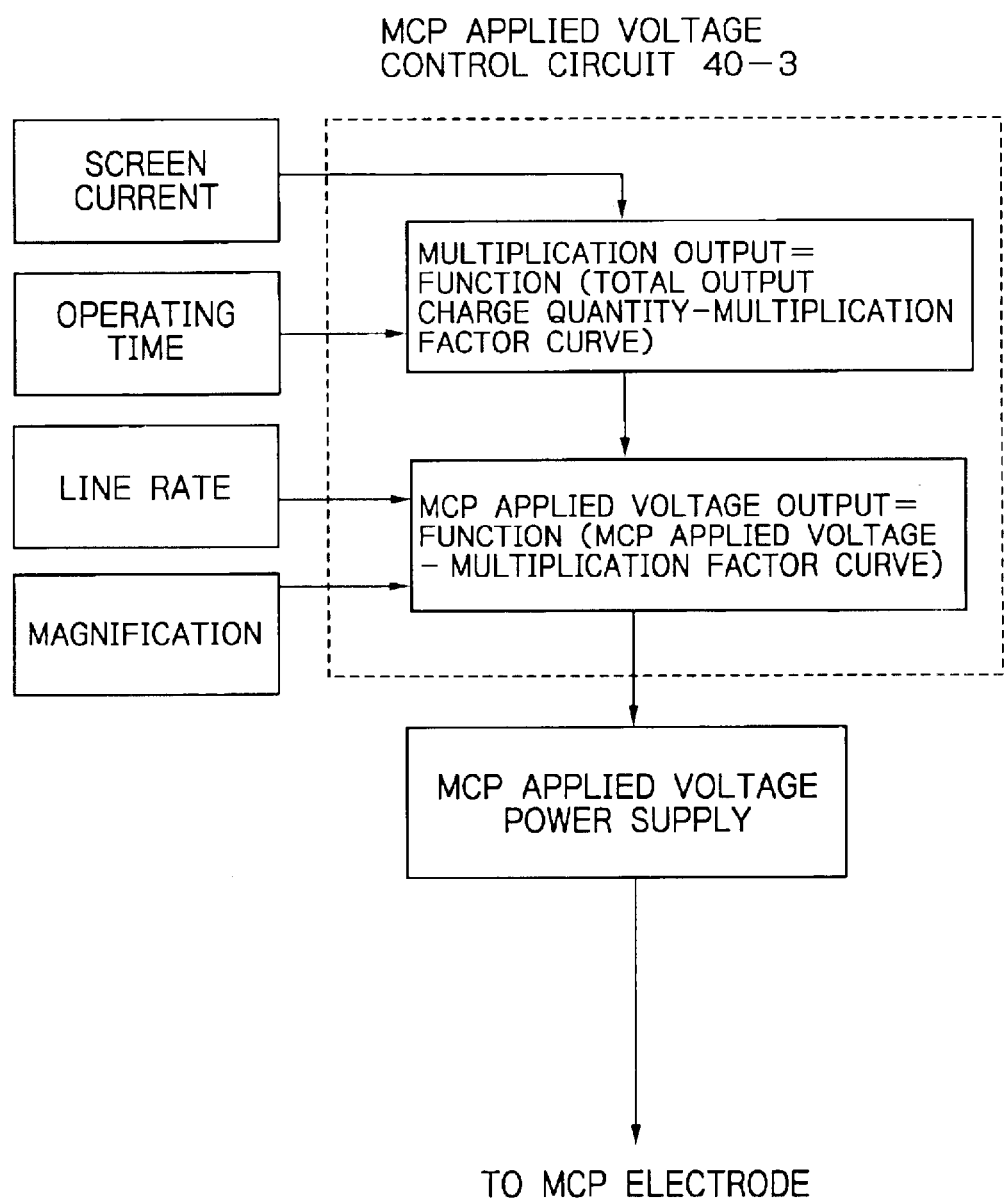
FIG. 7 is a flow chart illustrating an operational flow in a control circuit for controlling a voltage to be applied to an MCP according to the third embodiment of the present invention.

For the MCP 14-1 of FIG. 1, it is obvious from FIG. 5, in which the operating time is represented along the lateral axis and the multiplication factor is represented along the longitudinal axis, that the multiplication factor decreases as the operating time increases. Further, it is also obvious from FIG. 6, which indicate the correlation between the voltage applied to the MCP (sometimes referred to as MCP applied voltage) and the MCP multiplication factor while representing the MCP applied voltage along the lateral axis and the MCP multiplication factor along the longitudinal axis, that the MCP multiplication factor increases in monotone up to a saturation value. Based on this study, the present invention employs an MCP applied voltage control circuit 40-3 for performing a control as shown in FIG. 7. This MCP applied voltage control circuit 40-3 calculates a current MCP multiplication factor from an MCP operating time and controls the voltage to be applied to the MCP such that the MCP multiplication factor is regularly kept at a constant level, based on an MCP applied voltage-MCP multiplication factor curve with respect to the current operating time. That is, the circuit controls the voltage to be applied to the MCP such that the voltage is shifted in the direction indicated by an arrow of FIG. 6. As for an image containing a defect, which has been taken through such a control, a constant level of contrast in the image can be regularly obtained in spite of the long time use of the MCP. Further, this MCP applied voltage control circuit 40-3 controls the voltage to be applied to the MCP in such a manner that if the line rate of the line sensor is changed to be doubled as compared to a current line rate, then the circuit controls the voltage to be applied to the MCP to such a level that can achieve a doubled MCP multiplication factor as compared to the current multiplication factor, and if the magnification factor is changed to be doubled as compared to the current magnification factor, then the circuit controls the voltage to be applied to the MCP to such a level that can achieve an MCP multiplication factor four times as high as the current multiplication factor, and thereby keeps the constant level of contrast of the image even in the case of any change in those parameters. It is to be noted that a flow chart of the MCP applied voltage control circuit 40-3 is shown in FIG. 7.

A specific embodiment will now be described in more detail in conjunction with a wafer defect inspection.

Figure 8:
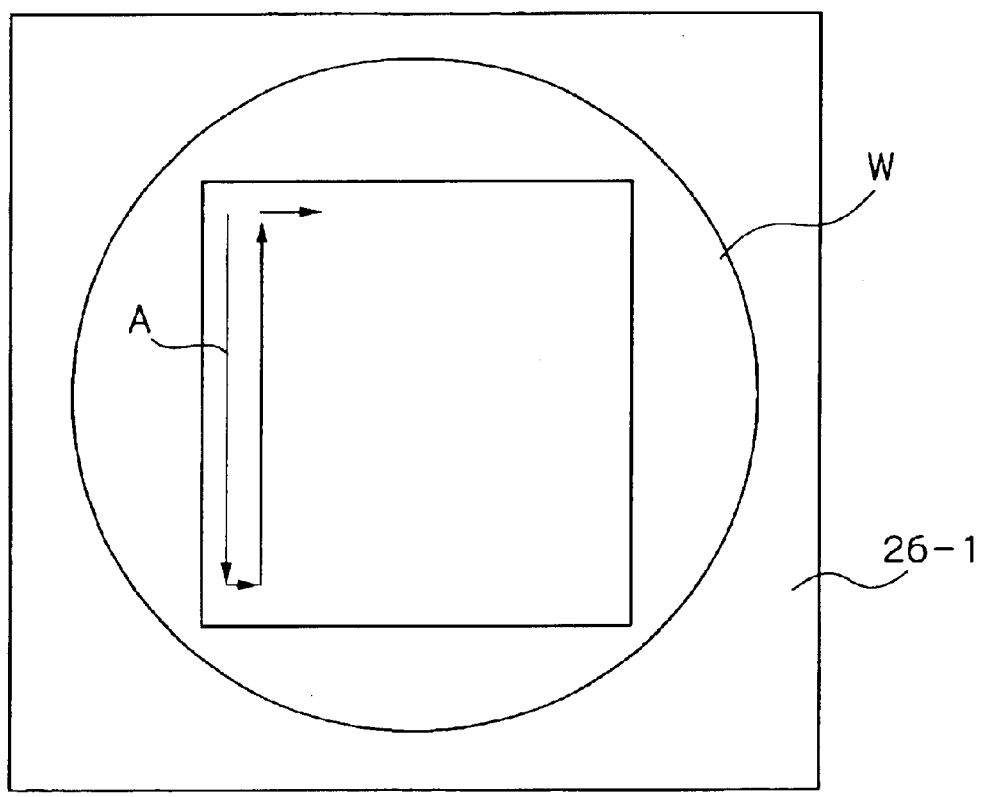
FIG. 8 shows an inspection procedure for a wafer W according to the third embodiment of the present invention.

A wafer W prepared as a sample subject to a defect inspection as shown in FIG. 8 was loaded on the X-Y stage 26-1, and the primary electron beam was radiated upon the wafer W by the aforementioned defect inspection apparatus 1-1 so as to scan the wafer W in the up and down directions as indicated by an arrows A in FIG. 8 thus to pick up images covering whole area on the wafer, and the images taken by the line sensor 18-1 were stored in the PC memory 34-1. These steps of the defect inspection were performed by the MCP applied voltage control circuit 40-3 continuously for 1000 hours. As a result, the MCP multiplication factor was about 4500 for the operating time of zero hour, and after the operating time of 1000 hours, G2 was changed to about 3000 for the same MCP applied voltage of 1200 V (see FIG. 5). However, when the MCP applied voltage control circuit of the present invention was used to change the MCP multiplication factor, the MVP applied voltage was shifted from about 1200 V to about 1400 V while the MCP multiplication factor of the constant level of 4500 having been steadily indicated through the period. Further, the defective image taken in such a manner had kept the almost same level of contrast in the image over 1000 hours.

According to the third embodiment, the following effects may be brought about.

(A) Any change or deterioration of the contrast in the defective image may be inhibited even after a long time operation of the defect inspection.

(B) By controlling the MCP applied voltage or the emission current of the beam, the deterioration of the multiplication factor due to the long time operation of the MCP can be prevented, and thereby the defective image contrast can be maintained in the same level through the operation.

(C) By determining the MCP applied voltage by referring to the current MCP applied voltage-MCP gain curve, the defective image contrast can be maintained in the same level through the operation (D) The performance in the defect inspection can be improved without any deterioration in throughput.

Fourth Embodiment

Figure 9:
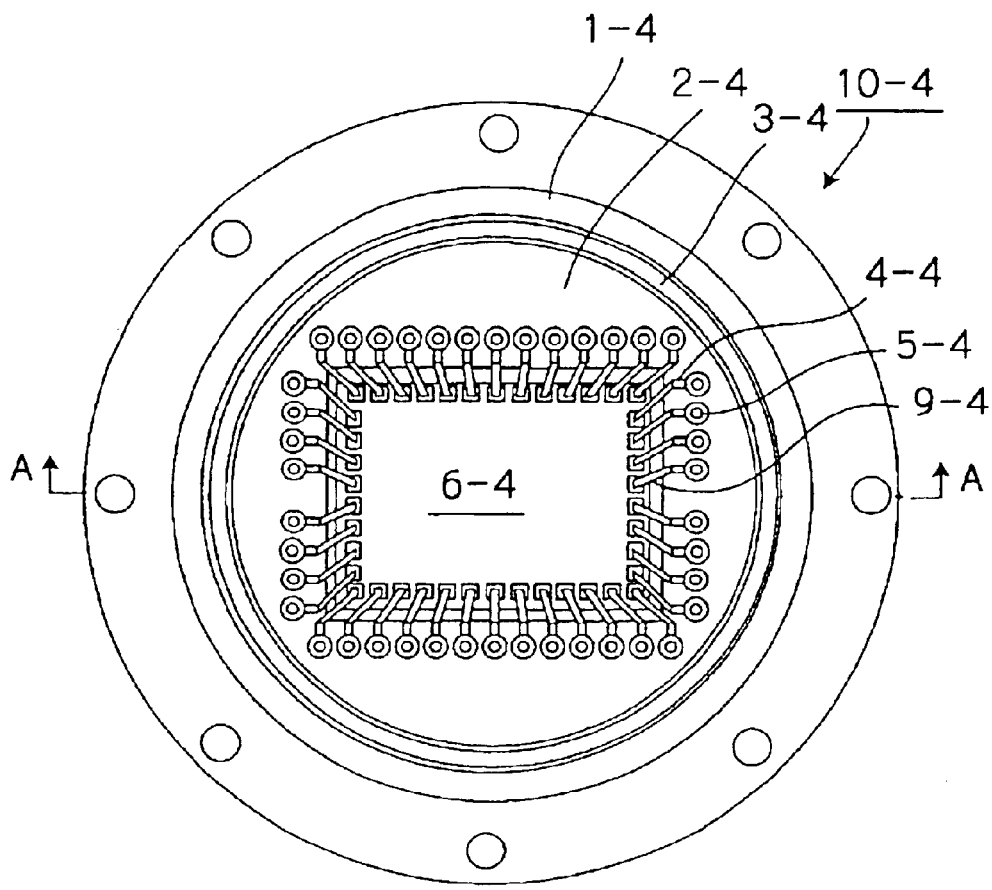
FIG. 9 is a schematic plan view of a feed-through unit according to a fourth embodiment of the present invention.
Figure 10:
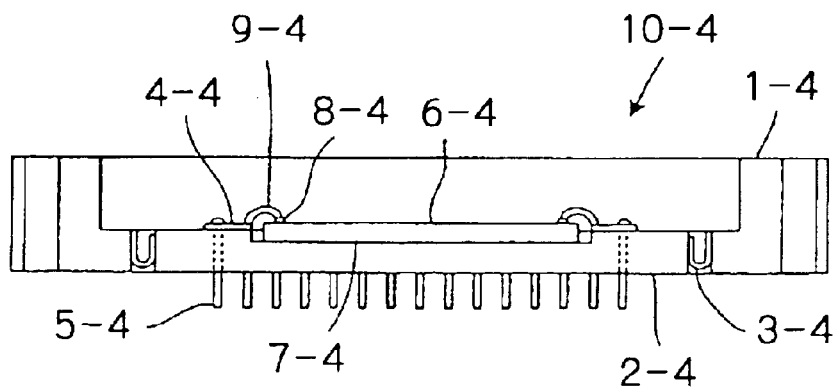
FIG. 10 is a schematic cross sectional view of the feed-through unit taken along the line A—A of FIG. 9.

FIG. 9 is a schematic plan view of a feed-through unit according to an embodiment of the present invention and FIG. 10 is a schematic cross sectional view of the filed-through unit of FIG. 9 taken along the line A—A. The feed-through unit 10-4 of FIG. 9 is composed of a semiconductor device forming a semiconductor package. As shown in FIG. 10, the feed-through unit 10-4 comprises a feed-through section 2-4, at least one electricity introduction pin 5-4 to be fixedly attached to said filed-through section 2-4, a wiring 9-4 for interconnecting said at least one electricity introduction pin 5-4 with a functional element, though not shown, and a metal flange 1-4.

The feed-through section 2-4 is made of material having an electric insulating ability, and typically made of alumina-based ceramic. The feed-through section 2-4 is coupled with the metal flange 1-4 via a shell 3-4. The shell 3-4 is made of metal such as Kovar or 42 alloy, and plays a role of preventing a damage which might be caused by a thermal stress due to a difference in coefficient of thermal expansion between the feed-through section 2-4 and the metal flange 1-4. Upon bonding the filed-through section 2-4 with the shell 3-4, for example, molybdenum-manganese metallized and silver solder are used to provide a sealing adhesion between them. Further, the coupling between the shell 3-4 and the metal flange 1-4 is provided with an air-tight treatment in a method such as the TIG full-arc welding.

The feed-through section 2-4 comprises a pattern metallized section 4-4 and a die (functional element) 6-4. The pattern metallized section 4-4 and the pin 5-4 are sealingly adhered to each other via the silver solder. The die 6-4 is fixedly attached to a die bonding section 7-4 formed in one of the surfaces of the feed-through section 2-4. The die 6-4 is constituted of a functional element including a sensor, an electric circuit and a semiconductor element. The field-though section 2-4 is adapted to allow an existence of different pressure conditions and different kinds of gas via the feed-through section 2-4.

In FIG. 10, the die 6-4 is arranged on a surface on a vacuum atmosphere side of the feed-through section 2-4, and the die 6-4 is connected to an electricity introduction terminal of the vacuum insulated pin 5-4. Further, the pin 5-4 is arranged in such a manner that the electric signal of the die 6-4 can be extracted out into the atmosphere via the electricity introduction terminal. The feed-through unit 10-4 shown in FIGS. 9 and 10 is composed of a semiconductor package having a function capable of vacuum-insulating, in specific, a package accommodating a semiconductor device such as CCD or TDI. This feed-through unit 10-4 is used as a detector for detecting a defect in the semiconductor device including an image projecting system, as will be described later with reference to FIG. 13.

In the unit shown in FIGS. 9 and 10, the functional element is fabricated on a top surface in the vacuum side of the feed-through section 2-4, though not shown. The interconnecting wiring 9-4 for connecting the electricity introduction pin 5-4 and the functional element which is not shown is formed in a net-like geometry on a top surface of the feed-through section 2-4. The feed-through section 2-4 is welded to the metal flange 1-4 or coupled with the metal flange 1-4 via the shell 3-4.

The feed-through section 2-4 may or may not include partially a drop-in section formed thereon as a die bonding section 7-4. As for a method to be used for the adhesion in the die bonding section 7-4, an adhesive, an adhesive tape and a soldering by a metal of low fusing point may be applicable. If it is to be used in the vacuum atmosphere, preferably a method which resultantly provides small quantity of outgassing in the vacuum should be used. In the embodiment of FIG. 10, although the interconnecting wiring 9-4 has been employed as the electric connection means between the die pad section 8-4 and the pattern metallized section 4-4, a flip chip connection or an ordinary electric wiring may be employed instead.

Figure 11:
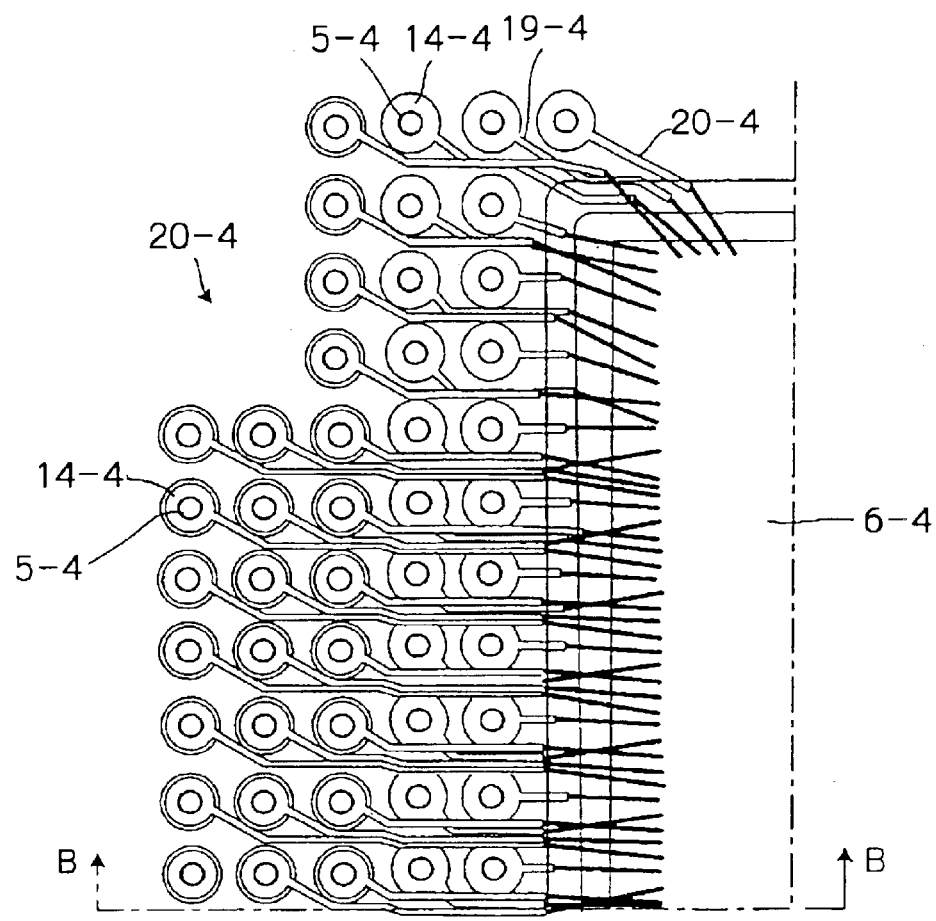
FIG. 11 is a schematic plan view encompassing approximately a quarter of an alternative feed-through unit according to the fourth embodiment of the present invention.
Figure 12:
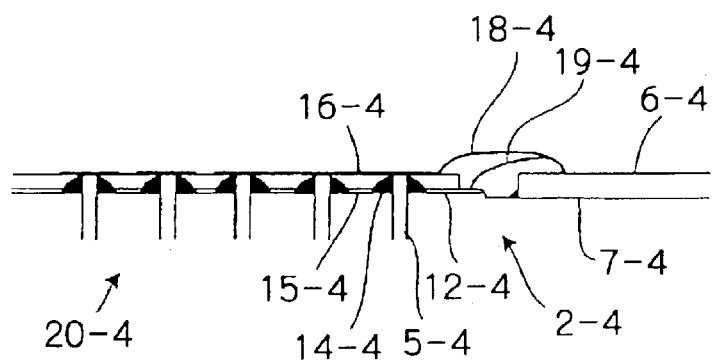
FIG. 12 is a schematic cross sectional view of the feed-through unit taken along the line B—B of FIG. 11.

FIG. 11 is a schematic plan view of a feed-through unit according to another embodiment of the present invention, showing one quarter of a plane of a functional element 6-4. FIG. 12 is a schematic cross sectional view of the feed-through unit 6-4 of FIG. 11 taken along the line B—B. FIGS. 11 and 12 shows a feed-through unit 20-4 having a larger number of pins 5-4. The same method as that used in the embodiment 10 is employed to secure sealingly the feed-through section 2-4 to the metal flange which is not shown.

If the feed-through unit 20-4 has an excessively large number of pins 5 as shown in FIGS. 11 and 12 and accordingly the lower pattern metallized 12-4 is not sufficient to form all of the wirings, then a wiring plate 15-4 equipped with an upper pattern metallized 16-4 fabricated on a top surface thereof may be built so as to be superimposed thereon, wherein the lower and the upper patterns metallized 12-4, 16-4 are electrically connected to the die 6-4 by using a lower and an upper connecting wirings 19-4, 18-4 respectively. The electric connection between the upper pattern metallized 16-4 and the pin 5-4 may be provided by using either one of a brazing, a soldering, or a wire bonding.

Figure 13:
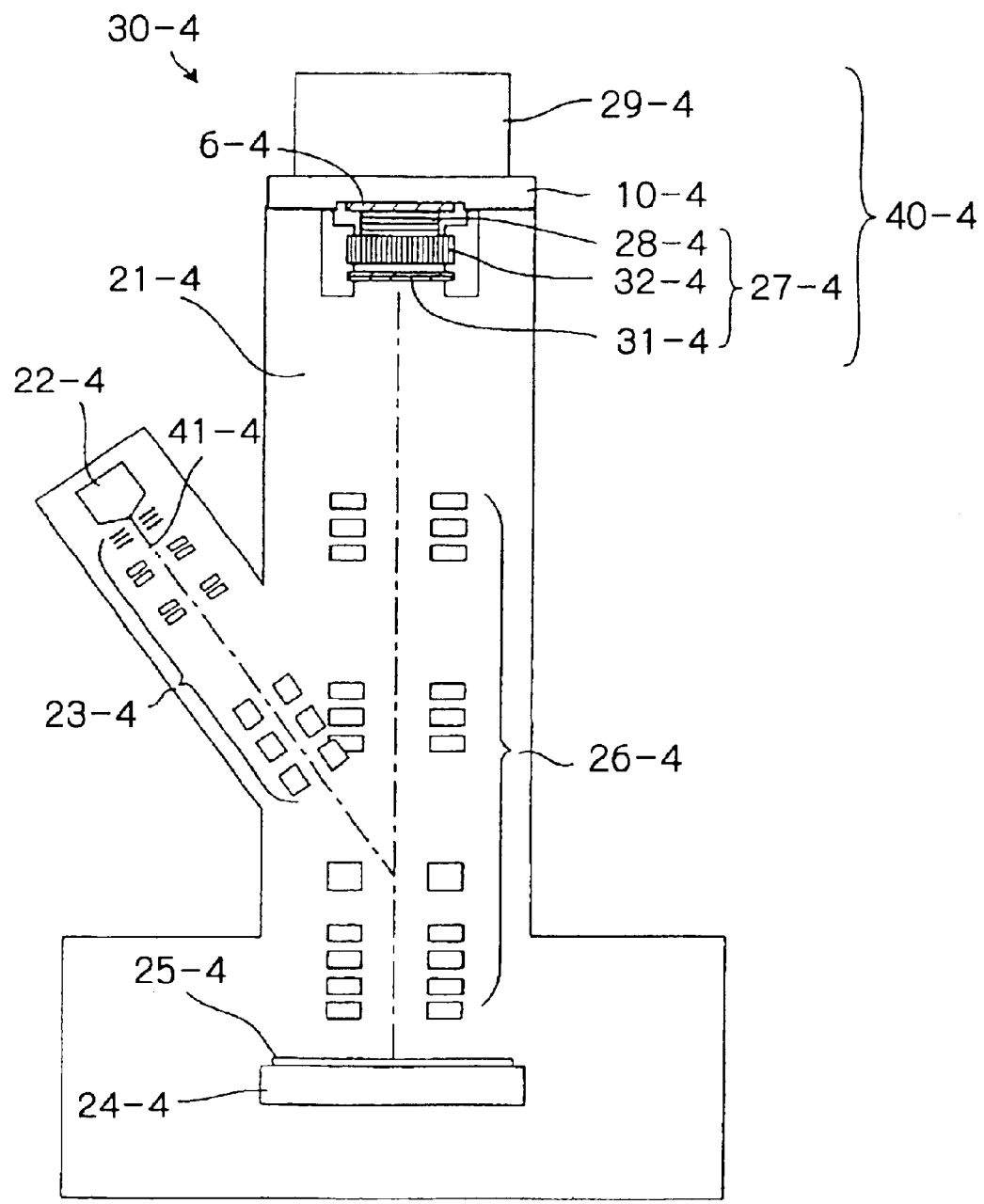
FIG. 13 is a schematic longitudinal cross sectional view of a defect inspection apparatus with the feed-through unit incorporated therein, according to the fourth embodiment of the present invention.

FIG. 13 is a schematic longitudinal cross sectional view of a wafer defect inspection apparatus 30-4 incorporated with the feed-through unit 10-4 or 20-4 according to the present invention. The wafer defect inspection apparatus 30-4 of FIG. 13 comprises an electron gun 22-4 for emitting an electron beam 41-4 into a vacuum chamber 21-4, an illumination optical system 23-4 consisting of a group of electrostatic lenses, a stage 24-4 for supporting a wafer to be inspected, an image projecting optical system 26-4 consisting of a group of electrostatic lenses, and a detector 40-4.

As shown in FIG. 13, the detector 40-4 comprises an MCP (Micro Channel Plate) 31-4 for amplifying a secondary electron image, a fluorescent screen 32-4 for converting the electron image amplified by the MCP 31-4 into an optical signal, a FOP (Fiber Optic Plate, designated with a reference numeral 28-4) disposed so as to be tightly attached to the fluorescent screen 32-4 for transmitting the optical image converted by the fluorescent screen 32-4, an element 20-4 (functional element 6-4) for converting the optical image output from the FOP 28-4 into a digital electric signal, the feed-through unit 10-4, and a camera 29-4 disposed just above the feed-through unit for converting the electric signal from the feed-through unit. The filed-through unit 10-4 transmits the electric signal to an outside while providing a sealing for the vacuum system within the vacuum chamber 21-4 against the outside. The MCP 31-4, the fluorescent screen 32-4 and the FOP 28-4 are all supported by a common support member so as to form an MCP/FOP assembly 27-4.

In the wafer defect inspection apparatus 30-4 of FIG. 13, the electron beam 41-4 emitted from the electron gun 22-4 is deflected and shaped appropriately by the illumination optical system 23-4 and then radiated upon a surface of the wafer 25-4 loaded on the stage 24-4. The secondary electrons emitted from the wafer 25-4 by the irradiation of the electron beam are formed into an image on the MCP/FOP assembly 27-4 by the image projecting optical system 26-4 at a predetermined magnification. The secondary electron image formed on the MCP/FOP assembly 27-4 is multiplied and converted into an optical signal by the fluorescent screen 32-4, and the signal enters to the feed-through unit 10-4, where the optical signal is converted into a digital signal by the functional element on the feed-through unit, and then this digital signal is transmitted to the camera 29-4. The camera 29-4 converts the digital signal into to a signal in such a form that an image processing unit (not shown) in the subsequent step can accept, and then outputs the signal thus to be used in the wafer defect inspection and the like.

According to the fourth embodiment of the present invention, since such a configuration has been employed that comprises at least one electricity introduction pin fixedly attached to the feed-through section and the interconnecting wiring for connecting said at least one electricity introduction pin and the functional element, wherein because said functional element includes a sensor, a signal delay may be prevented and a disturbance may be reduced with a shorter signal line in comparison with a configuration where an image taking sensor and a vacuum flange are formed separately, and thus the sensor may be driven at a high speed, therefor the throughput of the defect inspection can be improved The wafer defect inspection apparatus using the electron beam apparatus incorporated with the feed-through unit according to the fourth embodiment of the present invention can inspect a semiconductor device having a fine pattern with a high level of throughput and can prevent any faulty products from being delivered.

Fifth Embodiment

Figure 14:
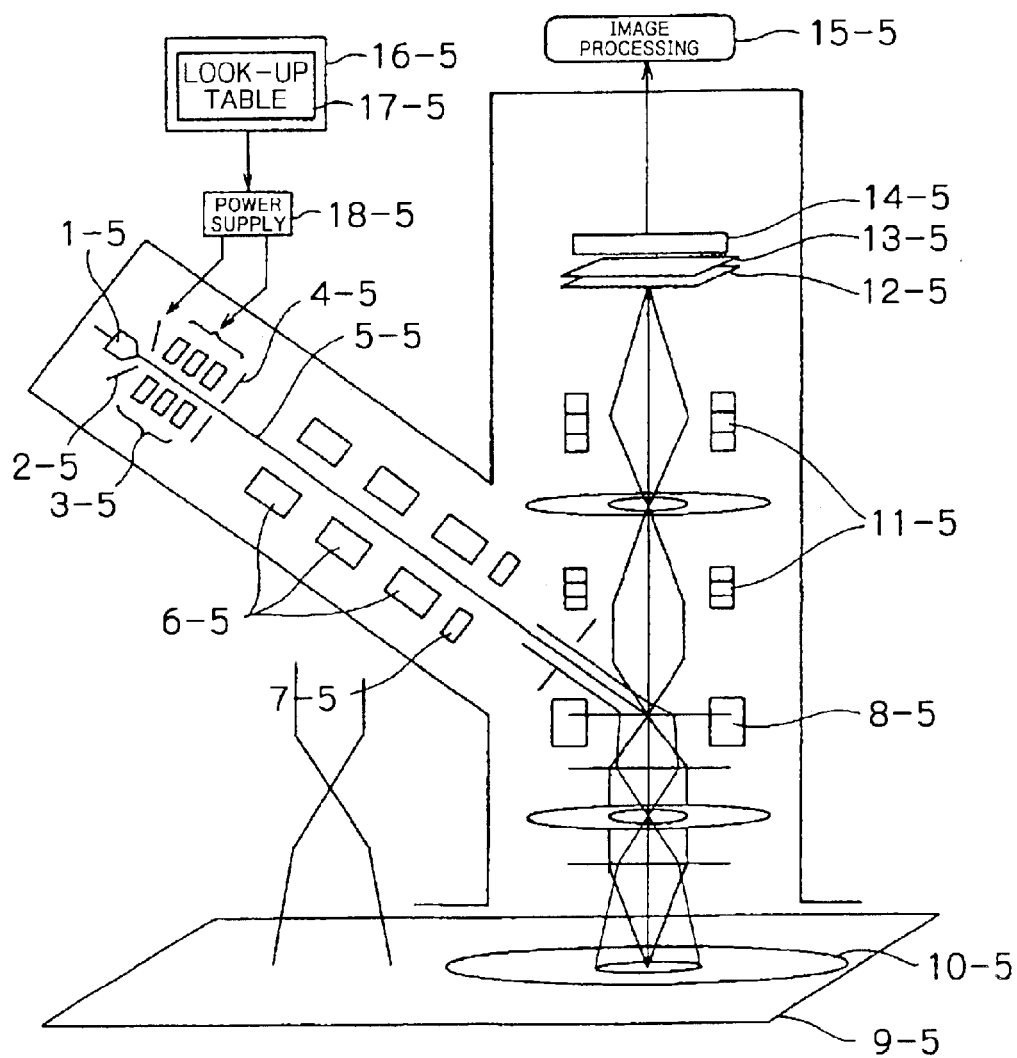
FIG. 14 is a schematic diagram of a defect inspection apparatus according to a fifth embodiment of the present invention.

FIG. 14 schematically shows a configuration of a defect inspection apparatus according to an embodiment of the present invention. The inspection apparatus of FIG. 14 is a defect inspection apparatus of the image projection type similar to that in the embodiment of FIG. 13, in which a primary electron beam 5-5 emitted from an electron gun 15 passes through a primary electron optical system and irradiates a sample 10-5, and a secondary electron beam emitted from the sample 10-5 by said irradiation is introduced into a detector 14-5 via a secondary electron optical system, where an image data representing a pattern of a surface of the sample 10-5 may be obtained so as to perform a defect inspection.

The electron gun 1-5 comprises a cathode made of $LaB_6$, said cathode having a flat <100> monocrystal surface with a diameter greater than 100 microns formed in a tip portion thereof. In the primary electron optical system, the primary electron beam 5-5 emitted from the electron gun 1-5 is, after the emission current amount having been controlled by the Wehnelt electrode 2-5, accelerated by a plurality of positive electrodes 3-5 and forms a crossover in a gun aperture 4-5. Then, the primary electron beam 5-5 enters to an electrostatic lens 6-5, in which the beam is shaped to be rectangular or elliptical in a sectional view and goes straight through an alignment electrode 7-5 and into a Wien filter 8-5. The Wien filter 8-5 deflects the primary electron beam 5-5 so that the beam is radiated onto the sample 10-5 at a right angle and thus, the beam irradiates the sample 10-5 loaded on an X-Y stage 9-5. At that time, the primary electron beam 5-5 may be, for example, elliptical in the section having the size of 400 microns×600 microns. The primary electron beam 5-5 is controlled by a retarding voltage applied to the sample 10-5 so as to have a predetermined landing energy and then is radiated onto the sample 10-5, and in response to this irradiation the sample emitts the secondary electrons.

The secondary electron beam thus emitted from the sample 10-5 is advanced straight forward through the Wien filter 8-5 and after having been magnified by an electrostatic lens 11-5 in the secondary electron optical system with a predetermined lens magnification, the beam is formed into an image on a micro channel plate 12-5. The secondary electron beam having been formed into the image on the micro channel plate 12-5 is multiplied by the micro channel plate 12-5 and projected onto a fluorescent screen 13-5. The secondary electron beam is converted by the fluorescent screen 13-5 into light, which is then entered into a detector 14-5 such as a CCD camera, a line sensor or the like. In this way, a pattern image for the surface of the sample 10-5 is obtained and the obtained image is fed to an image processing section 15-5.

Further, the defect inspection apparatus of FIG. 14 comprises a control section 16-5 for controlling a voltage applied to the Wehnelt electrode 2-5 and the positive electrode 3-5, and a power supply 18-5 for supplying the Wehnelt electrode 2-5 and the positive electrode 3-5 with the voltage at a certain level based on a command from the control section 16-5. The reason why the control section 16-5 has been provided is that only by changing the voltage to be applied to the Wehnelt electrode 2-5 in association with the elapsed time measured from the beginning of the current emission of the electron gun 1-5, the emission current of the electron gun 1-5 can be maintained at a certain value. However, if the applied voltage to the Wehnelt electrode 2-5 is changed, a cross over diameter of the primary electron beam is also changed. To prevent this, the control section 16-5 also changes a voltage applied to the positive electrode 3-5 while changing the voltage applied to the Wehnelt electrode 2-5, so that the primary electron beam may always form a crossover at the center of the gun aperture 4-5. Such a controlling allows the image processing section 15-5 to obtain an image having a certain level of contrast.

To accomplish this, in the defect inspection apparatus of FIG. 14, a relationship between the elapsed time measured from the beginning of the current emission and the applied voltage to the Wehnelt electrode 2-5 required to control the emission current of the electron gun 1-5 to be maintained at a constant level and also a relationship between the change in the applied voltage to the Wehnelt electrode 2-5 and the voltage applied to the positive electrode 3-5 required for the primary electron beam to form the crossover at the center of the gun aperture 4-5 should be measured in advance, and for said emission current, the relationship between the elapsed time and the applied voltage should be stored in the control section 16-5 in a form of a look-up table 17-5.

When the defect inspection apparatus of FIG. 14 is operated after the above-described pre-processing having been finished, the control section 16-5 monitors the elapsed time from the beginning of the current emission and refers to the look-up table 17-5 with a predetermined time interval while reading a value representing a voltage to be applied corresponding to said elapsed time from the beginning of the current emission and applying said value to the power supply 18-5 so as to control the emission current of the electron gun 1-5 to be kept at a constant level, and thereby the control section 16-5 can set the voltage to be applied to the Wehnelt electrode 2-5 to a certain level corresponding to said elapsed time. At the same time, the control section 16-5 also reads out a value representing the voltage to be applied to the positive electrode 5-3 corresponding to a change in the voltage applied to the Wehnelt electrode 2-5 from the look-up table 17-5 and applies the read value to the power supply 18-5, thereby adjusting the voltage to be applied to the positive electrode 3-5 to a desired value.

Figure 15:
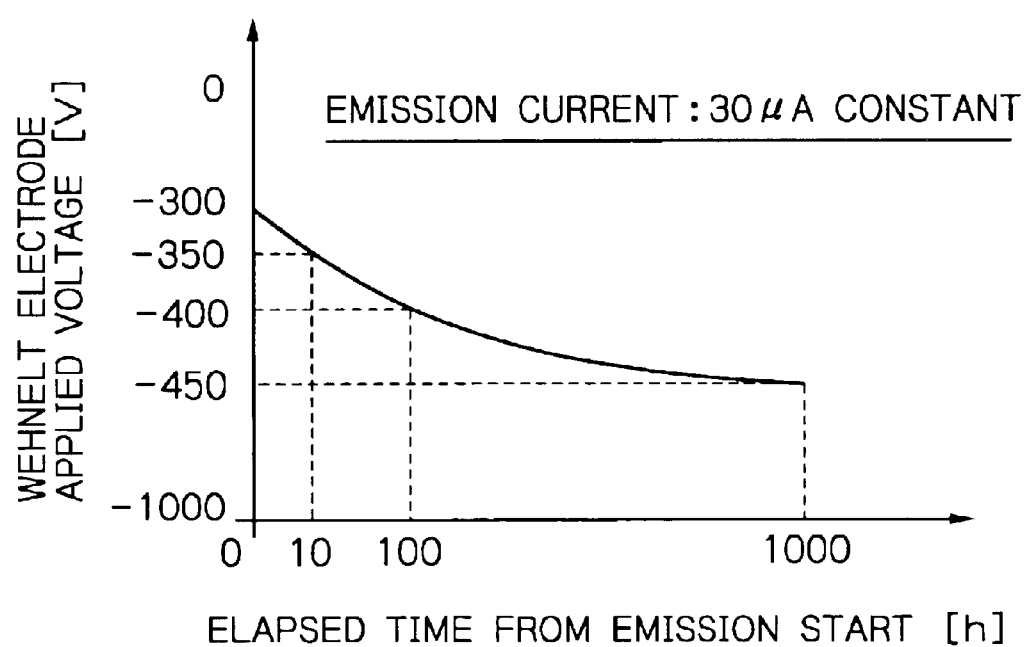
FIG. 15 is a graph illustrating a relationship between a voltage applied to a Wehnelt electrode and an elapsed time, for controlling an emission current from an electron gun to be maintained at a constant level according to the fifth embodiment.

According to an actual experiment in which a level of voltage to be applied to the Wehnelt electrode 2-5 in order to maintain the emission current at a constant level of 30 microampere was measured as a function of the elapsed time from the beginning of the current emission by using the defect inspection apparatus having the configuration shown in FIG. 14, it has been observed that the voltage to be applied to the Wehnelt electrode 2-5 was around the level of −300 volts at the beginning of the current emission, around the level of −350 volts after 10 hours, around the level of −400 volts after 100 hours, and around the level of −450 volts after 1000 hours, as shown in FIG. 15. Further, the apparatus could successful control such that the primary electron beam might formed the crossover at the center of the gun aperture 4-5.

Figure 16:
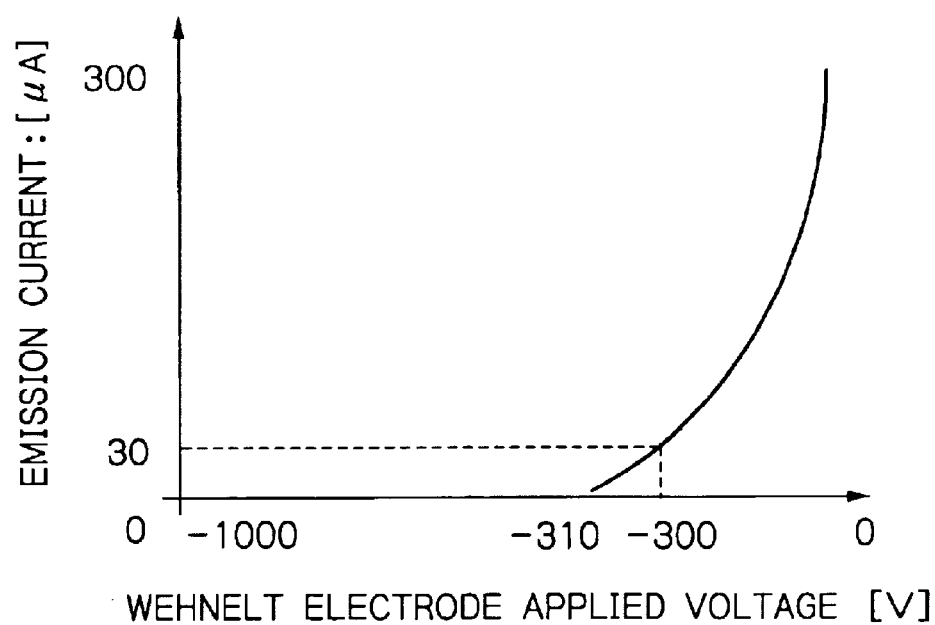
FIG. 16 is a graph indicating a relationship between an emission current from an electron gun and a voltage applied to a Wehnelt electrode in the fifth embodiment according to the prior art.

In contrast to the result shown in FIG. 15, it is obvious from FIG. 16 of a graph indicating a relationship between the voltage applied to the Wehnelt electrode (by volt) and the emission current of the electron gun (by microampere) according to the prior art, that the emission current increases rapidly as the voltage applied to the Wehnelt electrode exceeds the level of −300 volts.

As having been understood from the description of the electron beam apparatus according to the fifth embodiment, since the apparatus of the present embodiment allows the voltage applied to the Wehnelt electrode to be changed in association with the passage of time so as to keep a certain level of emission current from the electron gun, therefore an image for a sample with a certain level of contrast can be obtained, and most effectively a sample can be inspected for a defect with high degree of throughput and accuracy.

Sixth Embodiment

A further detailed system for an entire defect inspection system including the conveying mechanism 40-1, the vibration isolating mechanism and the vacuum system as described with reference to FIG. 1 will now be described as a sixth embodiment of the present invention.

Figure 17:
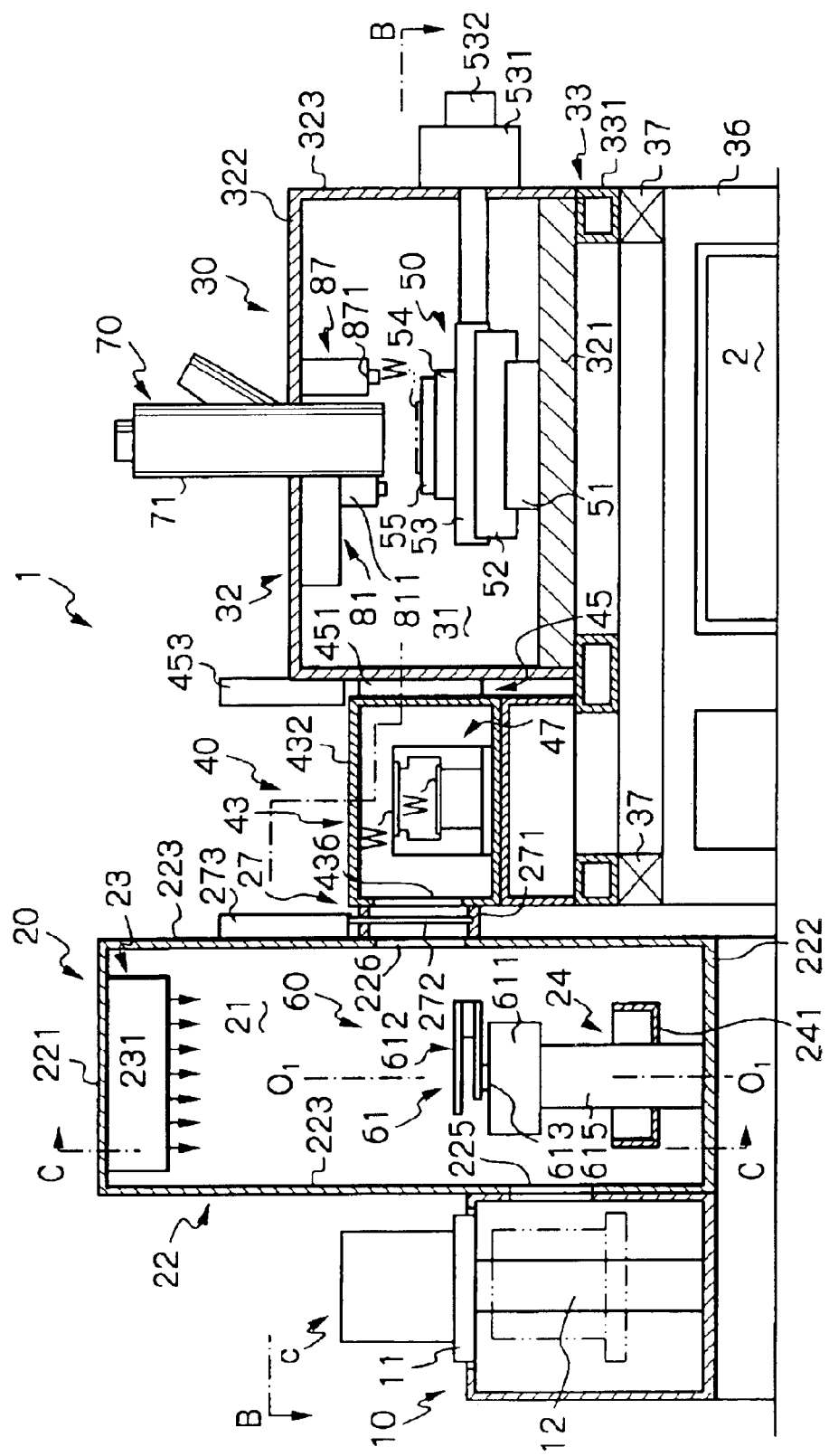
FIG. 17 is an elevation view illustrating main components of an inspection apparatus according to a sixth embodiment of the present invention, taken along the line A—A of FIG. 18.
Figure 18:
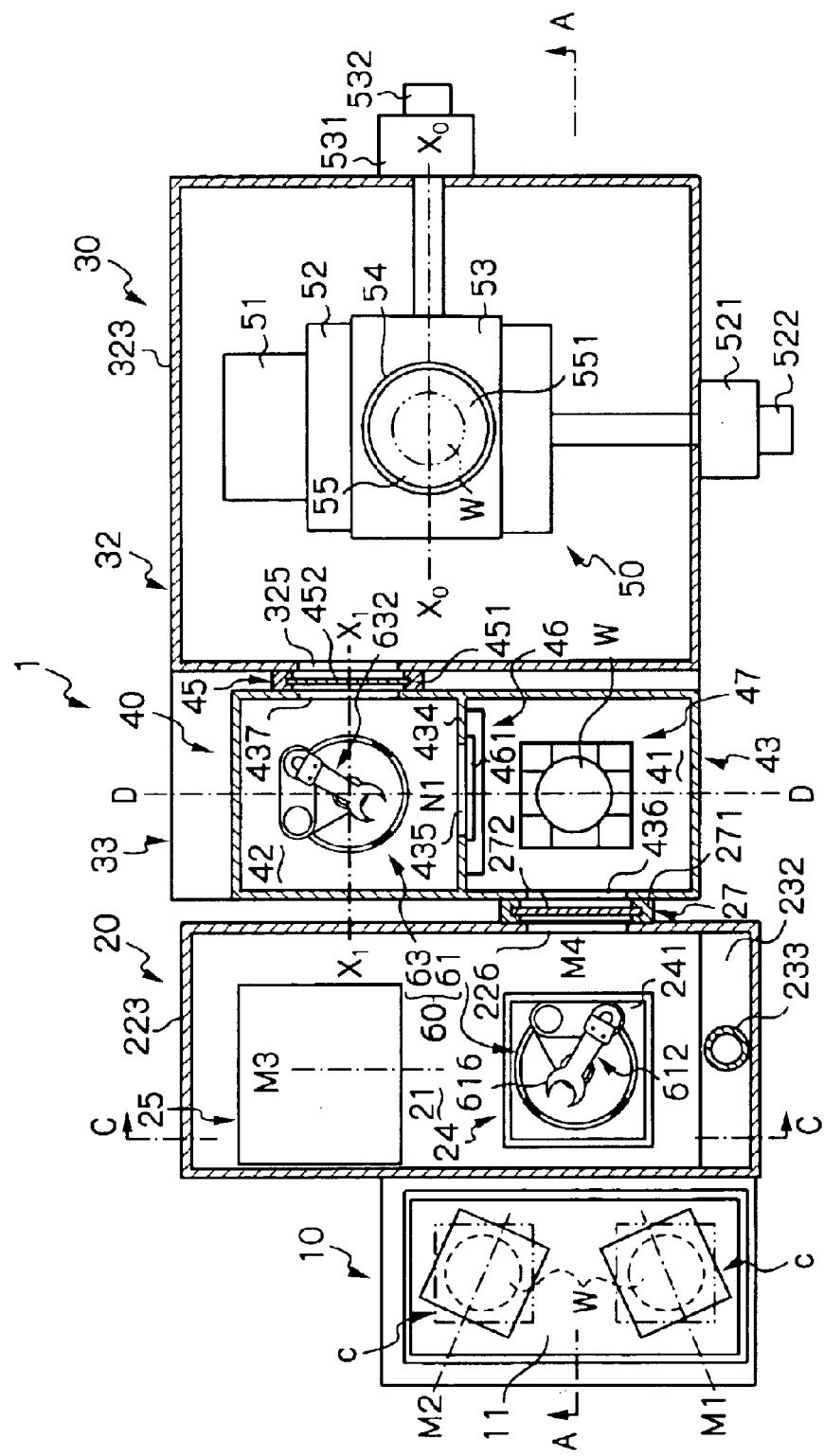
FIG. 18 is a plan view illustrating main components of the inspection apparatus taken along the line B—B of FIG. 17.

FIGS. 17 and 18 show main components of a semiconductor inspection apparatus 1 according to the sixth embodiment, in an elevation view and a plan view respectively.

The semiconductor inspection apparatus 1 of the present embodiment comprises a cassette holder 10 for holding a cassette accommodating a plurality of wafers, a mini-environment device 20, a main housing 30 defining a working chamber, a loader housing 40 disposed between the mini-environment device 20 and the main housing 30 so as to define two loading chambers, a loader 60 for loading a wafer from the cassette holder 10 onto a stage unit 50 located within the main housing 30, and an electron optical unit 70 installed within a vacuum housing, all of which are arranged with the physical relationship as shown in FIGS. 17 and 18. The semiconductor inspection apparatus 1 further comprises a pre-charge unit 81 disposed within the vacuum main housing 30, a potential applying mechanism 83 (shown in FIG. 25) for applying a potential to the wafer, an electron beam calibration mechanism 85 (shown in FIG. 27), and an optical microscope 871 which is a component of an alignment control unit 87 used for positioning the wafer on the stage unit.

The cassette holder 10 has been designed so that it can hold a plurality (two in this embodiment) of cassettes "c" (e.g., a closed cassette such as SMIF or FOUP available from Assist Corp.) accommodating a plurality of wafers (e.g., 25 pieces of wafers) which are arranged in parallel in the up and down direction within the cassette. As for this cassette holder, any cassette holder may be arbitrarily selected and installed in the apparatus depending on the circumstance, wherein for example, if the cassette is conveyed by a robot or the like and is automatically loaded to the cassette holder 10, the cassette holder in a structure suitable for such specific operation may be selected, and if the cassette is loaded manually, a cassette holder in an open cassette structure may be selected. In this embodiment, such type of cassette holder 10 is employed that is suitable for the circumstance where the cassette c is automatically loaded, wherein said cassette holder 10 comprises, for example, an elevating table 11 and an elevating mechanism 12 for moving up and down the elevating table 11, in which the cassette c is allowed to be set on the elevating table automatically in a state indicated by a chained line of FIG. 18 and after having been set thereon, to be rotated automatically into a state indicated by a solid line of FIG. 18 so that the cassette is oriented to a rotary movement axis line of a first conveying unit in the mini-environment device. Further, the elevating table 11 is lowered into a state indicated by a chained line of FIG. 17. In this way, since any cassette holders in any known structures may be used appropriately depending on the circumstance, including the cassette holder used in the automatic loading or the cassette holder used in the manual loading, the detailed description on those structures and functions will be herein omitted.

Figure 28:
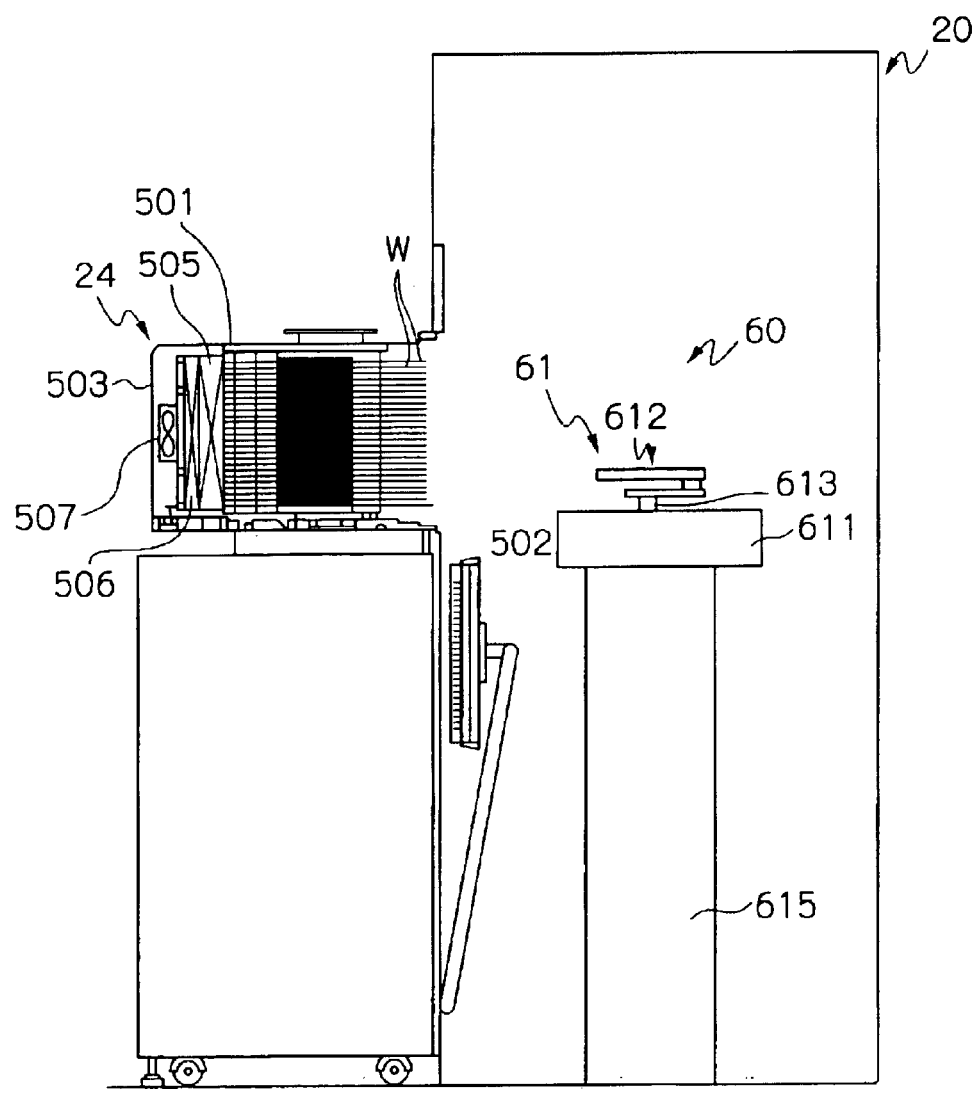
FIG. 28 is a side elevation view illustrating an alternative embodiment of a mechanism for loading/unloading a substrate.

In another embodiment shown in FIG. 28, a plurality of 300 mm substrates W is accommodated in a state of being contained in a slot type pocket (not shown) fixedly attached to an inner side of a box main body 501 so as to be ready for the conveying and storing. This substrate storage box 24 comprises: a box main body 501 of rectangular-cylindrical shape; a door 502 for carrying in/out the substrate, which is coupled with an automatic door opening/closing unit for selectively opening or closing said door 502 so that an opening in a side face of the box main body 501 can be opened or closed by this mechanism; a lid body 503 disposed in an opposite side of said opening for covering another opening through which filters and a fun motor are to be attached or detached; said slot type pocket for holding the substrate W; a ULPA filter 505; a chemical filter 506; and a fan motor 507. In this embodiment, the substrate is carried in or out by a first conveying unit 61 of robot type in the loader 60.

It is to be noted that the substrate or the wafer received in the cassette c is a wafer to be subjected to an inspection, and such inspection may be carried out after or in a course of a process for processing the wafer in the semiconductor manufacturing process. In specific, such a substrate or a wafer as having been subjected to a membrane deposition process, a CMP process or an ion implantation process, a wafer with a wiring pattern formed thereon, or a wafer with a wiring pattern not yet formed thereon is received in the cassette. Since a plurality of wafers are received in the cassette c so as to be arranged horizontally and parallelly placing a space therebetween and stacked vertically, an arm of the first conveying unit is designed to be movable vertically so that the first conveying unit can catch the wafer in any arbitrary location.

Figure 19:
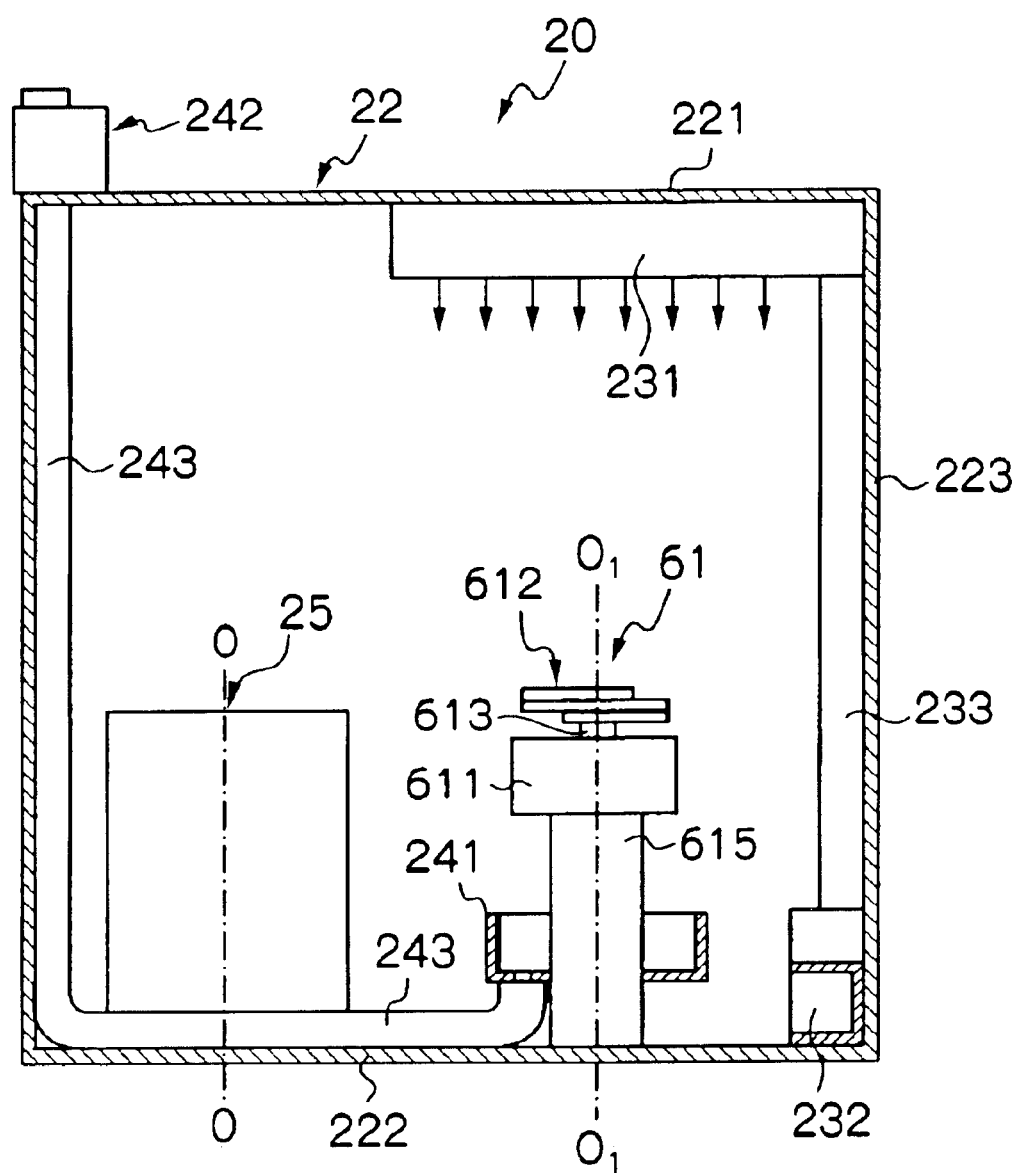
FIG. 19 is a cross sectional view of a mini-environment device taken along the line C—C of FIG. 17.

In FIGS. 17 to 19, the mini-environment device 20 comprises a housing 22 defining a mini-environmental space 21 subject to an atmosphere control, a gas circulation unit 23 for circulating a gas such as a clean air within the mini-environmental space 21 for the atmosphere control, a pumping unit 24 for recovering and exhausting a part of the air supplied to the mini-environmental space 21, and a pre-aligner 25 disposed in the mini-environmental space 21 for roughly positioning the substrate or the wafer as an objective material to be inspected.

The housing 22 has a top wall 221, a bottom wall 222 and four side walls for forming a closed space, thus having a structure to shield the mini-environmental space 21 from the outside. In order to control the atmosphere within the mini-environmental space 21, the gas circulation unit 23, as shown in FIG. 19, comprises a gas supply unit 231 attached to the top wall 221 within the mini-environmental space 21 for cleaning a gas (an air in this embodiment) and blowing the clean air just downward in laminar flow through one or more gas outlets (not shown), a recovery duct 232 disposed on the bottom wall 222 within the mini-environmental space for recovering the air which has flowed down toward the bottom, and a conduit 233 interconnecting the recovery duct 232 and the gas supply unit 231 for returning the recovered air back to the gas supply unit 231. Although in this embodiment the gas supply unit 231 has been designed so that about 20% of the supply air may be taken from the outside of the housing 22 so as to clean the air, the ratio of the air to be taken from the outside may be selected arbitrarily. The gas supply unit 231 is equipped with either of the HEPA filter or the ULPA filter with a known structure for generating a clean air. A down flow of the clean air in laminar flow, namely, a down flow of the air is mainly supplied so as to flow through a conveying plane by means of the first conveying unit disposed in the mini-environment device 21, thereby preventing dust from depositing on the wafer, which otherwise may be probably caused by the conveying unit. Accordingly, the injection port of the down flow is not necessarily arranged in the location near the top wall as illustrated, but it may be arranged at any location above the conveying plane by means of the conveying unit. Also, the down flow is not necessarily supplied to flow over the entire area of the mini-environmental space. It is to be noted, in some cases, an ionic wind may be used as the clean air to ensure the level of cleanness. Further, a sensor may be arranged in the mini-environmental space so that the unit can be shut down in case of deterioration in the level of cleanness. An entrance and exit port 225 is formed in a portion adjacent to the cassette holder 10 among the side walls 223 of the housing 22. A shutter unit of known structure may be provided in the vicinity of the entrance and exit port 225 so that the entrance and exit port can be closed from the side of the mini-environment device. The down flow in the laminar flow generated in the vicinity of the wafer may have a flow velocity of, for example, 0.3 to 0.4 m/sec. The gas supply unit is not necessarily arranged within the mini-environmental space but may be arranged in the outside of the space.

The pumping unit 24 comprises a suction duct 241 disposed in an under portion of said conveying unit at a location lower than the wafer conveying plane of the conveying unit, a blower 242 disposed in the outside of the housing 22, and a conduit 243 interconnecting the suction duct 241 and the blower 242. This pumping unit 24 sucks from the suction duct 241 the gas flowing down around the conveying unit and including the dust, which may be possibly generated by the conveying unit, and exhaust the gas to the outside via the conduit 243, 244 and the blower 242. In that case, the gas may be exhausted into an exhaust pipe (not shown) lying in the vicinity of the housing 22.

The aligner 25 arranged within the mini-environmental space 21 is designed such that it may detect optically or mechanically an orientation-flat formed in the wafer (which is a flat portion formed in an outer periphery of a circular wafer, and hereafter referred to as ori-fla) and/or a one ore more V-shaped cut-outs, namely, notches formed in an outer-peripheral edge of the wafer, and then position the wafer in advance in the rotational direction around the axis line O—O with a precision of +/-1 degree. The pre-aligner is a component of a mechanism for determining a coordinate of the objective sample to the inspection according to the present invention as defined in the attached claim, and plays a role for roughly positioning the objective material to be inspected. This pre-aligner itself may be of known structure and an explanation on the structure and operation thereof will be herein omitted.

It is to be noted that a recovery duct may be additionally provided in a lower portion of the pre-aligner, though not shown, so that an air including the dust, which has been discharged from the pre-aligner, can be exhausted to the outside.

In FIGS. 17 and 18, the main housing 30 defining a working chamber 31 comprises a housing main body 32, and the housing main body 32 is supported by a housing support unit 33 mounted on a vibration isolating unit, namely, a vibration isolating unit 37 disposed on a table frame 36. The housing support unit 33 comprises a frame structure 331 configured in a rectangular shape. The housing main body 33 is fixedly installed on the frame structure 331 and comprises a bottom wall 321 mounted on the frame structure 331, a top wall 322 and four side walls 323 connected to the bottom wall 321 and the top wall 322, thereby defining a closed space so as to isolate the working chamber 31 from the outside. Although the bottom wall 321, in this embodiment, is made of relatively thick steel plate so as to prevent a distortion which may possibly be generated by a load applied from a device such as the stage to be mounted thereon, other structure may be used. In this embodiment, the housing main body and the housing support unit 33 has been constructed in a rigid structure, and the vibration isolating unit 37 is provided to prevent the vibration from being transmitted to this rigid structure from a floor on which the table frame is installed. An entrance and exit port 325 for carrying in/out a wafer is formed in one of the side walls 323 of the housing main body 32 adjacent to the loader housing, which will be described later.

It is to be noted that the vibration isolating unit may be of active type or passive type, either of which may have an air spring, a magnetic bearing or the like. The vibration isolating unit may be of any known structure and an explanation on its structure and functions will be omitted. The working chamber 31 is designed to be held in vacuum atmosphere by a vacuum unit (not shown) of known structure. A control unit 2 is arranged under the table frame 36 so as to control a general operation of the unit.

Figure 20:
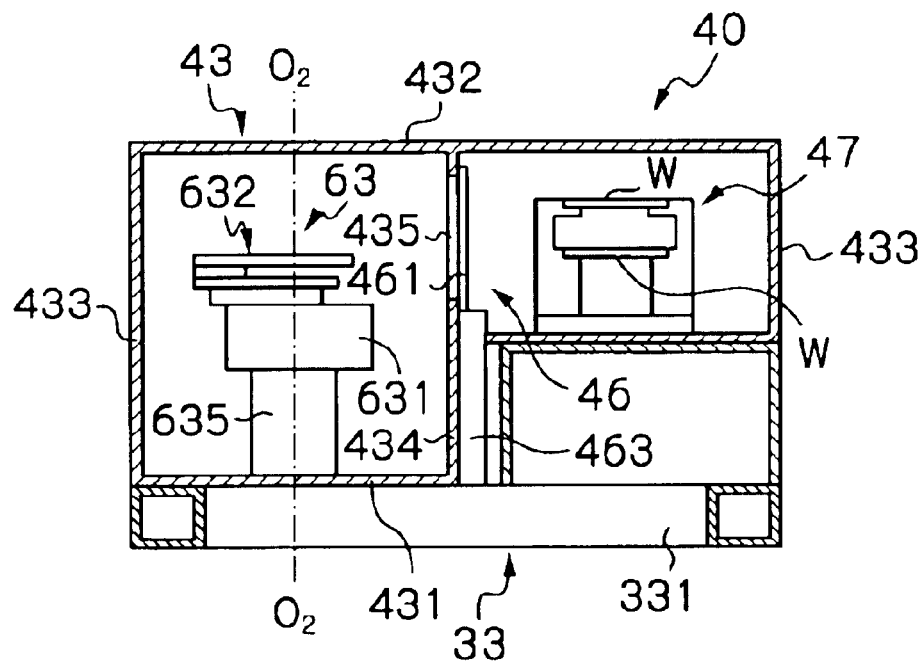
FIG. 20 is a side elevation view of a loader housing of FIG. 17, taken along the line D—D of FIG. 18.
Figures 21A, 21B:
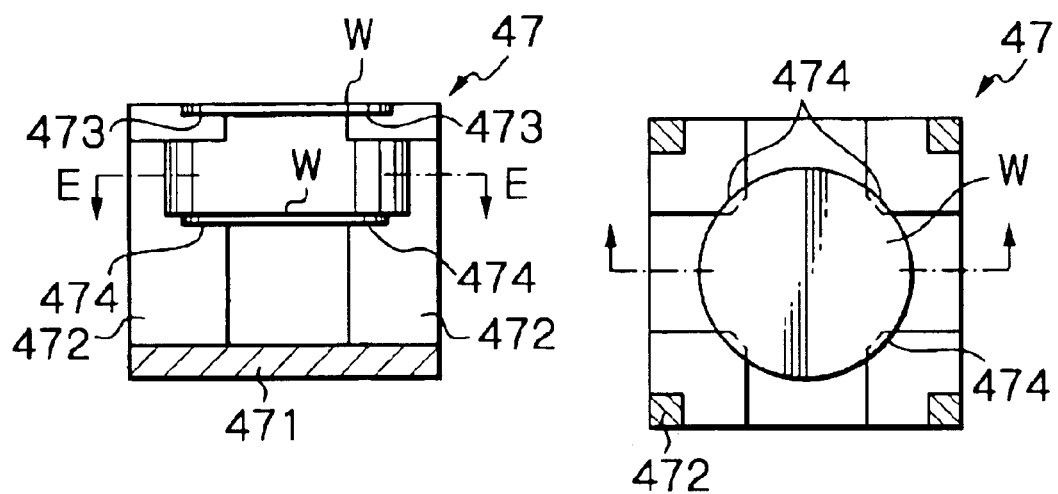
FIG. 21 is an enlarged view of a wafer rack, wherein [A] is a side view and [B] is a cross sectional view taken along the line E—E of [A]

In FIGS. 17, 18 and 20, the loader housing 40 comprises a housing main body 43 defining a first loading chamber 41 and a second loading chamber 42. The housing main body 43 has a bottom wall 431, the top wall 432, four side walls 433 defining a closed space, and a partition wall 434 for partitioning the housing into the first loading chamber 41 and the second loading chamber 42 so as to isolate the both loading chambers from the outside. An opening, namely, an entrance and exit port 435 is formed in the partition wall 434 for giving and taking the wafer between the both loading chambers. In addition, entrance and exit ports 436 and 437 are formed in the side walls 433 in those portions adjacent to the mini-environment device 20 or the main housing 30 respectively. The housing main body 43 of this loader housing 40 is mounted on and supported by the frame structure 331 of the housing support unit 33. Accordingly, also this loader housing 40 is designed so as to be isolated from the vibration of the floor. The entrance and exit port 436 of the loader housing 40 and the entrance and exit port 226 of the housing 22 of the mini-environment device are in alignment with each other, and a shutter unit 27 is arranged therebetween so as to block selectively a communication between the mini-environmental space 21 and the first loading chamber 41. The shutter unit 27 has a sealing member 271 surrounding the peripheries of the entrance and exit ports 226 and 436 and secured by way of a tight contact to the side wall, a door 272 for working cooperatively with the sealing member 271 to block an air flow through the entrance and exit ports, and a driving unit 273 for driving the door. Further, the entrance and exit port 437 of the loader housing 40 and the entrance and exit port 325 of the housing main body 32 are in alignment with each other, and a shutter unit 45 is arranged therebetween so as to block selectively a communication between the second loading chamber 42 and the working chamber 31. The shutter unit 45 has a sealing member 451 surrounding the peripheries of the entrance and exit ports 437 and 325 and secured by way of a tight contact to the side walls 433 and 323, a door 452 for working cooperatively with the sealing member 451 to block an air flow through the entrance and exit ports, and a driving unit 453 for driving the door. Still further, the opening formed in the partition wall 433 is provided with a shutter unit 46 so that the opening may be closed by a door 461 and a communication may be selectively blocked by way of sealing between the first and the second loading chambers. Those shutter units 27, 45 and 46 are adapted to seal air-tightly the respective chambers when they are in the closing mode. Since those shutter units may be of known structures, explanations on their structures and operations will be omitted. It is to be appreciated that the supporting manner of the housing 22 of the mini-environment device 20 is different from the supporting manner of the loader housing 40, and accordingly a damping material for isolating the vibration may be arranged between the housing 22 and the loader housing 40 surrounding the peripheries of the entrance and exit ports in the air-tight manner in order to prevent the vibration from the floor from being transmitted to the loader housing 40 and thus the main housing 30 via the mini-environment device 20.

A wafer rack 47 is installed within the first loading chamber 41, which wafer rack holds a plurality of wafers (two wafers in this embodiment) in a horizontal state while isolating one from another in the up and down direction. The wafer rack 47 comprises support rods 472 secured to a rectangular base plate 471 at four corners respectively in upright state separately from one another, and a two-step of support sections 473 and 474 is formed in each of the support rods 472 so as to support the wafers W in the peripheral edges thereof loaded on the support sections respectively. Then, tip portions of arms of the first and the second conveying units, which will be described later, are advanced through a space between the adjacent support rods and approach the wafers so as to grip the wafers with the arms.

The loading chambers 41 and 42 are specifically designed such that the atmosphere in the chambers can be controlled to high level of vacuum condition (a vacuum level of $10^{-5}$ to $10^{-6}$ Pa) by a vacuum pumping unit (not shown) of known structure including a vacuum pump, though not shown. In that case, the first loading chamber 41 may be controlled to be a low level of vacuum atmosphere as a low level vacuum chamber and the second loading chamber 42 may be controlled to be a high level of vacuum atmosphere as a high level vacuum chamber, so as to prevent effectively a contamination of the wafer. Employing such a structure allows the wafer, which has been contained within the loading chamber and is going to be inspected subsequently for a defect, to be fed into the working chamber without any delay. Employing such a loading chamber together with the principle of an electron beam apparatus of the multi-beam type, which will be described later, helps improve the throughput of the defect inspection and also allows the vacuum level in the surrounding of the electron source to be kept as high as possible, said electron source being required to be held in a storage condition having a high level of vacuum atmosphere.

The first and the second loading chambers 41 and 42 are connected with a vacuum pumping pipe and a vent pipe for an inert gas (e.g., dry pure nitrogen) respectively (both not shown). In this way, the conditions of an atmospheric pressure in the respective loading chambers may be accomplished by the inert gas vent (injecting the inert gas and thereby preventing other gas than the inert gas such as oxygen gas from being adsorbed on the surface). Since the unit itself for performing such an inert gas vent may have a known structure, the detailed explanation thereof will be omitted.

It is to be noted that in an inspection apparatus using an electron beam according to the present invention, if a substance such as lanthanum hexaboride (LaB$_6$), which is typically used as an electron source in an electron optical system as will be described later, is once heated to such high temperature as it emits thermal electron, it becomes important that the LaB$_6$ should be isolated from any contact with oxygen or the likes in order not to shorten its life-time, and this will be much ensured by applying the atmosphere control as described above in a stage prior to carrying the wafer into the working chamber in which the electron optical system is located.

The stage unit 50 comprises a stationary table 51 located on the bottom wall 321 of the main housing 30, a Y table 52 which moves in the Y-direction (the direction normal to page space in FIG. 17) on the stationary table, an X table 53 which moves in the X-direction (the left and right direction in FIG. 17) on the Y table, a turn table 54 capable of turning on the X table, and a holder 55 located on the turn table 54. The holder 55 holds a wafer on a wafer loading face 551 thereof while allowing the wafer to be released. The holder 55 may be of known structure so far as it can hold the wafer while allowing the wafer to be released mechanically or by way of an electrostatic chuck method. The stage unit 50 has been designed such that it uses a servo motor, an encoder and a variety of sensors (not shown) to actuate a plurality of tables as described above, and thereby it can position the wafer held by the holder on the loading face 551 with high level of accuracy in the X, Y and Z directions (Z directions designating the up and down direction in FIG. 17) with respect to the electron beam radiated from the electron optical system as well as the rotational direction (θ direction) around an axis line perpendicular to the support face of the wafer. It is to be appreciated that the positioning in the Z direction may be accomplished, for example, by a design allowing a fine tuning of the position of the loading face on the holder in the Z direction. In that case, a reference position of the loading face is detected by a position measuring unit by means of a laser having an minute diameter (a laser-interferometer taking advantage of an interferometer) and the position may be controlled by using a feedback circuit though not shown, and additionally or alternatively the notch or the ori-fla of the wafer is measured so as to detect a planer location and a rotational location of the wafer with respect to the electron beam and the turn table may be rotated by, for example, a stepping motor controllable by a minute angle, thereby controlling the position of the wafer. In order to prevent the generation of dust within the working chamber as much as possible, servo motors 521, 531 and encoders 522, 532 for the stage unit are disposed in the outside of the main housing 30. It is to be noted that since the stage unit 50 may be of known structure, for example, the one which has been typically used in the stepper, a detailed description on the structure and operation thereof will be omitted. Further, above-described laser-interferometer may be of known structure, a detailed description on the structure and operation thereof will be omitted also.

A signal obtained by entering in advance the rotational position and/or the X and the Y positions of the wafer with respect to the electron beam to a signal detecting system or an image processing system, which will be described later, may also be standardized. Further, a wafer chucking mechanism arranged in this holder has been designed such that a voltage for chucking the wafer may be applied to an electrode of an electrostatic chuck so as to press and thus position the wafer at three points on the outer periphery of the wafer (preferably, equally spaced in the circumferential direction). The wafer chucking mechanism comprises two stationary positioning pins and one cramp pin of compressive type. The cramp pin is adapted to accomplish an automatic chucking and an automatic releasing and constitutes a conductive part for the voltage application.

It is to be appreciated that although in this embodiment, a table traveling in the left and right direction has been designated as the X table and a table traveling in the up and down direction as the Y table in FIG. 18, the table traveling in the left and right direction may be designated as the Y table and the table traveling in the up and down direction as the X table in FIG. 18.

The loader 60 comprises a first conveying unit 61 of robot type disposed within the housing 22 of the mini-environment device 20 and a second conveying unit 63 of robot type disposed within the second loading chamber 42.

The first conveying unit 61 has a multi-joint arm 612 capable of rotating around an axis line $O_1$—$O_1$ with respect to a driving section 611. Although any multi-joint arm in an arbitrary structure may be used, this embodiment has employed the arm composed of three parts rotatably coupled to each other. One of those parts forming the arm 612 of the first conveying unit 61, which is a first part closest to the driving section 611, is attached to a shaft 613 capable of being rotationally driven by a driving mechanism (not shown) having a known structure arranged within the driving section 611. The arm 612 can be rotated around the axis line $O_1$—$O_1$ by the shaft 613, and also is made stretchable as a whole unit in a radial direction with respect to the axis line $O_1$—$O_1$ by way of relative rotation of the parts to one another. A tip portion of a third part farthest to the shaft 613 of the arm 612 is provided with a gripping unit 616 by means of a mechanical chuck, an electrostatic chuck or the like having a known structure for gripping the wafer. The driving section 611 is movable in the up and down direction by an elevating mechanism 615 of known structure.

In this first conveying unit 61, the arm 612 stretches toward one of two cassettes "c" held by the cassettes holder, that is, along a direction of either of M1 or M2, and loads one of the wafers accommodated in the cassette c onto the arm or grips the wafer with the chuck (not shown) attached in the tip portion of the arm so as to take out the wafer. After that, the arm is retracted (into a state as shown in FIG. 18) and turns and stops a position where the arm can stretch toward the direction of M3 of the pre-aligner 25. Then, the arm stretches again and loads the wafer having held by the arm, on the pre-aligner 25. On the other hand, after the arm having received the wafer from the pre-aligner 25 in the procedure reversely to the aforementioned, the arm turns again and stops at a position where the arm can stretch toward the second loading chamber 41 (in the direction of M4) and passes the wafer to a wafer receiver 47 within the second loading chamber 41. It is to be noted that when the wafer is mechanically gripped, the wafer should be gripped in a rim portion (in a range of about 5 mm from the peripheral edge). This is because the wafer includes devices (circuit wirings) formed in the entire region thereof excluding the rim portion and gripping of the wafer in this device region may cause a break or defect in the device.

Since the second conveying unit 63 has a structure which is basically same as that for the first conveying unit 61 but they are different only in the point that the second conveying unit 63 carries the wafer between the wafer rack 47 and a loading face of the stage unit, a detailed description will be omitted.

In this loader 60, the first and the second conveying units 61 and 63 convey the wafer from the cassette held by the cassette holder onto the stage unit 50 disposed within the working chamber 31 or vice versa while holding the wafer almost horizontally, and accordingly the occasions that the arms of the conveying units move upward or downward are only limited to the time of taking/inserting the wafer out of/into the cassette, the time of loading/taking the wafer onto/out of the wafer rack, and the time of loading/taking the wafer onto/out of the stage unit. Therefore, the conveying of a large wafer having a diameter of, for example, 30 cm may be performed smoothly.

Now, how to convey the wafer from the cassette c held by the cassette holder to the stage unit 50 disposed within the working chamber 31 will be described according to the sequence.

As discussed above, if the cassette is loaded manually, a cassette holder in a structure suitable for the manual operation may be selected and if the cassette is automatically set, a cassette holder in a structure suitable for the automatic operation may be selected. In this embodiment, when the cassette c is set on the elevating table 11 of the cassette holder 10, the elevating table 11 is lowered by the elevation mechanism 12 so as for the cassette c to be in alignment with the entrance and exit port 225.

When the cassette is in alignment with the entrance and exit port 225, a cover (not shown) arranged in the cassette is opened, while the cylindrical cover is arranged between the cassette c and the entrance and exit port 225 of the mini-environment device so as to shield the interior of the cassette and the inner space of the mini-environment device from the outside. Since this structure has been well known in the art, a detailed description on its structure and operation will be omitted. It is to be appreciated that if the shutter unit for opening and closing the entrance and exit port 225 is arranged on the side of the mini-environment device 20, the shutter unit is actuated to open the entrance and exit port 225.

On the other hand, the arm 612 of the first conveying unit 61 has stopped in the position toward either of the direction M1 or M2 (toward the direction of M1 in this description), and as the entrance and exit port 225 is opened, the arm stretches and receives in its tip portion one of the wafers accommodated in the cassette. It is to be noted that the adjustment of the relative positions of the arm and the wafer to be taken out from the cassette in the up and down direction has been performed by the upward and downward movement of the driving section 611 and the arm 612 of the first conveying unit 61 in this embodiment, but the adjustment may be accomplished by the upward and downward movement of the elevating table of the cassette holder or otherwise by the combination of both.

As the arm 612 has received the wafer, the arm is retracted and the shutter unit is actuated to close the entrance and exit port (if the shutter unit has been provided), and then the arm 612 rotates around the axis line $O_1$—$O_1$ and positions itself to be stretchable toward the direction M3. Next, the arm stretches and loads the wafer having loaded on the tip portion of the arm or having gripped by the chuck onto the pre-aligner 25, and the pre-aligner 25 positions the wafer in an orientation in the rotational direction (the orientation of the wafer around the central axis line perpendicular to the plane of the wafer) within a determined range. After the positioning having been finished, the conveying unit 61 receives the wafer from the pre-aligner 25 into the tip portion thereof and then retracts the arm so as to be ready for stretching out the arm toward the direction M4. Then, the door 272 of the shutter unit 27 moves to open the entrance and exit ports 226 and 436, and the arm 612 stretches to load the wafer onto an upper rack or a lower rack of the wafer rack 47 in the first loading chamber 41. As described above, before the shutter unit 27 opens the door and the wafer is passed to the wafer rack 47, the opening 435 formed in the partition wall 434 has been closed in the air tight condition by the door 461 of the shutter unit 46.

In the conveying process of the wafer by the first conveying unit as described above, a clean air flows in a laminar flow (as a down flow) from the gas supply unit 231 arranged in the upper portion of the housing of the mini-environment device, which prevents dust from depositing on the wafer in the course of conveying. A portion of the air in the surrounding of the conveying unit (about 20% of the air supplied from the supply unit and mainly the dirty air in this embodiment) is sucked from the suction duct 241 of the pumping unit 24 and evacuated to the outside of the housing. The rest of the air is recovered via the recovery duct 232 arranged in the bottom portion of the housing and again returned to the air supply unit 231.

When the wafer is loaded into the wafer rack 47 within the first loading chamber 41 of the loader housing 40 by the first conveying unit 61, the shutter unit 27 closes the door to seal up the loading chamber 41. Then, after the first loading chamber having been full up with the inert gas and the air having been cleaned out, said inert gas is also exhausted, and then the loading chamber 41 is brought into the vacuum atmosphere. The level of this vacuum atmosphere in the first loading chamber may be set to low. As a certain level of the vacuum is obtained in the loading chamber 41, the shutter unit 46 is actuated to open the entrance and exit port 434 which has been closed with the door 461, and an arm 632 of the second conveying unit 63 stretches and receives one wafer from the wafer receiver 47 with the gripping unit in the tip portion thereof (by loading the wafer on the tip portion thereof or gripping the wafer by the chuck attached to the tip portion thereof). As the wafer has been received, the arm is retracted, and the shutter unit 46 is actuated again to close the entrance and exit port 435 with the door 461. It is to be noted that before the shutter unit 46 opens, the arm 632 has been already brought into a position ready for stretching toward the direction N1 for the wafer rack 47. Further, as described above, before the shutter unit 46 opens, the entrance and exit ports 437, 325 have been closed with the door 452 of the shutter unit 45 so as to block the communication between the interior of the second loading chamber 42 and the interior of the working chamber 31 in the air tight condition, and the second loading chamber 42 has been evacuated to vacuum.

As the shutter unit 46 closes the entrance and exit port 435, the second loading chamber is evacuated to vacuum again, so that a level of the vacuum in the second loading chamber may be higher than that in the first loading chamber. During this operation, the arm of the second conveying unit 61 is rotated to a position where it can stretch toward the stage unit 50 in the working chamber 31. On the other hand, in the stage unit within the working chamber 31, the Y table 52 moves upward in FIG. 18 to a position where the centerline $X_0$—$X_0$ of the X table 53 is approximately in alignment with the X-axis line $X_1$—$X_1$ crossing a rotational axis line $O_2$—$O_2$ of the second conveying unit 63, and the X table 53 moves to a position closest to the left most location in FIG. 18, and resultantly the stage unit stands by in this condition. As the second loading chamber is evacuated to vacuum at approximately same level as the vacuum environment in the working chamber, the door 452 of the shutter unit 45 moves thus to open the entrance and exit ports 437, 325, and the arm stretches with the tip portion holding the wafer approaching the stage unit within the working chamber 31. Then, it loads the wafer on the loading face 551 of the stage unit 50. As the loading of the wafer has been completed, the arm is retracted and the shutter unit 45 closes the entrance and exit ports 437, 325.

The above explanation has been made to the operations to be taken until the wafer within the cassette c is finally placed on the stage unit, and when the wafer which has been loaded on the stage unit and finished with the processing is to be returned back into the cassette c, the same operation but in the reverse sequence with respect to the above description would be conducted. Further, since a plurality of wafers is loaded in the wafer rack 47, while the second conveying unit conveying a wafer between the wafer rack and the stage unit, the first conveying unit can convey another wafer between the cassette and the wafer rack, thereby allowing the inspection process to be performed efficiently.

In specific, if there are a wafer A which has been already processed and a wafer B which has not yet processed in the wafer rack 47 of the second conveying unit, the operation may be conducted according to the following procedure.

(1) At first, the wafer B which has not yet processed is transferred to the stage unit 50 and the processing is started.

(2) During this processing, the wafer A which has been processed is transferred from the stage unit 50 to the wafer rack 4 by the arm, and the wafer C which has not yet processed is withdrawn from the wafer rack similarly by the arm and, after having been positioned by the pre-aligner, is moved to the wafer rack 47 of the loading chamber 41. This procedure allows the wafer A, which has been processed, to be replaced by the wafer C, which has not yet processed, in the wafer rack 47 during the wafer B being processed.

Further, a plurality of stage unit 50 may be arranged in parallel in dependence on the application of the apparatus for performing an inspection and evaluation, and in that case a plurality of wafers may be processed equally by transferring the wafers from one wafer racks 47 to respective units.

Figure 22:
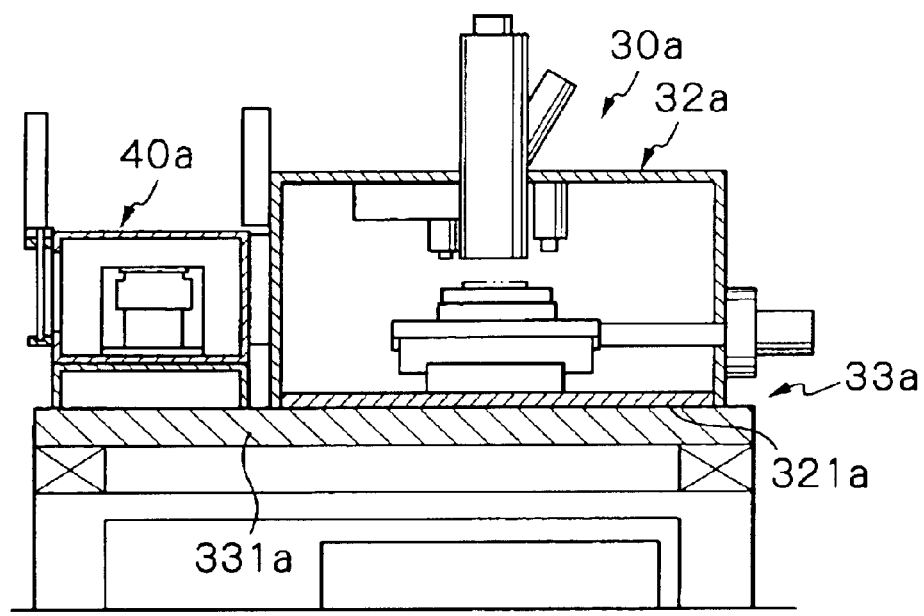
FIG. 22 shows an alternative method for supporting a main housing.
Figure 23:
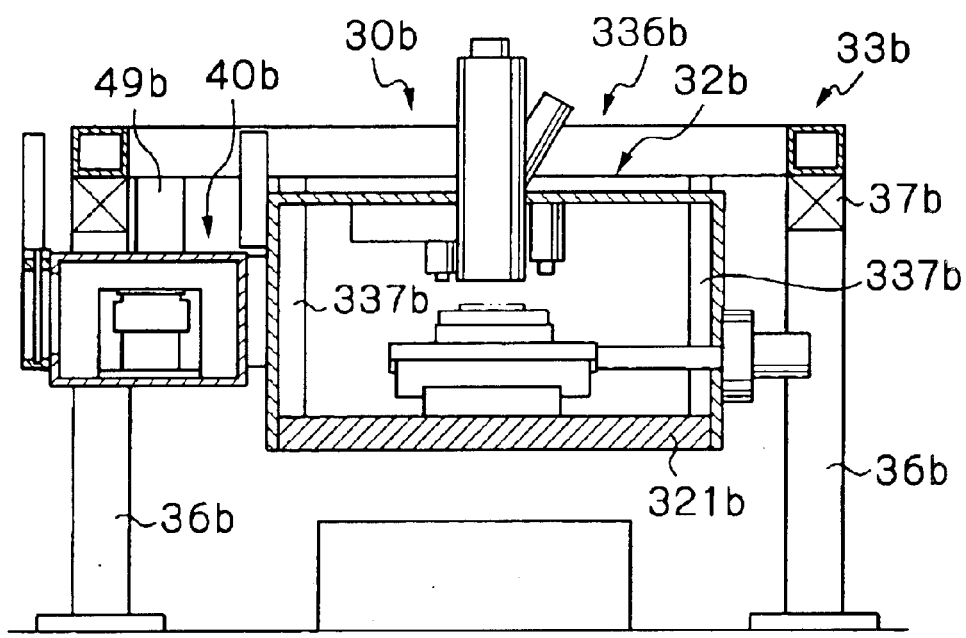
FIG. 23 shows further alternative method for supporting the main housing.

FIGS. 22 and 23 show alternative embodiment of supporting systems of the main housing. In the alternative embodiment shown in FIG. 22, a housing supporting unit 33a is made of thick rectangular steel plate 331a, and a housing main body 32a is mounted on that steel plate. Accordingly a bottom wall 321a of the housing main body 32a has much thinner structure as compared to the bottom wall in the preceding embodiment. In another alternative embodiment shown in FIG. 23, a housing main body 32b and a loader housing 40b are suspended and thus supported by a frame structure 336b of a housing supporting unit 33b. Lower end portions of a plurality of longitudinal frames 337b fixedly attached to the frame structure 336b are secured to the bottom wall 321b of the housing main body 32b in four corners thereof, and this design allows the bottom wall to support side walls and a top wall. A vibration isolating unit 37b is arranged between the frame structure 336b and a table frame 36b. Further, a loader housing 40 is also suspended by a suspender member 49b secured to the frame structure 336. In the housing main body 32b of this alternative embodiment shown in FIG. 23, since the method of suspending type has been employed, the low center of gravity may be accomplished for the whole unit consisting of the main housing and those variety of devices arranged inside thereof. According to the present supporting system of the main housing and the loader housing including the alternative systems described above, the system is designed so as to prevent the vibration from the floor from being transmitted to the main housing and the loader housing.

In still another alternative embodiment, through not shown, only the housing main body of the main housing may be supported by the support unit from under side but the loader housing may be located on the floor in the same method used for the adjacent mini-environment device. Further, yet another alternative embodiment, though not shown, only the housing main body of the main housing may be supported by the frame structure by way of the suspending method but the loader housing may be located on the floor in the same method used for the adjacent mini-environment device.

Figure 24:
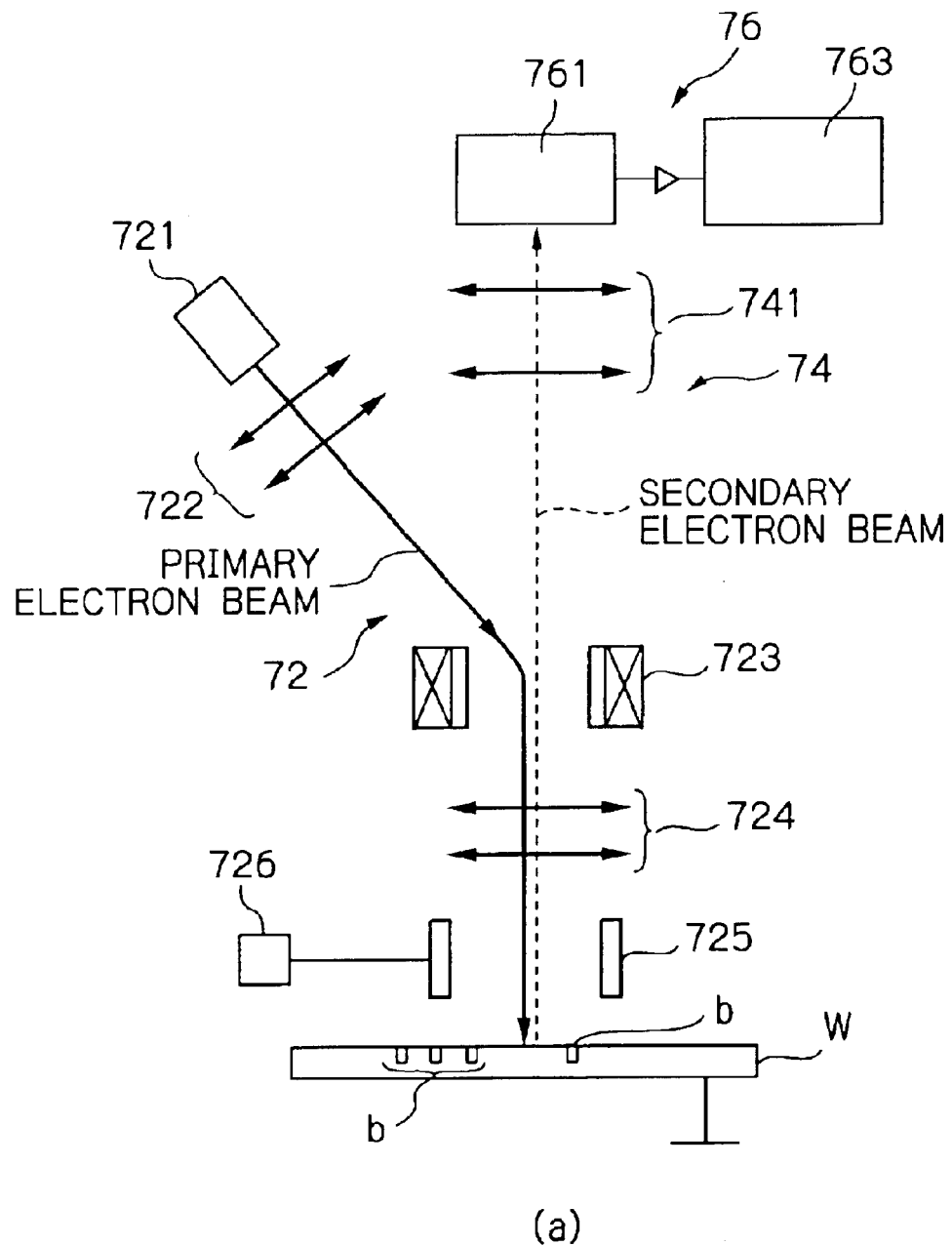
FIG. 24 is a schematic diagram illustrating a general configuration of an electron optical unit of the inspection apparatus of FIG. 17.

The electron optical unit 70 may use an electron beam apparatus of the image projection type shown in FIG. 1. In an alternative embodiment, another electron beam apparatus of the image projection type shown in FIG. 24 may be used. The electron beam apparatus of the image projection type as shown schematically in FIG. 24 comprises an electron optical column 71 secured to a housing main body 32, and the electron optical column 71 contains inside thereof an electron optical system consisting of a primary electron optical system (hereafter referred to as a primary optical system for simplicity) 72 and a secondary electron optical system (hereafter referred to as a secondary optical system for simplicity) 74, and a detecting system 76. The primary optical system 72 is such an optical system that radiates an electron beam onto a top surface of a wafer W to be inspected, and comprises an electron gun 721 for emitting an electron beam, a lens system 727 consisting of an electrostatic lens for converging the primary electron beam emitted from the electron gun 721, an E×B separator 723, and an objective lens system 724, each being arranged sequentially in this order placing the electron gun 721 in the topmost level as shown in FIG. 24. The objective lens system 724 of this embodiment is a decelerating electric field type objective lens. In this embodiment, an optical axis of the primary electron beam emitted from the electron gun 721 is inclined with respect to an irradiation optical axis along which the primary electron beam is radiated onto the wafer to be inspected (perpendicular to the surface of the wafer). An electrode 725 is arranged between the objective lens system 724 and the wafer W to be inspected. This electrode 725 is formed to be axially symmetrical with respect to the irradiation optical axis of the primary electron beam and a voltage applied to this electrode is controlled by a power supply 726.

The secondary optical system 74 comprises a lens system 741 consisting of an electrostatic lens for passing therethrough secondary electrons separated from the primary optical system by the E×B type deflector 723. This lens system 741 functions as a magnifying lens for magnifying a secondary electron image.

The detecting system 76 comprises a detector 761 disposed in an image forming plane for the lens system 741 and an image processing section 763.

An operation of the electron optical unit 70 having a configuration described above will now be described.

The primary electron beam emitted from the electron gun 721 is converged by the lens system 722. The converged electron beam enters to the E×B type deflector 723, which deflects the beam so as to be radiated onto the surface of the wafer W at a right angle, and then by the objective lens system 724, the beam is formed into an image on the surface of the wafer W.

The secondary electrons emitted from the wafer by the irradiation of the primary electron beam are accelerated by the objective lens system 724, and the accelerated secondary electrons are entered into the E×B type deflector 723, advanced straight ahead through the E×B type deflector and guided by a lens system 741 of the secondary optical system to a detector 761. Then, the detector 761 detects the secondary electrons and sends that detection signal to the image processing section 763.

It is assumed in this embodiment that a voltage as high as 10 to 20 kV is applied to the objective lens system 724 and the wafer 27 is grounded.

Then, in the case where the wafer W included a via "b" and the voltage of −200 V was applied to the electrode 725, the resulting electric field in the electron beam irradiation plane of the wafer was observed to be within the range from 0 to −0.1 V/mm ("−" indicates that the wafer W has a higher potential). In this condition, although the defect inspection of the wafer W was conducted without any electric discharge occurring between the objective lens system 724 and the wafer W, a detection efficiency for the secondary electron was somewhat decreased. For this reason, a series of operations comprising the irradiation of the electron beam and the detection of the secondary electrons was repeated, for example, four times, and the obtained detection results were processed with the accumulative addition or averaging operation, so that a predetermined detection sensitivity was obtained.

Further, even in the case where the wafer W included no via "b" and the voltage of +350 V was applied to the electrode 725, the defect inspection of the wafer W was successfully conducted without any electric discharge occurring between the objective lens system 724 and the wafer W. In this case, since the secondary electrons were converged by the voltage applied to the electrode 725 and further converged by the objective lens system 724, the detection efficiency of the secondary electrons at the detector 761 was thus improved. Accordingly, the processing speed achieved by the apparatus in serving as a wafer defect inspection apparatus was also increased, and the inspection was performed with a higher throughput.

The pre-charge unit 81 has been installed within the working chamber 31 at a location adjacent to the electron optical column 71 of the electron optical unit 70, as shown in FIG. 17. Since the inspection apparatus of the present invention is such type of apparatus that inspects a device pattern or the like formed on a surface of a substrate or a wafer subject to an inspection by irradiating an electron beam on and scanning thereby the surface thereof, wherein data of the secondary electrons generated by the irradiation of the electron beam is used as the data of the wafer surface, there is a fear that the surface of the wafer could be charged up depending on the condition of the material of the wafer, the energy of the radiated electron and so on. Also, there is a possibility that some locations on the surface of the wafer may be charged up to a high degree and some locations on the surface of the wafer may be charged up to a low degree. Unevenness in an amount of charge-up on the surface of the wafer may lead to unevenness in the secondary image data and prohibit acquisition of accurate data. From this viewpoint, this embodiment has employed the pre-charge unit 81 having a charged particle irradiation section 811 in order to prevent this unevenness in charge-up. In order to eliminate the unevenness in charge-up, before the scanning electron beam is radiated onto a predetermined spot on the wafer to be inspected, the charged particles are radiated onto the surface from the charged particle irradiation section 811 of the pre-charge unit, thereby eliminating the unevenness in charge-up. The charge-up on the surface of the wafer may be detected by forming in advance an image of the surface of the wafer subject to the inspection and then evaluating that image, and the pre-charge unit 81 may be operated based on that detection result.

Further, with this pre-charge unit, the primary electron beam may be defocused upon irradiation.

Figure 25:
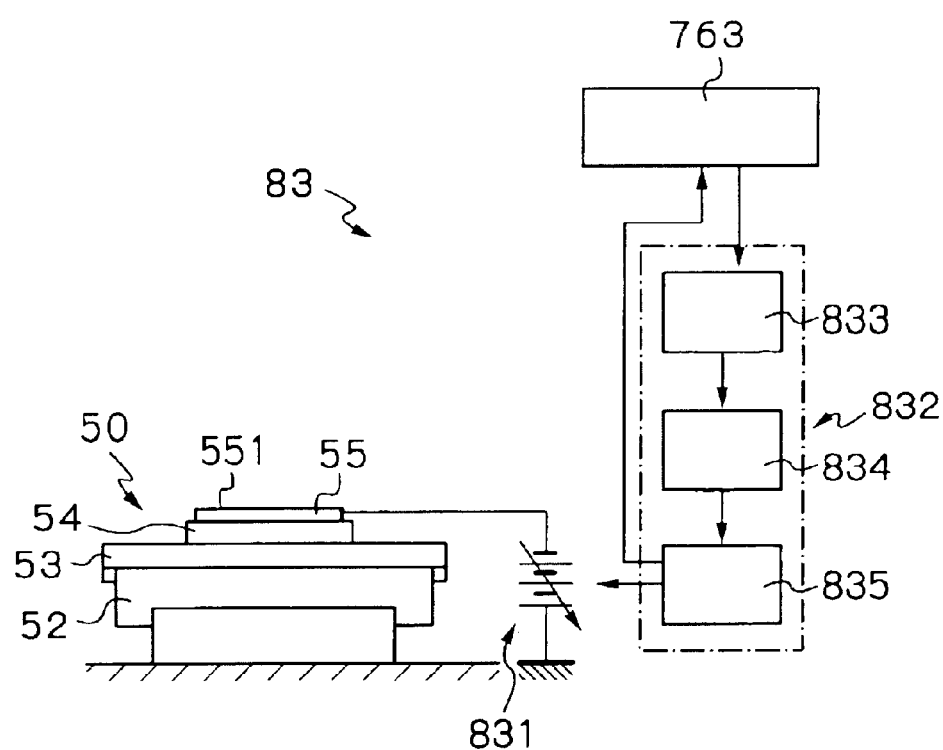
FIG. 25 shows a potential applying mechanism.

In FIG. 25, a potential applying mechanism 83 is to control the generation of the secondary electrons by applying the potential of +/− a few V to an apron of the stage, on which a wafer is loaded, based on the fact that the data for the secondary electrons emitted from the wafer (a rate of secondary electron generation) depends on the potential of the wafer. Further, this potential applying mechanism also plays a role for decelerating an energy originally pertained to the emitted electron so as to make an irradiation electron energy on the order of 100 to 500 eV onto the wafer.

The potential applying mechanism 83, as shown in FIG. 25, comprises a voltage applying unit 831 having an electric contact with a loading face 541 of the stage 50 and a charge-up investigation and voltage determination system (hereafter referred to as an investigation and determination system) 832. The investigation and determination system 832 comprises a monitor 833 having an electric contact with an image forming section 763 of the detecting system 76 of the electron optical unit 70, an operator console 834 connected to the monitor 833, and a CPU 835 connected to the operator console 834. The CPU 835 has been designed so as to supply a signal to said voltage applying unit 831.

This potential applying mechanism has been designed so as to search for a potential with which the wafer subject to inspection is hardly charged up and apply that potential to the apron of the stage.

Figure 26A:
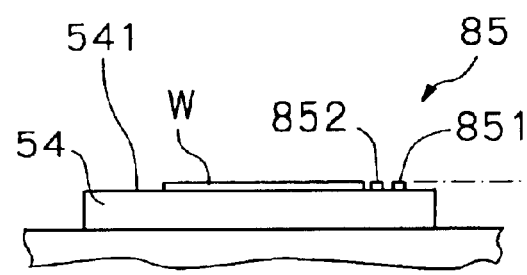
FIG. 26 is a diagram illustrating an electron beam calibration mechanism, wherein [A] is a side elevation view and [B] is a plan view.
Figure 26B:
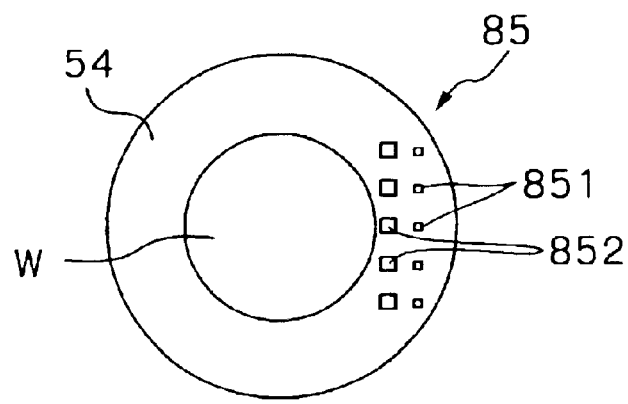

Referring to FIG. 26, an electron beam calibration mechanism 85 comprises a plurality of Faraday cups 851 and another plurality of Faraday cups 852, each for measuring a beam current and being arranged at a plurality of locations in a side portion of the wafer loading face 541 on the turn table described above. The Faraday cups 851 are designed for a thin beam (about $\phi 2$ $\mu$m) and the Faraday cups 852 are designed for a thick beam (about $\phi 30$ $\mu$m). The Faraday cups 851 for the thin beam measure a beam profile by a step-forwarding of the turn table, while the Faraday cups 852 for the thick beam measure a total current volume of the beam. Those sets of Faraday cups 851 and 852 have been arranged such that the level of the top surfaces thereof are in flash with the level of the top surface of the wafer W loaded on the loading face 541. With such arrangements, the primary electron beam emitted from the electron gun may be monitored regularly. This is because the electron gun may not always emit an electron beam of constant quantity but the emission quantity of the beam may vary over operation time.

Figure 27:
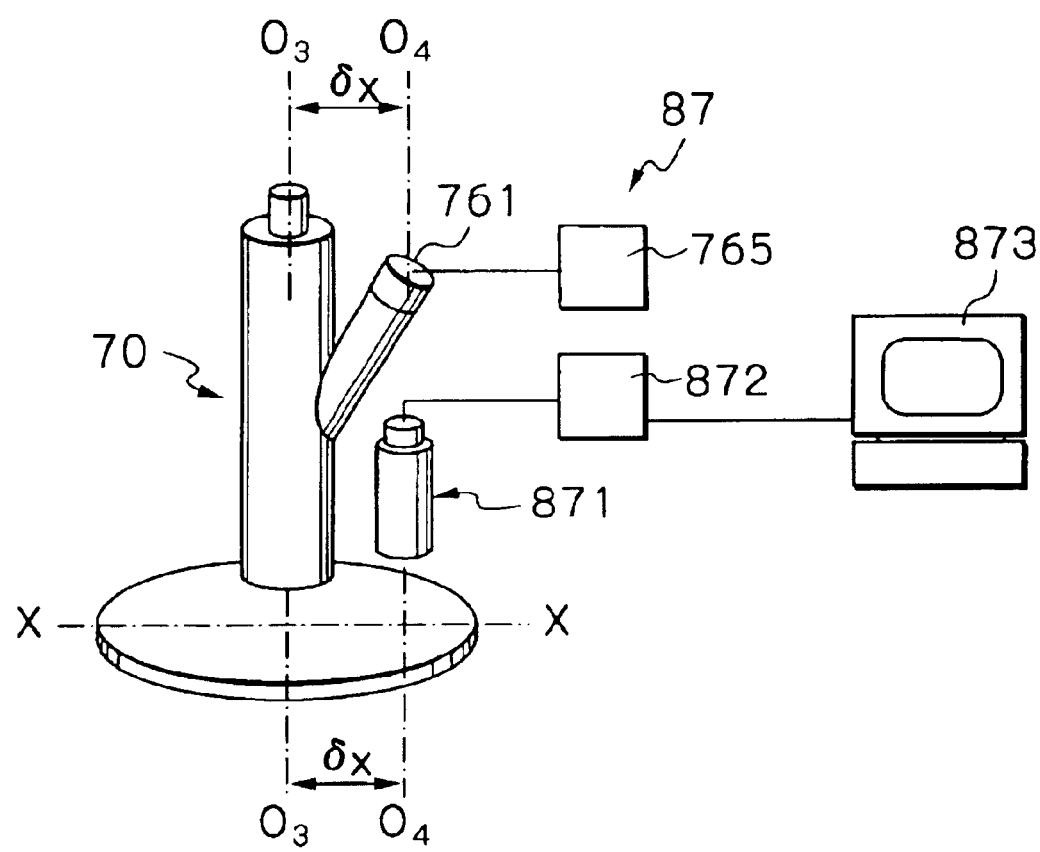
FIG. 27 is a schematic perspective view illustrating a wafer alignment control unit.

An alignment control unit 87 shown in FIG. 27 is a unit for positioning the wafer W with respect to the electron optical unit 70 by using the stage unit 50 and it allows for a control operation including a rough alignment of the wafer by way of a wide field observation using an optical microscope 871 (a measurement with a lower magnification than the electron optical system), an alignment with a higher magnification by using the electron optical system of the electron optical unit 70, a focal tuning, a setting of an inspection region, a pattern alignment and so on. The reason why the optical system is used to inspect the wafer with the lower magnification in such a manner as described above is that the automatic inspection of the pattern on the wafer requires that the alignment mark should be easily detected by the electron beam when the pattern of the wafer is observed in a narrow field by using the electron beam thus to perform the wafer alignment.

An optical microscope 871 is arranged in the housing (may be arranged so as to be movable within the housing), and a light source for actuating the optical microscope may be also arranged within the housing, though not shown. Further, the electron optical system used for the observation with the high magnification may be the electron optical system (the primary optical system 72 and the secondary optical system 74) of the electron optical unit 70, which will be used in common. The configuration thereof, if illustrated schematically, may be shown, for example, by FIG. 27. To observe a point on the wafer subject to observation with a low magnification, the X stage 53 of the stage unit 50 is moved in the X direction to bring the point on the wafer subject to the observation into a field of the optical microscope. After the visual recognition of the wafer in the wide field by using the optical microscope, the point to be observed on the wafer is displayed on a monitor 873 via a CCD 872 and the point to be observed is roughly determined. In that case, the magnification applied to the optical microscope may be changed gradually from the lower scale to the higher scale.

Then, the stage 50 is moved by a distance equivalent to an interval $\delta x$ between an optical axis of the electron optical unit 70 and an optical axis of the optical microscope 871 thus to place the point to be observed on the wafer, which has been determined in advance by the optical microscope, in a field position of the electron optical unit. In that case, since the interval $\delta x$ between the optical axis $O_3$—$O_3$ of the electron optical unit 70 and the optical axis $O_4$—$O_4$ of the optical microscope 871 has been known in advance (in this embodiment, it is assumed that the optical axes are displaced from each other only in the direction along the X-axis line, but they may be displaced in the X-axis direction and the Y-axis direction at the same time), the movement corresponding to the value of $\delta x$ can bring the point to be observed into the visually recognizable location. After the movement of the point to be observed to the visually recognizable location of the electron optical unit having been completed, the electron optical system performs the SEM image taking of the point to be observed with a high magnification, and the obtained image will be stored or displayed on the monitor 765 via the CCD 761.

In this way, after the observed point on the wafer having been displayed on the monitor by the electron optical system with the high magnification, a displacement of the wafer in the rotational direction with respect to the rotation center of the turn table 54 of the stage unit 50, i.e., the displacement $\delta\theta$ of the wafer in the rotational direction around the optical axis $O_3$—$O_3$ of the electron optical system is detected by a known method, and also the displacements of a predetermined pattern in the X-axis and the Y-axis directions is detected with respect to the electron optical unit. Then, based on the detected values and separately obtained data for an inspection mark given to the wafer or data regarding a geometry of the pattern on the wafer or the like, the operation of the stage unit 50 is controlled so as to adjust the alignment of the wafer.

According to the sixth embodiment, the following effects may be obtained.

(A) An overall configuration for the inspection apparatus of the image projection type using the electron beam can be obtained, and thereby an objective sample to the inspection can be processed with high throughput.

(B) Since the clean air flow is applied to the objective material to be inspected within the mini-environmental space so as to prevent the deposition of dust to the material and also the sensor is provided for observing a level of cleanness, the objective sample to the inspection can be inspected while monitoring the dust within the space.

(C) Since the loading chamber and the working chamber are supported as one unit by a vibration isolating unit, the supply of the objective material to be inspected into the stage unit and the inspection thereof can be carried out without any affection from the outer environment.

(D) Since the pre-charge unit has been provided, even a wafer made of insulating material may be hardly affected by the charge-up.

Seventh Embodiment

A seventh embodiment relates to an improvement of the stage. Prior to the explanation of this embodiment, a stage according to the prior art will be described.

A stage for accurately positioning a sample in a vacuum atmosphere has been used in an apparatus in which a charged particle beam such as an electron beam is radiated onto a surface of a sample such as a semiconductor wafer so as to expose the surface of the sample to a pattern of a semiconductor circuit or the like, or so as to inspect a pattern formed on the surface of the sample, and also in another apparatus in which the charged particle beam is radiated onto the sample so as to apply an ultra-precise processing thereto.

When said stage is required to be positioned highly accurately, one structure has been conventionally employed, in which the stage is supported in non-contact manner by a hydrostatic bearing. In this case, the vacuum level in a vacuum chamber is maintained by forming in an extent of the hydrostatic bearing a differential pumping mechanism for exhausting a high pressure gas so that the high pressure gas supplied from the hydrostatic bearing may not be directly exhausted into the vacuum chamber.

Figure 29A:
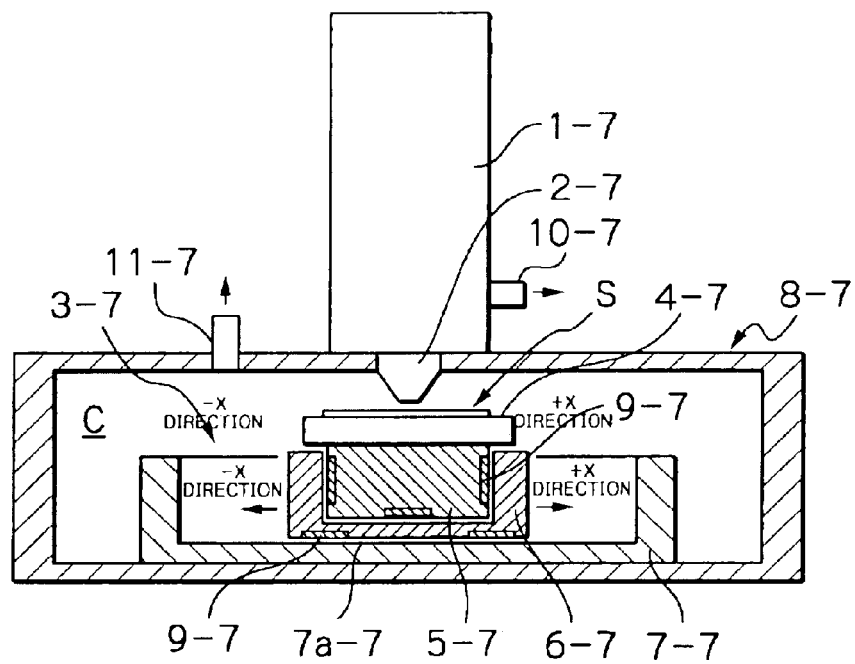
FIG. 29 is a cross sectional view illustrating a vacuum chamber and an XY stage of a charged particle beam apparatus according to the prior art in a seventh embodiment of the present invention, wherein [A] is an elevation view and [B] is a side elevation view.
Figure 29B:
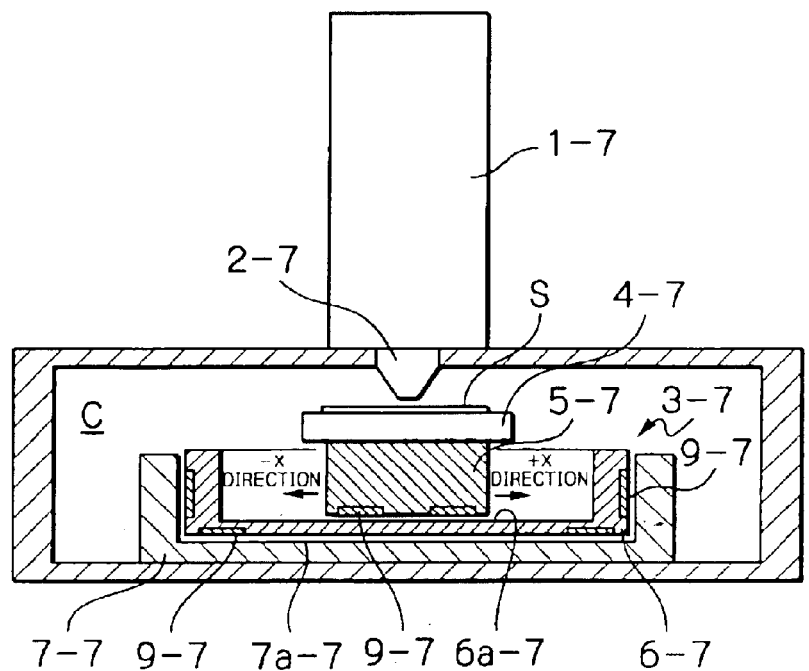

FIG. 29 shows one of the examples of such stage according to the prior art. In the configuration of FIG. 29, a tip portion of an electron optical column 1-7 or a charged particle beam irradiating section 2-7 of a charged particle beam apparatus for generating a charged particle beam and irradiating it onto a sample is attached to a housing 8-7 which defines a vacuum chamber C. An interior of the electron optical column is exhausted to vacuum through a vacuum pipe 10-7 and so as the chamber C through a vacuum pipe 11-7. Herein, the charged particle beam is radiated from the tip portion 2-7 of the electron optical column 1-7 onto a sample S such as a wafer or the like placed thereunder.

Figure 30:
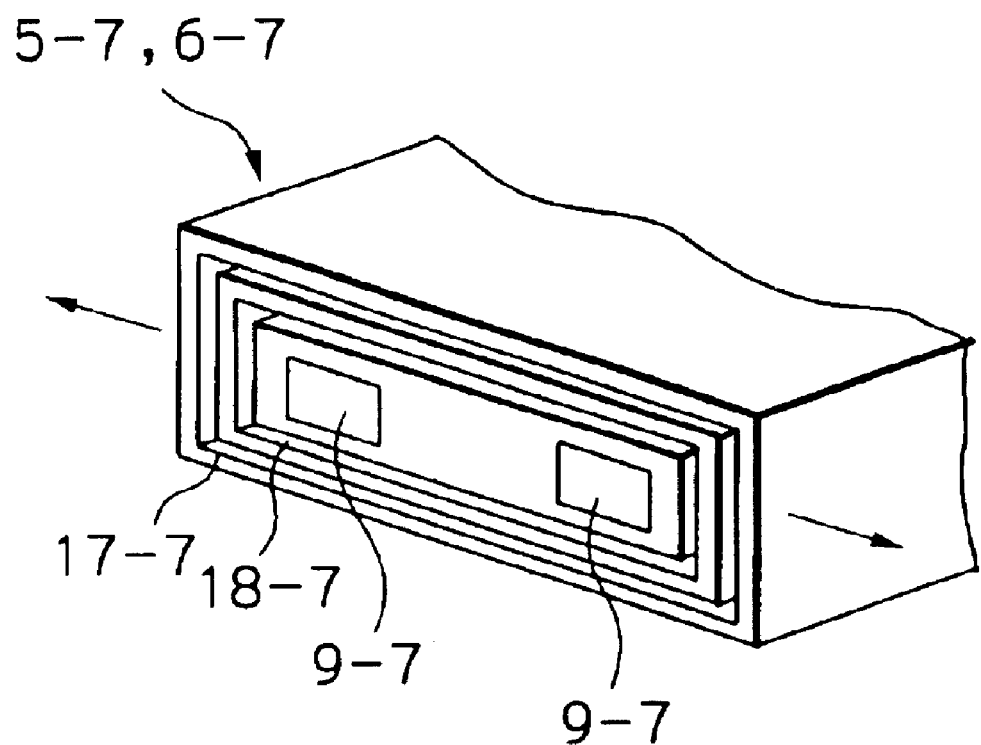
FIG. 30 is a diagram illustrating an intensity distribution of electrons emitted from an electron gun used in the XY stage of FIG. 29.

The sample S is detachably held on a sample table 4-7 by a known manner, and the sample table 4-7 is mounted on an upper face of a Y directionally movable section 5-7 of an XY stage (hereafter, referred to as a stage for simplicity) 3-7. The above-mentioned Y directionally movable section 5-7 is equipped with a plurality of hydrostatic bearings 9-7 attached on respective planes facing to respective guide planes 6a-7 of an X directionally movable section 6-7 of the stage 3-7 (on both of the right and left faces and also on a bottom face in FIG. 29[A]), so that the section 5-7 may be moved in the Y direction (lateral direction in FIG. 29[B]) while keeping a micro gap formed between the guide planes and said respective planes facing thereto owing to an operation of said hydrostatic bearings 9-7. Further, a differential pumping mechanism is provided surrounding the hydrostatic bearing so that the high-pressure gas supplied to the hydrostatic bearing might not leak into the vacuum chamber C. This configuration is shown in FIG. 30. Doubled grooves 18-7 and 17-7 are formed surrounding the hydrostatic bearings 9-7, and these grooves are regularly exhausted to vacuum through a vacuum pipe by a vacuum pump, though not shown. Owing to such structure, the Y directionally movable section 5-7 is allowed to move freely in the Y direction in the vacuum atmosphere as supported in non-contact manner. Those doubled grooves 18-7 and 17-7 are formed in a plane of the movable section 5-7 on which the hydrostatic bearing 9-7 is arranged, so as to circumscribe said hydrostatic bearing. It is to be noticed that the structure of the hydrostatic bearing may be any conventional one and its detailed description will be omitted.

The X directionally movable section 6-7 on which said Y directionally movable section 5-7 is mounted is formed to be concave in shape with the top face opened, as obviously seen from FIG. 29, and said X directionally movable section 6-7 is also provided with completely similar hydrostatic bearings and grooves, so that the section 6-7 may be supported in the non-contact manner with respect to the stage table 7-7 so as to be movable freely in the X direction.

Combining said Y directionally movable section 5-7 with the X directionally movable section 6-7 allows the sample S to be moved to a desired position in the horizontal direction relative to the tip portion of the electron optical column or the charged particle beam irradiating section 2-7, so that the charged particle beam can be radiated to a desired location of the sample.

With the stage including a combination of the hydrostatic bearing and the differential pumping mechanism as described above, the guide plane 6a-7 or 7a-7 facing to the hydrostatic bearing 9-7 makes a reciprocating motion between a high-pressure atmosphere in the hydrostatic bearing portion and a vacuum environment within the chamber while the stage moves. During this reciprocating motion, such a gas supply cycle is repeated in which while the guide plane being exposed to the high-pressure atmosphere, the gas is adsorbed onto the guide plane, and upon being exposed to the vacuum environment, the adsorbed gas is desorbed into the environment. Because of this gas supply cycle, every time when the stage moves, there has occurred such an event that the vacuum level in the chamber C is degraded, which has caused such problems that the exposure, inspection, or processing with the charged particle beam described above could not be carried out stably, and the sample might be contaminated.

Now, referring to the attached drawings, an embodiment of an electron beam apparatus according to the seventh embodiment of the present invention, which has been made in order to solve the above problems, will be described. It is to be noted that the same reference numerals are used to designate the same components in common to both of the embodiment according to the prior art shown in FIG. 29 and a plurality of embodiments of the present invention.

Figure 31A:
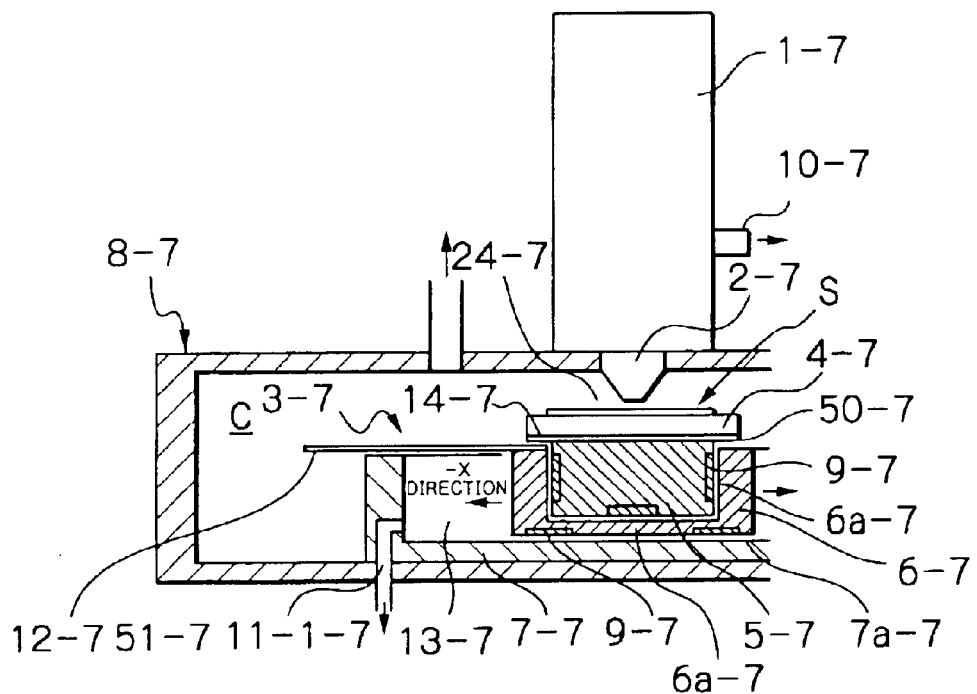
FIG. 31 is a cross sectional view illustrating a vacuum chamber and an XY stage of an example of a charged particle beam apparatus according to the seventh embodiment of the present invention, wherein [A] is an elevation view and [B] is a side elevation view.
Figure 31B:
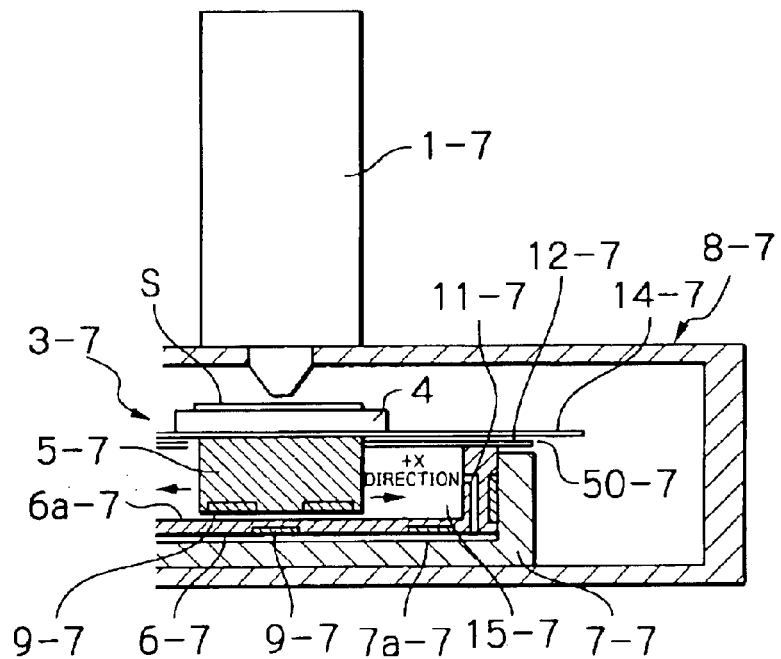

FIG. 31 shows a first mode for carrying out the seventh embodiment.

A division plate 14-7 is attached onto an upper face of the Y directionally movable section 5-7 of the stage 3, wherein said division plate 14-7- overhangs to a great degree approximately horizontally in the +Y direction and the −Y direction (the lateral direction in FIG. 31[B]), so that between an upper face of the X directionally movable section 6-7 and the division plate 14-7 may be always provided a narrow gap 50-7 with small conductance therebetween. Also, a similar division plate 12-7 is attached onto the upper face of the X directionally movable section 6-7 so as to overhang in the +/−X direction (the lateral direction in FIG. 31[A]), so that a narrow gap 51-7 may be constantly formed between an upper face of a stage table 7-7 and said division plate 12-7. The stage table 7-7 is fixedly secured onto a bottom wall within a housing 87 with a known method.

In this way, since the narrow gap 50-7 and 51-7 are constantly formed wherever the sample table 4-7 may move to, and the gaps 50-7 and 51-7 can prevent the movement of a discharged gas even if a gas is discharged or leaked along the guide plane 6a-7 or 7a-7 upon movement of the movable sections 5-7 or 6-7, a pressure increase can be regulated to significantly low level in a space 24-7 adjacent to the sample to which the charged particle beam is radiated.

Since in a side face and an under face of the movable section 3-7 and also in an under face of the movable section 6-7 of the stage, there are provided grooves for differential pumping formed surrounding hydrostatic bearings 9-7, as shown in FIG. 30, and accordingly spaces nearby there grooves are exhausted to vacuum through those grooves, therefore in a case where narrow gaps 50-7 and 51-7 have been formed, the discharged gas from the guiding planes is mainly evacuated by those differential pumping sections. Owing to this, the pressure in those spaces 13-7 and 15-7 within the stage are kept to be higher level than the pressure within a chamber C. Accordingly, if there are more portions provided for vacuum pumping the spaces 13-7 and 15-7 in addition to the differential pumping grooves 17-7 and 18-7, the pressure within the spaces 13-7 and 15-7 can be decreased, and the pressure rise of the space 24-7 in the vicinity of the sample can be controlled to be further low. For this purpose, vacuum pumping channels 11-1-7 and 11-2-7 are provided. The vacuum pumping channel 11-1-7 extends through the stage table 7-7 and the housing 8-7 to communicate with the outside of the housing 8. On the other hand, the pumping channel 11-2-7 is formed in the X directionally movable section 6-7 and opened in an under face thereof.

It is to be noted that though arranging the division plates 12-7 and 14-7 might cause a problem requiring the chamber C to be extended so as not to interfere with the division plates, this can be improved by employing those division plates of stretchable material or structure. There may be suggested one embodiment in this regard, which employs the division plates made of rubber or in a form of bellows, and the ends portions thereof in the direction of movement are fixedly secured respectively, so that each end of the division plate 14-7 is secured to the X directionally movable section 6-7 and that of the division plate 12-7 to the inner wall of the housing 8-7.

Figure 32:
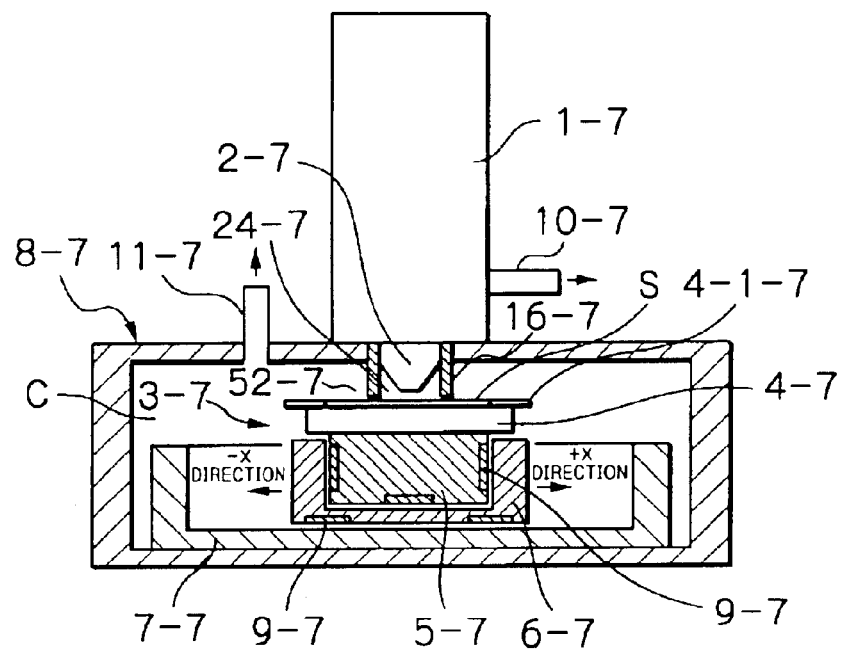
FIG. 32 is a cross sectional view illustrating a vacuum chamber and an XY stage of an alternative example of a charged particle beam apparatus according to the seventh embodiment of the present invention.

FIG. 32 shows a second mode for carrying out this embodiment.

In this embodiment, a cylindrical divider 16-7 is disposed surrounding the tip portion of the electron optical column or the charged particle beam irradiating section 2-7, so that a narrow gap may be produced between an upper face of a sample S and the cylindrical divider 16-7. In such configuration, even if the gas is discharged from the XY stage to increase the pressure within the chamber C, since a space 24-7 within the divider has been isolated by the divider 16-7 and exhausted with a vacuum pipe 10-7, there could be generated a pressure deference between the pressure in the chamber C and that in the space 24-7 within the divider, thus to control the pressure rise in the space 24-7 within the divider to be low. Preferably, the gap between the divider 16-7 and the sample surface should be approximately some ten $\mu$m to some mm, depending on the pressure level to be maintained within the chamber C and in the surrounding of the irradiating section 2-7. It is to be understood that the interior of the divider 16-7 is made to communicate with the vacuum pipe by the known method.

On the other hand, the charged particle beam irradiation apparatus may sometimes apply a high voltage of about some kV to the sample S, and so it is feared that any conductive materials located adjacent to the sample could cause an electric discharge. In this case, the divider 16-7 made of insulating material such as ceramic may be used in order to prevent any discharge between the sample S and the divider 16-7.

It is to be noted that a ring member 4-1-7 arranged so as to surround the sample S (a wafer) is a plate-like adjusting part fixedly attached to the sample table 4-7 and set to have the same height with the wafer so that a micro gap 52-7 may be formed throughout a full circle of the tip portion of the divider 16-7 even in a case of the charged particle beam being radiated onto an edge portion of the sample such as the wafer. Thereby, whichever location on the sample S may be irradiated by the charged particle beam, the constant micro gap 52-7 can be always formed in the tip portion of the divider 16-7 so as to maintain the pressure stable in the space 24-7 surrounding the electron optical column tip portion.

Figure 33:
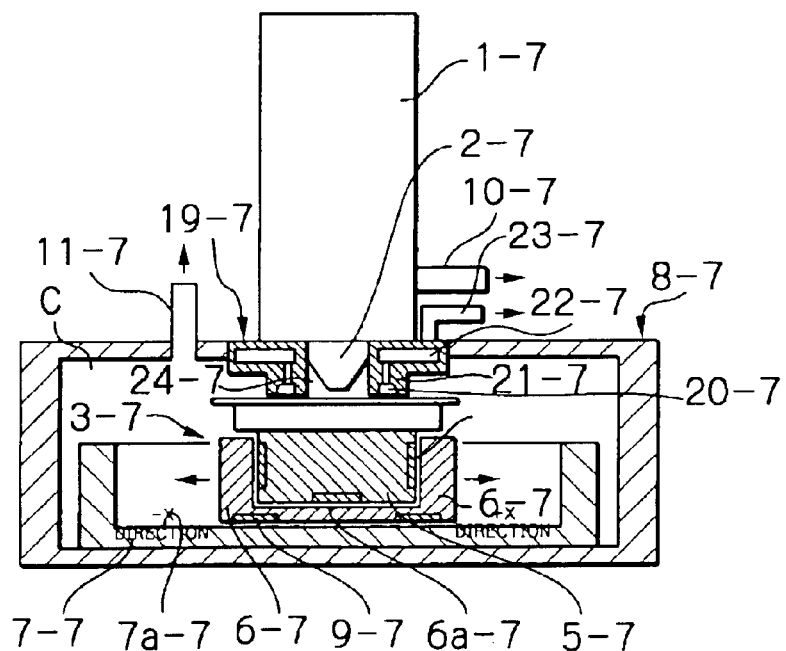
FIG. 33 is a cross sectional view illustrating a vacuum chamber and an XY stage of a still alternative example of a charged particle beam apparatus according to the seventh embodiment of the present invention.

Further, FIG. 33 shows a third mode for carrying out the seventh embodiment.

A divider 19-7 having a differential pumping structure integrated therein is arranged so as to surround the charged particle beam irradiating section 2-7 of an electron optical column 1-7. The divider 19-7 is cylindrical in shape and has a circular channel 20-7 formed inside thereof and an exhausting path 21-7 extending upwardly from said circular channel 20-7. Said exhausting path 21-7 is connected to a vacuum pipe 23-7 via an inner space 22-7. A micro space as narrow as dozens of $\mu$m to few mm is formed between the lower end of the divider 19-7 and the upper face of the sample S.

With such configuration as described above, even if the gas is discharged from the stage in association with the movement of the stage resulting in an increase of the pressure within the chamber C, and eventually is to possibly flow into the space of tip portion or the charged particle beam irradiating section 2-7, the gas is blocked to flow in by the divider 19-7, which has reduced the gap between the sample S and itself so as to make the conductance very low, thus to reduce the flow-in rate. Further, since any gas that has flown into is allowed to be exhausted through the circular channel 20-7 to the vacuum pipe 23-7, there will be almost no gas remained to flow into the space 24-7 surrounding the charged particle beam irradiating section 2-7, and accordingly the pressure of the space surrounding the charged particle beam irradiating section 2-7 can be maintained to be a desired high vacuum level.

Figure 34:
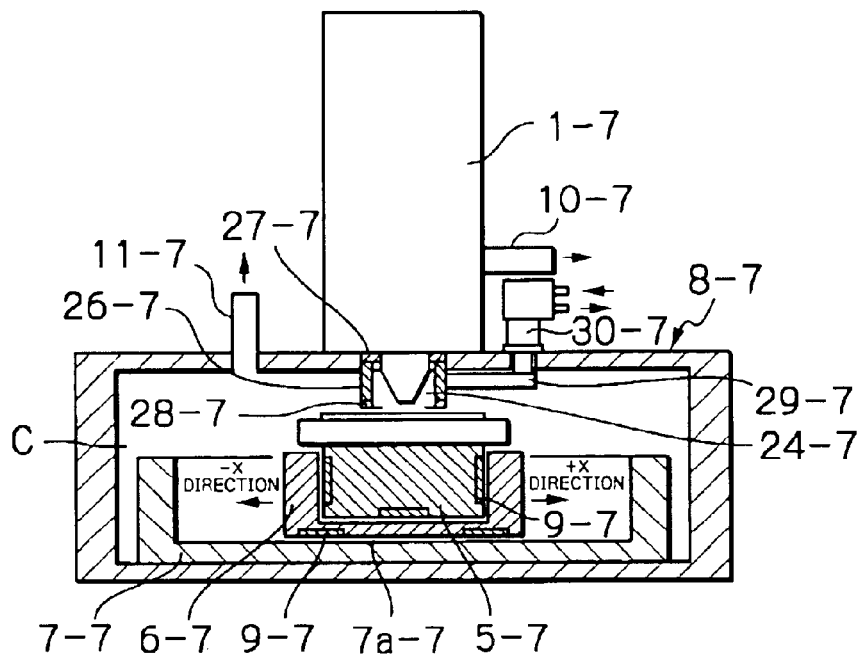
FIG. 34 is a cross sectional view illustrating a vacuum chamber and an XY stage of a still alternative example of a charged particle beam apparatus according to the seventh embodiment of the present invention.

FIG. 34 shows a fourth mode for carrying out the seventh embodiment.

A divider 26-7 is arranged so as to surround the charged particle beam irradiating section 2-7 in the chamber C and accordingly to isolate the charged particle beam irradiating section 2-7 from the chamber C. This divider 26-7 is coupled to a refrigerating machine 30-7 via a support member 29-7 made of material of high thermal conductivity such as copper or aluminum, and is kept as cool as −100° C. to −200° C. A member 27-7 is provided for blocking a thermal conduction between the cooled divider 26-7 and the electron optical column and is made of material of low thermal conductivity such as ceramic, resin or the like. Further, a member 28-7 is made of insulating material such as ceramic or the like and is attached to the lower end of the divider 26-7 so as to prevent any electric discharge between the sample S and the divider 26-7.

With such configuration as described above, any gas molecules attempting to flow into the space surrounding the charged particle beam irradiating section from the chamber C are blocked by the divider 26-7, and even if there are any molecules successfully flown into the section, they are frozen to be trapped on the surface of the divider 26-7, thus allowing the pressure in the space 24-7 surrounding the charged particle beam irradiating section to be kept low.

It is to be noted that a variety type of refrigerating machines may be used for the refrigerating machine in this embodiment, for example, a cooling machine using liquid nitrogen, a He refrigerating machine, a pulse-tube type refrigerating machine or the like.

Figure 35:
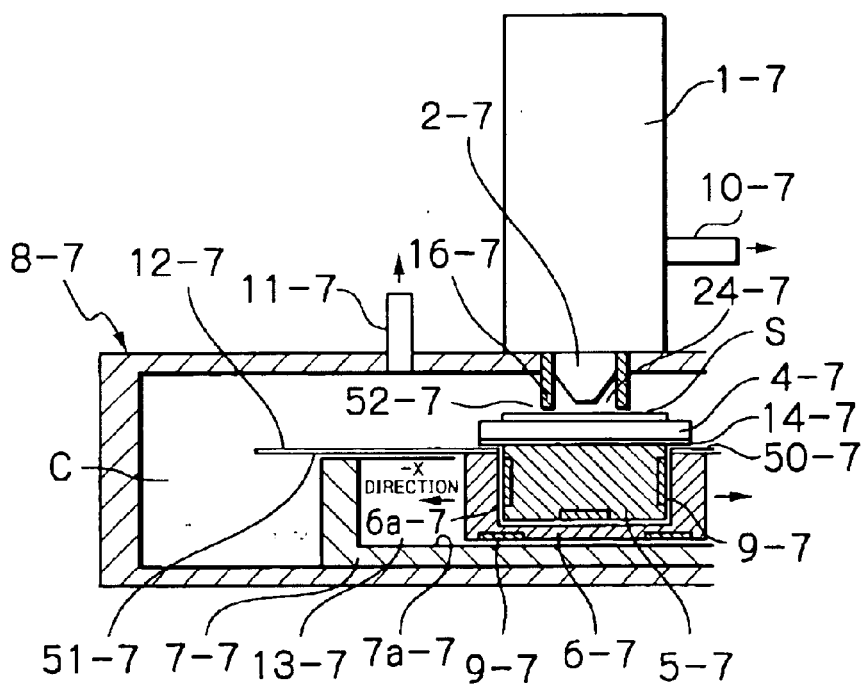
FIG. 35 is a cross sectional view illustrating a vacuum chamber and an XY stage of a still alternative example of a charged particle beam apparatus according to the seventh embodiment of the present invention.

FIG. 35 shows a fifth mode for carrying out the seventh embodiment.

The division plates 12-7 and 14-7 are respectively arranged on both of the movable sections of the stage 3-7 similarly to those illustrated in FIG. 31, and thereby, if the sample table 4-7 is moved to any locations, the space 13-7 within the stage is separated from the inner space of the chamber C by those division plates via the narrow gaps 50-7 and 51-7. Further, another divider 16-7 similar to that as illustrated in FIG. 32 is formed surrounding the charged particle beam irradiating section 2-7 so as to separate a space 24-7 accommodating the charged particle beam irradiating section 2-7 therein from the interior of the chamber C with a narrow gap 52-7 disposed therebetween. Owing to this, upon movement of the stage, even if the gas having been adsorbed on the stage is discharged into the space 13-7 to increase the pressure in this space, the pressure increase in the chamber C is kept to be low, and the pressure increase in the space 24-7 is also kept to be much lower. This allows the pressure in the space 24-7 for irradiating the charged particle beam to be maintained at low level. Alternatively, employing the divider 19-7 having the differential pumping mechanism integrated therein as explained with reference to the divider 16-7, or the divider 26-7 cooled with the refrigerating machine as shown in FIG. 33 allows the space 24-7 to be maintained stably with further lowered pressure.

The electron beam apparatus to be installed in the electron optical column 1-7 may employ any optical system and detector as desired. For example, either of the image projection type shown in FIG. 1 and the like or the scanning type shown in FIG. 41 and the like may be employable.

According to the seventh embodiment of the present invention, the following effects may be brought about.

(A) The stage unit can bring out a good performance of accurate positioning within vacuum atmosphere, and further the pressure in the space surrounding the charged particle beam irradiating location is hardly increased. That is, this allows the charged particle beam processing to be applied to the sample with high accuracy.

(B) The gas discharged or leaked from the hydrostatic bearing hardly goes though the divider and reaches to the space for the charged particle beam irradiating system. Thereby, the vacuum level in the space surrounding the charged particle beam irradiating location can be further stabilized.

(C) The desorbed gas hardly goes through to the space for the charged particle beam irradiating system, and it is facilitated to maintain the vacuum level in the space surrounding the charged particle beam irradiating region stable.

(D) The interior of the vacuum chamber is partitioned into three chambers, i.e., a charged particle beam irradiation chamber, a hydrostatic bearing chamber, and an intermediate chamber, which communicate with each other via a small conductance. Further, the vacuum pumping system is constructed to control the pressures in the respective chambers sequentially, so that the pressure in the charged particle beam irradiation chamber is the lowest, the intermediate chamber medium, and the hydrostatic bearing chamber the highest. The pressure fluctuation in the intermediate chamber can be reduced by the divider, and the pressure fluctuation in the charged particle beam irradiation chamber can be further reduced by another step of divider, so that the pressure fluctuation therein can be reduced substantially to a non-problematic level.

(E) According to the first mode for carrying out the seventh embodiment, the pressure increase upon movement of the stage can be controlled to be low.

(F) According to the second mode for carrying out the seventh embodiment, the pressure increase upon movement of the stage can be further controlled to be lower.

(G) According to the third mode for carrying out the seventh embodiment, since the defect inspection apparatus with highly accurate stage positioning performance and with a stable vacuum level in the charged particle beam irradiating region can be accomplished, the inspection apparatus with high inspection performance and without any fear of contamination of the sample can be provided.

(H) According to the fourth mode for carrying out the seventh embodiment, since an exposure apparatus with highly accurate stage positioning performance and with a stable vacuum level in the charged particle beam irradiating region can be accomplished, the exposure apparatus with high exposing accuracy and without any fear of contamination of the sample can be provided.

(I) According to the fifth mode for carrying out the seventh, manufacturing the semiconductor by using the apparatus with highly accurate stage positioning performance and with a stable vacuum level in the charged particle beam irradiating region allows to form a miniaturized micro semiconductor circuit.

Eighth Embodiment

An eighth embodiment relates to an improvement of the stage. Prior to explaining this embodiment, a stage according to the prior art will be described.

Figure 36A:
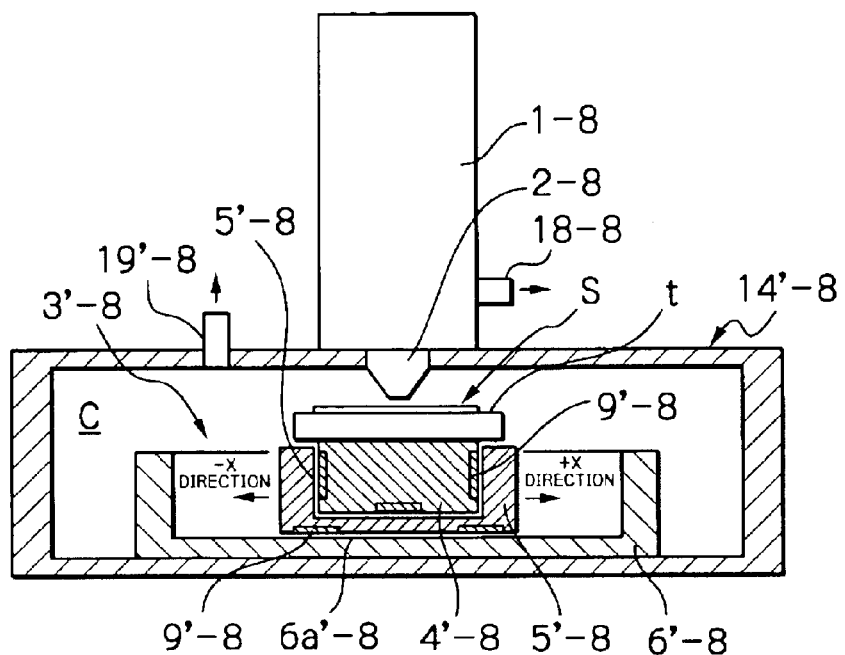
FIG. 36 is a cross sectional view illustrating a vacuum chamber and an XY stage of a conventional charged particle beam apparatus employed in an eighth embodiment of the present invention, wherein [A] is an elevation view and [B] is a side elevation view.
Figure 36B:
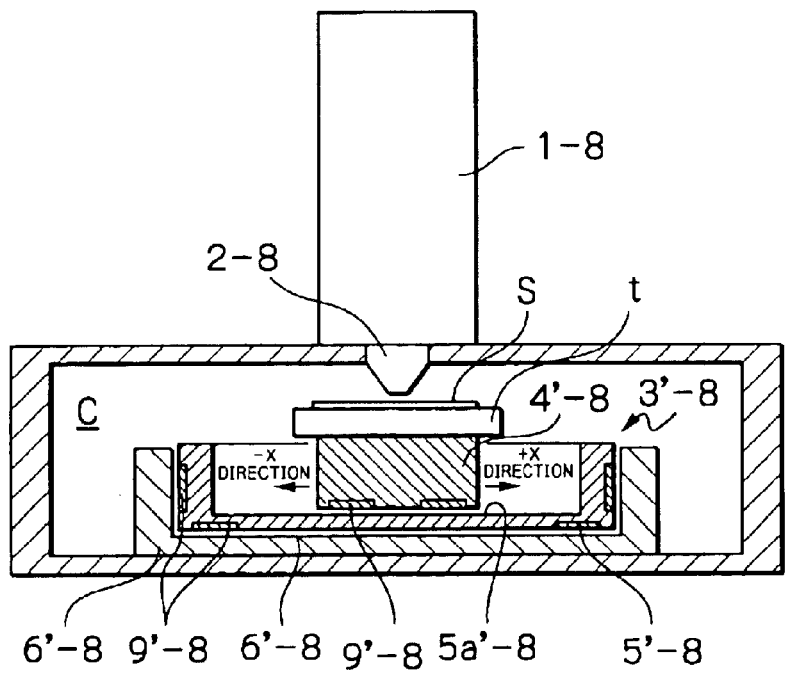

FIG. 36 shows an example of the stage according to the prior art similarly to the seventh embodiment. In the configuration of FIG. 36, a tip portion of an electron optical column 1-8 or a charged particle beam irradiating section 2-8 of a charged particle beam apparatus for generating a charged particle beam and irradiating it onto a sample is attached to a housing 14'-8 which defines a vacuum chamber C. The interior of the electron optical column is exhausted to vacuum through a vacuum pipe 18-8 and so as the chamber C through a vacuum pipe 19'-8. Herein, the charged particle beam is radiated from the tip portion 2-8 of the electron optical column 1-8 onto a sample S such as a wafer or the like placed thereunder.

Figure 37:
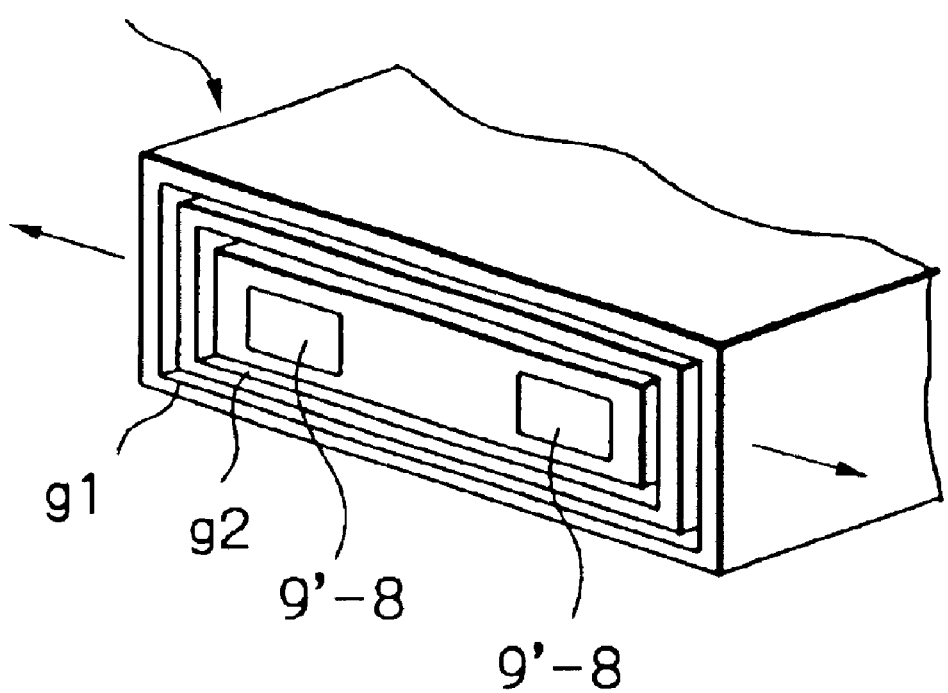
FIG. 37 is a perspective view illustrating a differential pumping unit used in the XY stage of FIG. 36.

The sample S is detachably held on a sample table "t" in a known manner, and the sample table t is mounted on an upper face of a Y directionally movable section 4'-8 of an XY stage (hereafter, referred to as a stage for simplicity) 3'-8. The above-mentioned Y directionally movable section 4'-8 is equipped with a plurality of hydrostatic bearings 9'-8 attached on respective planes facing to respective guide planes 5a'-8 of an X directionally movable section 5'-8 of the stage 3-8 (on both of the right and left faces and also on a bottom face in FIG. 36[A]), so that the section 4'-8 may be moved in the Y direction (lateral direction in FIG. 36[B]) while keeping a micro gap formed between the guide planes and said respective planes facing thereto owing to an operation of said hydrostatic bearings 9'-8. Further, a differential pumping mechanism is provided surrounding the hydrostatic bearing so that a high-pressure gas supplied to the hydrostatic bearing might not leak into the vacuum chamber C. This is shown in FIG. 37. Doubled grooves g1 and g2 are formed surrounding the hydrostatic bearings 9'-8, and these grooves are regularly exhausted to vacuum through a vacuum pipe by a vacuum pump, though not shown. Owing to such structure, the Y directionally movable section 4'-8 is allowed to move freely in the Y direction in the vacuum atmosphere as supported in the non-contact manner. Those doubled grooves g1 and g2 are formed in a plane of the movable section 4'-8 on which the hydrostatic bearing 9'-8 is arranged, so as to circumscribe said hydrostatic bearing. It is to be noticed that the structure of the hydrostatic bearing may be any conventional one and its detailed description will be omitted.

The X directionally movable section 5'-8 on which said Y directionally movable section 4'-8 is mounted is formed to be concave in shape with the top face opened, as obviously seen from FIG. 36, and said X directionally movable section 5'-8 is also provided with completely similar hydrostatic bearings and grooves, so that the section 5'-8 may be supported in a non-contact manner with respect to the stage table 6'-8 so as to be movable freely in the X direction.

Combining said Y directionally movable section 4'-8 with the X directionally movable section 5'-8 allows the sample S to be moved to a desired position in the horizontal direction relative to the tip portion of the electron optical column or the charged particle beam irradiating section 2-8, so that the charged particle beam can be radiated to a desired location of the sample.

However, there have been such problems in the above-described stage including a combination of the hydrostatic bearing and the differential pumping mechanism that because of the differential pumping mechanism having been added, the structure has become more complicated and increased in size but the reliability as a stage has decreased in contrast with the increased cost as compared to a stage having a hydrostatic bearing used in the atmospheric pressure.

Now, referring to the attached drawings, a mode for implementing an electron beam apparatus according to the eighth embodiment of the present invention, which has been made to solve the above problems, will be described. It is to be noted that the same reference numerals are used to designate the same components in common to both of the embodiment according to the prior art shown in FIG. 36 and the respective modes for implementing the eighth embodiment. It is also to be appreciated that a term "vacuum" used in the content of this specification means a vacuum as referred to in this field of art.

Figure 38:
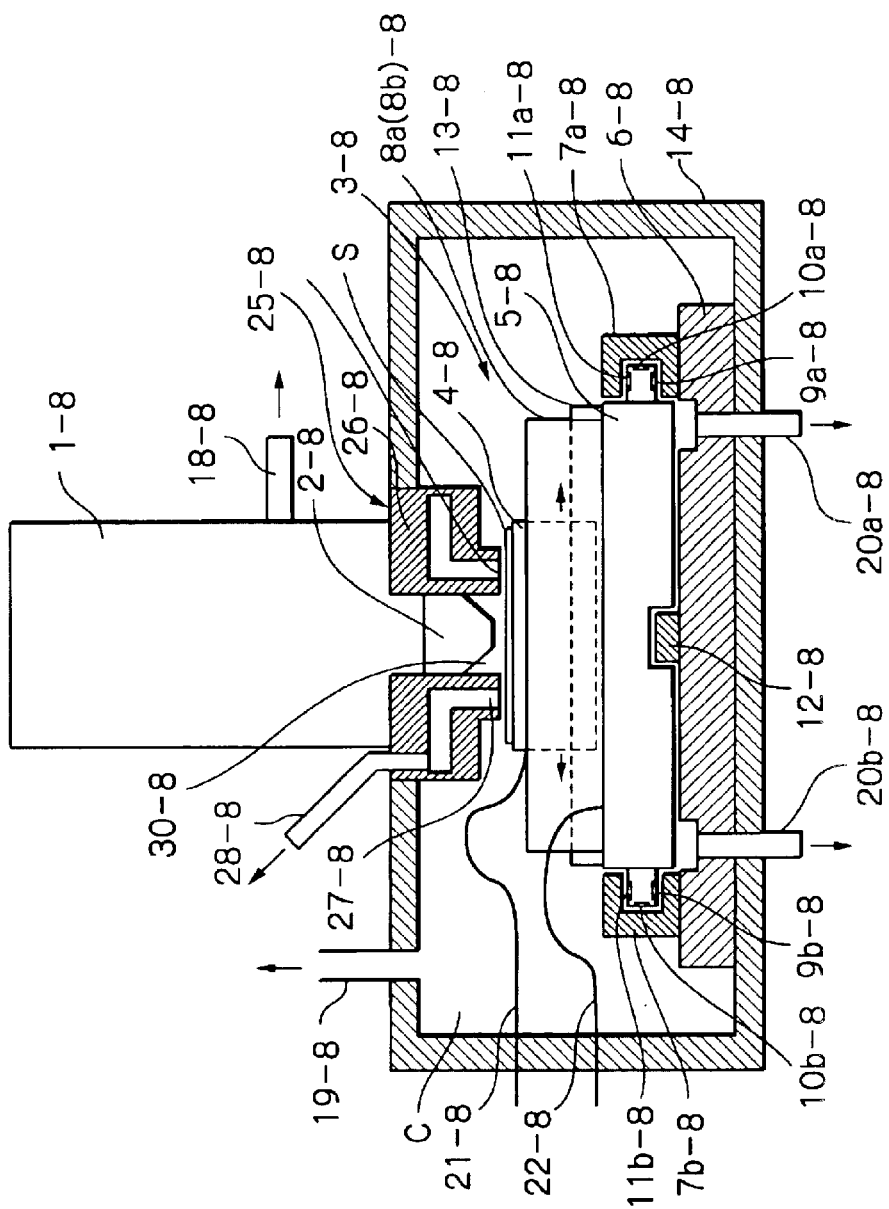
FIG. 38 is a cross sectional view illustrating a vacuum chamber and an XY stage of an example of a charged particle beam apparatus according to the eighth embodiment of the present invention.

FIG. 38 shows a first mode for carrying out the eighth embodiment of the present invention.

A tip portion of an electron optical column 1-8 or a charged particle beam irradiating section 2-8, which functions to radiate a charged particle beam onto a sample, is mounted to a housing 14-8 defining a vacuum chamber C. The sample "S" loaded on an X directionally movable table of an XY stage 3-8 (movable in the lateral direction in FIG. 38) is adapted to be positioned immediately under the electron optical column 1-8. The XY stage 3-8 of high precision allows the charged particle beam to be radiated onto this sample S accurately in any arbitrary location on the sample surface.

A pedestal 6-8 of the XY stage 3 is fixedly mounted on a bottom wall of the housing 14-8, and a Y table 5 movable in the Y direction (the vertical direction on page of FIG. 38) is mounted on the pedestal 6-8. Convex portions are formed on both of opposite sidewall faces (the left and the right side faces in FIG. 38) of the Y table 58 respectively, each of which protrudes into a concave groove formed on a side surface facing to the Y table in either of a pair of Y-directional guides 7a-8 and 7b-8 mounted on the pedestal 6-8. The concave groove extends approximately along the full length of the Y directional guide in the Y direction. A top, a bottom and side faces of respective convex portions protruding into the grooves are provided with known hydrostatic bearings 11a-8, 9a-8, 11b-8, and 9b-8 respectively, through which a high-pressure gas is blown out and thereby the Y table 5-8 is supported by the Y directional guides 7a-8 and 7b-8 in non-contact manner so as to be movable smoothly forth and back in the Y direction. Further, a linear motor 12-8 of known structure is arranged between the pedestal 6-8 and the Y table 5-8 for driving the Y table 5 in the Y direction. The Y table is supplied with the high-pressure gas through a flexible pipe 22-8 for supplying a high-pressure gas, and the high-pressure gas is further supplied to the above-described hydrostatic bearings 9a-8 to 11a-8 and 9b-8 to 11b-8 though a gas passage (not shown) formed within the Y table. The high-pressure gas supplied to the hydrostatic bearings blows out into a gap of some microns to some ten microns formed respectively between the bearings and the opposing guide planes of the Y directional guide so as to position the Y table accurately with respect to the guide planes in the X and Z directions (up and down directions in FIG. 38).

The X table 4-8 is mounted on the Y table so as to be movable in the X direction (the lateral direction in FIG. 38). A pair of X directional guides 8a-8 and 8b-8 (only 8a-8 is illustrated) with the same configuration as of the Y directional guides 7a-8 and 7b-8 is arranged on the Y table 5-8 with the X table 4-8 sandwiched therebetween. Concave grooves are also formed in the X directional guides on the sides facing to the X table and convex portions are formed on the side portions of the X table (side portions facing to the X directional guides). The concave groove extends approximately along the full length of the X directional guide. A top, a bottom and side faces of respective convex portions of the X table 4-8 protruding into the concave grooves are provided with hydrostatic bearings (not shown) similar to those hydrostatic bearings 11a-8, 9a-8, 10a-8, 11b-8, 9b-8 and 10b-8 in the similar arrangements. A linear motor 13-8 of known configuration is disposed between the Y table 5-8 and the X table 4-8 so as to drive the X table in the X direction. Further, the X table 4-8 is supplied with a high-pressure gas through a flexible pipe 21-8, and thus the high-pressure gas is supplied to the hydrostatic bearings. The X table 4-8 is supported highly precisely with respect to the Y directional guide in a non-contact manner by way of said high-pressure gas blowing out from the hydrostatic bearings to the guide planes of the X directional guides. The vacuum chamber C is exhausted through vacuum pipes 19-8, 20a-8 and 20b-8 coupled to a vacuum pump of known structure. Those pipes 20a-8 and 20b-8 penetrate through the pedestal 6-8 to the top surface thereof to open their inlet sides (inner side of the vacuum chamber) in the proximity of the locations to which the high-pressure gas is ejected from the XY stage 3-8, so that the pressure in the vacuum chamber may be prevented to the utmost from rising up by the blown-out gas from the hydrostatic bearings.

A differential pumping mechanism 25-8 is arranged so as to surround the tip portion of the electron optical column 1-8 or the charged particle beam irradiating section 2-8, so that the pressure in a charged particle beam irradiation space 30-8 can be controlled to be sufficiently low even if there exists high pressure in the vacuum chamber C. That is to say, an annular member 26-8 of the differential pumping mechanism 25-8 mounted so as to surround the charged particle beam irradiating section 2-8 is positioned with respect to the housing 14-8 so that a micro gap (in a range of some microns to some-hundred microns) 40-8 can be formed between the lower face thereof (the surface facing to the sample) and the sample, and an annular groove 27-8 is formed in the lower face thereof. That annular groove 27-8 is coupled to a vacuum pump or the like, though not shown, through an exhausting pipe 28-8. Accordingly, the micro gap 40-8 can be exhausted through the annular groove 27-8 and the exhausting pipe 28-8, and if any gaseous molecules from the chamber C attempt to enter the space 30-8 circumscribed by the annular member 26-8, they may be exhausted. Thereby, the pressure within the charged particle beam irradiation space 30-8 can be maintained to be low and thus the charged particle beam can be radiated without any troubles.

That annular groove may be made doubled or tripled, depending on the pressure in the chamber C and the pressure within the charged particle beam irradiation space 30-8.

Typically, dry nitrogen is used as the high-pressure gas to be supplied to the hydrostatic bearings. If available, however, a much higher-purity inert gas should be preferably used instead. This is because any impurities, such as water contents or oil and fat contents, included in the gas could stick on the inner surface of the housing defining the vacuum chamber or on the surfaces of the stage components leading to the deterioration in vacuum level, or could stick on the sample surface leading to the deterioration in vacuum level in the charged particle beam irradiation space.

It should be appreciated that though typically the sample S is not placed directly on the X table, but may be placed on a sample table having a function to detachably carry the sample and/or a function to make a fine tuning of the position of the sample relative to the XY stage 3-8, an explanation thereof is omitted in the above description for simplicity due to the reason that the presence and structure of the sample table has no concern with the principal concept of the present invention.

Since a stage mechanism of a hydrostatic bearing used in the atmospheric pressure can be used in the above-described charged particle beam apparatus mostly as it is, a stage having an equivalent level of precision with equivalent cost and size to those of the stage of high-precision fitted for a use in the atmospheric pressure, which is typically used in an exposure apparatus or the likes, may be accomplished for an XY stage to be used in a charged particle beam apparatus.

It should be also appreciated that the configuration and arrangement of the hydrostatic guide and the actuator (the linear motor) have been only illustratively explained in the above description, and any hydrostatic guides and actuators usable in the atmospheric pressure may be applicable.

Figure 39:
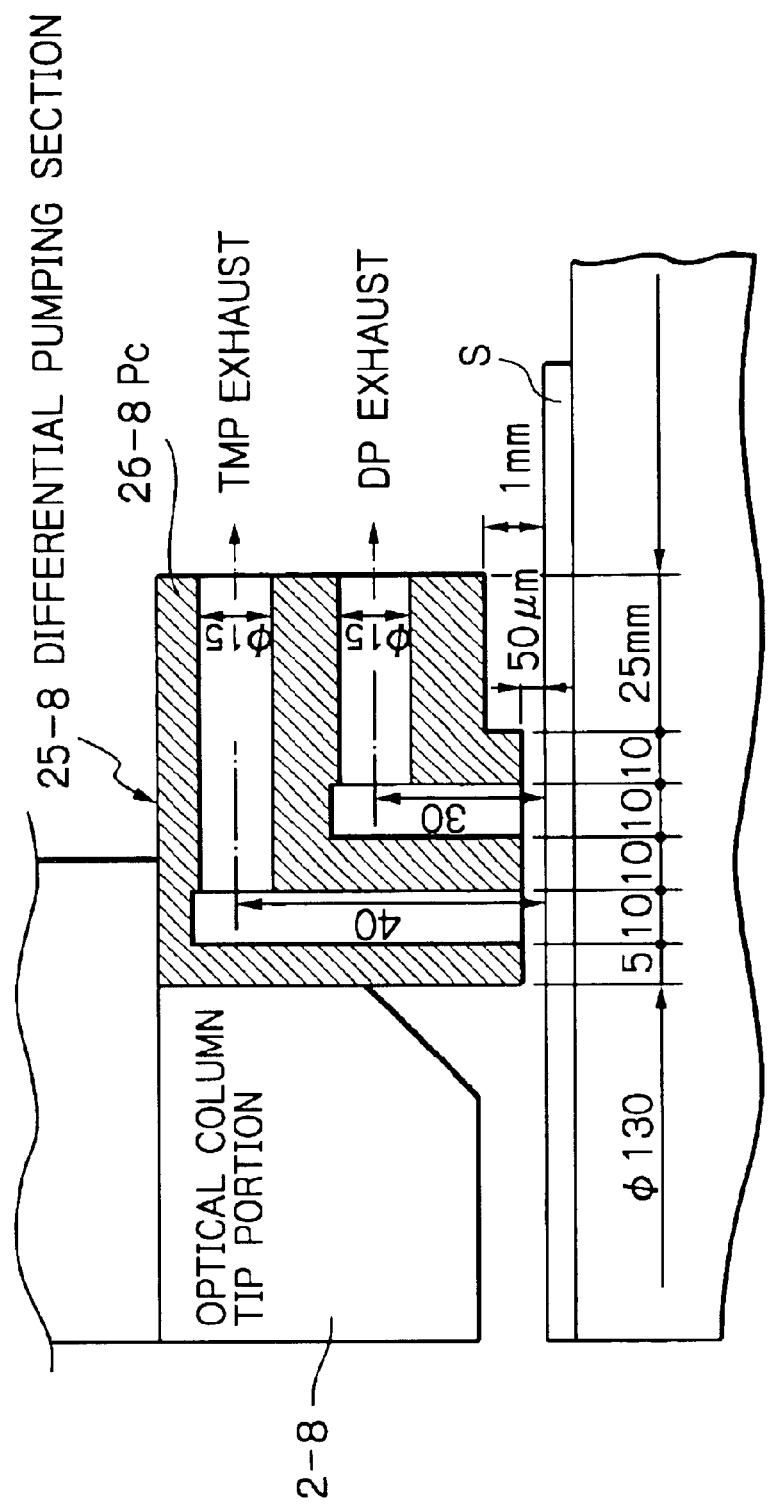
FIG. 39 is a cross sectional view illustrating an example of a differential pumping mechanism arranged in the unit shown in FIG. 38.

FIG. 39 shows an example of numeric values representative of the sizes of the annular member 26-8 and the annular groove formed in the annular member 26-8 of the differential pumping mechanism. It is to be noted that in this example, the annular groove has a doubled structure of 27a-8 and 27b-8, which are spaced from each other in the radial direction.

The flow rate of the high-pressure gas supplied to the hydrostatic bearing is in the order of about 20 L/min (in the conversion into the atmospheric pressure). Assuming that the vacuum chamber C is exhausted by a dry pump having an exhaust velocity of 20,000 L/min via a vacuum pipe having an inner diameter of 50 mm and a length of 2 m, the pressure in the vacuum chamber C will be about 160 Pa (about 1.2 Torr). At that time, with the applied size of the annular member 26-8, the annular groove and others of the differential pumping mechanism as designated in FIG. 39, the pressure within the charged particle beam irradiation space 30-8 can be controlled to $10^{-4}$ Pa ($10^{-6}$ Torr).

It is to be appreciated that the differential pumping mechanism is not necessarily formed in a concentric circular geometry as in this mode but a rectangular or polygonal geometry may be applicable so far as the differential pumping mechanism in such a shape can control the pressure within the charged particle beam irradiating space 30-8 to be maintained at a predetermined level. Further, the differential pumping mechanism is not necessarily provided along an entire circumference but may be provided in some portions along the circumferential region.

Figure 40:
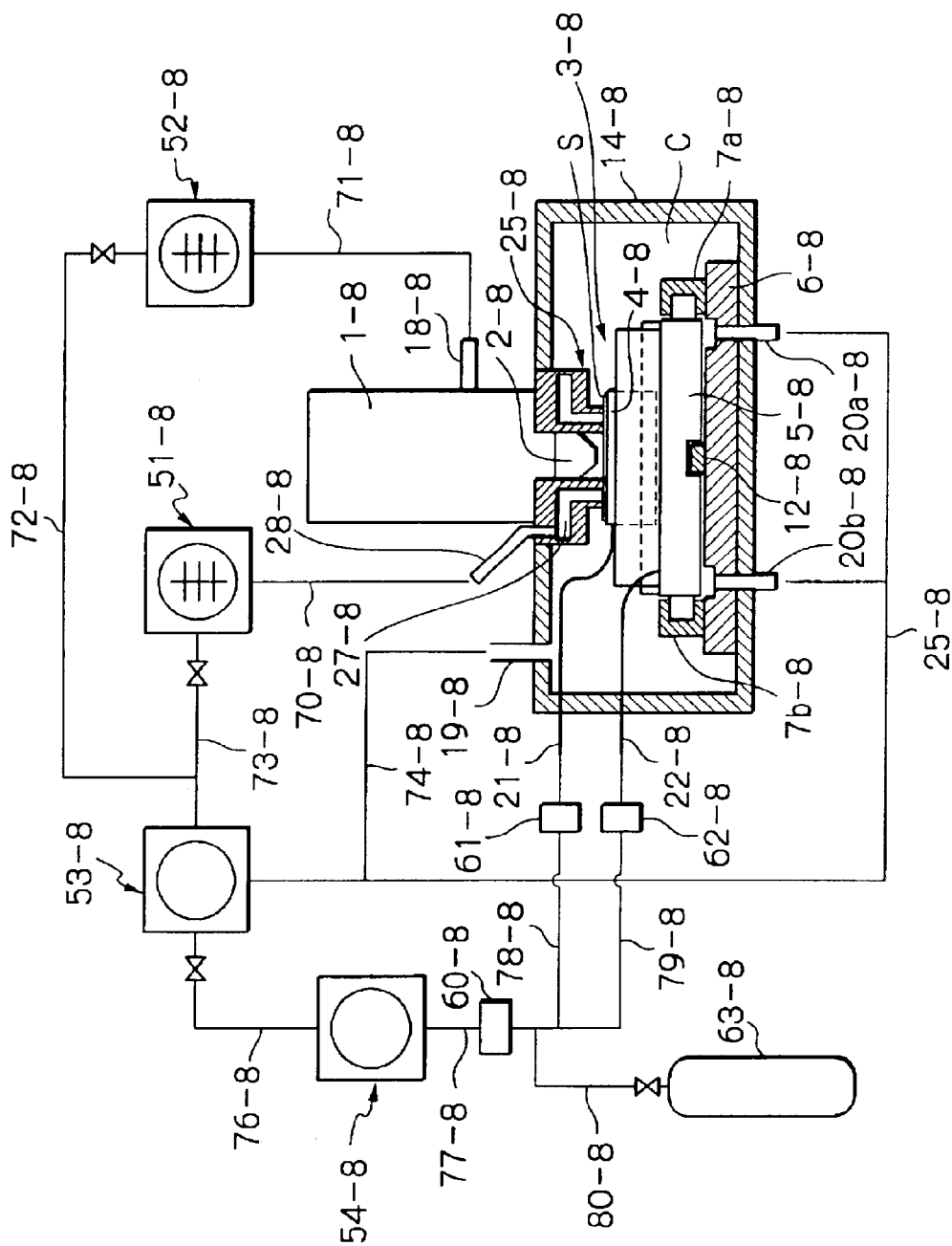
FIG. 40 is a diagram illustrating a circulation piping system for a gas used in the unit shown in FIG. 38.

FIG. 40 shows a second mode for carrying out the eighth embodiment. A vacuum chamber C defined by a housing 14-8 is connected with a dry vacuum pump 53-8 via vacuum pipes 74-8 and 75-8. An annular groove 27-8 of a differential pumping mechanism 25-8 is connected with an ultra-high vacuum pump or a turbo molecular pump 51-8 via a vacuum pipe 70-8 connected to an exhaust port 28-8. Further, the interior of an electron optical column 1-8 is connected with a turbo molecular pump 52-8 via a vacuum pipe 71-8 connected to an exhaust port 18-8. Those turbo molecular pumps 51-8 and 52-8 are connected to the dry vacuum pump 53-8 through vacuum pipes 72-8 and 73-8. (In FIG. 40, the single dry vacuum pump has been used to serve both as a roughing vacuum pump of the turbo molecular pump and as a pump for vacuum pumping of the chamber, but multiple dry vacuum pumps of separate systems may be employed for exhausting, depending on the flow rate of the high-pressure gas supplied to the hydrostatic bearings of the XY stage, the volume and inner surface area of the vacuum chamber and the inner diameter and length of the vacuum pipes.)

A high-purity inert gas ($N_2$ gas, Ar gas or the like) is supplied to a hydrostatic bearing of an XY stage 3-8 through a flexible pipes 21-8 and 22-8. Those gaseous molecules blown out of the hydrostatic bearing are diffused into the vacuum chamber and exhausted by the dry vacuum pump 53-8 through exhaust ports 19-8, 20a-8 and 20b-8. Further, those gaseous molecules having invaded into the differential pumping mechanism and/or the charged particle beam irradiation space are sucked from the annular groove 27-8 or the tip portion of the electron optical column 1-8 through the exhausting ports 28-8 and 18-8 to be exhausted by the turbo molecular pumps 51-8 and 52-8, and then those gaseous molecules, after having been exhausted by the turbo molecular pumps, are further exhausted by the dry vacuum pump 53-8.

In this way, the high-purity inert gas supplied to the hydrostatic bearing is collected into the dry vacuum pump and then exhausted away.

On the other hand, the exhaust port of the dry vacuum pump 53-8 is connected to a compressor 54-8 via a pipe 76-8, and the exhaust port of the compressor 54-8 is connected to flexible pipes 21-8 and 22-8 via pipes 77-8, 78-8 and 79-8 and regulators 61-8 and 62-8. Owing to this configuration, the high-purity inert gas exhausted from the dry vacuum pump 53-8 is compressed again by the compressor 54-8 and then the gas, after being regulated to an appropriate pressure by the regulators 61-8 and 62-8, is supplied again to the hydrostatic bearings of the XY stage.

In this regard, since the gas to be supplied to the hydrostatic bearings is required to be as highly purified as possible in order not to have any water contents or oil and fat contents included therein, as described above, the turbo molecular pump, the dry pump and the compressor are all required to have such structures that prevent any water contents or oil and fat contents from entering the gas flow path. It is also considered effective that a cold trap, filter or the like (60-8) is provided in the course of the outlet side piping 77 of the compressor so as to trap the impurities such as the water contents or oil and fat contents, if any, included in the circulating gas and prevent them from being supplied to the hydrostatic bearings.

This may allow the high purity inert gas to be circulated and reused, and thus allows the high-purity inert gas to be saved, while the inert gas would not remain discharged into a room where the present apparatus is installed, thereby eliminating a fear that any accidents such as suffocation or the like would be caused by the inert gas.

It is to be noted that a circulation piping system is connected with the high-purity inert gas supply system 63-8, and the system 63-8 serves both to fill up with the high-purity inert gas all of the circulation systems including the vacuum chamber C, the vacuum pipes 70-8 to 75-8, and the pipes in compression side 76-8 to 80-8, prior to the starting of the gas circulation, and to supply a deficiency of gas if the flow rate of the circulation gas decreases by some reason.

Further, a single dry vacuum pump 53-8, if provided with a function of compressing to the level equal or greater than the atmospheric pressure, may be employed so as to serve both as the dry vacuum pump 53-8 and the compressor 54-8.

Further, as to the ultra-high vacuum pump to be used for exhausting the electron optical column, other pumps including an ion pump and a getter pump may be used instead of the turbo molecular pump. It is to be note that in the case where those reservoir type pumps are used, the circulation systems are prohibited to build in those areas. Further, it is also apparent that instead of the dry vacuum pump, a dry pump of other type, for example, a dry pump of diaphragm type may be used.

The electron beam apparatus to be installed in the electron optical column 1-8 may employ any optical systems and detectors as desired. For example, either of the image projection type shown in FIG. 1 and the like or the scanning type shown in FIG. 41 and the like may be employable.

According to the eighth embodiment of the present invention, the following effects may be brought about.

(A) A processing by the charged particle beam can be stably applied to a sample on the stage by the use of the stage having a structure similar to that of a stage of hydrostatic bearing type which is typically used in the atmospheric pressure (a stage supported by the hydrostatic bearing having no differential pumping mechanism).

(B) Affection on the vacuum level in the charged particle beam irradiation region can be minimized, and thereby the processing by the charged particle beam to the sample can be stabilized.

(C) Such an inspection apparatus can be provided in low cost that accomplishes positioning performance of the stage with high precision and provides a stable vacuum level in the irradiation region of the charged particle beam.

(D) Such an exposure apparatus can be provided in low cost that accomplishes positioning performance of the stage with high precision and provides a stable vacuum level in the irradiation region of the charged particle beam.

(E) A micro semiconductor circuit can be formed by manufacturing the semiconductor using an apparatus which accomplishes positioning performance of the stage with high precision and provides a stable vacuum level in the irradiation region of the charged particle beam.

Ninth Embodiment

Figure 41:
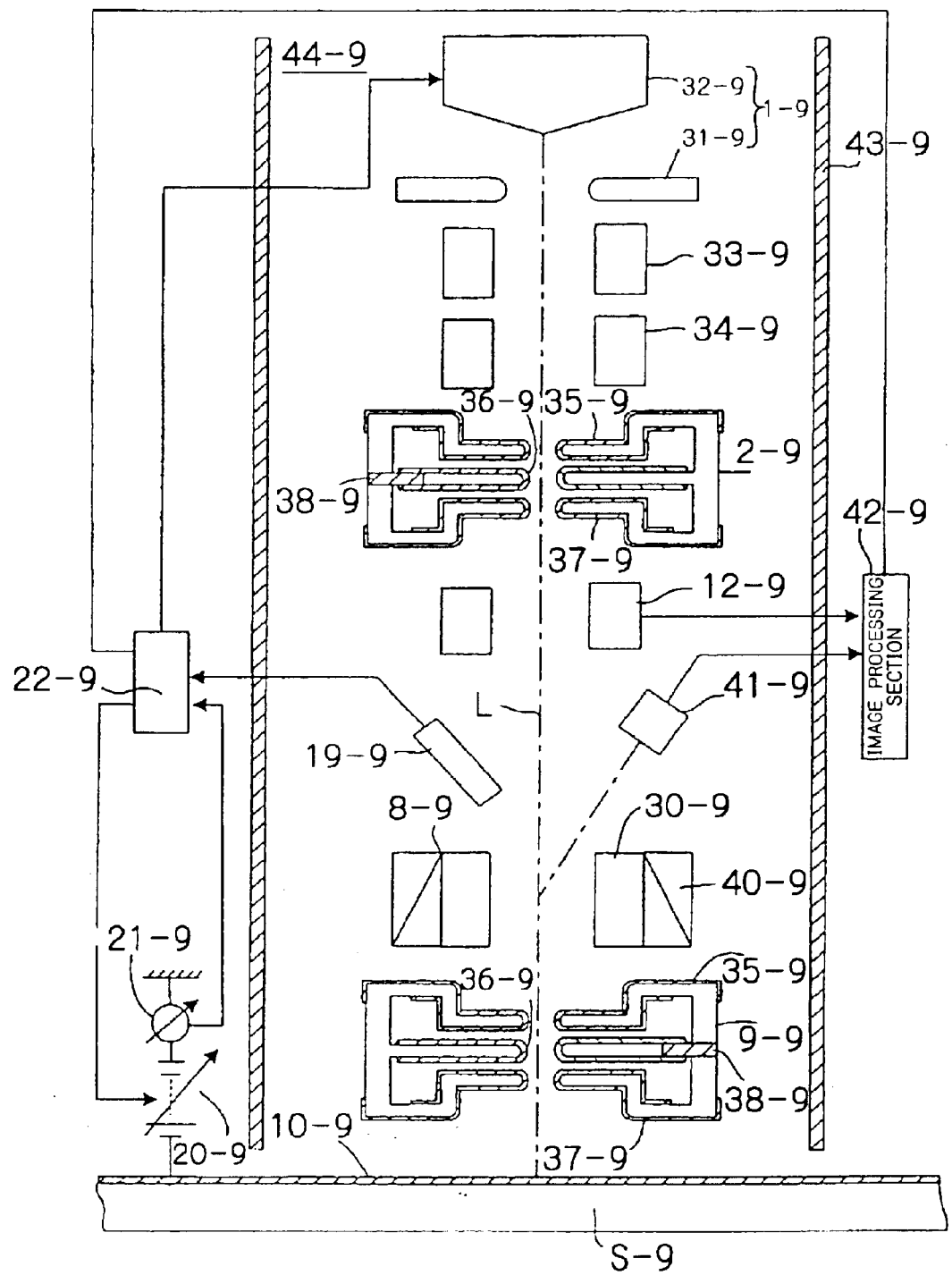
FIG. 41 is a schematic diagram of an electron beam apparatus according to a ninth embodiment of the present invention.

The defect inspection apparatus of FIG. 1 may be replaced with an electron beam apparatus of scanning type. A configuration and operation of a ninth embodiment of the present invention relating to such a scanning type electron beam apparatus will now be described in conjunction with FIG. 41. In FIG. 41, an electron gun 1-9 comprises a Wehnelt 31-9 and a cathode 32-9 and emits a primary electron beam having a crossover of approximately 10 microns in diameter. The primary electron beam emitted in this way passes through deflectors 33-9 and 34-9 for the axial alignment and then a condenser lens 2-9, where the beam is converged thereby, and then after having passed through a deflector 12-9 and a Wien filter 8-9, the primary electron beam is contracted by an objective lens 9-9 to form a probe of not greater than 100 nm. Then, the contracted primary beam is formed into an image on one of a plurality of, for example, rectangular circuit patterns formed on a surface of a sample 10-9 loaded on a stage S-9. The sample 10-9 is applied with a scanning by the primary electron beam using the deflectors 12-9 and 40-9.

A secondary electron beam, which has been emitted from the surface of the sample 10-9 as a result of the scanning with the primary electron beam, is attracted and accelerated by an electric field of the objective lens 9-9 and deflected by the Wien filter 8-9 so as to depart from an optical axis L and thus to be separated from the primary electron beam. In this way, the secondary electron beam is detected by a secondary electron beam detecting section 41-9. The secondary electron detecting section 41-9 outputs an electric signal representing an intensity of the secondary electron beam entered therein. The electric signal output from this secondary electron detecting section 41-9 is amplified by a corresponding amplifier (not shown) and then entered into an image processing section 42-9.

As shown in FIG. 41, the electron gun 1-9, the deflectors 33-9 and 34-9 for the axial alignment, the condenser lens 2-9, the deflector 12-9, the Wien filter 8-9, the objective lens 9-9 and the secondary electron detecting section 41-9 are all accommodated in an electron optical column 43-9 having a diameter corresponding to a predetermined extent on the sample 10-9 thus to make up a single unit of electron beam scanning and detecting system 44-9, and this single unit of electron beam scanning and detecting system 44-9 is used to scan a circuit pattern on the sample 10-9. In specific, there is a plurality of dies formed on a surface of the sample 10-9. Another electron beam scanning and detecting system (not shown) having a similar configuration to that of the electron beam scanning and detecting system 44-9 may be arranged in parallel with the electron optical column 43-9 so as to scan the same location on a different die on the sample 10-9.

As having been described already in conjunction with the electron beam scanning and detecting system 44-9, the electric signal output from each of the secondary electron detecting systems in the electron beam scanning and detecting system is entered into the image processing section 42-9. Then, the image processing section 42-9 converts the electric signal having been entered from the each of the detecting systems into a binary information, and further converts this binary information into an image data with reference to the electron beam scanning signal. To accomplish this, a signal waveform having applied to the electrostatic deflector 12-9 is supplied to the image processing section 42-9. The image data obtained for each of the dies formed on the surface of the sample 10-9 is compared with a reference die pattern while being accumulated in an appropriate storage means. This allows any defects to be detected for every one of the plurality of die patterns formed on the surface of the sample 10-9.

It is to be noted that in the mode for carrying out the embodiment shown in FIG. 41, a variety of circuit patterns may be used as a reference circuit pattern to be used by the image processing section 42-9 for making a comparison with a specific image data representing a certain die pattern on the sample 10-9, and for example, such image data obtained from the CAD data for the die pattern, to which the scanning has been applied so as to generate said specific image data, may be used.

The Wien filter 8-9 comprises an electrostatic deflector 39-9 and an electromagnetic deflector 40-9 arranged so as to circumscribe said electrostatic deflector 39-9. As for this electromagnetic deflector 40-9, preferably a permanent magnet made of platinum alloy may be used instead of an electromagnetic coil. This is because applying a current in a vacuum environment is not adequate. Further, the deflector 12-9 may be used also as an axial aligner for aligning the direction of the primary electron beam with the axis of the objective lens 9-9.

To fabricate the condenser lens 2-9 and the objective lens 9-9 in the electron beam scanning and detecting system 44-9, at first a ceramic block is processed in high precision to be formed into a shape of sectional geometry shown in FIG. 41 and then a metal coating is selectively applied to a surface of the processed ceramic so as to form an upper electrode 35-9, a central electrode 36-9 and a lower electrode 37-9, respectively. To the upper electrode 35-9 is applied a voltage proximal to a ground voltage and to the central electrode 36-9 is applied a positive or negative voltage having a high absolute value through a current introduction terminal 38-9 made of metal, thereby producing a lens effect.

In this way, since the condenser lens 2-9 and the objective lens 9-9 are fabricated by way of machining of the ceramic, it is possible to process those lenses with high level of precision and to reduce outer diameters thereof. Accordingly, if the outer diameters of the condenser lens 2-9 and the objective lens 9-9 are reduced to, for example, not greater than 20 mm, then six electron beam scanning and detecting systems can be arranged in the case of the inspection of the wafer having a diameter of 200 mm with a range defined by a diameter of 140 mm to be inspected, thus achieving the throughput increased by six times.

A characteristic part in the embodiment of the electron beam apparatus according to the present invention will be described below. The objective lens 9-9 is constituted of an electrostatic lens, and to either one of the electrodes of the electrostatic lens is applied a high positive voltage. On the other hand, to the sample wafer 10-9 is applied a high negative voltage by a power supply 20-9. This produces a decelerating electric field between the objective lens 9-9 and the sample wafer 10-9.

If the wafer 10-9 is a wafer having a via and the primary electron beam enters into the via, then a large amount of secondary electrons would be emitted because the via is made of metal with high atomic number. Further, in the vicinity of the via, much larger electric field would have been generated locally due to the decelerating electric field. Because of those facts, a wafer with the via is in a condition where an electric discharge is likely to occur thereabound.

However, given all of those conditions, the electric discharge would not necessarily occur instantly. At first, a corona discharge would occur in which a residual gas in a space of intense electric field emits light locally, and then the corona discharge is to be shifted to an arc discharge through a transient state of a spark discharge. In this specification, a period from the event of this corona discharge to the beginning of the spark discharge will be referred to as a "precursory phenomenon of the electric discharge".

It has been found that in the period corresponding to this precursory phenomenon of the electric discharge, if the beam current is decreased so as to limit the generation of the primary electron beam to a quantity not greater than a certain level or the voltage of the decelerating electric field between the objective lens 9-9 and the sample wafer 10-9 is decreased, or otherwise both of those arrangements are performed, then it can inhibit the precursory phenomenon from proceeding to the arc discharge and thus can prevent any damage to the wafer.

Beside, since critical levels for the decelerating electric field voltage or the primary electron beam dose not to trigger the electric discharge are different between an easily discharged wafer and a hardly discharged wafer, therefore those values should not be fixed at low levels but it is preferable to obtain limit values for prohibiting the electric discharge for each type of the wafer.

In an electron beam apparatus according to the present invention as shown in FIG. 41, a PMT 19-9 and an ampere meter for a sample 21-9 are provided as a detector for detecting the electric discharge or the precursory phenomenon of the electric discharge between the sample wafer 10-9 and the objective lens 9-9 and generating a signal. The PMT 19-9 can detect the light emission by the corona discharge or the arc discharge and the ampere meter for the sample 21-9 can detect an irregular current at the time of the corona discharge or the arc discharge.

If the PMT 19-9 detects the light emission by the corona discharge or the ampere meter for the sample 21-9 detects the irregular current in the period of the precursory phenomenon of the electric discharge, such information may be entered to a CPU 22-9. A voltage value of the decelerating electric field and a beam current value (corresponding to the primary electron beam dose) of the electron gun 1-9 measured at that time may be used as basic data for determining a condition not to trigger the electric discharge. The CPU 22-9, in response to the entry indicating the presence of the light emission or the irregular current or both of them, performs such a control that, for example, it reduces the voltage of the decelerating electric field 20-9 or it sends a feedback signal to the electron gun 1-9 to decrease the beam current thus to control the primary electron beam dose to a value not greater than a specified level. The CPU 22-9 may perform both of those two controls.

Preferably both of the PMT 19-9 and the ampere meter for the sample 21-9 should be employed, but either one of them may be omitted.

Figure 42:
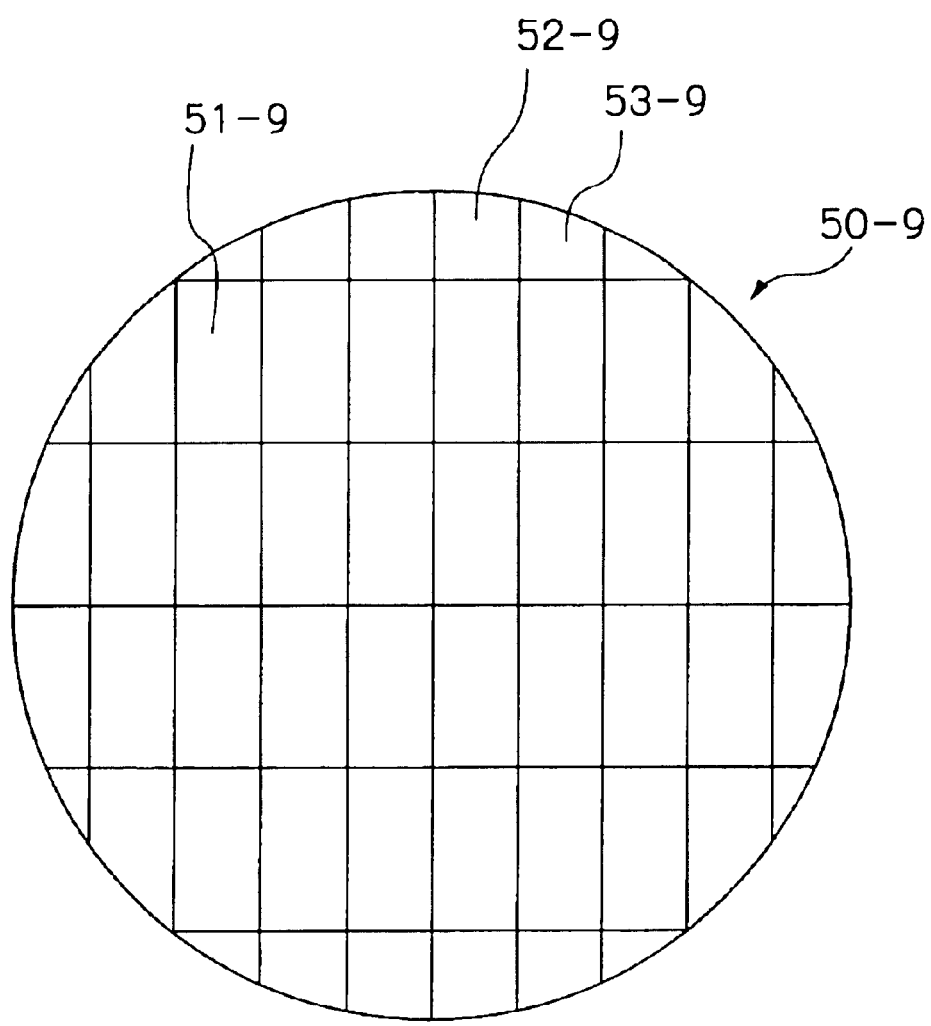
FIG. 42 is a plan view illustrating an arrangement of devices on a single wafer according to the ninth embodiment of the present invention.

FIG. 42 shows an arrangement of devices on a single wafer. A plurality of rectangular chips 51-9 is obtained from a single circular wafer 50-9, and there are defective chips existing in a circumferential region thereof, which are insufficient in size for a single chip. A normal lithography is also applied to those regions having defective chips and various processes are also applied to those regions similarly to the region having a complete chip 51-9. On the other hand, since those defective chips would not be used as finished products and any damages to those regions would not be a problem. In this viewpoint, if said regions having the defective chips are used so as not only to detect the precursory phenomenon of the electric discharge but also to detect further the phenomenon of the electric discharge without flinching from the possible break, then it can help determine more precisely a condition for preventing the electric discharge. In this case, the PMT 19-9 may detect the light emission by the arc discharge, and the ampere meter for the sample 21-9 may detect the irregular current at the time of the arc discharge and then send a signal to the CPU 22-9. Further, the CPU 22-9 can designate accurately the limit values representing the voltage value of the decelerating electric filed and the beam current value (corresponding to the primary electron beam dose) not to trigger the electric discharge.

According to the electron beam apparatus of the ninth embodiment, the condition not to trigger the electric discharge can be determined individually depending on the wafer which is easily discharged or hardly discharged.

Further, if the regions having defective chips (incomplete chips) are used to perform a further level of detection such as the detection of the phenomenon of the electric discharge, a critical condition not to trigger the electric discharge can be known accurately. Alternatively, in the case where the regions having normal chips (complete chips) are used, if the detection is limited to a level of the detection of the precursory phenomenon of the electric discharge, the condition not to trigger the discharge can be known to an effective level still with no damage to the normal chips. In either case, since the normal chips are never be broken, an evaluation procedure of a wafer can be conducted with high throughput, that is, with a favorable condition for the detection efficiency of the secondary electrons. Use of the multi-beam may further improve the throughput.

Tenth Embodiment

Figure 43:
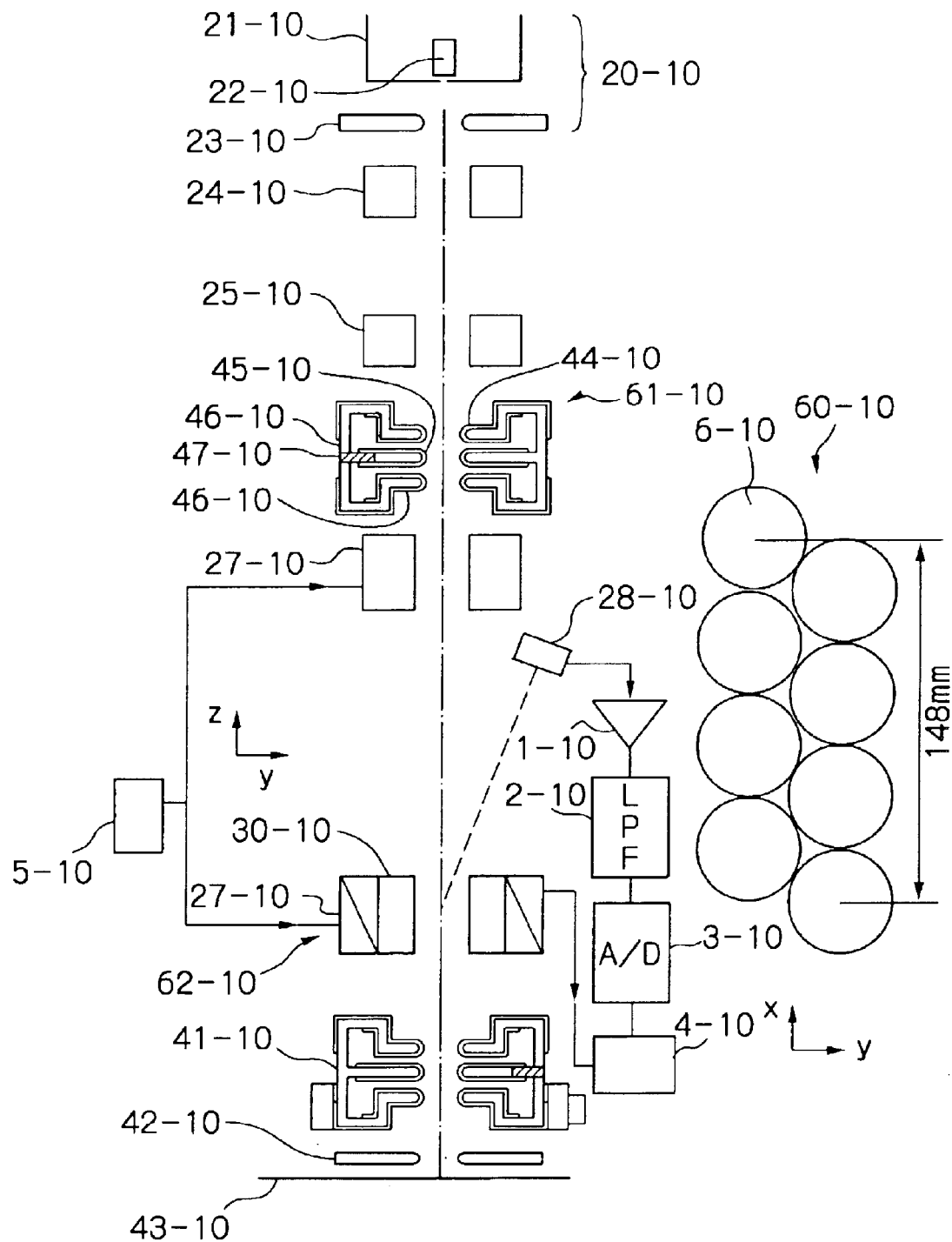
FIG. 43 is a schematic diagram illustrating an electron beam apparatus according to a tenth embodiment of the present invention.

Preferred embodiments of a scanning type electron beam apparatus according to a tenth embodiment of the present invention will now be described with reference to the attached drawings. FIG. 43 shows schematically an electron beam apparatus according to the tenth embodiment of the present invention. As shown in FIG. 43, the electron beam apparatus comprises a plurality of electron optical columns 60-10 (eight lens columns shown in this embodiment), each being composed of the same components, arranged in parallel above a sample 43-10. One of those electron optical columns 6-10 has an electron gun 20-10, axial aligning electrodes 24-10 and 25-10 for the axial alignment of a primary electron beam, a condenser lens 61-10, an electrostatic deflector 27-10 for scanning with the primary electron beam, an ExB separator 62-1 consisting of an electromagnetic deflector 29-10 and an electrostatic deflector 30-10, an objective lens 41-10, an axially symmetric electrode 42-10 for measuring a voltage contrast, and a detector 28-10 serving as a detecting means on which a secondary electron beam separated from the primary electron beam forms an image and which detects a detection signal of the secondary electron beam.

The electron gun 20-10 comprises a Schottky shield 21-10, a shottokey cathode 22-10, and an anode 23-10, and it works to emit the primary electron beam. The primary electron beam emitted from the electron gun 20-10 is controlled to be in axial alignment with respect to a condenser lens 61-10 by the axial aligning electrodes 24-10, 25-10, and then is converged by the condenser lens 61-10. The primary electron beam converged by the condenser lens 61-10 forms an image on a sample 43-10 with an aid of the objective lens 41-10. At the same time, the electrostatic deflector 27-10 and the electromagnetic deflector 29-10 of the ExB separator 62-10 deflect the beam so as to scan a surface of the sample 43-10. Since an angle of deflection by the electromagnetic deflector 29-10 has been set to approximately doubled angle of deflection by the electrostatic deflector 27-10, there would be generated no chromatic aberration by deflection.

The secondary electron beam emitted from the scanned point on the sample 43-10 is attracted and accelerated by a high positive voltage applied to a central electrode of the objective lens 41-10, separated from the primary optical system by the ExB separator 62-10, introduced into the secondary optical system, and then formed into an image on the detector 28-10.

The detector 28-10 outputs the image of the secondary electron beam formed thereon to a low-pass filter (LPF) 2-10 in a form of an electric signal representing its intensity (a detection signal of the secondary electron beam). To explain in more specific, the electric signal output from the detector 28-10 is firstly amplified by the amplifier 1-10 and then output to the low-pass filter (LPF) 2-10. The low-pass filter 2-10 is such a device that allows only the electric signal having a frequency of pass band to pass though it, and the electric signal which has passed through the low-pas filter 2-10 is converted by an A/D converter 3-10 from the analog signal to a digital signal, which in turn is sent to an image forming unit 4-10. Further, the image forming unit 4-10 is further supplied with a scanning signal, which has given to the electrostatic deflector 27-10 and the electromagnetic deflector 29-10 from a deflector control power supply 5-10 for deflecting the primary electron beam. The image forming unit 4-10 can synthesize image data from the scanning signal and the electric signal to constitute or display the image representing the scanned surface of the sample 43-10. Comparing this image data with a reference image data having no defect allows a defect on the sample 43-10 to be detected.

Figure 44A:
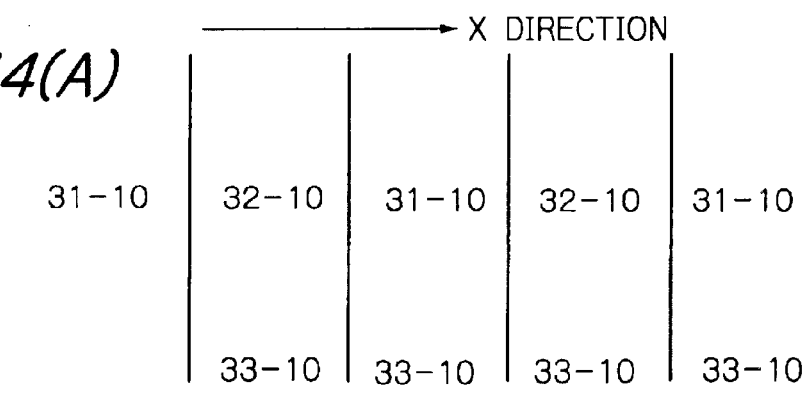
FIG. 44 is a waveform diagram representing a pattern on a sample and a detection signal of a secondary electron beam from said pattern, in the tenth embodiment.

The low-pass filter 2-10 will now be described in detail, which is a characteristic part of the present invention. The low-pass filter 2-10 is such a device that allows only the electric signal having a frequency of pass band to pass though it, as described before. FIG. 44(A) shows a pattern on a sample. This pattern includes portions 31-10 that have been recessed by 0.5 μm by etching and portions 32-10 that are not etched and are 0.5 μm higher than the etched portions 31-10, which two kinds of portions have been alternately formed therein.

Figure 44B:
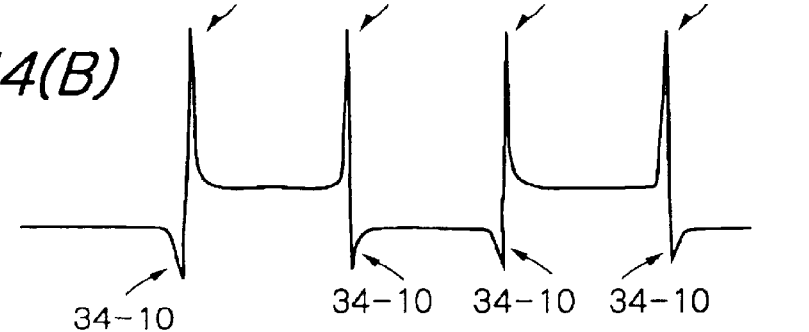
Figure 44C:
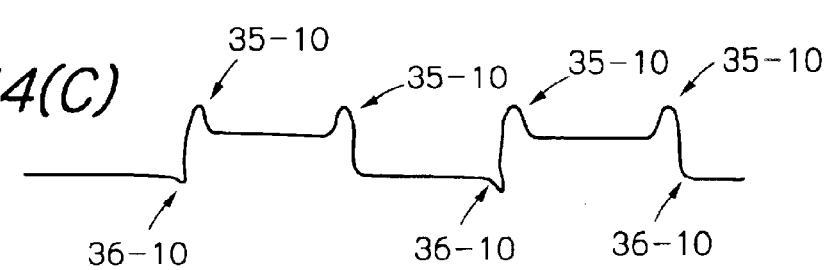

FIGS. 44(B) and (C) show waveforms of aforementioned electric signal (detection signal of the secondary electron beam) received by the image forming unit 4-10, wherein FIG. 44(B) shows a signal waveform in a case where the electric signal outputted from the detector 28-10 is received by the image forming unit 4-10 without passing through the low-pass filter 2-10, while FIG. 44(C) shows another signal waveform in a case where the electric signal outputted from the detector 28-10 is received by the image forming unit 4-10 after having passed through the low-pass filter 2-10. It is to be noted that herein the pixel frequency is 10 MHz and the amplifier 1-10 allows the frequency up to 100 MHz to pass. Further, the low-pass filter 2-10 has frequency characteristics with a frequency of 20 MHz for 3 db signals dropping at the rate of 12 db/octave.

It is observed that the signal waveform shown in FIG. 44(B) has the intensity of the electric signal increased at the edge portions of the pattern as indicated by reference numeral 33-10. Besides, it is also observed that the intensity of the electric signal is reduced at the end portions of the grooves of the pattern as indicated by reference numeral 34-10. On the other hand, it is found that, as indicated by reference numeral 35-10, the signal waveform shown in FIG. 44(C) has the intensity of the electric signal observed at the edge portions of the pattern being smaller than that as shown in FIG. 44(B). Further, as indicated by reference numeral 36-10, the intensity of the electric signal observed at the end portions of the grooves of the pattern appears to be shallow in depth as compared to that shown in FIG. 44(B).

In this way, allowing the electric signal outputted from the detector 28-10 to pass through the low-pass filter 2-10 and then to be received by the image forming unit 4-10 can reduce the intensity of the electric signal at the edge portions of the pattern where the secondary electron emission rate is extremely high. Thus, this can prohibit that the electric signal at the portions having the extremely high secondary electron emission rate would mask such a signal as occurred from a defect, and can improve the defect inspection speed.

On the other hand, for an aluminum pattern, the intensity of the electric signal at the edge portions would not be increased to that high, so that, in this case, a more accurate pattern image can be obtained by allowing the image forming unit 4-10 to receive high frequency signal. Therefore, if said low-pass filter 2-10 has been designed to have the variable cut-off frequency, the image data can be successfully detected for any patterns and thus the detection rate can be further improved.

Further, although in the above embodiment, having been arranged between the amplifier 1-10 and the A/D converter 3-10, the low-pass filter 2-10 may be located between the detector 28-10 and the amplifier 1-10 or between the A/D converter 3-10 and the image forming unit 4-10.

On the other hand, a shot noise "$i_n^2$" can be represented by an equation, $i_n^2 = 2eIB$, which means that the noise could be made smaller as a signal bandwidth "B" is reduced, which provides the signal with large S/N ratio. Where, "e" denotes a charge of an electron and "I" denotes a current.

Further, as shown in FIG. 43, the condenser lens 61-10 is such a lens that is made by processing an insulating material or ceramic to form a plurality of electrodes in one unit and then selectively applying a metal coating onto a surface thereof. The plurality of electrodes in the condenser lens 61-10 is composed of an upper electrode 44-10, a central electrode 45-10, and a lower electrode 46-10, and to the condenser lens 61-10 is applied a voltage via a lead mounting bracket 47-10. Besides, similarly to the condenser lens 61-10, the objective lens 41-10 is also a lens that is made by processing an insulating material or ceramic to form a plurality of electrodes in one unit and then selectively applying a metal coating onto a surface thereof. Since the condenser lens 61-10 and the objective lens 41-10, which have been processed in such a manner, can be made as the lens of smaller outer diameters and thereby allows the outer diameter of the electron optical column 6-10 to be made smaller, therefore a large number of electron optical columns 6-10 can be arranged in parallel above a single sample 43-10.

According to the tenth embodiment, since there is provided an electron beam apparatus comprising a plurality of electron optical columns arranged in parallel, each being designed so as to form the primary electron beam into an image on the sample and to form the secondary electron beam emitted from the sample into an image on the detecting means, wherein said apparatus further comprises a low-pass filter, and said detecting means outputs the detection signal of the secondary electron beam to said low-pass filter, therefore the apparatus can reduce a signal intensity of the detection signal having a high level of secondary electron emission rate and also exhibiting a waveform of pulse shape with narrow width, thereby improving the defect detection rate.

Eleventh Embodiment

First of all, referring to FIG. 45, an evaluation apparatus for evaluating a condition of a wafer for a semiconductor device after having been processed according to the present invention will be described.

Figure 45:
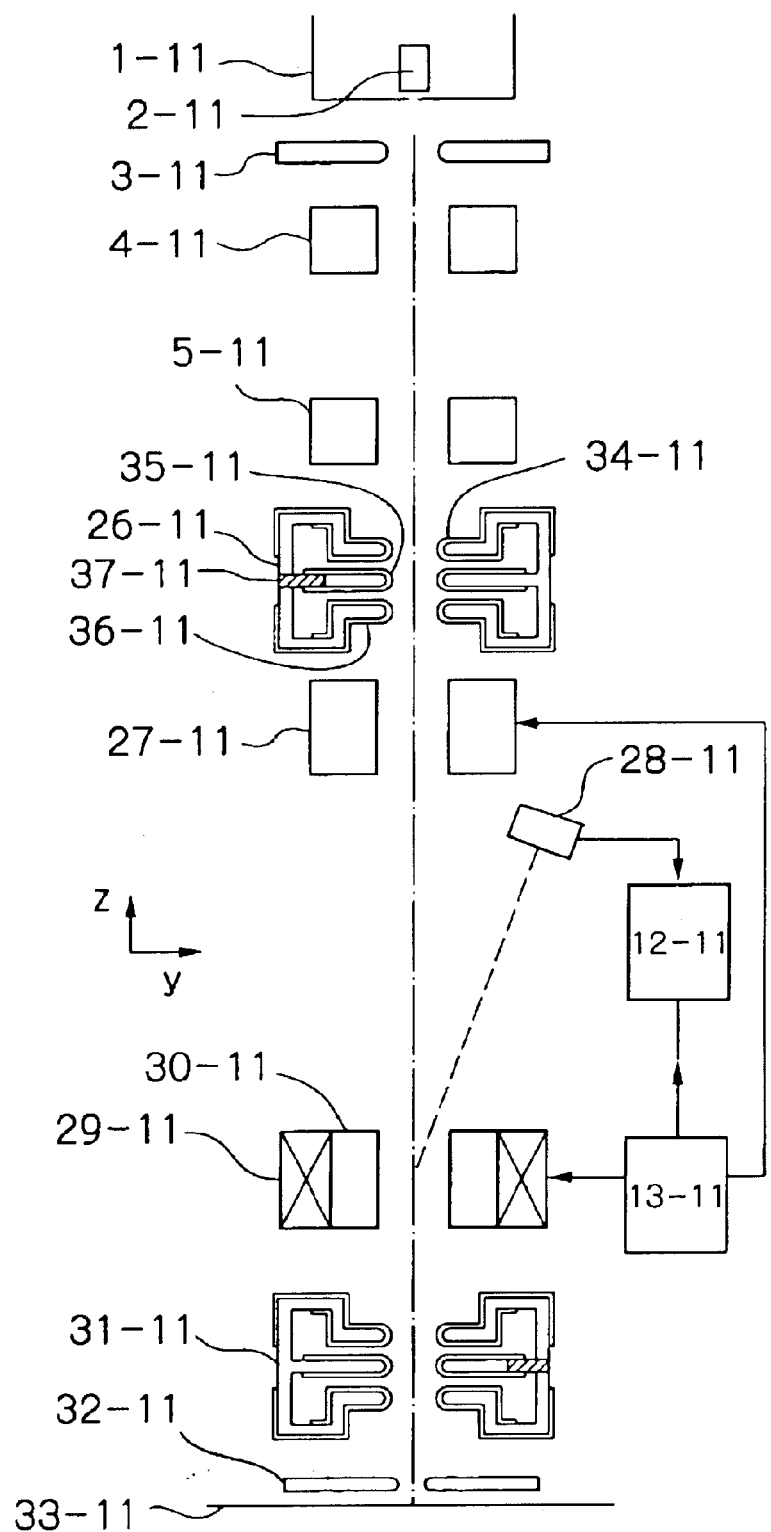
FIG. 45 is a schematic block diagram illustrating a configuration of a first example of an evaluation apparatus according to an eleventh embodiment of the present invention.

In FIG. 45, reference numeral 1-11 is an electron gun for emitting an electron beam, 2-11 is a cathode, 3-11 is an anode, 4-11, 5-11 and 27-11 are deflectors, 26-11 is a condenser lens, and 29-11 and 30-11 are deflectors which make up an E×B separator. The reference numeral 31-11 is an objective lens, 33-11 is a wafer prepared as an inspection sample, and 28-11 is an electron beam detector. Further, the reference numeral 12-11 is an image forming unit, and 13-11 is a scanning control unit, which supplies the deflectors 27-11 and 29-11 with a scanning signal used for scanning operation of the electron beam.

In the evaluation apparatus of FIG. 45, the electron beam emitted from the electron gun 1-11 forms an image on a surface of the wafer 33-11 with an aid of the condenser lens 26-11 and an objective lens 31-11, while scanning the surface of the wafer 33-11 with an aid of the deflectors 27-11 and 29-11. Under the condition where a stage (not shown) holding the wafer 33-1 has been held stationary, the scanning control circuit 13-11 controls the deflectors 27-11 and the 29-11 so that either one of them may control the electron beam to scan in the X-axis direction and the other may control the electron beam to scan in the Y-axis direction. This allows a raster scanning to be applied to the surface of the wafer 33-11 while the wafer 33-11 being fixed, and the electron beam spot may be formed on every point within a predetermined area on the surface of the wafer 33-11.

In this stage, if one time of the raster scanning is not enough to cover entire region to be inspected on the wafer, which has been determined in advance, the stage having the wafer 33-11 loaded thereon should be moved step by step in the X-axis and/or the Y-axis directions, so that the areas adjacent to those areas which have been previously scanned can be similarly scanned.

A secondary electron beam emitted by the electron beam forming an image on the wafer 33-11 is deflected by the E×B separator or the deflectors 29-1, 30-11, converted into an electric signal by the secondary electron beam detector 28-11, and supplied as a detection signal to the image forming unit 12-11.

The condenser lens 26-11 comprises an upper electrode 34-11, a central electrode 35-11 and a lower electrode 36-11 formed therein, which have been formed in such a way that a single cylindrical body of ceramic is skived so as to be axially symmetric in sectional geometry and to have three arms whose surfaces are then selectively applied with a metal coating to be formed into respective electrodes. The central electrode 35-11 is supplied with an electric power through a current introducing terminal 37-11, and the upper electrode 34-11 and the lower electrode 36-11 are supplied with the electric power respectively through those metal-coated sections in the outer peripheral portion of the condenser lens 26-11 serving as power supplying terminals. With the condenser lens 26-11 which has been constituted by an axially symmetric lens formed as one body in the manner as described above, the outside dimension thereof has been successfully reduced with a diameter reduced to about 40 mm.

The objective lens 31-11 has been made so as to have approximately similar configuration and dimension to the condenser lens 26-11.

The image forming unit 12-11 is also supplied with the scanning signal from the scanning control unit 13-11, in which the output signal from the detector is coordinated so as to correspond to the scanning signal and then stored in an image data storage (not shown) as a signal representing a pixel locations. With this signal, the image of the surface of the wafer 33-11 can be formed by the image forming unit 12-11.

The image representing the wafer surface which has been formed in such a manner as described above is then compared as per pixel by a mismatch/match detecting unit (not shown) with a reference image pattern or an image pattern with no defect stored in advance, and if any mismatching pixel is found out, then it may be determined that the wafer has a defect. If the evaluation result of a wafer is different from the evaluation results of large majority of wafers, it may be determined that said wafer has a defect. Further, the image representing the wafer surface may be displayed on the monitor screen, and in that case an experienced operator or the like may monitor the image to inspect the wafer surface for a defect.

Still further, upon measuring a line width of a wiring pattern or an electrode pattern formed on the wafer, a pattern area to be evaluated is moved to a location on or near to an optical axis and said area is line-scanned to take out an electric signal to be used for evaluating the line width, while applying a calibration to the signal if necessary, thereby detecting the line width.

With an evaluation apparatus having such a configuration as described above, the present invention has suggested a method in order to inspect the wafer surface which has been processed by a processing apparatus, in which the evaluation apparatus is arranged in the proximity to the processing apparatus and further a controller (not shown) controls an overall operation of the evaluation apparatus to inspect only a region consisting of a predetermined one area or a plurality of predetermined areas on the wafer surface so that an inspection time may be made approximately equal to a processing time per wafer by said processing apparatus. In this control, at first the wafer is secured to the evaluation apparatus, and then minimal required evaluation parameter of a wafer and a processing time required for each wafer are input to the controller of the evaluation apparatus. The evaluation parameter includes, for example, a fluctuation of a minimum line width in the case of the processing apparatus being a lithography apparatus and a defect inspection in the case of the processing apparatus being an etching apparatus. Subsequently, the controller determines an evaluation area on the wafer based on the entered evaluation parameter and the entered processing time required so that the time required per wafer for evaluating a processed condition of the wafer may be made within or approximately equal to the processing time required per wafer.

Since the inspection is only applied to the predetermined area and inevitably the range of movement of the wafer 33-11 within the evaluation apparatus should be made smaller, therefore a floor area of the evaluation apparatus can be reduced in comparison to the case where the inspection is applied to the entire area on the wafer. Further, since the evaluation time has been made approximately equal to the processing time, therefore if any defect is found out, it will be more easier to find out any irregular operation in the processing apparatus corresponding to the defective condition.

A second mode for implementing an evaluation apparatus according to the eleventh embodiment of the present invention will now be described. In this second mode, the evaluation apparatus of the first mode as shown in FIG. 45 has been used as a single unit of electron optical column, and the entire evaluation apparatus comprises eight units of electron optical columns arranged in an array of 4×2 (4 electron optical columns in the X-axis direction and 2 electron optical columns in the Y-axis direction) as shown in FIG. 46, thus constituting the evaluation apparatus.

As having been discussed in conjunction with the first mode, the outer diameter of the condenser lens 26-11 and the objective lens 31-11 could have been reduced to about 40 mm, and thereby the outer diameter of the electron optical column could have been reduced to about 42 mm. Accordingly, with the electron optical column having the diameter of 42 mm, four electron optical columns may be arranged in a tight contact to each other along the X-axis on an 8-inch (about 203 mm) wafer with a total length of 189 mm (147 mm+42 mm) as shown in FIG. 46. Beside, as shown in FIG. 46, if the electron optical columns are also arranged in a tight contact to each other along the Y-axis so as to form the array of 4×2, totally 8 of the electron beams can be used for raster-scanning on the wafer surface all at once.

Figure 46:
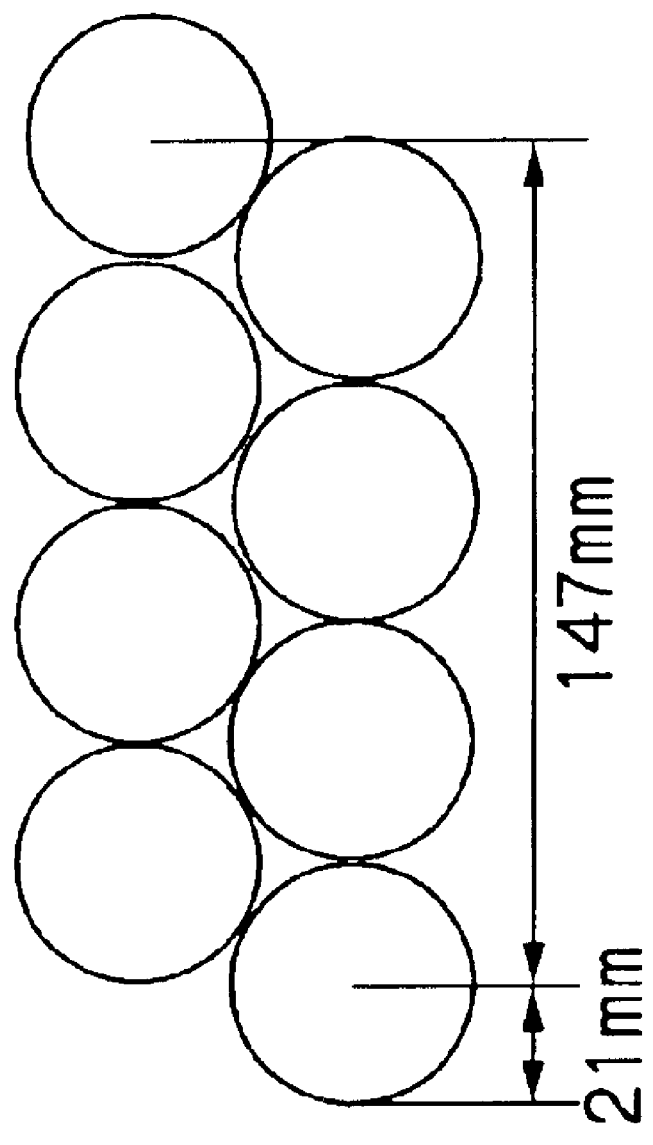
FIG. 46 is a diagram illustrating a locational relationship of electron optical columns for explaining a second example of an evaluation apparatus having a plurality of electron optical columns according to the eleventh embodiment of the present invention.

It is to be appreciated that the physical relationship among a plurality of electron optical columns and the number of the electron optical columns are not limited to those shown in FIG. 46, but of course, M×N array may be employed (M and N are integers selected arbitrarily). In that case, they are required to be arranged such that the optical axes of those electron beams are equally spaced along the X-axis.

Even in the second mode employing a plurality of electron optical columns, similarly to the fist mode, the evaluation apparatus is arranged in the proximity to the processing apparatus and further a controller (not shown) controls the operation of the evaluation so that the inspection time may be made approximately equal to the processing time required for each wafer by said processing apparatus. In this case, since the inspection time has been made shorter by employing a plurality of electron optical columns, therefore the entire area on the wafer may be determined to be the region subject to inspection if the processing time allows to do so. Alternatively, some of the wafers may be applied with a full-face inspection and the other may be applied with no inspection. The point is that the inspection condition should be set such that the processing time per a wafer or per a lot may be made approximately equal to the inspection time therefor.

With the second mode also, since the range of movement of the stage on which the wafer is loaded should be made smaller, therefore a floor area of the evaluation apparatus can be reduced. Further, since the throughput of the evaluation apparatus is made approximately equal to the throughput of the processing apparatus, if a defect is found out, it will be much easier to find out an abnormal operation in the processing apparatus.

Besides, upon evaluating a processed condition in a processing apparatus with an especially shorter processing time, a sampling inspection on the basis of one for every two wafers or one for every three wafers may be applied so as to make the evaluation time required per a lot approximately equal to the processing time required a per lot.

According to the evaluation apparatus of eleventh embodiment which has been configured as described above, the miniaturization of an evaluation apparatus for a wafer of a semiconductor device can be accomplished, while the throughput of the evaluation apparatus can be matched with the throughput of the processing apparatus. Thereby, at the point of detection of a wafer having a defect, a real time checking of the operation can be applied to the processing apparatus and it may reduce a fear that the processing apparatus would continue to manufacture defective wafers undesirably.

Twelfth Embodiment

Figure 47:
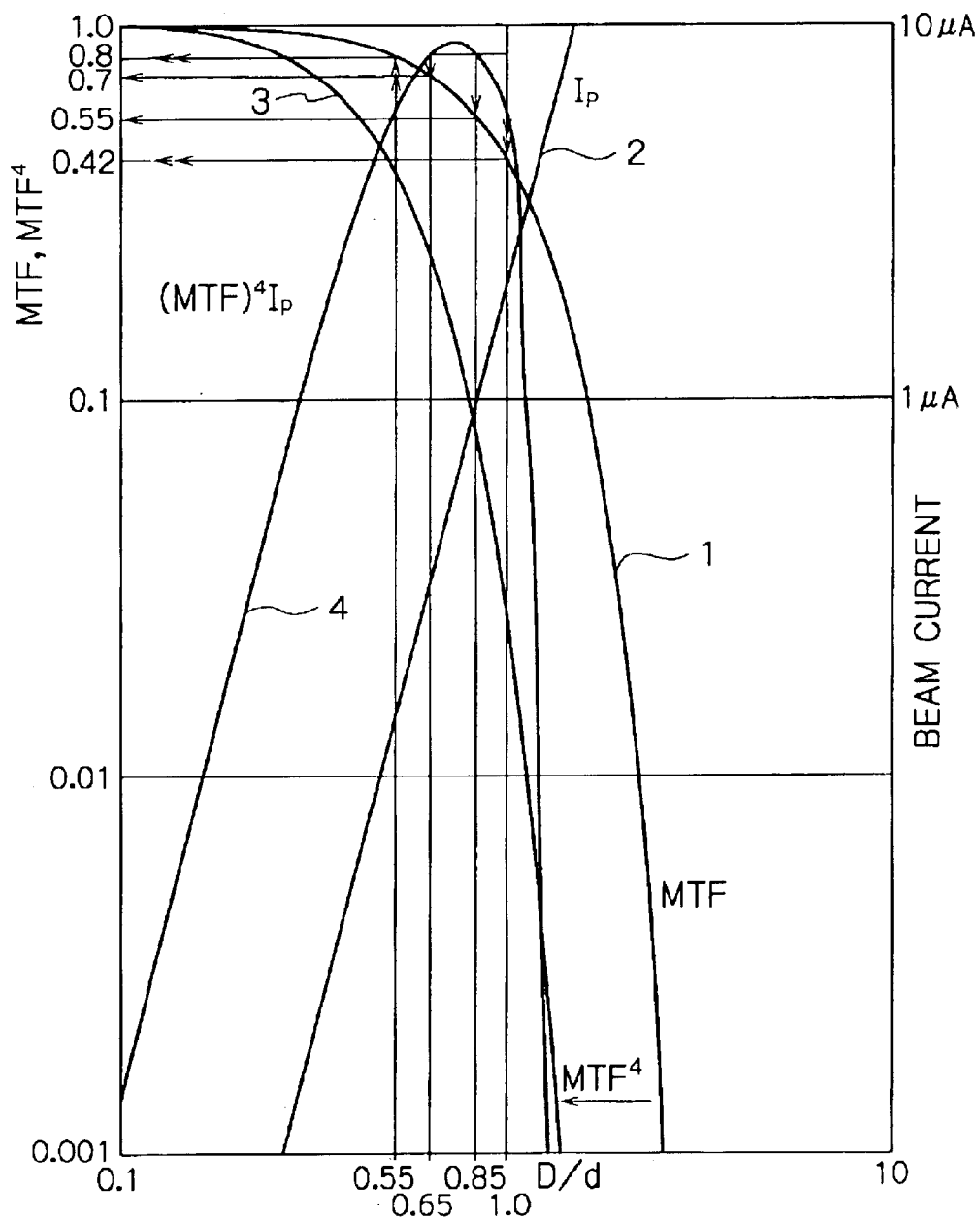
FIG. 47 is a graph indicating a relationship among MTF, $(MTF)^2$, $I_p$, $(MTF)^4 I_p$ and D/d according to a twelfth embodiment.
Figure 48:
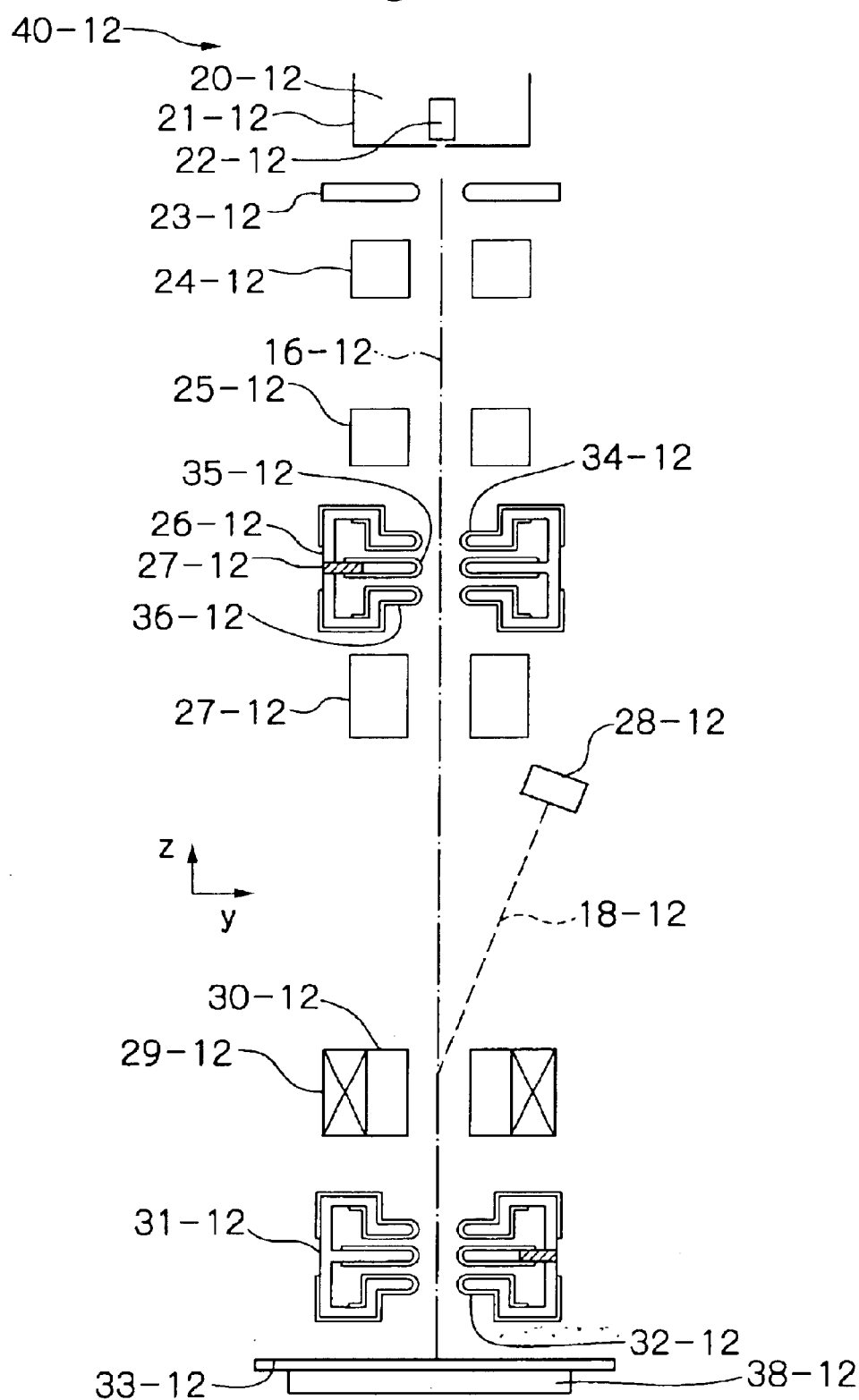
FIG. 48 is a block diagram illustrating a schematic configuration of an optical system in an electron beam apparatus according to the twelfth embodiment of the present invention.

A twelfth embodiment of the present invention will now be described with reference to the drawings. FIG. 47 is a graph indicating relationships of MTF, (MTF)$^2$, $I_p$, and (MTF)$^4 I_p$ as a function of D/d, while FIG. 48 is a block diagram illustrating a general configuration of an optical system of an electron beam apparatus of the scanning type according to the twelfth embodiment. As shown in FIG. 48, the electron gun 20-12 comprises a TFE cathode 22-12 to be located within a Wehnelt 21-12 and an anode 23-12 to be located outside to the Wehnelt 21-12, in which an electron beam is emitted from the TFE cathode 22-12 toward the anode 23-12 and the electron beam, after passing through the anode 23-12, is axially aligned by axially aligning deflectors 24-12 and 25-12 so as to pass through a condenser lenses 34-12, 35-12 and 36-12 at the central locations thereof.

The electron beam converged by the condenser lenses 34-12, 35-12 and 36-12 forms a crossover on a deflection center of an E×B separator 30-12 and the beam is further focused on a sample 33-12 by an objective lens 31-12. The electron beam scans a surface of the sample 33-12 with an aid of an electrostatic deflector 27-12 to be located beneath the condenser lens and an electromagnetic deflector 29-12 to be located over the E×B separator 30-12. A secondary electron beam emitted from a point of scanning on the sample 33-12 is accelerated by an electric field generated by the objective lens 31-12, where the beam is further converged to be narrower and passes through the objective lens 31-12. The converged secondary electron beam is deflected by the E×B separator 30-12 disposed right above the objective lens 31-12, into the direction indicated by the dotted line so as to be separated from the primary electron beam, and then the secondary electron beam is detected by the secondary electron detector 28-12 to be converted into an image signal.

In the electron beam apparatus of FIG. 48, a defect inspection of a sample may be performed in such a way that the electron beam scans the surface of the sample 33-12 with a width of 200 μm in the x-direction (vertical direction in page space of FIG. 48) while the stage 38-12 being successively moved in the y-direction. When the defect inspection with the width of 200 μm has been finished up to an end along the y-direction on the sample (a limited region), the stage 38-12 is moved in the x-direction by only 201 μm to inspect an adjacent stripe (an adjacent region). Because the stage has been moved by 1 μm more than the width of the limited region, there would be a region of 1 μm remained not-inspected, but this can eliminate any overlaps of the scanning regions and prevent a damage to the sample. Further, the damage to the sample can be minimized by no electron beam radiated onto the sample during no date of the electron beam scanning being taken in.

Although in the above case, there is a not-inspected region of 1 μm remained due to avoiding the scanning regions overlapping one on the other, the area for non inspected region is only 0.5%, which would not be a big problem. The ratio of this not-inspected region can be further reduced to 0.05% by reducing a distortion in scanning and feeding back accurately a yaw and/or snaking of the stage 38-12 to the beam position.

Figure 49:
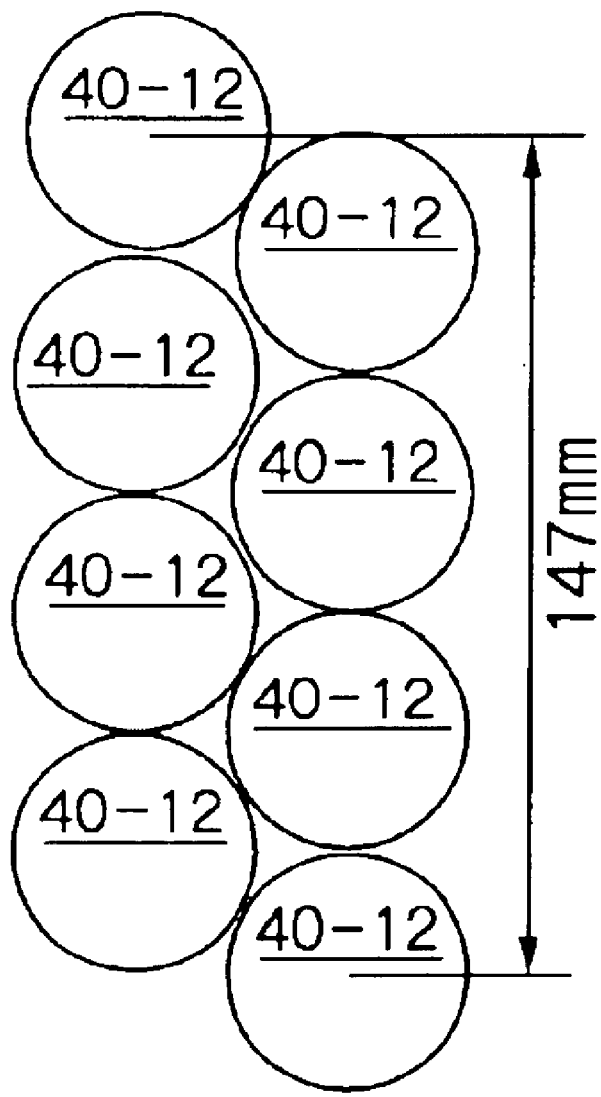
FIG. 49 is a diagram illustrating an arrangement of a multi-optical column comprising a plurality of electron optical columns, which is a variation of the electron optical column 40 in the electron beam apparatus of FIG. 47.

FIG. 49 is an arrangement plan for a multi-optical column comprising a plurality of electron optical columns, each of which being a variation of the optical column 40-12 of the electron beam apparatus of FIG. 48. The multi-optical column of FIG. 49 is composed of a plurality of optical columns 40-12 arranged on a 8-inch wafer, which has been accomplished by reducing an outer diameter of each electron optical column by employing an axially symmetric lens made of insulating material with a metal coating applied to the surface thereof in the electron beam apparatus of FIG. 48. FIG. 49 shows an arrangement of a plurality of electron optical columns 40-12 in an array of 4 rows×2 columns. In the case of FIG. 49 where a plurality of electron optical columns 40-12 are used, a scanning width of an adjacent electron optical column is adjusted similarly to the case of FIG. 48, so that any overlapping between scanning regions may be prevented. Besides, damage to the sample can be minimized by irradiating no electron beam onto the sample during no data of the electron beam scanning being taken in.

FIG. 47 is a graph indicating relationships of a modulation transfer function MTF, (MTF)$^2$, a beam current $I_p$, and (MTF)$^4 I_p$ as a function of D/d, when an electron beam having a beam diameter of D was used to scan a cyclic pattern with a pitch of 2d on a sample. In FIG. 47, the curve 1 shows a relationship between the MTF and the D/d (dependence) where the intensity distribution of the electron beam with the beam diameter of D is assumed to be in the Gauss distribution. In FIG. 47, the curve 2 shows a relationship between the beam current $I_p$ and the D/d. The curve 3 shows a value (MTF)$^4$ representing the fourth power of the MTF.

In the electron beam apparatus, assuming that "$I_p$" denotes the beam current of the primary electron beam, "t" denotes a time period required for scanning one pixel, and "e" denotes an elementary charge, then the S/N ratio can be expressed by the following equation (1) (Shinada, et al. "Proceeding of LSI testing symposium/2000", p.151, Nov. 9–10, 2000).

$$S/N = (I_p \cdot t)^{1/2} / [3(2e)^{1/2}] \tag{1}$$

Assuming that since the beam diameter being finite, the signal contrast is reduced by (MTF) times upon scanning the cyclic pattern with the pitch of 2d, then the equation (1) may be modified to the following equation (2).

$$S/N = (I_p \cdot t)^{1/2} \cdot (MTF) / [3(2e)^{1/2}] \tag{2}$$

On the other hand, a dose "C" representing an irradiation quantity per unit area is expressed by the following equation (3).

$$C = I_p \cdot t \tag{3}$$

The measurement time "t" can take a small value if the S/N ratio is high, while if the S/N ratio is low, the measurement time "t" must take a large value, or no required image should be obtained. It has been know from the information theory that the measurement time "t" is in inverse proportion to (S/N)$^2$, that is, t ∝ 1/(S/N)$^2$. Accordingly, the equation (3) can be expressed by the following formula, $$C \propto I_p / (S/N)^2 t \tag{3'}$$

In general, the dose C is required to be small from the viewpoint of preventing a break of a gate oxide, while the measurement time "t" is required to be reduced in order to increase the throughput. To satisfy both of these two requirements, it is only required to minimize a product of (dose C)×(measurement time t), and accordingly an inverse of the product "Q", i.e., $$Q = 1/[(\text{dose } C) \times (\text{measurement time } t)]$$

should be maximized.

Substituting the equation (3') and said measurement time $t \propto 1/(S/N)^2$, then;

$$Q=(S/N)^4/I_p$$

Substituting the equation (2), then $$Q=[(I_p \cdot t)^{1/2}/[3(2e)^{1/2}]]^4 (MTF)^4/I_p$$

$$Q=[(I_p)^2 \cdot t^2/[81 \times 4e^2]](MTF)^4/I_p$$

$$Q \propto (MTF)^4 \cdot I_p \qquad (4)$$

From the preceding, in the present invention, a requirement for minimizing the break of the gate oxide as well as maximizing the throughput is to maximize the $(MTF)^4 \cdot I_p$.

In FIG. 47, the curve 1 shows a relationship between the MTF and the D/d (dependence) where the intensity distribution of the electron beam with the beam diameter of D is assumed to be in the Gauss distribution. In FIG. 47, the curve 2 shows a relationship between a relative value of the beam current $I_p$ and the diameter D of the electron beam. The curve 3 shows a value $(MTF)^4$ representing the fourth power of the MTF represented by the curve 1. Assuming that the value Q in the formula (4) is a product of the $(MTF)^4$ and $I_p$, that is, $Q=a (MTF)^4 \cdot I_p$, then the curve 4 is formed. The curve 4 has a maximum value when the D/d is 0.75 and it exhibits a sudden dropping once the D/d is out of 0.75.

The Q has a value proximal to the maximum value of Q when the D/d is in a range of 0.65 to 0.85, and the range of the MTF corresponding thereto is 0.55 to 0.7. Further, if the D/d is in a range of 0.55 to 1.0, the Q appears still favorable without departing so far from the maximum value of Q, wherein the MTF value is in a range of 0.42 to 0.8. See what indicated by the arrows of FIG. 47. Accordingly, if the beam diameter is determined so that the D/d is in the range of 0.55 to 1.0, then the S/N ratio (signal/noise) may be maximized.

Although above description has been made to the case of forming a plurality of electron beam by using a single electron gun and a multi-aperture plate, a similar simulation may be applicable even to the case where a single optical system is used to project the electron beams emitted from a plurality of electron guns onto the surface of the sample, because the electron beam emitted from the plurality of electron guns form crossovers. Further, in the case of a single beam, since the space-charge effect is not great and the beam current $I_p$ is in proportion to (beam diameter D)$^{8/3}$ if the spherical aberration is superior, therefore it can be shown by the curve 2 of FIG. 47.

The electron beam apparatus according to the twelfth embodiment of the present invention can make the dose doubled without giving any damage to the gate oxide, as compared to an electron beam apparatus permitting a duplicated scanning. Besides, the dose can be increase by 10 to 20% by irradiating no electron beam during no data being taken in. Further, in the electron beam apparatus of the present invention, since a point of compromise could have been found for reducing the dose and also for increasing the throughput, the higher throughput can be obtained without giving any damage to the gate oxide. Further, according to the present invention, a duplicated scanning region can be eliminated even in the case of the multi-optical column. Still further, according to the present invention, an optimal value of (D/d) can be made known for either of the case where a single beam is used or the case where a plurality of beams is used, and thereby problems including too low beam current and too small MTF can be solved.

Thirteenth Embodiment

An evaluation apparatus according to a thirteenth embodiment will now be described with reference to the drawings.

Figure 50:
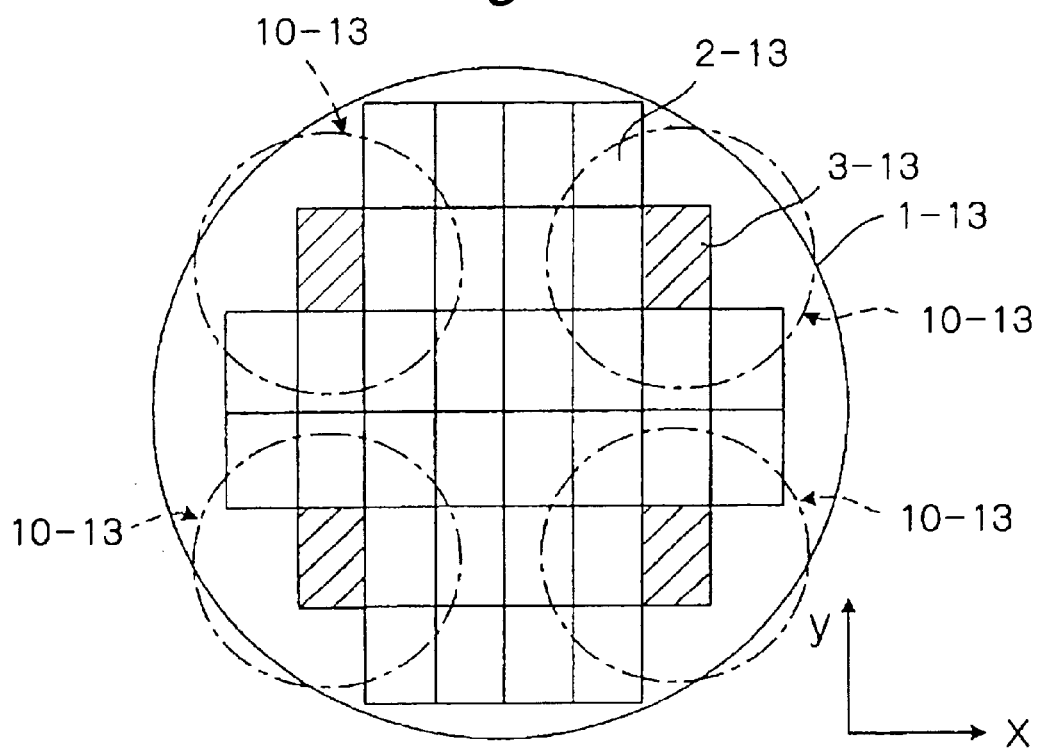
FIG. 50 is a diagram illustrating a method for evaluating a sample according to a thirteenth embodiment of the present invention.

FIG. 50 is a plan view of a silicon wafer 1-13 having a plurality of chips (or dies) formed thereon and in specific, 36 chips have been formed on the wafer in total. According to this embodiment, an evaluation such as a defect inspection is applied only to four chips with hatching 3 among those chips but the evaluation may be omitted to the remaining 32 chips 2-13, thus the evaluation procedure for one piece of wafer being completed.

Figure 51:
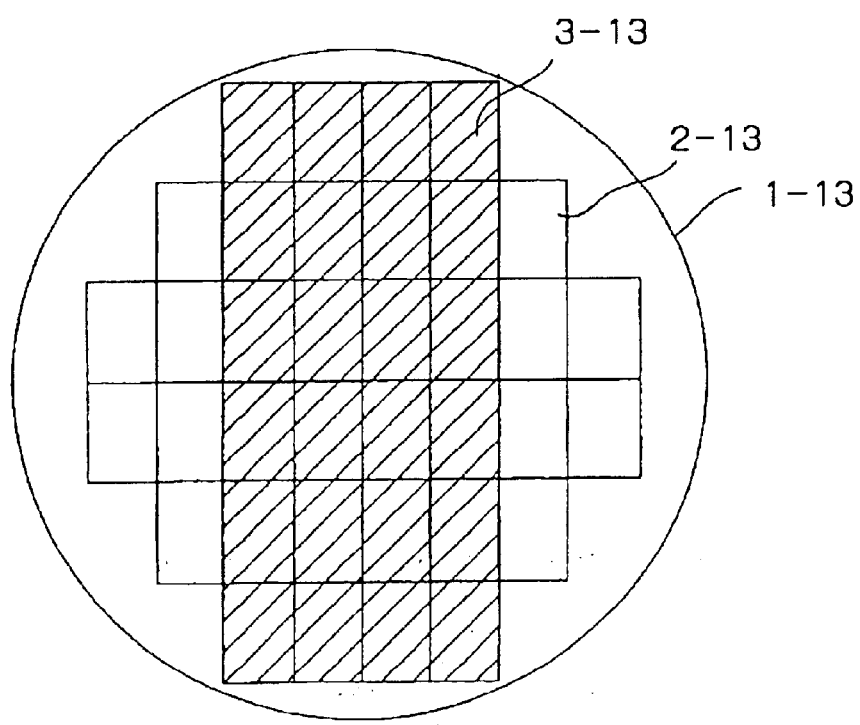
FIG. 51 is a diagram illustrating a conventional method for evaluating a wafer, in the thirteenth embodiment of the present invention.

In contrast, in an evaluation method according to the prior art, for a wafer having the same number of chips, the evaluation has been made to 24 chips located in the central portion of the wafer as indicated similarly with hatching in FIG. 51 but the evaluation has been omitted to the remaining 12 chips, thus the evaluation procedure for one piece of wafer having been completed. In this way, since a large number of chips had to be evaluated, the evaluation time of about 7 hours has been required for each wafer. In that case, since the evaluation has been conducted while moving the XY stage successively in the Y direction with the wafer loaded thereon, the XY stage must have a high degree of precision, while the extensive movement of the XY stage has made the sample chamber larger and thus a large area of footprint therefor has been required.

To the contrast, according to the present invention, as illustrated schematically in FIG. 50, four optical columns 10-13 are arranged in total on the basis of one for each location of said four chips so that the inspection can be conducted with one optical column for one chip. Owing to this, the XY stage with the wafer loaded thereon is only required to move by a distance equivalent to one chip in the step and repeat method. Accordingly, since the movement of the XY stage can be reduced and thus the sample chamber can be made smaller, and also the XY stage is no more required to move successively, the stage can be manufactured at a low cost.

Figure 52A:
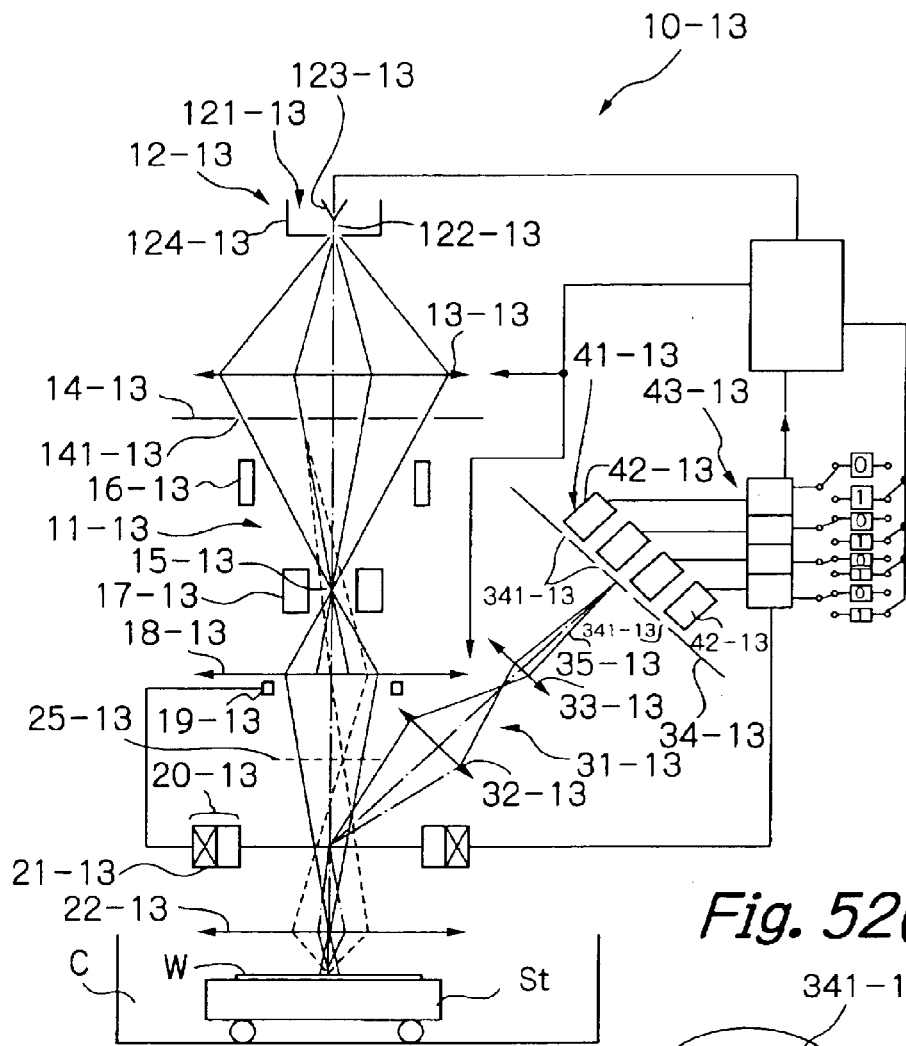
FIG. 52 is schematic diagram illustrating an electron beam apparatus of an evaluation apparatus according to the thirteenth embodiment of the present invention.
Figure 52B:
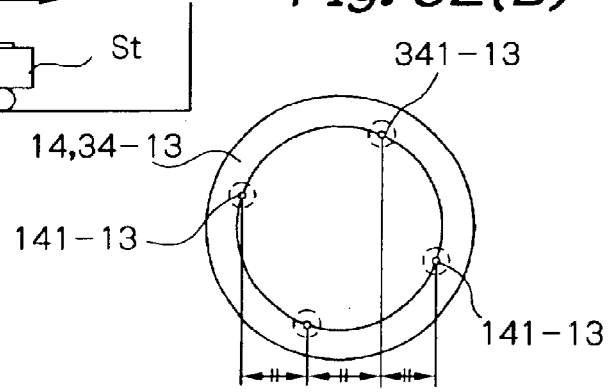

FIG. 52 shows schematically the interior of the optical column 10-13 of the electron beam apparatus according to the thirteenth embodiment. In FIG. 52, the electron beam apparatus of the present embodiment comprises a primary electron optical system (hereafter referred to as a primary optical system for simplicity) 11-13 and a secondary electron optical system (hereafter referred to as a secondary optical system for simplicity) 31-13, and a detecting system 41-13 for detecting secondary electrons.

The primary optical system 11-13 is such an optical system that radiates an electron beam onto a top surface of a wafer S, and comprises an electron gun 12-13 for emitting an electron beam, a condenser lens 13-13 for converging the electron beam emitted from the electron gun 12-13, an aperture plate 14-13 having a plurality of small apertures formed therethrough, a reducing lens 18-13 for converging the electron beam, an axial aligning deflector 16-13, an astigmatic correcting lens 17-13, a lens 18-13, a scanning deflector 19-13, an E×B type separator 20-13, and an objective lens 22-13, which are sequentially arranged with the electron gun 12-13 in the topmost level as shown in FIG. 52, and which are arranged such that an optical axis of the electron beam emitted from the electron gun may be perpendicular to the surface of the wafer W. The electron gun 12-13 has been made in such a manner in this embodiment, in which a field-emission chip 122-13 of W-Zr has been attached to a filament 123-13 by spot-welding to form a cathode 121-13 with a tip portion of the field-emission chip 122-13 of the cathode being protrusive over a Schottky shield 124-13 by a small degree. With this structure, this electron gun has been adapted to emit five electron beams. Since the structure and the function for each of the other devices contained in the primary optical system may be of well known types in the prior art, description therefor will be omitted. The aperture plate 14-13 includes four apertures 141-13 formed therethrough, which are located on a circle around a center of the optical axis so as to be equally spaced from the optical axis. The arrangements of the apertures 141-13 are shown by four small circles of solid line in FIG. 52[B]. It is to be noticed that a reference numeral 21-13 designates a magnetic field generation coil for the E×B separator. The secondary optical system 31-13 works to send the secondary electron beam separated from the primary optical system by the E×B separator of the primary optical system, to the detecting system, and comprises magnifying lenses 32-13, 33-13 and a multi-detecting plate 34-13. The detecting system 41-13 comprises a set of detectors 42-13 each being arranged so as to correspond to each aperture of the multi-detecting plate 34-13, and a set of processing devices 43-13 each being connected to each of the set of detectors on one to one basis. The multi-detecting plate 34-13 also includes four apertures 341-13 located on the same circle corresponding to the apertures of the aperture plate 14-13 of the primary optical system, each of those apertures 341-13 having been made larger than the aperture 141-13 of the aperture plate 14-13 as indicated by a broken line in FIG. 52[B]. The apertures 341-13 of the multi-aperture plate 34-13 has been formed such that images of four secondary electron beams generated by four electron beams may be approximately matched to their centers. It is to be noticed that St designates a stage carrying the wafer thereon and C designates a sample chamber.

In this electron beam apparatus 10-13, five electron beams emitted from the electron gun 12-13 are converged by the condenser lens 13-13 so as to form a crossover at a point 15-13. Although one matching to the optical axis among five electron beams having passed through the condenser lens is interrupted by the aperture plate 14-13, the remaining four electron beams are advanced toward the reducing lens 18-13 through respectively corresponding apertures 141-13. Four of these electron beams are contracted by the reducing lens 18-13 to form reduced images on a plane 25-13 and further form images on the surface of the wafer W though the objective lens 22-13.

The secondary electron beams emitted from respective points on the wafer are accelerated by the objective lens 22-13, separated from the primary optical system 11-13 by the E×B separator 20-13 and advanced to the secondary optical system 31-13. These secondary electron beams are formed into images respectively on the locations of the aperture plate 34-13 through the magnifying lenses 32-13, 33-13. Since to the set of detectors arranged adjacent to those respective apertures of the multi-aperture plate 34-13 has been applied a high voltage of about 20 kV, any secondary electron beam approaching to the aperture is forced to pass though the apertures. One typical orbit of such secondary electron beam is indicated by the reference numeral 35-13. The image of the secondary electron beam formed in the aperture 341-13 is detected by the corresponding detector 42-13 and then processed by the corresponding processing device 43-13.

This embodiment, in order to arrange a plurality of electron optical columns facing to an 8-inch or 12-inch wafer, has employed an optical component made of ceramic with a metal coating applied to a surface thereof, thus downsizing an outer diameter of the optical column. A vacuum envelope which is made of permalloy and functions also as a magnetic shield have been arranged outside to the plurality of optical columns so as to circumscribe them. A typical ceramic deflector will now be described with reference to FIG. 53.

Figure 53A:
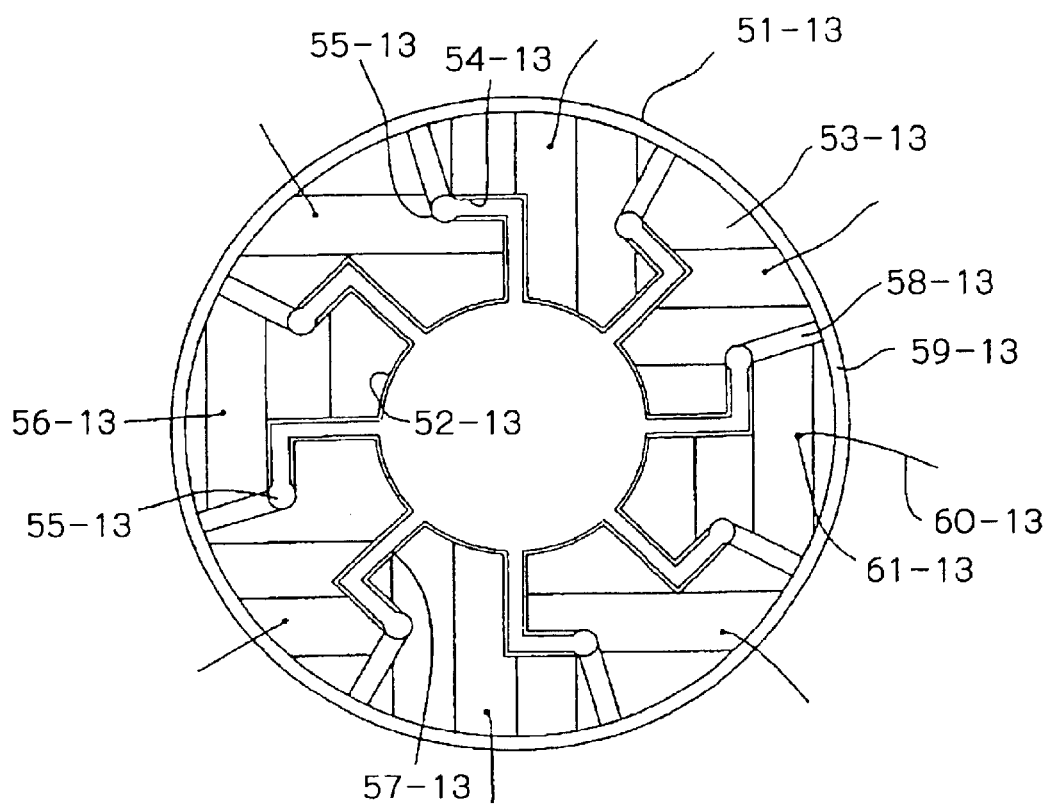
FIG. 53 is a diagram illustrating an electrostatic deflector made of ceramic with a surface treatment applied thereto, an axially symmetric lens or an astigmatic correcting lens, wherein [A] is an end view of the electrostatic deflector or the axially symmetric lens and [B] is a cross sectional view of the axially symmetric lens.
Figure 53B:
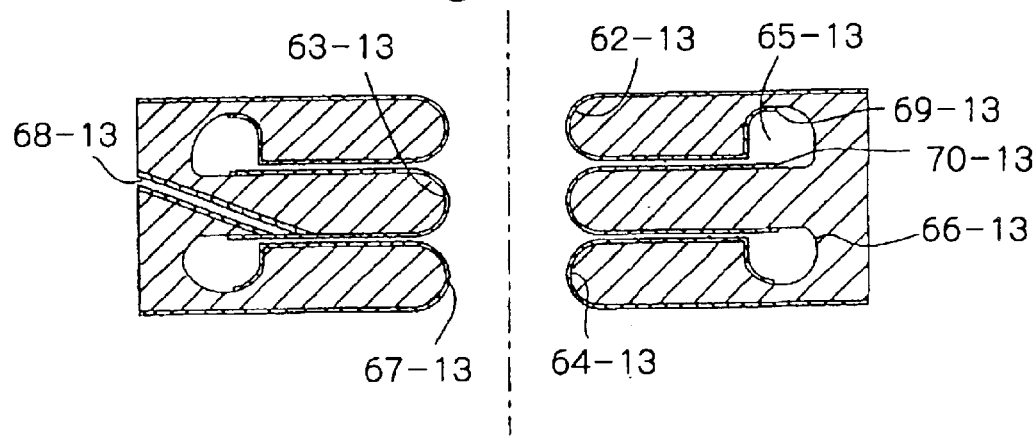

FIG. 53[A] is an end view of an electrostatic deflector or an astigmatic correcting lens. A pipe-shaped component of ceramic having an outer face 51-13, an inner face 52-13 and an end face 53-13 has been provided with a slit 57-13 for separating electrodes and a treatment of electroless plating and electroplating with metal (NiP, platinum) is applied thereto excluding faces 58-13. 59-13, where no plating should be applied for insulation. Then, a through-hole 55-13 has been formed in parallel with the optical axis. Lastly, a lead 60-13 made of aluminum has been connected to the component by wire bonding as indicated by 61-13.

FIG. 53[B] is a cross sectional view of an uni-potential lens implementing an axially symmetric lens. To an upper electrode 62-13 and a lower electrode 64-13 is applied a voltage proximal to the ground while to a central electrode 63-13 is applied a high voltage or a high negative voltage. A cavity 65-13 has been arranged as a structure for providing a spacing between metal coated edges 69-13 and 70-13 thus to avoid an electric discharge therebetween. The cavity 68-13 is a channel for applying the high voltage to the central electrode 63-13 and an inner face thereof has been provided with a metal coating.

According to the thirteenth embodiment of the present invention, the following effects may be brought about.

(A) Since only a small number of chips are evaluated, an evaluation time per wafer can be reduced.

(B) By using a plurality of optical columns with a plurality of electron beams emitted from each electron optical column, an evaluation time can be reduced in inverse proportion to the number of beams.

(C) Since an electrostatic deflector and lens made of ceramic are employed, an outer diameter of an optical system can be reduced, so that a large number of optical systems can be arranged over one piece of sample.

Fourteenth Embodiment

Figure 54:
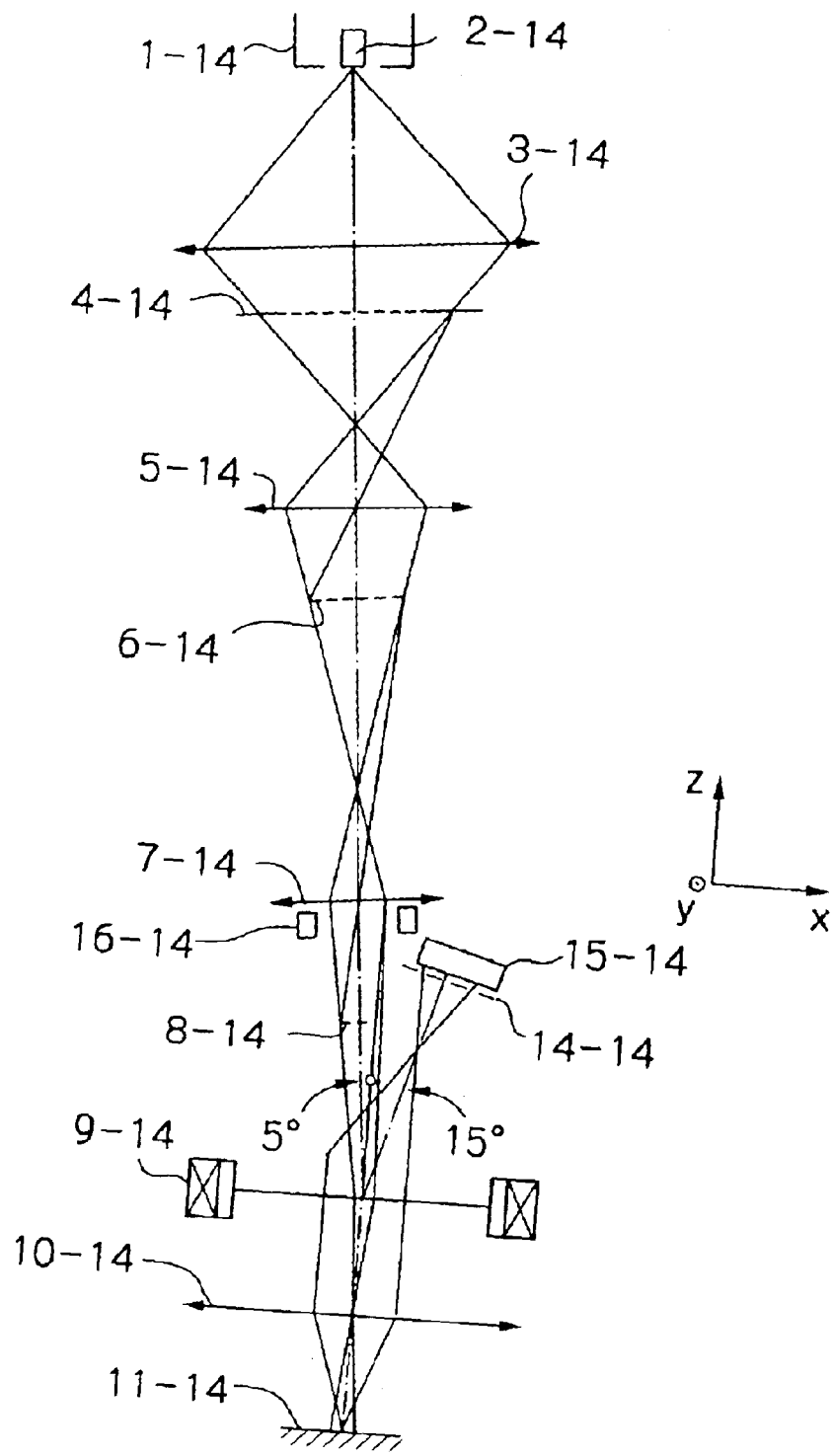
FIG. 54 is a schematic diagram illustrating an electron optical unit according to a fourteenth embodiment of the present invention.

FIG. 54 shows an electron beam apparatus according to the fourteenth embodiment of the present invention. A cathode 2-14 is disposed at a center of an electron gun 1-14, said cathode 2-14 being made of LaB$_6$ single crystal which has been processed to be a multi-emitter.

An electron beam emitted from the cathode is focused by a condenser lens 3-14 to form a crossover. A multi-aperture plate 4-14 is arranged between a lens 3-14 and the crossover so that each of apertures may be matched approximately to a location where each of the beams has a high intensity. The beam, after passing through the multi-aperture plate, is contracted first by reducing lenses 5-14, 7-14 and then by an objective lens 10-14 to be formed into an image on a surface of a sample 11-14 such as a semiconductor substrate. In FIG. 54, reference numerals 6-14 and 8-14 designate a first and a second contracted images, respectively.

An electron beam emitted from the sample surface 1-14 is converged to be narrower by an accelerating electric field generated by the objective lens 10-14, deflected by an E×B separator 9-14 to be separated from the primary optical system, passed through a multi-aperture detecting plate 14-14 having apertures located on the same circle, detected by a detector 15-14 and then a signal processing is applied thereto.

Figure 55:
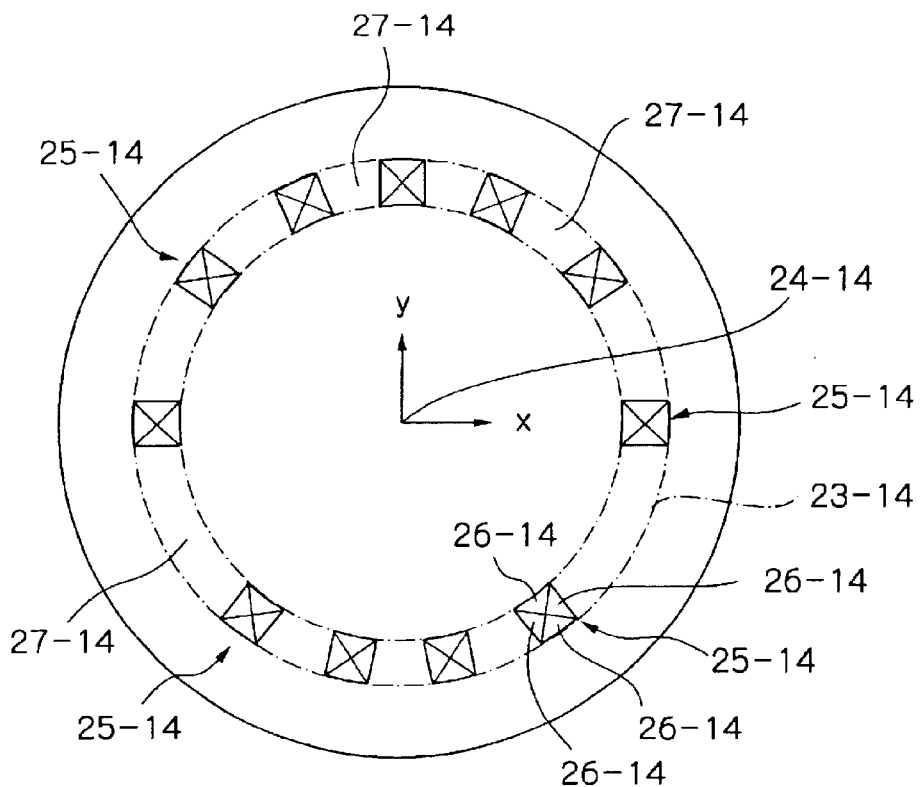
FIG. 55 is a plan view illustrating a tip portion of a mono-crystal $LaB_6$ cathode of an electron gun used in the electron optical unit of FIG. 54.
Figure 56:
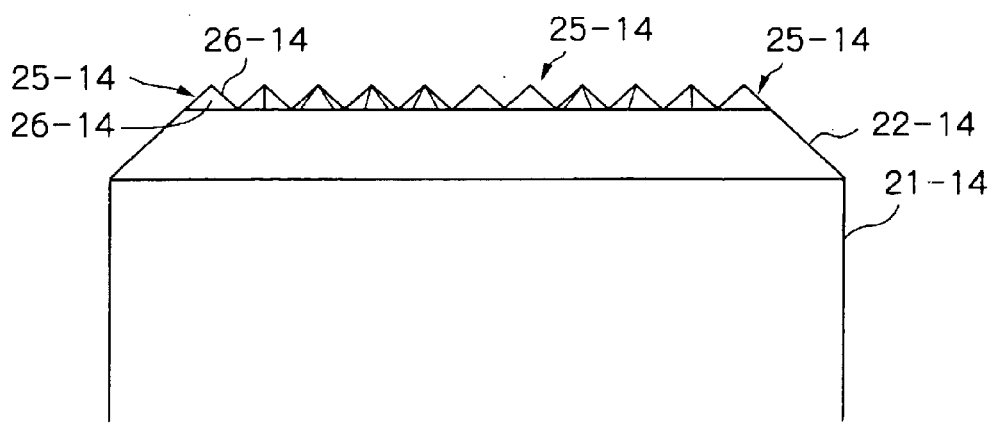
FIG. 56 is a side elevation view of the cathode of the electron gun used in the electron optical unit of FIG. 54.

A detailed geometry of a tip portion of the LaB$_6$ single crystal cathode 2-14 is shown in FIGS. 55 (a plan view) and 56 (a side view).

As illustrated, the cathode is generally made of $LaB_6$ circular cylinder of 2 mmφ, in which a tip portion thereof 22-14 has been cut at an angle of 45° with projections 23-14 triangular in sectional view remaining annularly on the tip face 24-14 along the periphery thereof, and said annular projections having been cut thus to form a plurality of projections or emitter regions 25-14, each being in the form of quadrangular pyramid having a slope of 45°. The emitter regions has been designed such that when they are projected on the line along the x-axis direction (the line in the direction along which the primary electron beam scans the sample) orthogonal to a centerline (identical with the optical axis of the primary electron optical system in this electron beam apparatus) of said tip face 24-14 viewed in FIG. 55, those projected emitter regions may be equally spaced along the line of the x-axis direction. In this design, in order to prevent any electrons from being emitted from regions between respective emitter regions and a region located in an inner side of the emitter regions on the tip face 24-14, there are sufficient differences provided in height between the tip portions of those emitters and said other regions.

According to the fourteenth embodiment of the present invention, an adequate multi-beam can be generated by a single electron gun. Further, since the field curvature can be almost completely corrected, more number of beams can be generated with the same aberration, and thereby throughput of an inspection apparatus can be significantly improved. Further, since the use of $LaB_6$ single crystal cathode enables an electron gun to be operated in a space charge limited region, a measurement with high S/N ration can be achieved.

Fifteenth Embodiment

Figure 57:
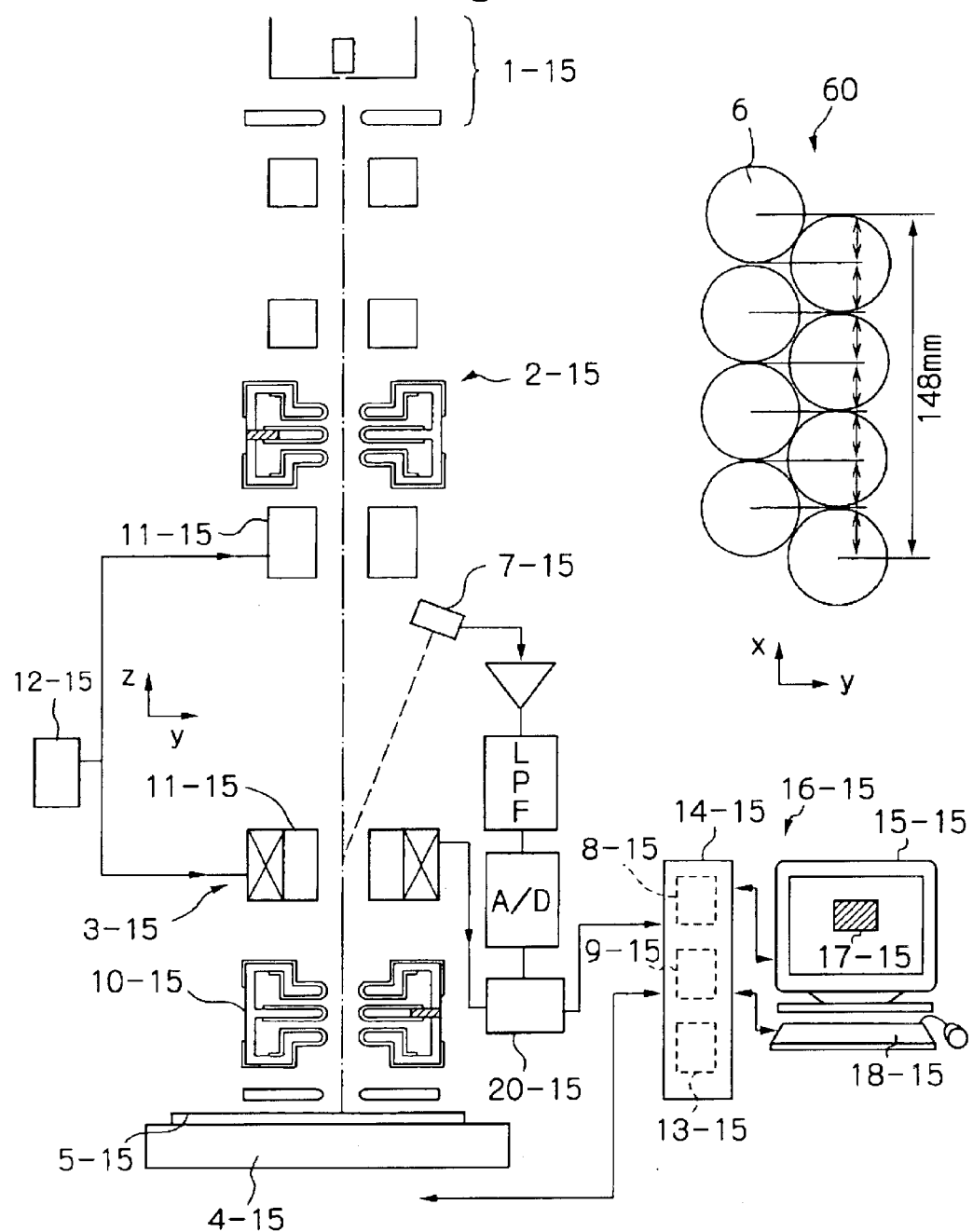
FIG. 57 is a schematic diagram illustrating a defect inspection apparatus according to a fifteenth embodiment of the present invention.

FIG. 57 shows a schematic diagram of a defect inspection apparatus according to a fifteenth embodiment of the present invention. This defect inspection apparatus is an inspection apparatus of, what is called, the multi-column type, which has been configured similarly to the electron beam apparatus 1-1. That is, the inspection apparatus has been configured so as to comprise an electron gun 1-15 for emitting a primary electron beam, an electrostatic lens 2-15 for deflecting and shaping the emitted primary electron beam, an E×B deflector 3-15 for forcing the shaped primary electron beam to be advanced straight ahead through a field where an electric field and a magnetic field are crossed at a right angle so as to impinge upon a semiconductor wafer 5-15 at an approximately right angle, an objective lens 10-15 for forming the deflected primary electron beam into an image on the wafer 5-15, a stage 4-15 installed in a sample chamber which can be evacuated to vacuum, though not shown, and allowed to move within a horizontal plane with the wafer 5-15 loaded thereon, a detector 7-15 for detecting a secondary electron beam emitted from the wafer 5-15 by the irradiation of the primary electron beam, and a control section 16-15 for controlling the overall apparatus and for executing a process of detecting a defect on the wafer 5-15 based on a secondary electron signal detected by the detector 7-15.

Further, a deflecting electrode 11-15 is interposed between the reducing lens 2-15 and the objective lens 10-15, for scanning the primary electron beam on the wafer 5-15. This deflecting electrode 11-15 is connected with a deflection controller 12-15 for controlling an electric field of said deflecting electrode. This deflection controller 12-15 is connected to the control section 16-15 and controls said deflecting electrode 11-15 so that the deflecting electrode 11-15 may generate the electric field in response to a command from the control section 16-15. It is to be noted that the deflection controller 12-15 may be implemented as a voltage controller for controlling a voltage to be applied to the deflecting electrode 11-15.

The detector 7-15 outputs the detection signal, and an image forming circuit 20-15 converts the signal into a secondary electron image.

The control section 16-15 may be constituted of a general-purpose personal computer and the like as shown in FIG. 57. This computer may comprise a control section main body 14-15 for executing a variety of controls and arithmetic processing according to a predetermined program, a CRT 15-15 for displaying a process result of the main body 14-15, and an input section 18-15 such as a key board or a mouse for enabling an operator to input a command, and, of course, the control section 16-15 may be built up of a hardware dedicated to a defect inspection apparatus, a workstation and the like.

The control section main body 14-15 comprises a variety of control boards, including a CPU, a RAM, a ROM, a hard disk, a video board and the like. A secondary electron image storage area 8-15 has been allocated on a memory such as the RAM or the hard disk for storing a digital image data of the secondary electron image for the wafer 5-15, which has been generated from the electric signal received from the detector 7-15. Further, on the hard disk, there is a reference image storage section 13-15 for storing beforehand a reference image data for the wafer having no defect. Still further, on the hard disk, in addition to the control program for controlling the whole unit of the defect inspection apparatus, a defect detection program 9-15 is stored for reading the secondary electron image data from the storage area 8-15 and automatically detecting a defect in the wafer 5-15 based on said image data according to the predetermined algorithm. This defect detection program 9-15, as will be described in more detail later, has such a function that it executes a matching operation of reference image read out from the reference image storage section 13-15 comparing with an actually detected secondary electron image in order to automatically detect any defective parts, so that it may indicate a warning to the operator when it determines there is the defect existing. In this operation, the secondary electron image 17-15 may be displayed on a display section of the CRT 15-15.

Figure 59:
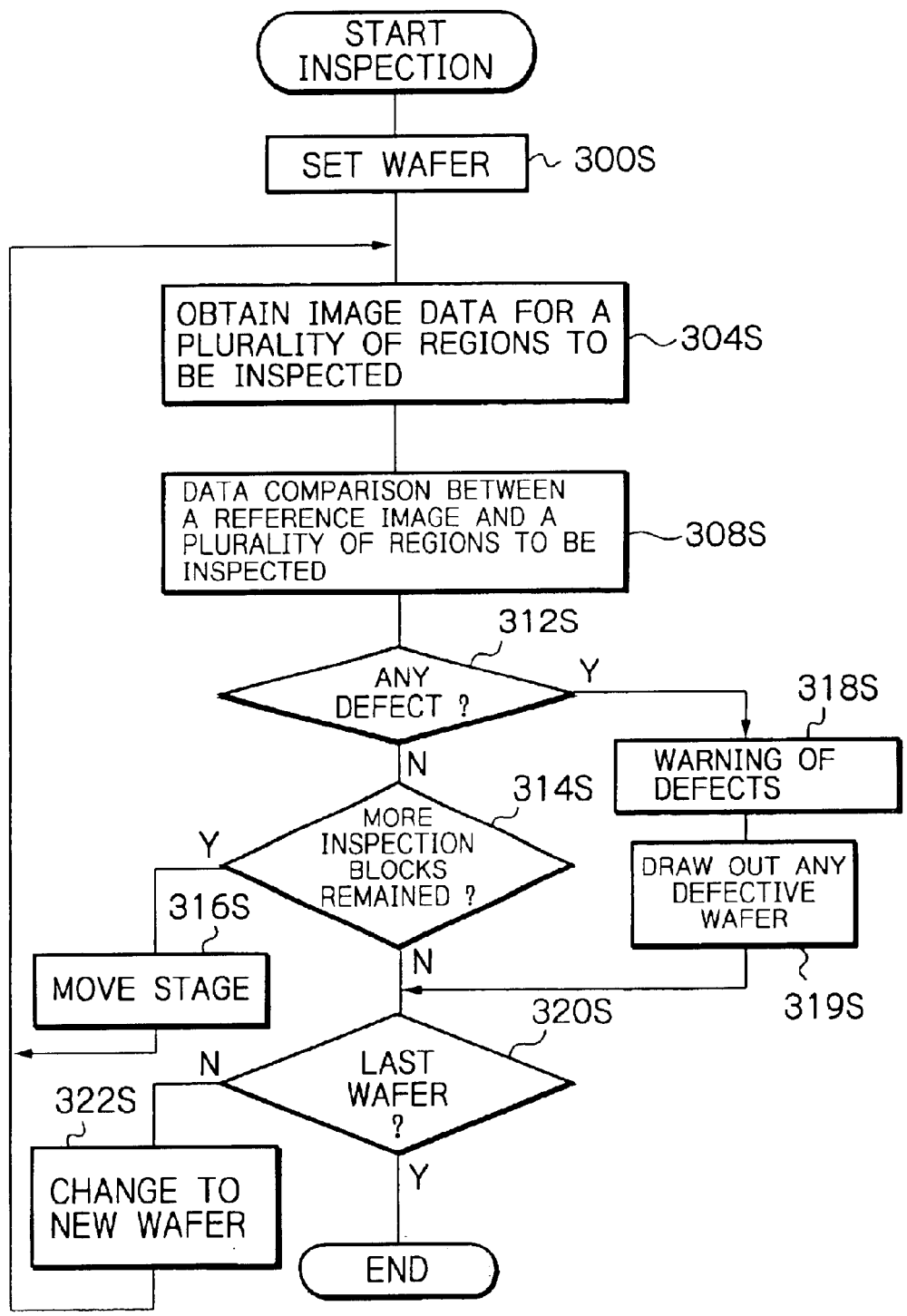
FIG. 59 is a flow chart illustrating a flow of a main routine of a wafer inspection in the defect inspection apparatus of FIG. 57.
Figure 60:
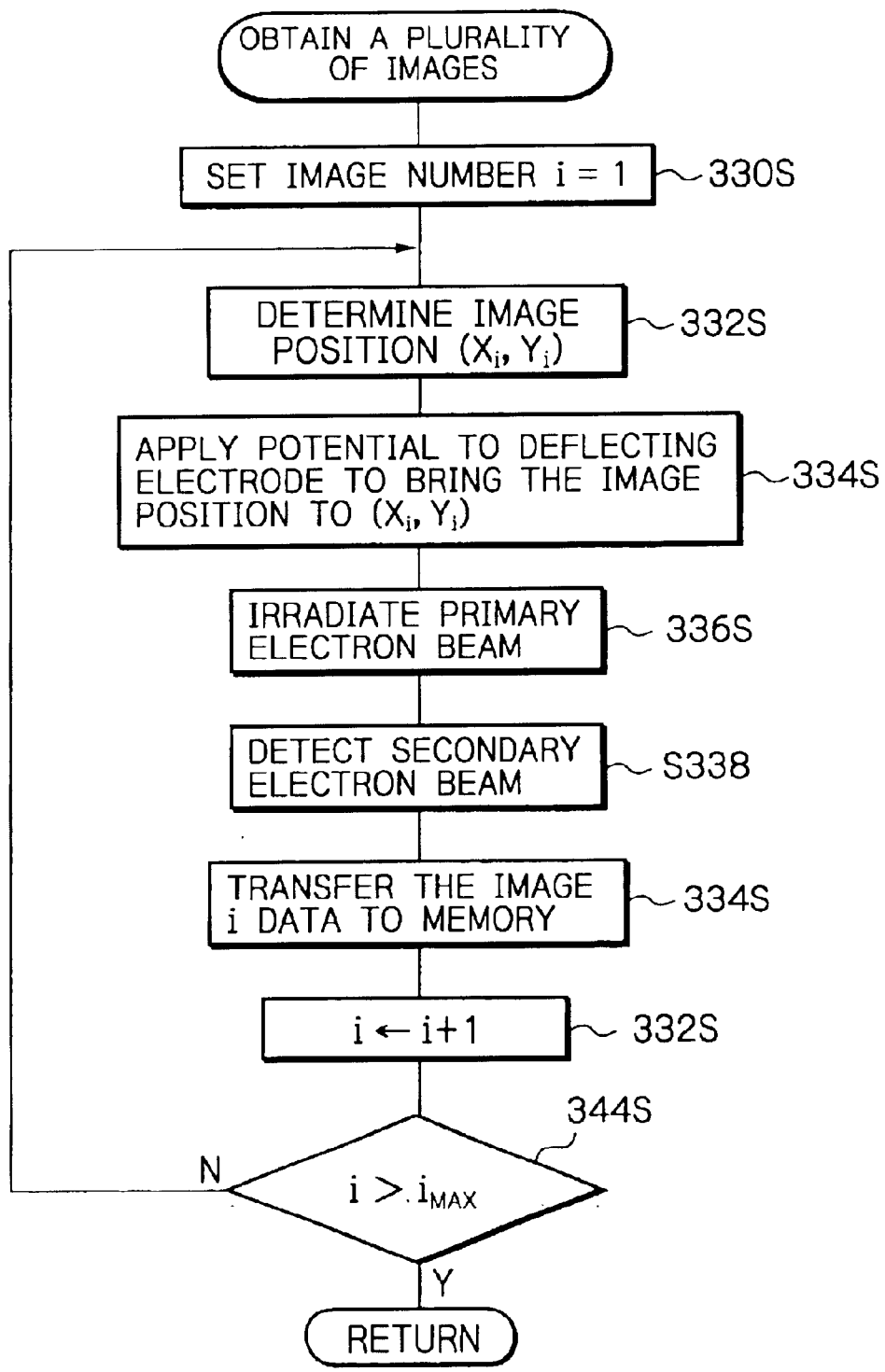
FIG. 60 is a flow chart illustrating a detailed flow of a sub routine of a process for obtaining data for a plurality of images to be inspected (step 304S) in FIG. 59.
Figure 61:
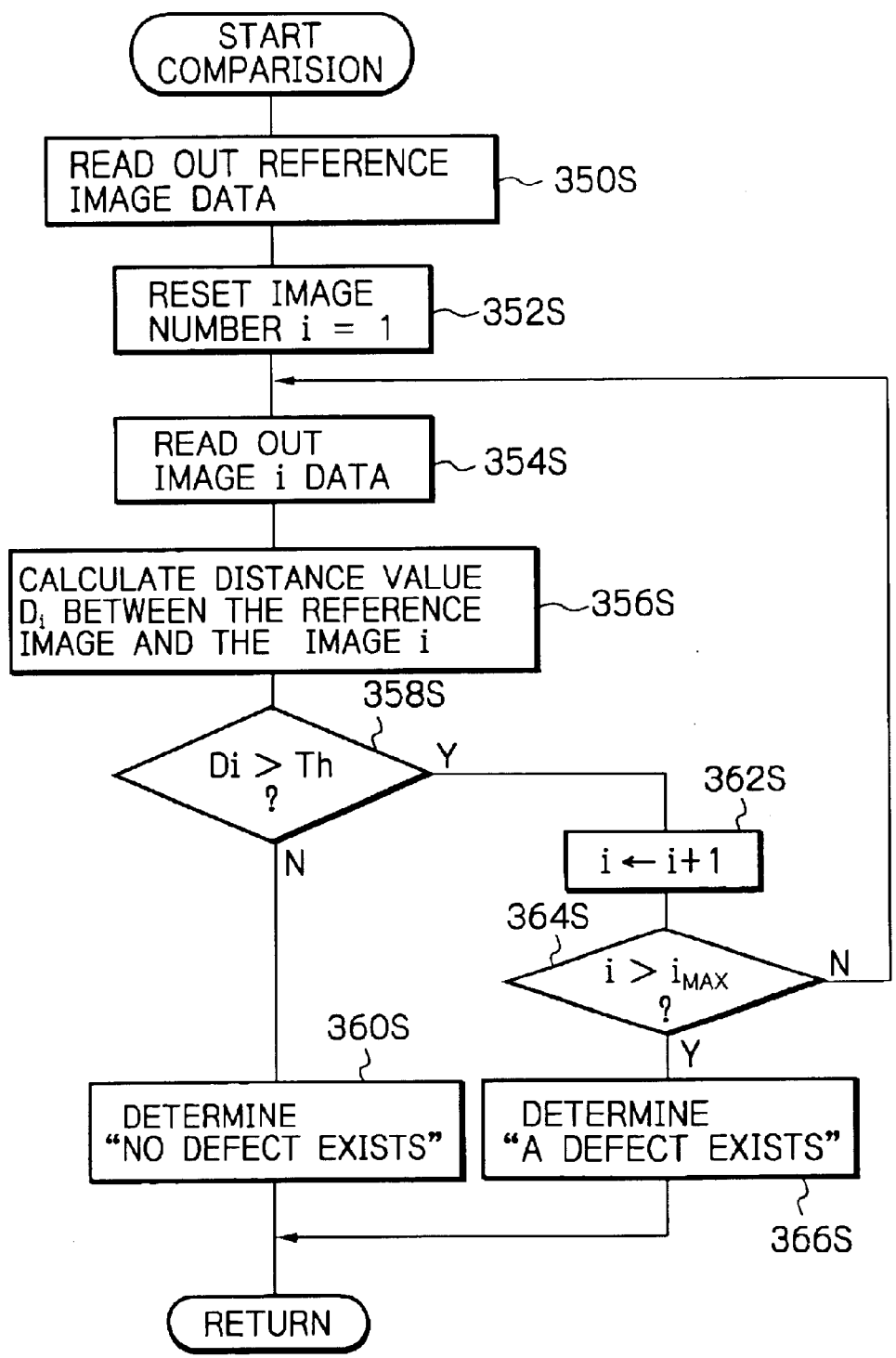
FIG. 61 is a flow chart illustrating a detailed flow of a sub routine of a comparing process (step 308S) in FIG. 59.

Then, an operation in the defect inspection apparatus according to the fifteenth embodiment will be exemplarily described referring to those flow charts of FIGS. 59 to 61.

First of all, as shown in the flow of the main routine of FIG. 59, the wafer 5-15 to be inspected is set on the stage 4-15 (step 300S). As for a detailed mechanism for performing this step, the implementation described in conjunction with the sixth embodiment may be applicable.

Figure 58:
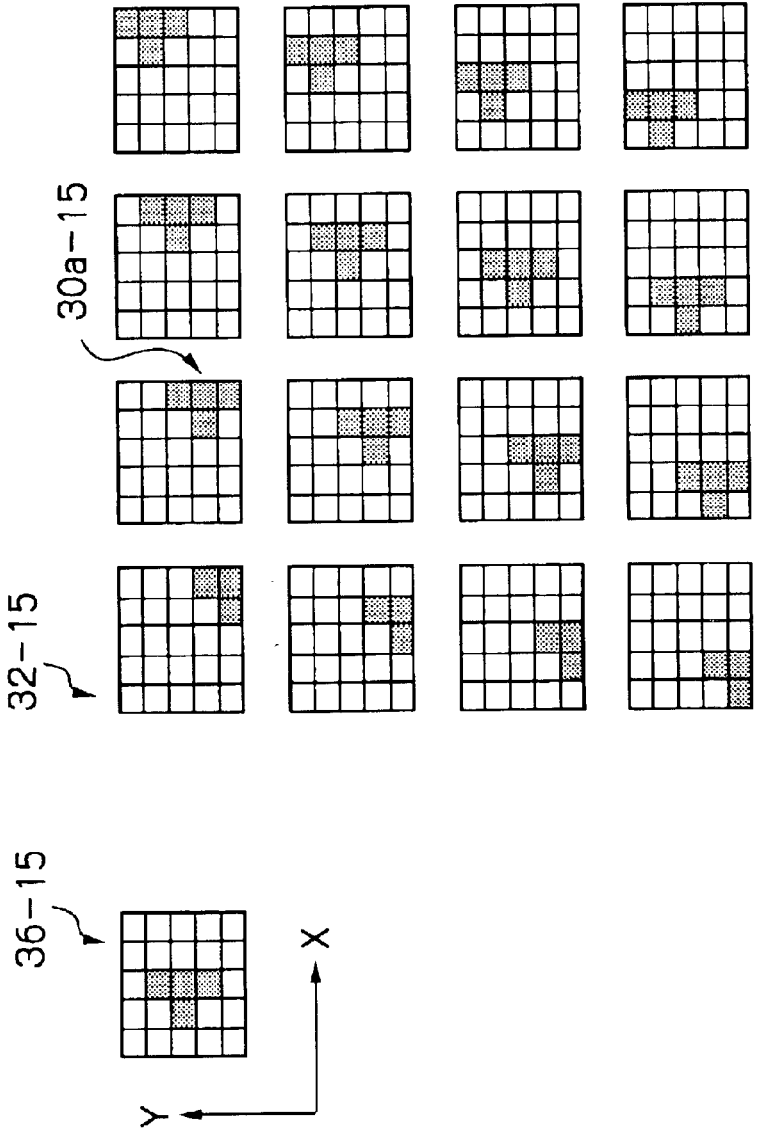
FIG. 58 shows a plurality of images to be inspected, which may be obtained in the defect inspection apparatus of FIG. 57, in conjunction with a reference image.

Then, images for a plurality of regions to be inspected are respectively obtained, which are displaces one from another while being superimposed partially one on another on the XY plane of the surface of the wafer 5-15 (Step 304S). Each of said plurality of regions to be inspected, from which the image is to be obtained, is, for example, a rectangular region on the wafer surface 34-15 to be inspected as designated by reference numerals 32a-15, 32b-15, . . . 32k-15, . . . , in FIG. 62, each of which is observed to be displaced relative to one another while being partially superimposed one on another around the inspection pattern 30-15 of the wafer. For example, 16 pieces of images 32-15 for the regions to be inspected (the images to be inspected) may be obtained as shown in FIG. 58. Herein, for the image as shown in FIG. 58, each square contained in the rectangle region corresponds to one pixel (or a block, whose unit is greater than the unit of pixel), and among those squares, shaded ones correspond to the imaged area of the pattern on the wafer 5-15. This step 304S will be described in more detail later with reference to the flow chart of FIG. 60.

Then, the image data for the plurality of regions to be inspected, which have been obtained at Step 304S, is respectively compared with the reference image stored in the storage section 13-15 to look for any matching (Step 308S in FIG. 59), and it is determined whether or not there is a defect existing in the wafer inspection plane encompassed by said plurality of regions to be inspected. This process performs, what is called, the matching operation between image data, which will be explained later in detail with reference to the flow chart shown in FIG. 61.

If the result from the comparing process at Step 308S indicates that there is a defect in the wafer inspection plane encompassed by said plurality of regions to be inspected (Step 312S, affirmative determination), the process gives a warning to the operator indicating the existence of the defect (Step 318S). As for the way of warning, for example, the display section of the CRT 15-15 may display a message notifying the operator that there is a defect, or at the same time may additionally display a magnified image 17-15 of the pattern determined to have the defect. Such defective wafers may be immediately taken out of a sample chamber 3-15 and stored in another storage separately from those wafers having no defect (Step 319S).

If the result from the comparing process at Step 308S indicates that there is no defect in the wafer 5-15 (Step 312S, negative determination), the it is determined whether or not there are remained more regions to be inspected for the current wafer 5-15 currently treated as the inspection object (Step 314S). If there are more regions remained for inspection (Step 314S, affirmative determination), the stage 4-15 is driven to move the wafer 5-15 so that other regions to be further inspected are positioned within the irradiation region of the primary electron beam (Step 316S). Subsequently, the process goes back to Step 304S to repeat the similar operations for said other regions to be inspected.

If there is no more regions remained to be further inspected (Step 314S, negative determination), or after a drawing out processing of the defective wafer (Step 319S), it is determined whether or not the current wafer treated as the inspection object is the last wafer to be inspected, that is, whether or not there are any wafers remaining for the inspection in the loader, though not shown (Step 320S). If the current wafer is not the last one (Step 3205, negative determination), the wafers having been inspected already are stored in a predetermined storing location, and a new wafer which has not been inspected yet is set instead on the stage 4-15 (Step 322S). Then, the process goes back to Step 304S to repeat the similar operations for said wafer. In contrast, if the current wafer is the last one (Step 320S, affirmative determination), the wafer having been inspected is stored in the predetermined storing location to end the whole process.

Then, the process flow of step 304S will now be described with reference to the flow chart of FIG. 60.

In FIG. 60, first of all, an image number "i" is set to the initial value "1" (Step 330S). This image number is an identification number assigned serially to each of the plurality of images for the regions to be inspected. Secondary, the process determines an image position $(X_i, Y_i)$ for the region to be inspected as designated by the set image number i (Step 332S). This image position is defined as a specific location within the region to be inspected for bounding said region, for example, a central location within said region.

Figure 62:
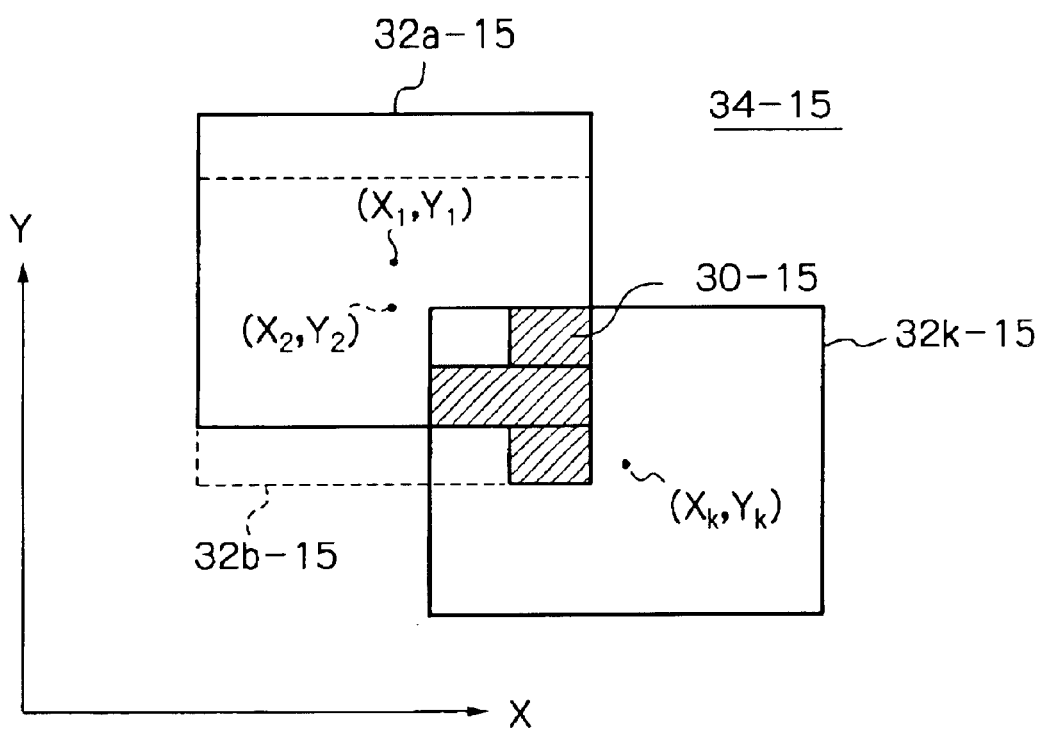
FIG. 62 is a diagram conceptually illustrating a plurality of regions to be inspected, which have been displaced from one another while superimposed one on another on a surface of a semiconductor wafer.

Currently, i=1 defines the image position as $(X_i, Y_i)$, which corresponds, for example, to a central location of the region to be inspected 32a-15 as shown in FIG. 62. The image position has been determined previously for every image region to be inspected, and stored, for example, in the hard disk of the control section 16-15 to be read out at Step 332S.

Then, the deflection controller 12-15 applies a potential to the deflecting electrode 11-15 (Step 334S in FIG. 60) so that the primary electron beam passing through the deflecting electrode 11-15 of FIG. 57 may be radiated onto the image region to be inspected in the image position $(X_i, Y_i)$ determined at Step 332S.

Then, the electron gun 1-15 emits the primary electron beam, which goes through the electrostatic lens 2-15, the ExB deflector 3-15, the objective lens 10-15 and the deflecting electrode 11-15, and eventually impinges upon a surface of the set wafer 5-15 (Step 336S). At that time, the primary electron beam is deflected by an electric field generated by the deflecting electrode 11-15 so as to be radiated onto the wafer inspection surface 34-15 covering the whole image region to be inspected at the image position $(X_i, Y_i)$. When i=1, the region to be inspected is 32a-15.

Secondary electrons are emitted from the region to be inspected, on which the primary electron beam has scanned. Then, the generated secondary electron beam is focused on the detector 7-15. The detector 7-15 detects the secondary electron beam, and outputs an electric signal. Subsequently, the image forming circuit 20-15 converts the electric signal into a digital image data to be output (Step 338S). Then, the formed digital image data for the image number i is sent to the secondary electron image storage area 8-15 (Step 340S).

Subsequently, the image number i is incremented by 1 (Step 342S), and the process determines whether or not the incremented image number (i+1) is greater than a predetermined constant value "$i_{MAX}$" (Step 344S). This $i_{MAX}$ is the number of images to be inspected that are required to obtain, which is "16" for the above example of FIG. 58.

If the image number i is not greater than the constant value $i_{MAX}$ (Step 344S, negative determination), the process goes back to Step 332S again, and determines again the image position $(X_{i+1}, 1, Y_{i+1})$ for the incremented image number (i+1). This image position is a position moved from the image position $(X_i, Y_i)$ determined at the previous routine by a specified distance $(\Delta X_i, \Delta Y_i)$ in the X-direction and/or the Y-direction. The region to be inspected in the example of FIG. 62 is at the location $(X_2, Y_2)$, i.e., the rectangular region 32b-15 indicated with the dotted line, which has been moved from the position $(X_i, Y_i)$ only in the Y direction. It is to be noted that the value for $(\Delta X_i, \Delta Y_i)$ (i=1,2, ... $i_{MAX}$) may have been appropriately determined from the data indicating practically and experimentally how much is the displacement of the pattern 30-15 on the wafer inspection surface 34-15 from the field of view of the detector 7-15 and a number and an area of the regions to be inspected.

Then, the operations for Step 332S to Step 342S are repeated in order for $i_{MAX}$ regions to be inspected. These regions to be inspected are continuously displaced while being partially superimposed one on another on the wafer inspection surface 34-15 so that the image position after k times of movement $(X_k, Y_k)$ corresponds to the inspection image region 32k-15, as shown in FIG. 62. In this way, the 16 pieces of inspection image data exemplarily illustrated in FIG. 58 are obtained in the image storage area 8-15. It is observed that a plurality of images 32-15 obtained for the regions to be inspected (i.e., inspection image) contains partially or fully the image 30a-15 of the pattern 30-15 on the wafer inspection surface 34-15, as illustrated in FIG. 58.

If the incremented image number i has become greater i than $i_{MAX}$ (Step 3445, affirmative determination), the process returns out of this subroutine and goes to the comparing process (Step 308S) in the main routine of FIG. 59.

It is to be noted that the image data that has been transferred to the memory at Step 334S is composed of intensity values of the secondary electrons for each pixel (so-called, raw data) detected by the detector 7-15, and these data may be stored in the storage area 8-15 after having been processed through various operations in order to use for performing the matching operation relative to the reference image in the subsequent comparing process (Step 308S of FIG. 59). Such operations includes, for example, a normalizing process for setting a size and/or a density of the image data to be matched with the size and/or the density of the reference image data, or the process for eliminating as a noise the isolated group of pixels including the pixels not greater than the predetermined number. Further, the image data may be converted by means of data compression into a feature matrix having extracted features of the detected pattern rather than the simple raw data, so far as it does not negatively affect to the accuracy in detection of the highly precise pattern. Such feature matrix includes, for example, m×n feature matrix, in which a two-dimensional inspection region composed of M×N pixels is divided into m×n (m<M, n<N) blocks, and respective sums of intensity values of the secondary electrons of the pixels contained in each block (or the normalized value defined by dividing said respective sums by a total number of pixels covering all of the regions to be inspected) should be employed as respective components of the matrix. In this case, the reference image data also should have been stored in the same form of representation. The image data in the context used in the embodiment of the present invention includes, of course, not only a simple raw data but also any image data having the feature extracted by any arbitrary algorithms as described above.

The process flow for Step 308S will now be described with reference to the flow chart of FIG. 61.

First of all, the CPU in the control section 16-15 reads the reference image data out of the reference image storage section 13-15 (FIG. 57) onto the working memory 20 such as the RAM or the like (Step 350S). This reference image is identified by reference numeral 36-15 in FIG. 58. Then, the image number "i" is reset to 1 (Step 352S), and then the process reads out the inspection image data having the image number "i" onto the working memory (Step 354S).

Then, the read out reference image data is compared with the data of the image "i" for any matching to calculate a distance value "$D_i$" between both data (Step 356S). This distance value $D_i$ indicates a similarity level between the reference image and the image to be inspected "i", wherein a greater distance value indicates the greater difference between the reference image and the inspection image. Any unit of amount representative of the similarity level may be used for said distance value "$D_i$". For example, if the image data is composed of M×N pixels, the secondary electron intensity (or the amount representative of the feature) of each pixel may be considered as an each of the position vector elements of M×N dimensional space, so that an Euclidean distance or a correlation coefficient between the reference image vector and the image "i" vector in the M×N dimensional space may be calculated. It will be easily appreciated that any distance other than the Euclidean distance, for example, the urban area distance may be calculated. Further, if the number of pixels is huge, which increases the amount of the operation significantly, then the distance value between both image data represented by the m×n feature vector may be calculated as described above.

Subsequently, it is determined if the calculated distance value $D_i$ is smaller than a predetermined threshold Th (Step 358S). This threshold Th is determined experimentally as a criterion for judging a sufficient matching between the reference image and the inspection image to be compared.

If the distance value $D_i$ is smaller than the predetermined threshold Th (Step 358S, affirmative determination), the process determines that the inspection plane 34-15 of said wafer 5-15 has "no defect" (Step 360S) and returns out of this sub routine. That is, if there has been found at least one image among those inspection images matching to the reference image, the process determines there is "no defect". Accordingly, since the matching operation shall not necessarily be applied to every inspection image, the high-speed judgment becomes possible. As for the example of FIG. 58, it is observed that the image to be inspected at the column 3 of the row 3 is approximately matching to the reference image without any offset thereto.

When the distance value $D_i$ is not smaller than the predetermined threshold Th (Step 358S, negative determination), the image number "i" is incremented by 1 (Step 362S), and then it is determined whether or not the incremented image number (i+1) is greater than the predetermined value $i_{MAX}$ (Step 364S).

If the image number "i" is not greater than the predetermined value $i_{MAX}$ (Step 364S negative determination), the process goes back to Step 354S again, reads out the image data for the incremented image number (i+1), and repeats the similar operations.

If the image number "i" is greater than the predetermined value $i_{MAX}$ (Step 364S, affirmative determination), then the process determines that said inspection plane 34-15 of said wafer 5-15 has "a defect existing" (Step 366S), and returns out of the sub routine. That is, if any one of the images to be inspected is not approximately matching to the reference image, the process determined that there is "a defect existing".

A defect inspection apparatus according to the present invention may use not only the electron beam apparatus of the multi-column type as described above but also an electron beam apparatus of, what is called, the scanning type by way of a multi-beam. This will now be explained as a second mode in the fifteenth embodiment with reference to FIG. 63.

Figure 63:
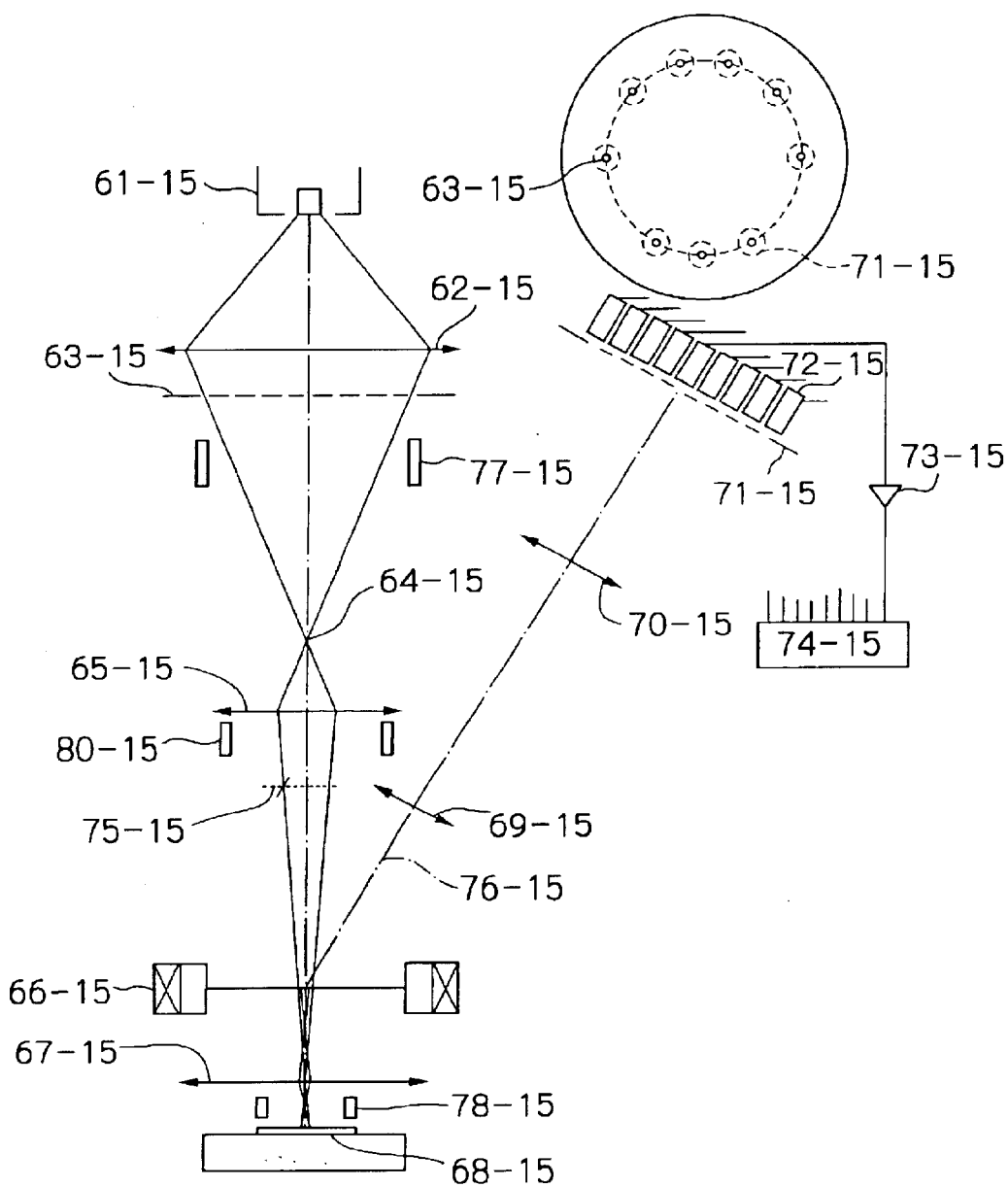
FIG. 63 is a schematic diagram illustrating an electron beam apparatus of the scanning type usable as a defect inspection apparatus according to the fifteenth embodiment of the present invention.

FIG. 63 is a schematic diagram of an electron beam apparatus of one embodiment according to the present invention, in which the electron beam emitted from an electron gun 61-15 is converged by a condenser lens 62-15 to form a crossover at a point 64-15.

Beneath the condenser lens 62-15 is disposed a first multi-aperture plate 63-15 having a plurality of apertures, thereby to form a plurality of primary electron beams. Each of those primary electron beams formed by the first multi-aperture plate 63-15 is contracted by a reducing lens 65-15 to be projected onto a point 75-15. After being focused on the point 75-15, the first electron beams are further focused onto a sample 68-15 by an objective lens 67-15. A plurality of first electron beams exited from the first multi-aperture plate 63-15 is deflected all together by a deflector 80-15 arranged between the reducing lens 65-15 and the objective lens 67-15 so as to scan the surface of the sample 68-15.

In order not to produce any field curvature aberration by the reducing lens 65-15 and the objective lens 67-15, as shown in FIG. 63, the multi-aperture plate 63-15 is provided with a plurality of small openings located along a circle such that projections thereof in the X direction are equally spaced.

A plurality of focused primary electron beams is radiated onto the sample 68-15 at a plurality of points thereon, and secondary electron beams emitted from said plurality of points are attracted by an electric field of the objective lens 67-15 to be converged narrower, and then deflected by an ExB separator 66-15 so as to be introduced into a secondary optical system. The secondary electron image is focused on a point 76-15 which is much closer to the objective lens 67-15 than the point 75-15. This is because each of the primary electron beams has the energy of 500 eV on the surface of the sample, while the secondary electron beam only has the energy of a few eV.

The secondary optical system has magnifying lenses 69-15 and 70-15, wherein the secondary electron beam after having passed through those magnifying lenses 69-15 and 70-15 is formed into an image on a plurality of apertures in a second multi-aperture plate 71-15. Then, the second electron beam passes through those apertures to be detected by a plurality of detectors 72-15. It is to be noted that the plurality of apertures formed through the second multi-aperture plate 71-15 disposed in front of the detectors 72-15 corresponds to the plurality of apertures formed through the first multi-aperture plate 63-15 on one to one basis.

Each of the detectors 72-15 converts the detected secondary electron beam into an electric signal representative of its intensity. Such electric signals output from respective detectors, after having been amplified respectively by an amplifier 73-15, are received by an image processing section 74-15 so as to be converted into image data. Since the image processing section 74-15 is further supplied with a scanning signal for deflecting the primary electron beam from the deflecting system 80-15, the image processing section 74-15 can display an image representing the surface of the sample 68-15. This image corresponds to one of those plural images to be inspected at the different locations (FIG. 58) described with reference to the first mode in the fifteenth embodiment. Comparing this image with the reference image 36-15 allows any defects in the sample 68-15 to be detected. Further, the line width of the pattern on the sample 68-15 can be measured in such a way that the evaluation pattern on the sample 68-15 is moved by a registration to the proximity to an optical axis of the primary optical system, and the evaluation pattern is then line-scanned to extract the line width evaluation signal, which is in turn appropriately calibrated.

In this regard, it is preferred to make arrangements when the primary electrons having passed through the apertures of the first multi-aperture plate 63-15 is focused onto the surface of the sample 68-15, and than the secondary electrons emitted from the sample 68-15 are formed into an image on the detector 72-15, in order to minimize the affection by the three aberrations, i.e., the coma aberration caused by the primary and the secondary optical systems, the image field curvature, and the field astigmatism.

Then, as to a relation between the spacing in the plurality of primary electron beams and the secondary optical system, if the space between respective primary electron beams is determined to be greater than the aberration of the secondary optical system, then any cross-talk among a plurality of beams could be prevented.

Also in the scanning electron beam apparatus of FIG. 63, the sample 68-15 is inspected according to the flow chart as illustrated in FIGS. 59 and 60. In this case, the image position $(X_i, Y_i)$ at Step 332S of FIG. 60 corresponds to the central location of the two-dimensional image made by synthesizing a plurality of line images obtained through scanning with the multi-beam. This image position $(X_i, Y_i)$ is changed sequentially in the subsequent processes, which may be performed by, for example, changing the offset voltage of the deflector 80-15. The deflector 80-15 performs the normal line scanning by changing the voltage around the set offset voltage. It is apparent that a separate deflecting means other than the deflector 80-15 may be employed to change the image position $(X_i, Y_i)$.

Although there has been described as above respective modes for implementing the fifteenth embodiment, it is to be appreciated that the present invention is not limited only to the preceding examples but also may be modified arbitrarily and preferably without departing from the scope and spirit of the present invention.

For example, although the description has illustratively employed a semiconductor wafer 5-15 as a sample to be inspected, the sample to be inspected in the present invention is not limited to this, but anything may be selected as the sample so far as it can be inspected for defects by using the electron beam. For example, the object to be inspected may be a mask with an exposure pattern formed thereon.

Further, the present invention may be applied not only to an apparatus which detects any defects with charged particle beams other than electrons but also to any apparatus which allows any images to be obtained for inspecting the sample for defects.

Still further, the deflecting electrode 80-15 may be disposed not only between the objective lens 67-15 and the wafer 68-15 but also at any arbitrary locations so far as the irradiation region of the primary electron beam can be controlled. For example, the deflecting electrode 80-15 may be disposed between the ExB deflector 66-15 and the objective lens 67-15, or between the electron gun 61-15 and the ExB deflector 66-15. Furthermore the ExB deflector 66-15 may be used for controlling the deflecting direction of the primary electron beam by controlling the field generated thereby. That is, the ExB deflector 66-15 may function also as the deflecting electrode 80-15.

Further, although in the above embodiment, either one of the matching between the pixels and the matching between the feature vectors has been employed for the matching operation between the image data, they may be combined together for it. For example, both of the high speed and the high precision may be satisfied by two-step matching, in which firstly a high-speed matching is performed with the feature vectors which requires fewer number of operations, and subsequently the more precise matching is performed with more detailed pixel data for the images to be inspected that have been found to be quite similar.

Still further, although in the embodiments of the present invention, the position mismatch for the image to be inspected has been resolved only by displacing the irradiating region of the primary electron beam, the procedure of the present invention may be combined with a process for retrieving an optimal matching region on the image data before or during the matching processes (e.g., first detecting the regions having higher correlation coefficient and then performing the matching). This can improve the accuracy in defect detection, because the major position mismatch for the image to be inspected could be rectified by displacing the irradiating region of the primary electron beam, while the relatively minor position mismatch could be absorbed subsequently with the digital image processing.

Still further, the flow in the flow chart of FIG. 59 is also not limited to the illustrated one. For example, although in the embodiment the process does not further perform the defect detection in any other regions of the sample that has been determined to have a defect at Step 312S, the flow may be modified so that the overall area would be inspected for any defects to be detected. Yet further, if the irradiating area of the primary electron beam can be expanded so as to cover almost overall area of the sample with one shot of irradiation, Steps 314S and 316S can be omitted.

As having been described above in detail, according to the detect inspection apparatus of the fifteenth embodiment, since the defect in the sample can be detected by firstly obtaining respective images of a plurality of regions to be inspected, which are displaced from one another while being partially superimposed one on another on the sample, and then comparing those images of the regions to be inspected with the reference image, therefore an advantageous effect can be provided in that the possible deterioration in accuracy in the defect detection can be prevented, which might be caused by position mismatch, Sixteenth Embodiment In a sixteenth embodiment, an electron beam apparatus described in either of preceding first to fifteenth embodiments is applied to an evaluation of a wafer in a semiconductor device manufacturing process.

Figure 64:
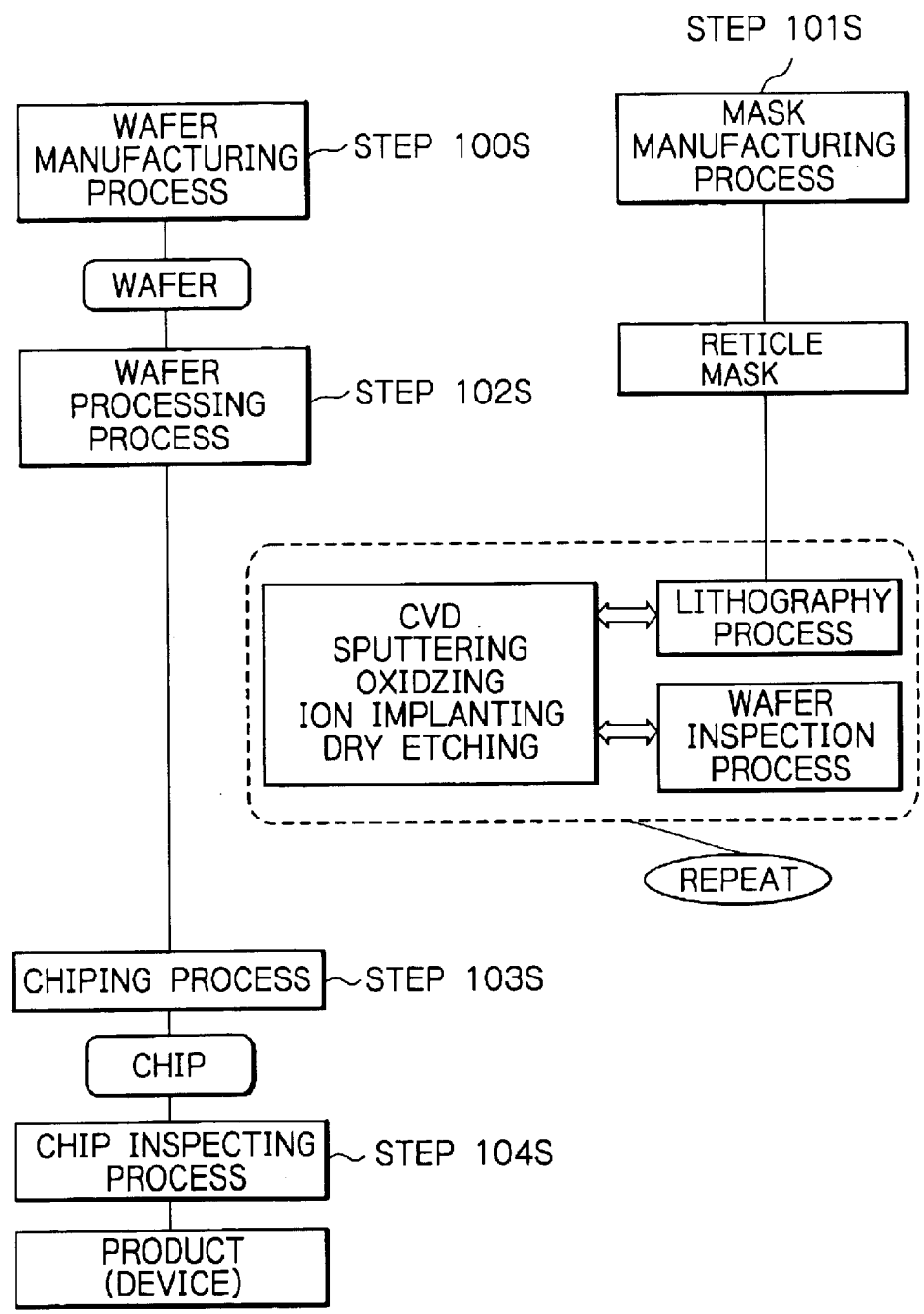
FIG. 64 is a flow chart illustrating a manufacturing process of semiconductor devices.

An example of the device manufacturing process will now be described with reference to a flow chart of FIG. 64.

The manufacturing process includes the following main processes.

(1) A wafer manufacturing process for manufacturing a wafer (or wafer preparing process for preparing a wafer). (Step 100S)

(2) A mask manufacturing process for fabricating a mask to be used in the exposure (or a mask preparing process). (Step 101S)

(3) A wafer processing process for performing any processing treatments necessary for the wafer. (Step 102S)

(4) A chip assembling process for cutting out those chips formed on the wafer one by one to make them operative. (Step 103S)

(5) A chip inspection process for inspecting an assembled chip. (Step 104S)

It is to be appreciated that each of those processes further comprises several sub-processes.

Among those main processes, the main process that gives a critical affection to the performance of the semiconductor device is the wafer processing process. In this wafer processing process, the designed circuit patterns are deposited on the wafer one on another, thus to form many chips, which will function as memories or MPUs. This wafer processing process includes the following sub-processes.

(1) A thin membrane deposition process for forming a dielectric thin film to be used as an insulation layer, a metallic thin film to be formed into a wiring section or an electrode section, and the like (by using the CVD process or the sputtering).

(2) An oxidizing process for oxidizing the formed thin film and/or the wafer substrate.

(3) A lithography process for forming a pattern of the resist by using a mask (reticle) in order to selectively process the thin film layer and/or the wafer substrate.

(4) An etching process for processing the thin film layer and/or the wafer substrate in accordance with the pattern of the resist (by using, for example, the dry etching technology).

(5) An ions/impurities implant and diffusion process.

(6) A resist stripping process.

(7) An inspection process for inspecting the processed wafer.

It should be noted that the wafer processing process must be performed repeatedly as desired depending on the number of layers contained in the wafer, thus to manufacture the device that will be able to operate as designed.

Figure 65:
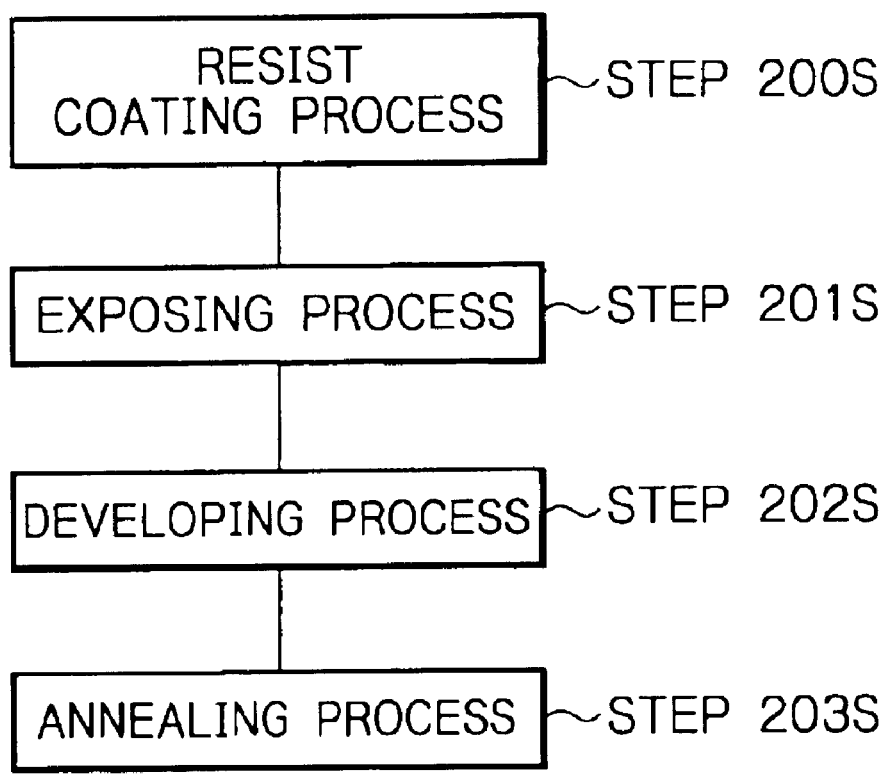
FIG. 65 is a flow chart illustrating a lithography process among the manufacturing process of semiconductor devices of FIG. 64.

A flow chart of FIG. 65 shows the lithography process included as a core process in said wafer processing process. The lithography process comprises the respective processes as described below.

(1) A resist coating process for coating the wafer having a circuit pattern formed thereon in the preceding stage with the resist. (Step 200S)

(2) An exposing process for exposing the resist. (Step 201S)

(3) A developing process for developing the exposed resist to obtain the pattern of the resist. (Step 202S)

(4) An annealing process for stabilizing the developed pattern. (Step 203S)

Known procedures may be applied to all of the semiconductor device manufacturing process, the wafer processing process, and the lithography process described above.

When an electron beam apparatus according to either of the preceding embodiments of the present invention is used in said (7) wafer inspection process, a defect can be detected with high level of accuracy under the condition without any image disorder in the secondary electron image, thereby allowing the yield of the product to be improved, while prohibiting any defective products from being delivered.

What is claimed is:

1. A substrate inspection apparatus comprising:

a. a beam source for emitting an electron beam having a specified width;

b. a primary electron optical system for introducing said electron beam to a surface of a substrate subject to an inspection;

c. a secondary electron optical system for guiding secondary electrons emitted from said substrate to a detecting system;

d. an image processing system for forming a secondary electron image based on a detection signal of a secondary electron beam obtained by said detecting system;

e. a stage for holding said substrate in such a manner that said substrate may be moved successively with at least one degree of freedom;

f. an inspection chamber for said substrate;

g. a substrate conveying mechanism capable of carrying said substrate into said inspection chamber and taking it out therefrom;

h. an image processing analyzer capable of detecting a defective location on the substrate loaded into said inspection chamber based on the secondary electron image formed by said image processing system;

i. a vibration isolating mechanism for said inspection chamber;

j. a vacuum system capable of controlling a vacuum atmosphere to be maintained in said inspection chamber;

k. a control system for indicating and/or storing said defective location on said substrate detected by said image processing analyzer;

l. a mini-environment device for inhibiting dust from adhering to the substrate by applying a purge gas flow against said substrate prior to the inspection; and m. at least one loading chamber which is disposed between said mini-environment device and said inspection chamber and controllable to the vacuum atmosphere independently from each other, wherein said substrate conveying mechanism includes a loader having one conveying unit capable of conveying said substrate between said mini-environment device and said loading chamber, and said vibration isolating mechanism includes a vibration isolating unit interposed between said inspection chamber and said loading chamber.

2. The substrate inspection apparatus in accordance with claim 1, further comprising a pre-charge unit for irradiating an electron beam onto said substrate disposed in said inspection chamber to reduce non-uniformity level in an electro static charge on said substrate and a potential applying mechanism for applying a potential to said substrate.

3. The substrate inspection apparatus in accordance with claim 1, further comprising an alignment control unit for observing a surface of said substrate and controlling an alignment thereof in order to position said substrate in place with respect to said primary electron optical system, and a laser-interferometer for measuring a coordinate of said substrate on said stage, wherein said alignment control unit uses a pattern existing on said substrate to determine the coordinate of a subject to be inspected.

4. The substrate inspection apparatus in accordance with claim 1, in which said detecting system comprises an MCP for multipling said secondary electron beam, a fluorescent screen for converting said amplified secondary electron beam into an optical signal and a CCD camera or a line sensor for taking out said optical signal as an image data, wherein a voltage applied to said MCP is controlled in association with a change in the amplification factor of the MCP in order to determine an optimal amount of exposure for the image containing said defect.

5. The substrate inspection apparatus in accordance with claim 4, which said voltage applied to said MCP is determined by referring to a current MCP applied voltage-MCP gain curve.

6. The substrate inspection apparatus in accordance with claim 1, in which said inspection system comprises an MCP for amplifying said secondary electron beam, a fluorescent screen for converting said amplified secondary electron beam into an optical signal and a CCD camera or a line sensor for taking out said optical signal as an image data, wherein an emission current of said electron beam is controlled in association with a change in the amplification factor of the MCP in order to determine an optimal amount of exposure for the image containing said defect.

7. The substrate inspection apparatus in accordance with any one of claims 4 to 5, in which said MCP applied voltage or said emission current of the beam is controlled in association with a multiplying factor of projection of the electron beam or a change in a line rate of said line sensor.

8. The substrate inspection apparatus in accordance with claim 1, in which said beam source is an electron beam source comprising a Wehnelt electrode, wherein said apparatus further comprises a control section for controlling a voltage applied to said Wehnelt electrode with time so that an emission current flowing to said electron beam source can be maintained at a constant level.

9. The substrate inspection apparatus in accordance with claim 8, in which said electron beam source comprises an electron gun having a cathode made of $LaB_6$.

10. The substrate inspection apparatus in accordance with claim 9, in which a flat <100> mono-crystalline orientation having a diameter of not less than 100 microns is arranged in a tip portion of said cathode.

11. The substrate inspection apparatus in accordance with claim 1, in which said stage is accommodated in a housing of said inspection chamber and supported by a hydrostatic bearing in a non-contact manner, wherein said housing containing said stage is evacuated to vacuum, and a differential pumping mechanism is arranged in a surrounding of a section irradiating the electron beam onto said substrate surface, for evacuating a region on said substrate subject to an electron beam irradiation.

12. The substrate inspection apparatus in accordance with claim 11, in which a gas supplied to said hydrostatic bearing of said stage is either of a dry nitrogen or a highly purified inert gas, wherein said dry nitrogen or said highly purified inert gas, after having been exhausted from said housing containing said stage, is pressurized and supplied again to said hydrostatic bearing.

13. The substrate inspection apparatus in accordance with claim 1, further having, in addition to an image projecting function comprising the steps of irradiating the electron beam having said specified width onto the substrate and projecting the secondary electron image onto said detecting system by means of said secondary electron optical system, a scanning electron microscopy function comprising the steps of firstly forming an electron beam to be narrower than said specified width, secondarily irradiating said narrower electron beam onto and scanning thereby the substrate surface, and lastly detecting the secondary electron beam emitted from said substrate.

14. The substrate inspection apparatus in accordance with claim 13, in which the function can be switched appropriately between said image projecting function and said scanning electron microscopy function to each other in response to a condition of the substrate during a single substrate being inspected.

15. The substrate inspection apparatus in accordance with claim 14, in which, on the same substrate, a pattern of a hardly charged sample area is inspected by using said image projecting function and a pattern of an easily charged sample area is inspected by using said scanning electron microscopy function.

16. The substrate inspection apparatus in accordance with claim 14, in which said scanning electron microscopy function is used in a mark detection for a registration in a wafer processing process, and said image projecting function is used in a subsequent pattern defect inspection.

17. The substrate inspection apparatus in accordance with claim 1, in which said image processing system captures each of images for a plurality of regions to be inspected which have been displaced one from another while being superimposed partially one on another, and said image processing system comprises:

a storage means for storing a reference image; and a defect determination means for determining the defect in said substrate by comparing the images of said plurality of regions to be inspected which have been captured by said image processing system with said reference image stored in said storage means.

18. The substrate inspection apparatus in accordance with claim 17, in which said beam source radiates the electron beam onto each of said plurality of regions to be inspected, and said detecting system detects the secondary electron beam emitted from each of said plurality of regions to be inspected.

19. The substrate inspection apparatus in accordance with claim 18, further comprising a deflecting means for deflecting said electron beam and thereby irradiating sequentially said electron beam onto said plurality of regions to be inspected.

20. A device manufacturing method in which a substrate is subjected in the course of process or after having been processed to an inspection for detecting any defects thereon by using the substrate inspection apparatus as defined in claim 1.

21. A device manufacturing method comprising:
   a. preparing wafers;
   b. processing a wafer-processing process;
   c. inspecting defect using a substrate inspection apparatus as defined in claim 2;
   d. repeating said steps b and c; and
   e. assembling devices from said processed wafer.

22. The substrate inspection apparatus in accordance with claim 1, further comprising:
   an objective lens provided in said primary electron optical system:
   a means for forming a decelerating electric field between the substrate and the objective lens:
   a detector for detecting a discharge or a precursory phenomenon of the discharge between the substrate and the objective lens and then generating a signal; and
   a means for receiving said signal from said detector to obtain a condition for inhibiting any discharge from occurring.

23. The substrate inspection apparatus in accordance with claim 22, in which said detector is a PMT for detecting a light occurring in said discharge or said precursory phenomenon of the discharge, or a substrate ampere meter for detecting an irregular current occurring in said discharge or said precursory phenomenon of the discharge.

24. The substrate inspection apparatus in accordance with claim 22 or 23, in which said means for obtaining a condition for inhibiting any discharge from occurring is a means for receiving said signal from said detector and then controlling a voltage of said decelerating electric field or an amount of said primary electron beam so as to inhibit the discharge from occurring.

25. The substrate inspection apparatus in accordance with any one of claim 22 or 23, in which said step of detecting said discharge or said precursory phenomenon of the discharge is performed on a partial area of said substrate where may not be used as an effective area of a product.

26. The substrate inspection apparatus in accordance with claim 1, further comprising a plurality of electron optical column systems arranged in parallel,
   each of said electron optical column systems including said primary and secondary electron optical systems, and further comprising:
   a low-pass filter, wherein
   said detecting system outputs a detection signal of the secondary electron beam to said low-pas filter.

27. The substrate inspection apparatus in accordance with claim 26, in which said low-pass filter can make a cut-off frequency variable and changes the cut-off frequency in dependence on the substrate.

28. The substrate inspection apparatus in accordance with claim 26 or 27, further comprising a lens including a plurality of electrodes made of insulating material with a metal coating applied selectively onto surfaces thereof.

29. The substrate inspection apparatus in accordance with claim 28, in which said plurality of electrodes is made of a single insulating material.

30. The substrate inspection apparatus in accordance with claim 1, wherein said beam source for emitting an electron beam is provided with a Wehnelt, and wherein
   said apparatus further comprises a control section for controlling a voltage applied to said Wehnelt electrode with time so that an emission current flowing to said electron beam source can be maintained at a constant level.

31. The substrate inspection apparatus in accordance with claim 30, in which said electron beam source comprises an electron gun having a cathode made of $LaB_6$.

32. The substrate inspection apparatus in accordance with claim 31, in which a flat <100> mono-crystalline orientation having a diameter of not less than 100 microns is arranged in a tip portion of said cathode.

33. The substrate inspection apparatus in accordance with claim 1, further comprising an evaluation apparatus disposed in the vicinity of at least one processing unit for manufacturing a semiconductor device so as to evaluate a resultant condition of a wafer after having been processed by said processing unit, said apparatus comprising:
   an evaluation condition setting system for setting an evaluation condition such that the resultant condition of a single wafer can be evaluated within a processing time per wafer by the processing unit.

34. The substrate inspection apparatus in accordance with claim 1, further comprising a plurality of electron optical columns, each including said primary and secondary electron optical systems.

35. The substrate inspection apparatus in accordance with claim 1, further comprising: an evaluation apparatus for evaluating a resultant condition of a processed semiconductor device, said apparatus including:
   an evaluation condition setting system for setting an evaluation condition such that the resultant condition of one lot can be evaluated within a processing time per lot by the processing unit.

36. The substrate inspection apparatus in accordance with claim 1, wherein
   after having scanned a certain region on the substrate with a predetermined scanning width by the primary electron beam, the apparatus scans another region adjacent to said certain region by way of a movement of a stage, wherein an amount of said movement of the stage is greater than said predetermined scanning width, so that the substrate can be evaluated for a larger region by repeating these steps.

37. The substrate inspection apparatus in accordance with claim 1, wherein said substrate has a pattern of a minimum line width "d" and said substrate is scanned with a predetermined scanning width, and wherein if a beam diameter of the primary electron beam is denoted by "D", then $0.55 \leq D/d \leq 1.0$.

38. The substrate inspection apparatus in accordance with claim 1, wherein said apparatus evaluates said substrate having a gate oxide, and wherein assuming that: a time period necessary for evaluating a unit area is denoted by "t"; an amount of irradiation or dose per unit area is denoted by "C" (Coulomb/cm$^2$); a beam current of the primary electron beam is denoted by "$I_p$"; and a modulation transfer function of a signal at a time when the primary electron beam has observed a cycle pattern having a pitch equivalent to a doubled minimum line width "d" is denoted by MTF, then the beam diameter of the primary electron beam is selected such that $1/(C \cdot t)$ or $(MTF)^4 I_p$ can be maximized.

39. The substrate inspection apparatus in accordance with claim 1, wherein when said apparatus evaluates a single substrate the evaluation is performed only with respect to a small number of chips among a large number of chips formed in said single substrate.

40. The substrate inspection apparatus in accordance with claim 39, wherein the number of said small number of chips is equivalent to the number of electron optical columns for forming the electron beam used for the inspection.

41. The substrate inspection apparatus in accordance with claim 1, further comprising a plurality of electron optical column, each of said electron optical column systems accommodating said primary and secondary electron optical systems, wherein an electrostatic lens provided in said electron optical column includes an electrode made of insulating material with a coating applied onto a surface thereof, and an electrostatic deflector or an electrostatic astigmatic correcting lens.

42. The substrate inspection apparatus in accordance with claim 41, in which each of said electron optical columns forms a plurality of electron beams.

43. A substrate inspection apparatus comprising:
a. a beam source for emitting an electron beam having a specified width;
b. a primary electron optical system for introducing said electron beam to a surface of a substrate subject to an inspection;
c. a secondary electron optical system for guiding secondary electrons emitted from said substrate to a detecting system;
d. an image processing system for forming a secondary electron image based on a detection signal of a secondary electron beam obtained by said detecting system;
e. a stage for holding said substrate in such a manner that said substrate may be moved successively with at least one degree of freedom;
f. an inspection chamber for said substrate;
g. a substrate conveying mechanism capable of carrying said substrate into said inspection chamber and taking it out therefrom;
h. an image processing analyzer capable of detecting a defective location on the substrate loaded into said inspection chamber based on the secondary electron image formed by said image processing system;
i. a vibration isolating mechanism for said inspection chamber;
j. a vacuum system capable of controlling a vacuum atmosphere to be maintained in said inspection chamber; and
k. a control system for indicating and/or storing said defective location on said substrate detected by said image processing analyzer, and
in which said detecting system is incorporated with a feed-through unit, said feed-through unit comprising: a feed-through section made of an electrical insulating material; at least one electricity introduction pin fixedly attached to said feed-through section; and a connecting wiring for connecting said at least one electricity introduction pin with a functional element, wherein said functional element includes a sensor, and both a pressure and a kind of gas in an inside of said feed-through section are different from those of an outside thereof, respectively.

44. The substrate inspection apparatus in accordance with claim 43, in which said functional clement is arranged on an inner surface of said feed-through section and said functional element includes a CCD or a TDI sensor.

45. The substrate inspection apparatus in accordance with claim 43 or 44, in which a wiring is formed in a net-like configuration on a surface of said feed-through section.

46. The substrate inspection apparatus in accordance with claim 43 or 44, further comprising a metal flange.

47. The substrate inspection apparatus in accordance with claim 43 or 44, in which said electricity introduction pin transmits a signal with frequency of not less than 10 MHz.

48. A substrate inspection apparatus comprising:
a. a beam source for emitting an electron beam having a specified width;
b. a primary electron optical system for introducing said electron beam to a surface of a substrate subject to an inspection;
c. a secondary electron optical system for guiding secondary electrons emitted from said substrate to a detecting system;
d. an image processing system for forming a secondary electron image based on a detection signal of a secondary electron beam obtained by said detecting system;
e. a state for holding said substrate in such a manner that said substrate may be moved successively with at least one degree of freedom;
f. an inspection chamber for said substrate;
g. a substrate conveying mechanism capable of carrying said substrate into said inspection chamber and taking out it therefrom;
h. an image processing analyzer capable of detecting a defective location on the substrate loaded into said inspection chamber based on the secondary electron image formed by said image processing system;
i. a vibration isolating mechanism for said inspection chamber;
j. a vacuum system capable of controlling a vacuum atmosphere to be maintained in said inspection chamber; and
k. a control system for indicating and/or storing said defective location on said substrate detected by said image processing analyzer, and in which said stage is provided with a non-contact supporting mechanism by means of a hydrostatic bearing and a vacuum sealing mechanism by means of a differential pumping, and
a divider is arranged between a location on said substrate subject to the electron beam irradiation and a hydrostatic bearing supporting section of said stage so as to reduce a conductance, so that
a pressure difference may be generated between the electron beam irradiated region and said hydrostatic bearing supporting section.

49. The substrate inspection apparatus in accordance with claim 48, in which said divider includes a differential pumping structure built therein.

50. The substrate inspection apparatus in accordance with claim 48 or 49, in which said divider has a cold trap function.

51. The substrate inspection apparatus in accordance with claim 48 or 49, in which said divider is arranged at each of two locations, which correspond to the vicinity of the charged particle beam irradiating location and the vicinity of the hydrostatic bearing, respectively.

52. The substrate inspection apparatus in accordance with claim 48 or 49, in which the gas supplied to said hydrostatic bearing of said stage is either of a dry nitrogen or a highly purified inert gas.

53. The substrate inspection apparatus in accordance with claim 48 or 49, in which at least a surface of a component of said stage facing to the hydrostatic bearing has been provided with a surface treatment for reducing gas emanated therefrom.

54. A substrate inspection apparatus comprising:

a. a beam source for emitting an electron beam having a specified width;

b. a primary electron optical system for introducing said electron beam to a surface of a substrate subject to an inspection;

c. a secondary electron optical system for guiding secondary electrons emitted from said substrate to a detecting system;

d. an image processing system for forming a secondary electron image based on a detection signal of a secondary electron beam obtained by said detecting system;

e. a stage for holding said substrate in such a manner that said substrate may be moved successively with at least one degree of freedom;

f. an inspection chamber for said substrate;

g. a substrate conveying mechanism capable of carrying said substrate into said inspection chamber and taking it out therefrom;

h. an image processing analyzer capable of detecting a defective location on the substrate loaded into said inspection chamber based on the secondary electron image formed by said image processing system;

i. a vibration isolating mechanism for said inspection chamber;

j. a vacuum system capable of controlling a vacuum atmosphere to be maintained in said inspection chamber; and k. a control system for indicating and/or storing said defective location on said substrate detected by said image processing analyzer, and wherein said substrate has a pattern of a minimum line width "d" and said substrate is scanned with a predetermined scanning width, and wherein a beam diameter "D" of the primary electron beam is selected such that a modulation transfer function MTF of a signal at a time when the primary electron beam has observed a cycle pattern having a pitch equivalent to a doubled minimum line width "d" should be $0.42 \leq MTF \leq 0.8$.

55. A device manufacturing method comprising:

a. preparing wafers;

b. processing a wafer-processing process;

c. inspecting defect using a pattern inspection apparatus as defined in claim 54;

d. repeating said steps b and c; and e. assembling devices from said processed wafer.

* * * * *

UNITED STATES PATENT AND TRADEMARK OFFICE
CERTIFICATE OF CORRECTION

PATENT NO. : 6,855,929 B2
DATED : February 15, 2005
INVENTOR(S) : Toshifumi Kimba et al.

It is certified that error appears in the above-identified patent and that said Letters Patent is hereby corrected as shown below:

Title page,
Item [30], Foreign Application Priority Data, should read
-- Feb. 9, 2001 (JP) ... 2001-033599 --.

Signed and Sealed this

Thirteenth Day of September, 2005

JON W. DUDAS
*Director of the United States Patent and Trademark Office*